US008642076B2

(12) United States Patent
Manoharan et al.

(10) Patent No.: US 8,642,076 B2
(45) Date of Patent: *Feb. 4, 2014

(54) LIPID CONTAINING FORMULATIONS

(75) Inventors: Muthiah Manoharan, Cambridge, MA (US); Kallanthottathil G. Rajeev, Cambridge, MA (US); Akin Akinc, Cambridge, MA (US); Narayanannair K. Jayaprakash, Cambridge, MA (US); Muthusamy Jayaraman, Cambridge, MA (US); Martin Maier, Cambridge, MA (US)

(73) Assignee: Tekmira Pharmaceuticals Corporation, Burnaby, British Columbia ( * ) Notice: Subject to any disclaimer, the term of this patent is extended or adjusted under 35 U.S.C. 154(b) by 0 days.

This patent is subject to a terminal disclaimer.

(21) Appl. No.: 13/211,094

(22) Filed: Aug. 16, 2011

(65) Prior Publication Data

US 2012/0046478 A1      Feb. 23, 2012

Related U.S. Application Data

(63) Continuation of application No. 12/056,230, filed on Mar. 26, 2008, now Pat. No. 8,034,376, which is a continuation of application No. PCT/US2007/080331, filed on Oct. 3, 2007.

(60) Provisional application No. 60/828,022, filed on Oct. 3, 2006, provisional application No. 60/870,457, filed on Dec. 18, 2006.

(51) Int. Cl.
*A61K 9/48*          (2006.01)
(52) U.S. Cl.
USPC ........................................................ 424/451
(58) Field of Classification Search
None
See application file for complete search history.

(56) References Cited

U.S. PATENT DOCUMENTS

| 5,679,852 A | 10/1997 | Platzek et al. |
| 2005/0064595 A1 | 3/2005 | MacLachlan et al. |
| 2006/0211642 A1 * | 9/2006 | McSwiggen et al. ........... 514/44 |

FOREIGN PATENT DOCUMENTS

| JP | 2003-505401 | 2/2003 |
| WO | WO-9626179 A1 | 8/1996 |
| WO | WO 01/05873 | 1/2001 |
| WO | WO 2005/007196 | 1/2005 |
| WO | WO-2005026372 A1 | 3/2005 |
| WO | WO-2006138380 A2 | 12/2006 |

OTHER PUBLICATIONS

Akinc, et al., A combinatorial library of lipid-like materials for delivery of RNAi therapeutics Nat. Biotech. 26:561-569 (2008).
Braun, et al., Structure/Function Relationships of Polyamidoamine/DNA Dendrimers as Gene Delivery Vehicles, J. Pharmaceutical Sciences 94:(2):423-436 (2005).
European Search Report dated Nov. 10, 2010 from European Application No. 07853756.
Pedroso De Lima, et al., Cationic Liposomes for Gene Delivery: From Biophysics to Biological Applications, Curr. Med. Chem. 10:1221-1231 (2003).
Westerberg, et al., Synthesis of Novel Bifunctional Chelators and Their Use in Preparing Monoclonal Antibody Conjugates for Tumor Targeting, J. Med. Chem. 32: 236-243 (1989).

* cited by examiner

*Primary Examiner* — Brian Gulledge
*Assistant Examiner* — Snigdha Maewall
(74) *Attorney, Agent, or Firm* — Viksnins Harris & Padys PLLP

(57) ABSTRACT

Compositions and methods useful in administering nucleic acid based therapies, for example association complexes such as liposomes and lipoplexes are described.

28 Claims, 13 Drawing Sheets

Fig. 6 ND98 formulation *in vivo* FVII assay result:

Figure 7: Formulation Tolerability is Increased as Lipid:siRNA Ratio is Reduced

Fig. 9
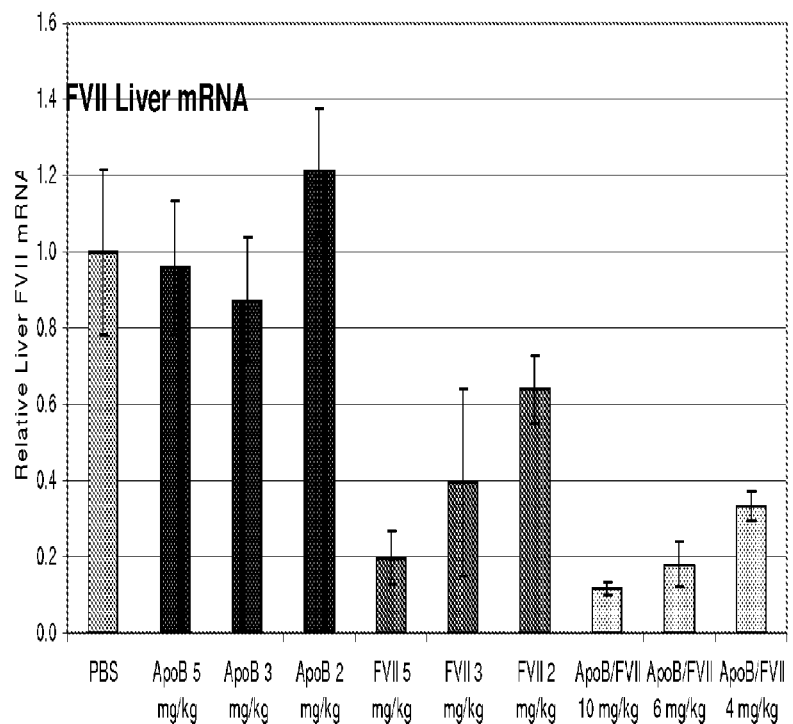
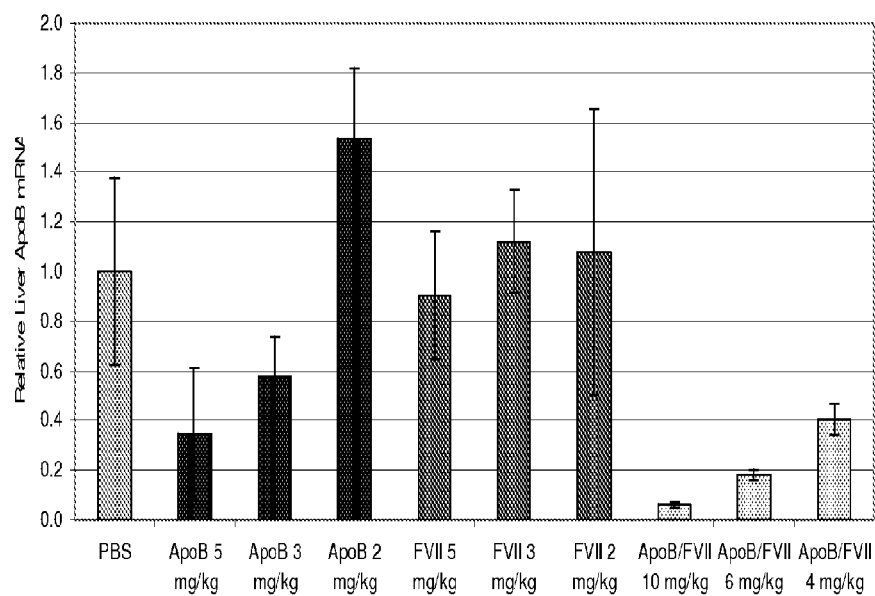

Unformulated

$T_{1/2} \sim 15$ min

Formulated

$T_{1/2} > 24$ h

LIPID CONTAINING FORMULATIONS

CLAIM OF PRIORITY

This application is a continuation of U.S. patent application Ser. No. 12/056,230, filed on Mar. 26, 2008, which is a continuation of International Application No. PCT/US2007/080331, filed Oct. 3, 2007, which claims priority to U.S. Provisional Application No. 60/828,022 filed on Oct. 3, 2006 and claims priority to U.S. Provisional Application No. 60/870,457 filed on Dec. 18, 2006, the entire contents of each are hereby incorporated by reference.

TECHNICAL FIELD

This invention relates to compositions and methods useful in administering nucleic acid based therapies, for example association complexes such as liposomes and lipoplexes.

BACKGROUND

The opportunity to use nucleic acid based therapies holds significant promise, providing solutions to medical problems that could not be addressed with current, traditional medicines. The location and sequences of an increasing number of disease-related genes are being identified, and clinical testing of nucleic acid-based therapeutics for a variety of diseases is now underway.

One method of introducing nucleic acids into a cell is mechanically, using direct microinjection. However this method is not generally effective for systemic administration to a subject.

Systemic delivery of a nucleic acid therapeutic requires distributing nucleic acids to target cells and then transferring the nucleic acid across a target cell membrane intact and in a form that can function in a therapeutic manner.

Viral vectors have, in some instances, been used clinically successfully to administer nucleic acid based therapies. However, while viral vectors have the inherent ability to transport nucleic acids across cell membranes, they can pose risks. One such risk involves the random integration of viral genetic sequences into patient chromosomes, potentially damaging the genome and possibly inducing a malignant transformation. Another risk is that the viral vector may revert to a pathogenic genotype either through mutation or genetic exchange with a wild type virus.

Lipid-based vectors have also been used in nucleic acid therapies and have been formulated in one of two ways. In one method, the nucleic acid is introduced into preformed liposomes or lipoplexes made of mixtures of cationic lipids and neutral lipids. The complexes thus formed have undefined and complicated structures and the transfection efficiency is severely reduced by the presence of serum. The second method involves the formation of DNA complexes with mono- or poly-cationic lipids without the presence of a neutral lipid. These complexes are prepared in the presence of ethanol and are not stable in water. Additionally, these complexes are adversely affected by serum (see, Behr, Acc. Chem. Res. 26:274-78 (1993)).

SUMMARY

The invention features novel preparations that include a polyamine compound or a lipid moiety described herein.

In some embodiments, the invention features a preparation comprising one or more compounds, each individually having a structure defined by formula (I) or a pharmaceutically acceptable salt thereof,

formula (I)

wherein each $X^a$ and $X^b$, for each occurrence, is independently $C_{1-6}$ alkylene;

n is 0, 1, 2, 3, 4, or 5; each R is independently H,

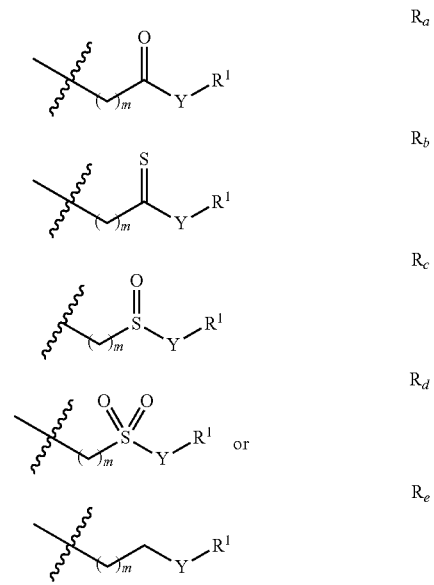

wherein at least n+2 of the R moieties in at least about 50% of the molecules of the compound of formula (I) in the preparation (e.g., at least about 55%, at least about 60%, at least about 65%, at least about 70%, at least about 75%, at least about 80%, at least about 85%, at least about 90%, at least about 95%, at least about 98%, at least about 99%, or substantially all) are not H;

m is 1, 2, 3 or 4; Y is O, $NR^2$, or S;

$R^1$ is alkyl alkenyl or alkynyl; each of which is optionally substituted with one or more substituents; and $R^2$ is H, alkyl alkenyl or alkynyl; each of which is optionally substituted each of which is optionally substituted with one or more substituents;

provided that, if n=0, then at least n+3 of the R moieties are not H.

In some embodiments, when R is not H, R is $R_a$, for example, when R is not H, R is $R_a$ for each occurrence.

In some embodiments, when R is not H, R is $R_b$, for example, when R is not H, R is $R_b$, for each occurrence.

In some embodiments, when R is not H, R is $R_c$, for example, when R is not H, R is $R_c$, for each occurrence.

In some embodiments, when R is not H, R is $R_d$, for example, when R is not H, R is $R_d$, for each occurrence.

In some embodiments, when R is not H, R is $R_e$, for example, when R is not H, R is $R_e$, for each occurrence.

In some embodiments, n+2 of the R moieties of formula (I) are not H. In some embodiments, n+3 of the R moieties of formula (I) are not H. In some embodiments, n+4 of the R moieties of formula (I) are not H.

In some embodiments, n+1 of the R moieties of formula (I) are not H.

In some embodiments, n>0, and at least one R of NR of formula (I) is H.

In some embodiments, at least one R of NR$_2$ of formula (I) is H.

In some embodiments, at least 80% of the molecules are a single structural isomer. For example, n+2 of the R moieties of formula (I) are not H, or n+3 of the R moieties of formula (I) are not H, or n+4 of the R moieties of formula (I) are not H.

In some embodiments, n is 2 or 0.

In some embodiments, $X^a$ and $X^b$ are $C_2$ alkylene.

In some embodiments, n is 0 and $X^b$ is ethylene or propylene.

In some embodiments, n>1 and $X^a$ varies with at least one occurrence.

In some embodiments, when R not H, R is

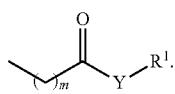

For example, Y can be O or $NR^2$. In some embodiments, m is 2. In some embodiments, Y is O or $NR^2$ and m is 2. In some embodiments, m is 1. In some embodiments, m is 1 and Y is O or $NR^2$.

In some embodiments, $R^1$ for at least one occurrence is alkyl, for example, $R^1$ for each occurrence is alkyl.

In some embodiments, $R^1$ is alkyl and $R^2$ is H, for at least one occurrence, e.g., for each occurrence.

In some embodiments, $R^1$ and $R^2$ are alkyl for at least one occurrence, e.g., for each occurrence.

In some embodiments, $R^1$ for at least one occurrence is alkenyl.

In some embodiments, $R^1$ for at least one occurrence is alkenyl.

In some embodiments, when R is not H, R is $R_a$, for at least one occurrence, e.g., for each occurrence, and Y is O or NH. In some embodiments, Y is O. In some embodiments, Y is NH. In some embodiments, $R^1$ is alkyl, e.g., $C_{10-30}$ alkyl or $C_{12}$ alkyl. In some embodiments, n is 2. In some embodiments, $X^a$, for each occurrence is $C_2$ alkylene and $X^b$ is $C_2$ alkylene. In some embodiments, m is 2.

In some embodiments, n is 2 and R, when R is not H, is $R_a$, for at least one occurrence, e.g., for each occurrence. In some embodiments, $R^1$ is alkyl, e.g., $C_{10-18}$ alkyl or $C_{12}$ alkyl. In some embodiments, Y is O or Y is NH. In some embodiments, $X^a$, for each occurrence is $C_2$ alkylene and $X^b$ is $C_2$ alkylene. In some embodiments, m is 2.

In some embodiments, at least 1 R of NR is H and R, when not H is $R_a$, for at least one occurrence, e.g. for each occurrence, and Y is O or NH. In some embodiments, Y is O or Y is NH. In some embodiments, $R^1$ is alkyl, e.g., $C_{10-18}$ alkyl or $C_{12}$ alkyl. In some embodiments, n is 2. In some embodiments, $X^a$, for each occurrence is $C_2$ alkylene and $X^b$ is $C_2$ alkylene. In some embodiments, m is 2.

In some embodiments, n is 2 and at least 1 R of NR is H and when R is not H, R is $R_a$, for at least one occurrence, e.g. for each occurrence, and Y is O or NH. In some embodiments, $R^1$ is alkyl, e.g., $C_{10-18}$ alkyl or $C_{12}$ alkyl. In some embodiments, Y is O or Y is NH. In some embodiments, $X^a$, for each occurrence is $C_2$ alkylene and $X^b$ is $C_2$ alkylene. In some embodiments, m is 2.

In some embodiments, at least 1 R of $NR_2$ is H and R is $R_a$, for at least one occurrence, e.g. for each occurrence, and wherein Y is O or NH. In some embodiments, Y is O or Y is NH. In some embodiments, $R^1$ is alkyl, e.g., $C_{10-30}$ alkyl, $C_{10-18}$ alkyl or $C_{12}$ alkyl. In some embodiments, n is 2. In some embodiments, $X^a$, for each occurrence is $C_2$ alkylene and $X^b$ is $C_2$ alkylene. In some embodiments, m is 2.

In some embodiments, n is 2 and at least 1 R of $NR_2$ is H and R is $R_a$, for at least one occurrence, e.g. for each occurrence, and wherein Y is O or NH. In some embodiments, $R^1$ is alkyl, e.g., $C_{10-18}$ alkyl or $C_{12}$ alkyl. In some embodiments, Y is O or Y is NH. In some embodiments, $X^a$, for each occurrence is $C_2$ alkylene and $X^b$ is $C_2$ alkylene. In some embodiments, m is 2.

In some embodiments, the preparation comprises one or a mixture of the formula below, wherein R is not H unless specified in the formula below.

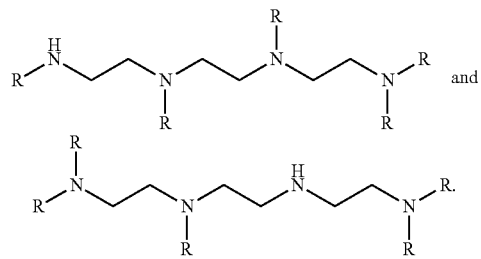

In some embodiments, the preparation consists essentially of one or a mixture of the formula below

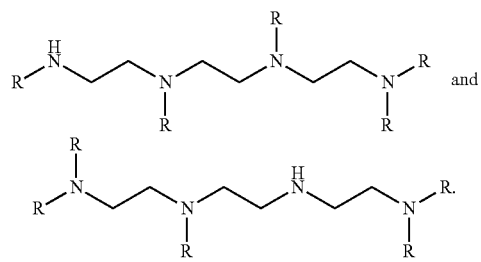

In some embodiments, each R is

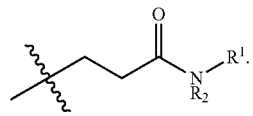

In some embodiments, each R is

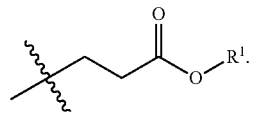

In some embodiments, $R^1$ is $C_{10}$-$C_{18}$ alkyl (e.g., $C_{12}$ alkyl), or $C_{10}$-$C_{30}$ alkenyl.

In some embodiments, R is

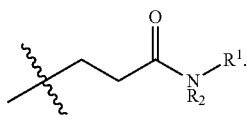

In some embodiments, $R^1$ is $C_{10}$-$C_{18}$ alkyl, e.g., $C_{12}$ alkyl. In some embodiments, $R^1$ is $C_{12}$ alkyl and $R^2$ is H.

In some embodiments, n is 0 and X is propylene. In some embodiments, 1 R is H. In some embodiments, when R is not H, R is $R_a$, for at least one occurrence, e.g. for each occurrence. In some embodiments, $R^1$ is alkyl, e.g., $C_{10\text{-}30}$ alkyl or $C_{12}$ alkyl. In some embodiments, Y is O or Y is NH. In some embodiments, m is 2.

In some embodiments, formula (I) is

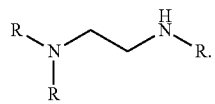

In some embodiments, R is

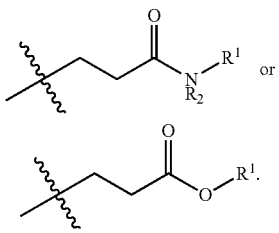

In some embodiments, $R^1$ is $C_{10}$-$C_{18}$ alkyl, or $C_{10}$-$C_{30}$ alkenyl. In some embodiments, R is

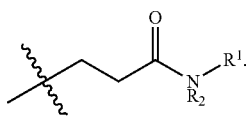

In some embodiments, $R^1$ is $C_{10}$-$C_{18}$ alkyl, or $C_{10}$-$C_{30}$ alkenyl and $R^2$ is H.

In some embodiments,
n is 2;
$X^a$, for each occurrence is $C_2$ alkylene and $X^b$ is $C_2$ alkylene; and
wherein
each R is H or

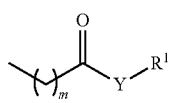

$R_a$, for at least one occurrence, e.g. for each occurrence, m is 2;
Y is NH or O;
$R^1$ is $C_{12}$ alkyl. In some embodiments, at least 80% of the molecules of the compound of formula (I) are a single structural isomer. In some embodiments, Y is NH, e.g., wherein at least 80% of the molecules of the compound of formula (I) are a single structural isomer. In some embodiments, R is $R^a$, for 5 occurrences. In some embodiments, in at least 80% of the molecules of the compound of formula (I), R is $R^a$, for 5 occurrences. In some embodiments, Y is NH.

In some embodiments, the compound of formula (I) is an inorganic or organic salt thereof, e.g., a hydrohalide salt thereof, such as a hydrochloride salt thereof. In some embodiments, the hydrochloride salt ranges from a single equivalent of HCL, to n+2 equivalents of HCl. In some embodiments, the compound of formula (I) is salt of an organic acid, e.g., an acetate, for example, the acetate salt ranges from a single equivalent of acetate, to n+2 equivalents of acetate or a formate, for example, the formate salt ranges from a single equivalent of acetate, to n+2 equivalents of formate.

In some embodiments, the compound of formula (I) is in the form of a hydrate.

In some embodiments, $R^1$, for at least one occurrence, e.g., for each occurrence, comprises an alkenyl moiety, for example, $R^1$ comprises a cis double bond.

In one aspect, the invention features a preparation including a compound of formula (I) and a nucleic acid (e.g., an RNA such as an siRNA or dsRNA or a DNA). In some embodiment, the preparation also includes an additional lipid such as a fusogenic lipid, or a PEG-lipid.

In some embodiments, the preparation comprises less than 11%, by weight, of

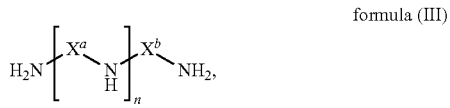

formula (III)

wherein X and n are defined as in formula (I) above.

In some embodiments, the preparation comprises less than 90% by weight of

formula (IV)

wherein Y and $R^1$ are defined as in formula (I) above.

In some embodiments, the preparation comprises a plurality of compounds of formula (I).

In some embodiments, the preparation comprises a mixture of compounds of the formulas below:

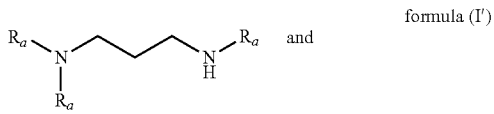

formula (I')

and

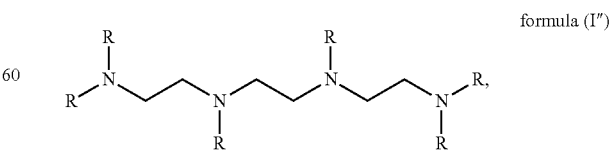

formula (I")

wherein in formula (I"), five of the R moieties are $R^a$. In some embodiments, formula (I') and (I") are present in a ratio of from about 1:2 to about 2:1.

In one aspect, the invention features a method of making a compound of formula

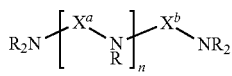
formula (II)

wherein
each $X^a$ and $X^b$, for each occurrence, is independently $C_{1-6}$ alkylene;
n is 0, 1, 2, 3, 4, or 5; and
wherein
each R is independently H or

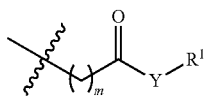

$R_a$;
m is 2;
Y is O, $NR^2$, or S;
$R^1$ is alkyl or alkenyl;
$R^2$ is H or C alkyl or alkenyl;
the method comprising reacting a compound of formula (III)

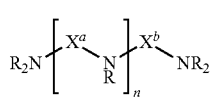
formula (III)

with a compound of formula (IV),

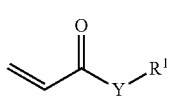
formula (IV)

in the presence of a promoter.

In one aspect, the invention features a method of making a compound of formula (II),

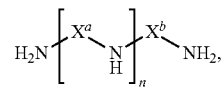
formula (II)

wherein
each $X^a$ and $X^b$, for each occurrence, is independently $C_{1-6}$ alkylene;
n is 0, 1, 2, 3, 4, or 5; and
wherein
each R is independently H or

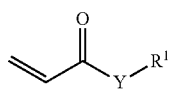

$R_a$
m is 2;
Y is O, $NR^2$, or S;
$R^1$ is alkyl or alkenyl;
$R^2$ is H or C alkyl or alkenyl;
the method comprising reacting a compound of formula (III)

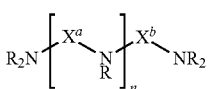
formula (III)

with a compound of formula (IV),

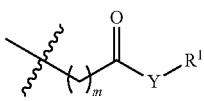
formula (IV)

in the presence of a quencher.

In one aspect, the invention features a method of making a compound of formula (II),

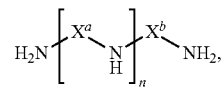
formula (II)

wherein
each $X^a$ and $X^b$, for each occurrence, is independently $C_{1-6}$ alkylene;
n is 0, 1, 2, 3, 4, or 5; and
wherein
each R is independently H or

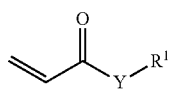

$R_a$;
m is 2;
Y is O, $NR^2$, or S;
$R^1$ is alkyl or alkenyl;
$R^2$ is H or alkyl or alkenyl; the method comprising reacting a compound of formula (III)

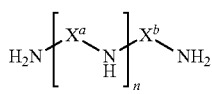

formula (III)

with a compound of formula (IV),

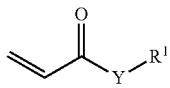

formula (IV)

wherein the reaction mixture comprises from about 0.8 about 1.2 molar equivalents of a compound of formula (III), with from about 3.8 to about 6.5 molar equivalents of a compound of formula (IV).

In some embodiments, the reaction mixture comprises from about 0.8 about 1.2 molar equivalents of a compound of formula (III), with from about 5.5 to about 6.5 molar equivalents of a compound of formula (IV). In some embodiments, the reaction mixture comprises about 1 molar equivalents of a compound of formula (III), with from about 6 molar equivalents of a compound of formula (IV). In some embodiments, the reaction mixture comprises about 1 molar equivalents of a compound of formula (III), with from about 5 molar equivalents of a compound of formula (IV).

In one aspect, the invention features a method of making a compound of formula (II),

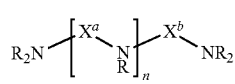

formula (II)

wherein
each $X^a$ and $X^b$, for each occurrence, is independently $C_{1-6}$ alkylene;
n is 0, 1, 2, 3, 4, or 5; and
wherein
each R is independently H or

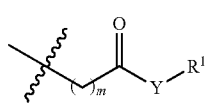

$R_a$;
m is 2;
Y is O, $NR^2$, or S;
$R^1$ is alkyl or alkenyl;
$R^2$ is H or alkyl or alkenyl;
the method comprising a two step process of reacting a compound of formula (III)

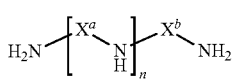

formula (III)

with a compound of formula (IV),

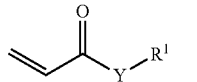

formula (IV)

in the presence of boric acid and water
wherein, the first step process involving the reaction mixture comprises from about 0.8 about 1.2 molar equivalents of a compound of formula (III), with from about 3.8 to about 4.2 molar equivalents of a compound of formula (IV) and the second step process involving addition of about 0.8 to 1.2 molar equivalent of compound of formula (IV).

In one aspect, the invention features a method of making a compound of formula (II),

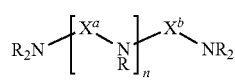

formula (II)

wherein
each $X^a$ and $X^b$, for each occurrence, is independently $C_{1-6}$ alkylene;
n is 0, 1, 2, 3, 4, or 5; and
wherein
each R is independently H or

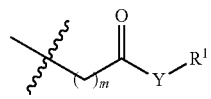

$R_a$
m is 2;
Y is O, $NR^2$, or S;
$R^1$ is alkyl or alkenyl;
$R^2$ is H or alkyl or alkenyl;
the method comprising reacting a compound of formula (III)

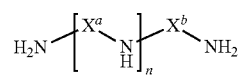

formula (III)

with a compound of formula (IV),

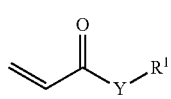

formula (IV)

and separating at least one structural isomer of formula (II) from the reaction mixture to provide a substantially purified preparation comprising a structural isomer of formula (II).

In some embodiments, the structural isomer of formula (II) is separated from the reaction mixture using chromatographic separation. In some embodiments, the chromatographic separation is using flash silica gel for separation of isomers. In some embodiments, the chromatographic separation is gravity separation of isomers using silica gel. In some embodiments, the chromatographic separation is using moving bed chromatography for separation of isomers. In some embodiments, the chromatographic separation uses liquid chromatography (LC) for separation of isomers. In some embodiments, the chromatographic separation is normal phase HPLC for separation of isomers. In some embodiments, the chromatographic separation is reverse phase HPLC for separation of isomers.

In some embodiments, the substantially purified preparation comprises at least about 80% of the structural isomer of formula (II), e.g., at least about 90% of the structural isomer of formula (II), at least about 95% of the structural isomer of formula (II).

In another aspect, the invention features a method of making a compound of formula (V) or a pharmaceutically acceptable salt thereof, $$R_2N \underset{}{\overset{}{\left[X^a\underset{R}{\overset{}{N}}\right]_n}} X^b NR_2 \quad \text{formula (V)}$$

wherein
each $X^a$ and $X^b$, for each occurrence, is independently $C_{1-6}$ alkylene;
n is 0, 1, 2, 3, 4, or 5; and
wherein
each R is independently H or

[structure: $-(\phantom{x})_m - C(=O) - Y - R^1$]

$R_a$;
m is 1;
Y is O, $NR^2$, or S;
$R^1$ is alkyl or alkenyl;
$R^2$ is H or alkyl or alkenyl;
the method comprising reacting a compound of formula (III)

$$H_2N \underset{}{\overset{}{\left[X^a\underset{H}{\overset{}{N}}\right]_n}} X^b NH_2 \quad \text{formula (III)}$$

with a compound of formula (VI), $$Q\underset{}{\overset{O}{\diagdown}}\underset{}{\overset{}{\diagup}}Y R^1 \quad \text{formula (VI)}$$

Q = Cl or Br or I to provide a compound of formula (V) or a pharmaceutically acceptable salt thereof.

In some embodiments, the pharmaceutically acceptable salt thereof is a hydrochloride salt of the compound of formula (V).

In one aspect, the invention features a compound of formula (X), $$R^1\underset{R^2}{\overset{}{N}}\underset{}{\left(\phantom{x}\right)_m}\underset{L^1\diagdown R^3}{\overset{}{\phantom{C}}}\underset{}{\left(\phantom{x}\right)_n}L^2\diagdown R^4 \quad \text{formula (X)}$$

wherein
$R^1$ and $R^2$ are each independently H, $C_1$-$C_6$ alkyl, optionally substituted with 1-4 $R^5$, $C_2$-$C_6$ alkenyl, optionally substituted with 1-4 $R^5$, or $C(NR^6)(NR^6)_2$;
$R^3$ and $R^4$ are each independently alkyl, alkenyl, alkynly, each of which is optionally substituted with fluoro, chloro, bromo, or iodo;
$L^1$ and $L^2$ are each independently —$NR^6C(O)$—, —$C(O)NR^6$—, —$OC(O)$—, —$C(O)O$—, —S—S—, —$N(R^6)C(O)N(R^6)$—, —$OC(O)N(R^6)$—, —$N(R^6)C(O)O$—, —O—N=C—, OR, —OC(O)NH—N=C—, or —NHC(O)NH—N=C—,
$L^1$-$R^3$ and $L^2$-$R^4$ can be taken together to form an acetal, a ketal, or an orthoester, wherein $R^3$ and $R^4$ are defined as above and can also be H or phenyl;
$R^5$ is fluoro, chloro, bromo, iodo, —$OR^7$, —$N(R^8)(R^9)$, —CN, $SR^{10}$, $S(O)R^{10}$, $S(O)_2R^{10}$
$R^6$ is H, $C_1$-$C_6$ alkyl,
$R^7$ is H or $C_1$-$C_6$ alkyl;
each $R^8$ and $R^9$ are independently H or $C_1$-$C_6$ alkyl;
$R^{10}$ is H or $C_1$-$C_6$ alkyl;
m is 1, 2, 3, 4, 5, or 6;
n is 0, 1, 2, 3, 4, 5, or 6;
and pharmaceutically acceptable salts thereof.

In some embodiments, the compound is an inorganic salt thereof, for example a hydrohalide salt thereof such as a hydrochloride salt thereof. In some embodiments, the compound is an organic salt thereof.

In some embodiments, $R^1$ and $R^2$ are each independently $C_1$-$C_3$ alkyl.

In some embodiments, $R^1$ is methyl.
In some embodiments, $R^2$ is methyl.
In some embodiments, $R^1$ and $R^2$ are both methyl.
In some embodiments, $R^1$ is H, methyl, ethyl, isopropyl, or 2-hydroxyethyl.
In some embodiments, $R^2$ is H.
In some embodiments, $R^2$ is methyl, ethyl, propyl, or isopropyl.
In some embodiments, $R^1$ is H, methyl, ethyl, isopropyl, or 2-hydroxyethyl and $R^2$ is H, methyl, ethyl, propyl, or isopropyl.
In some embodiments, m is 1.
In some embodiments, n is 1.
In some embodiments, both m and n are 1.
In some embodiments, $L^1$ is —$NR^6C(O)$—, or —$C(O)NR^6$—.
In some embodiments, $L^1$ is -OC(O)— or —C(O)O—.
In some embodiments, $L^1$ is S—S—.
In some embodiments, $L^1$ is —$N(R^6)C(O)N(R^6)$—.
In some embodiments, $L^1$ is —$OC(O)N(R^6)$— or —$N(R^6)C(O)O$—.
In some embodiments, $L^1$ is —O—N=C—.
In some embodiments, $L^1$-OC(O)NH—N=C— or —NHC(O)NH—N=C—. In some embodiments, $L^2$ is —$NR^6C(O)$—, or —$C(O)NR^6$—.
In some embodiments, $L^2$ is -OC(O)— or —C(O)O—.

In some embodiments, $L^2$ is —S—S—.

In some embodiments, $L^2$ is —N($R^6$)C(O)N($R^6$)—.

In some embodiments, $L^2$ is —OC(O)N($R^6$)— or —N($R^6$)C(O)O—.

In some embodiments, $L^2$ is —O—N=C—.

In some embodiments, $L^2$-OC(O)NH—N=C— or —NHC(O)NH—N=C—.

In some embodiments, both $L^1$ and $L^2$ are —N$R^6$C(O)—, or —C(O)N$R^6$—.

In some embodiments, both $L^1$ and $L^2$ are —OC(O)— or —C(O)O—.

In some embodiments, both $L^1$ and $L^2$ are S—S—.

In some embodiments, both $L^1$ and $L^2$ are —N($R^6$)C(O)N($R^6$)—.

In some embodiments, both $L^1$ and $L^2$ are —OC(O)N($R^6$)— or —N($R^6$)C(O)O—.

In some embodiments, $L^1$ is —N$R^6$C(O)— and $L^2$ is —S—S—.

In some embodiments, $L^1$ is —OC(O)— and $L^2$ is —S—S—.

In some embodiments, $L^1$ is —OC(O)N($R^6$) or —N($R^6$)C(O)O— and $L^2$ is —S—S—.

In some embodiments, $L^1$ is —N($R^6$)C(O)N($R^6$)— and $L^2$ is —S—S—.

In some embodiments, $L^1$-$R^3$ and $L^2$-$R^4$ are taken together to form an acetal, a ketal, or an orthoester.

In some embodiments, each $R^3$ and $R^4$ are independently alkyl.

In some embodiments, both $R^3$ and $R^4$ are $C_6$-$C_{28}$ alkyl.

In some embodiments, each $L^1$ and $L^2$ are independently —S—S—, —OC(O)N($R^6$)— or —N($R^6$)C(O)O—.

In some embodiments, $R^3$ is alkyl.

In some embodiments, $R^4$ is alkyl.

In some embodiments, $R^3$ is alkenyl.

In some embodiments, $R^4$ is alkenyl.

In some embodiments, each $R^3$ and $R^4$ are independently alkenyl, for example, each $R^3$ and $R^4$ are independently $C_6$-$C_{30}$ alkenyl or each $R^3$ and $R^4$ are the same alkenyl moiety.

In some embodiments, each $R^3$ and $R^4$ includes two double bond moieties. In some embodiments, at least one of the double bonds have a Z configuration. In some embodiments, both of the double bonds have a Z configuration. In some embodiments, at least one of $R^3$ and $R^4$ is provided in formula (II) below

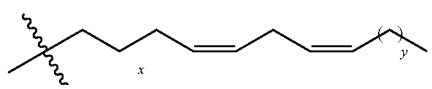

formula (II)

wherein x is an integer from 1 to 8; and y is an integer from 1-10. In some embodiments, both of $R^3$ and $R^4$ are of the formula (II). In some embodiments, at least one of the double bonds have an E configuration, e.g., both of the double bonds have an E configuration. In some embodiments, at least one of $R^1$ and $R^2$ is provided in formula (III) below

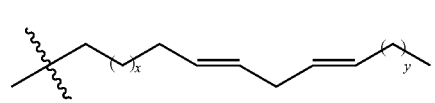

formula (III)

wherein x is an integer from 1 to 8; and y is an integer from 1-10.

In some embodiments, each $R^1$ and $R^2$ includes three double bond moieties. In some embodiments, at least one of the double bonds have a Z configuration. In some embodiments, at least two of the double bonds have a Z configuration. In some embodiments, all three of the double bonds have a Z configuration. In some embodiments, at least one of $R^1$ and $R^2$ is provided in formula (IV) below

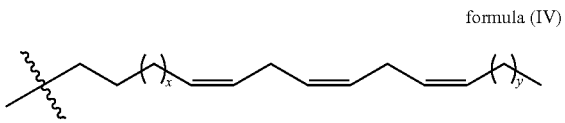

formula (IV)

wherein x is an integer from 1 to 8; and y is an integer from 1-10. In some embodiments, both of $R^1$ and $R^2$ are as provided in formula (IV). In some embodiments, at least one of the double bonds have an E configuration. In some embodiments, at least two of the double bonds have an E configuration. In some embodiments, all three of the double bonds have an E configuration. In some embodiments, at least one of $R^1$ and $R^2$ is provided in formula (IV) below

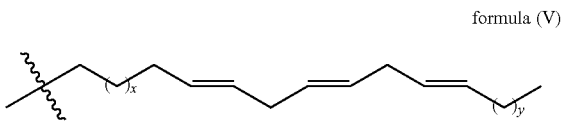

formula (V)

wherein x is an integer from 1 to 8; and y is an integer from 1-10. In some embodiments, both of $R^1$ and $R^2$ are as provided in formula (V).

In some embodiments, $R^1$ and $R^2$ are each $C_1$-$C_6$ alkyl (e.g., methyl), L1 and L1 are each —OC(O)—, and $R^3$ and $R^4$ are each alkenyl. In some embodiments, $R^3$ and $R^4$ are the same. In some embodiments, $R^3$ and $R^4$ both include two double bonds (e.g., having cis linkages). In some embodiments $R^3$ and $R^4$ are provided in formula (II) below

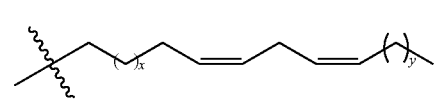

formula (II)

wherein x is an integer from 1 to 8 e.g., 5; and y is an integer from 1-10 e.g., 4.

In one aspect, the invention features a preparation including a compound of formula (X).

In one aspect, the invention features a preparation including a compound of formula (X) and a nucleic acid (e.g., an RNA such as an siRNA or dsRNA or a DNA). In some embodiment, the preparation also includes an additional lipid such as a fusogenic lipid, or a PEG-lipid.

In one aspect, the invention features a method of making a compound of formula (X),

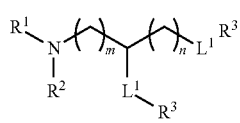

formula (X)

wherein $R^1$ and $R^2$ are each independently $C_1$-$C_6$ alkyl, optionally substituted with 1-4 $R^5$;

$R^3$ is alkyl, alkenyl, alkynyl $L^1$ is —OC(O)—

$R^5$ is $-OR^7$, $-N(R^8)(R^9)$, $-CN$, $SR^{10}$, $S(O)R^{10}$, $S(O)_2R^{10}$ $R^6$ is H, $C_1$-$C_6$ alkyl;

$R^7$ is H or $C_1$-$C_6$ alkyl;

each $R^8$ and $R^9$ are independently H or $C_1$-$C_6$ alkyl;

$R^{10}$ is H or $C_1$-$C_6$ alkyl;

m and n are each independently 1, 2, 3, 4, 5, or 6, the method comprising reacting a compound of formula (VI),

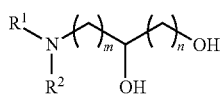

formula (VI)

with a compound of formula (VII)

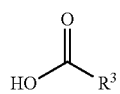

formula (VII)

in the presence of a coupling agent, thereby providing a compound of formula (X).

In some embodiments, the coupling agent is a carbodiimide such as EDCI.

In one aspect, the invention features a compound of formula (XV) below

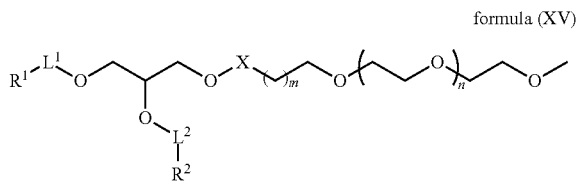

formula (XV)

wherein;

each $L^1$ and $L^2$ are independently a bond or C(O);

each $R^1$ and $R^2$ are independently alkyl alkenyl or alkynyl; each of which is optionally substituted with one or more substituents;

X is —C(O)NH—, C(S)NH, —C(O)$C_{1-3}$alkylC(O)NH—; or —C(O)$C_{1-3}$alkylC(O)O—;

m is an integer from 0-11 and n is an integer from 1-500.

In some embodiments, $L^1$ and $L^2$ are both a bond.

In some embodiments, $L^1$ and $L^2$ are both C(O).

In some embodiments, each $R^1$ and $R^2$ are independently alkyl, for example $C_6$-$C_{28}$ alkyl, e.g., $C_{10}$-$C_{18}$ alkyl, e.g., $C_{13}$ alkyl, $C_{14}$ alkyl, $C_{15}$ alkyl, or $C_{16}$ alkyl, In some embodiments, both $R^1$ and $R^2$ are alkyl, e.g., straight chain alkyl having the same length, e.g., $C_6$-$C_{28}$ alkyl, e.g., $C_{10}$-$C_{18}$ alkyl, e.g., $C_{13}$ alkyl, $C_{14}$ alkyl, $C_{15}$ alkyl, or $C_{16}$ alkyl. In some preferred embodiments, both $R^1$ and $R^2$ are $C_{14}$ alkyl.

In some embodiments, the formula XV represents a racemic mixture

In some embodiments, the compound of formula XV has an enantiomeric excess of the R isomer, e.g., at least about 65%, 70%, 75%, 80%, 85%, 90%, 95%, 97%, 98%, or 99%. In some embodiments the formula XV represents enantiomerically pure 'R' isomer.

In some embodiments, the compound of formula XV has an enantiomeric excess of the S isomer, e.g., at least about 65%, 70%, 75%, 80%, 85%, 90%, 95%, 97%, 98%, or 99%. In some embodiments the formula XV represents enantiomerically pure 'S' isomer.

In some embodiments, each $R^1$ and $R^2$ are independently alkenyl, for example, each $R^1$ and $R^2$ are independently $C_6$-$C_{30}$ alkenyl or each $R^1$ and $R^2$ are the same alkenyl moiety. In some embodiments, each $R^1$ and $R^2$ includes a single double bond, for example a single double bond in the E or Z configuration.

In some embodiments, each $R^1$ and $R^2$ includes two double bond moieties. In some embodiments, at least one of the double bonds has a Z configuration. In some embodiments, both of the double bonds have a Z configuration. In some embodiments, at least one of $R^1$ and $R^2$ is provided in formula (II) below

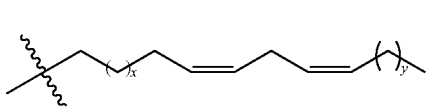

formula (II)

wherein x is an integer from 1 to 8; and y is an integer from 1-10. In some embodiments, both of $R^1$ and $R^2$ are of the formula (II). In some embodiments, at least one of the double bonds has an E configuration, e.g., both of the double bonds have an E configuration. In some embodiments, at least one of $R^1$ and $R^2$ is provided in formula (III) below

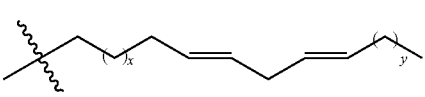

formula (III)

wherein x is an integer from 1 to 8; and y is an integer from 1-10.

In some embodiments, each $R^1$ and $R^2$ includes three double bond moieties. In some embodiments, at least one of the double bonds has a Z configuration. In some embodiments, at least two of the double bonds have a Z configuration. In some embodiments, all three of the double bonds have a Z configuration. In some embodiments, at least one of $R^1$ and $R^2$ is provided in formula (IV) below

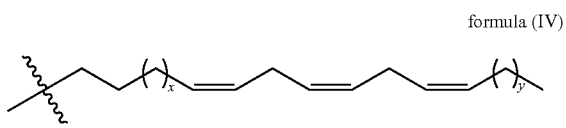

formula (IV)

wherein
x is an integer from 1 to 8; and
y is an integer from 1-10. In some embodiments, both of $R^1$ and $R^2$ are as provided in formula (IV). In some embodiments, at least one of the double bonds has an E configuration. In some embodiments, at least two of the double bonds have an E configuration. In some embodiments, all three of the double bonds have an E configuration. In some embodiments, at least one of $R^1$ and $R^2$ is provided in formula (IV) below

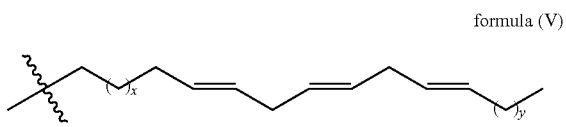

formula (V)

wherein
x is an integer from 1 to 8; and
y is an integer from 1-10. In some embodiments, both of $R^3$ and $R^4$ are as provided in formula (V).

In some embodiments, X is —C(O)NH—, providing a compound of formula (XV') below:

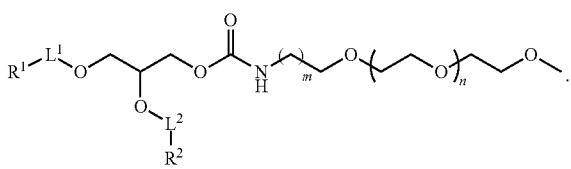

formula (XV')

In some embodiments, each $R^1$ and $R^2$ are independently alkyl, for example $C_6$-$C_{28}$ alkyl, e.g., $C_{10}$-$C_{18}$ alkyl, e.g., $C_{13}$ alkyl, $C_{14}$ alkyl, $C_{15}$ alkyl, or $C_{16}$ alkyl. In some embodiments, both $R^1$ and $R^2$ are alkyl, e.g., straight chain alkyl having the same length, e.g., $C_6$-$C_{28}$ alkyl, e.g., $C_{10}$-$C_{18}$ alkyl, e.g., $C_{13}$ alkyl, $C_{14}$ alkyl, $C_{15}$ alkyl, or $C_{16}$ alkyl. In some preferred embodiments, both $R^1$ and $R^2$ are $C_{14}$ alkyl.

In some embodiments, X is —C(O)$C_{1-3}$alkylC(O)O—.

In some embodiments, m is an integer from 1-10, for example an integer from 2-4 or an integer 2.

In some embodiments, n is an integer from 1-500, for example an integer from 40-400, from 100-350, from 40-50 or from 42-47.

In some embodiments, the compound is a compound of formula (XV'), formula (XV')

$$R^1\text{-}L^1\text{-}O\text{-}CH_2\text{-}CH(O\text{-}L^2\text{-}R^2)\text{-}CH_2\text{-}O\text{-}C(O)\text{-}NH\text{-}(CH_2)_m\text{-}O\text{-}(CH_2CH_2O)_n\text{-}CH_3$$

wherein both $L^1$ and $L^2$ are a bond. In some embodiments, each $R^1$ and $R^2$ are independently alkyl, for example $C_6$-$C_{28}$ alkyl, e.g., $C_{10}$-$C_{18}$ alkyl, e.g., $C_{14}$ alkyl, $C_{15}$ alkyl, or $C_{16}$ alkyl. In some embodiments, both $R^1$ and $R^2$ are alkyl, e.g., straight chain alkyl having the same length, e.g., $C_6$-$C_{28}$ alkyl, e.g., $C_{10}$-$C_{18}$ alkyl, e.g., $C_{14}$ alkyl, $C_{15}$ alkyl, or $C_{16}$ alkyl. In some preferred embodiments, both $R^1$ and $R^2$ are $C_{14}$ alkyl. In some embodiments, m is an integer from 1-10, for example an integer from 2-4 or an integer 2 In some embodiments, n is an integer from 1-500, for example an integer from 40-400, or from 40-50.

In some embodiments, the compound is a compound of formula (XV'), wherein L1 and L2 are both bonds, $R^1$ and $R^2$ are both alkyl (e.g., $C_6$-$C_{28}$ alkyl, e.g., $C_{10}$-$C_{18}$ alkyl, preferably $C_{14}$ alkyl), and n is an integer from about 40-400.

In some embodiments, the compound has a formula (XVI) below:

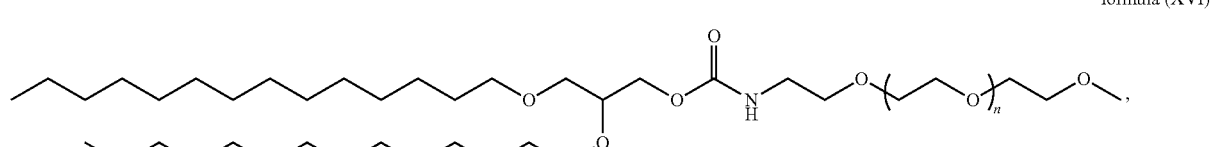

formula (XVI)

wherein the repeating PEG moiety has an average molecular weight of 2000 with n value between 42 and 47.

In some embodiments, the compound of formula XV has an enantiomeric excess of the R isomer, e.g., at least about 65%, 70%, 75%, 80%, 85%, 90%, 95%, 97%, 98%, or 99%. In some embodiments the compound of formula XVI is a stereo isomer with preferred absolute configuration 'R'.

In one aspect, the invention features a PEG lipid conjugated to a cholesterol moiety. For example, the compound of formula (XX) below:

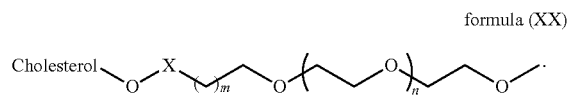

formula (XX)

X is —C(O)NH—, C(S)NH, —C(O)C$_{1-3}$alkylC(O)NH—; or —C(O)C$_{1-3}$alkylC(O)O—;

M is an integer from 0-11 and n is an integer from 1-500.

In some embodiments the 0 attached to the cholesterol in formula (XX) is part of the cholesterol moiety.

In some preferred embodiments, X is —C(O)NH—, or —C(O)C$_{1-3}$alkylC(O)O—.

In some embodiments, the compound of formula (XX) is as provided below in formula (XX')

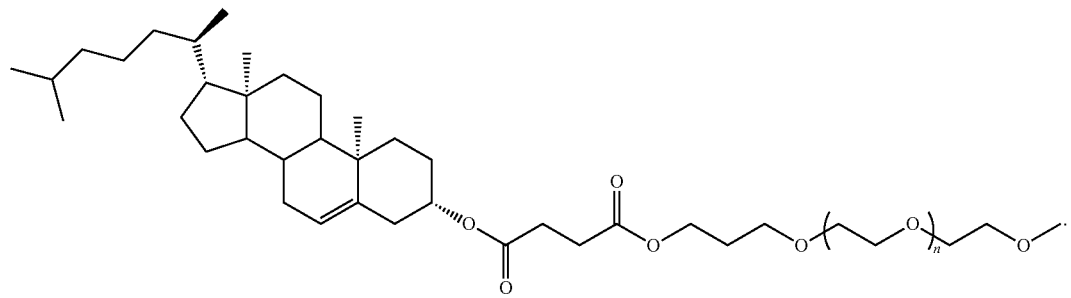

formula (XX')

In one aspect, the invention features a PEG lipid bound to a targeting moiety, for example a sugar residue. For example, the compounds of formula (XV) or (XX) are modified at the OMe terminal end with a targeting moiety. In some embodiments, the targeting moiety is bound to the PEG moiety via a linker Examplary targeted PEG lipids are provided in formulas (XXI) and (XXII) below.

In one embodiment, the lipid is a compound of formula (XXI)

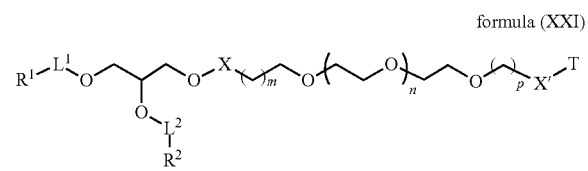

formula (XXI)

wherein;

each L$^1$ and L$^2$ are independently a bond or C(O);

each R$^1$ and R$^2$ are independently alkyl alkenyl or alkynyl; each of which is optionally substituted with one or more substituents;

each X and X' is independently —C(O)NH—, —NHC(O)—, C(S)NH, C(S)NH, —C(O)C$_{1-3}$alkylC(O)NH—; NHC(O)C$_{1-3}$alkylC(O)—; —C(O)C$_{1-3}$alkylC(O)O—; NHC(O)C$_{1-3}$alkyl-; or C$_{1-3}$alkylC(O)NH—;

m is an integer from 0-11 and n is an integer from 1-500 p is an integer from 1-6, e.g., 3;

T is a targeting moiety such as a glycosyl moiety (e.g., a sugar residue). Examplary targeting moieties include

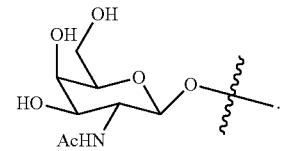 [SMILES: *OC1OC(CO)C(O)C(O)C1NC(C)=O]

In some embodiments, L$^1$ and L$^2$ are both a bond.

In some embodiments, L$^1$ and L$^2$ are both C(O).

In some embodiments, each R$^1$ and R$^2$ are independently alkyl, for example C$_6$-C$_{28}$ alkyl, e.g., C$_{10}$-C$_{18}$ alkyl, e.g., C$_{14}$ alkyl, C$_{15}$ alkyl, or C$_{16}$ alkyl. In some embodiments, both R$^1$ and R$^2$ are alkyl, e.g., straight chain alkyl having the same length, e.g., C$_6$-C$_{28}$ alkyl, e.g., C$_{10}$-C$_{18}$ alkyl, e.g., C$_{14}$ alkyl, C$_{15}$ alkyl, or C$_{16}$ alkyl. In some preferred embodiments, both R$^1$ and R$^2$ are C$_{14}$ alkyl.

In some embodiments, the formula (XXI) represents a racemic mixture

In some embodiments, the compound of formula (XXI) has an enantiomeric excess of the R isomer, e.g., at least about 65%, 70%, 75%, 80%, 85%, 90%, 95%, 97%, 98%, or 99%. In some embodiments the formula (XXI) represents enantiomerically pure 'R' isomer.

In some embodiments, the compound of formula (XXI) has an enantiomeric excess of the S isomer, e.g., at least about 65%, 70%, 75%, 80%, 85%, 90%, 95%, 97%, 98%, or 99%. In some embodiments the formula (XXI) represents enantiomerically pure 'S' isomer.

In some embodiments, each R$^1$ and R$^2$ are independently alkenyl, for example, each R$^1$ and R$^2$ are independently C$_6$-C$_{30}$ alkenyl or each R$^1$ and R$^2$ are the same alkenyl moiety. In some embodiments, each R$^1$ and R$^2$ includes a single double bond, for example a single double bond in the E or Z configuration.

In some embodiments, each R$^1$ and R$^2$ includes two double bond moieties. In some embodiments, at least one of the double bonds has a Z configuration. In some embodiments, both of the double bonds have a Z configuration. In some embodiments, at least one of R$^1$ and R$^2$ is provided in formula (II) below

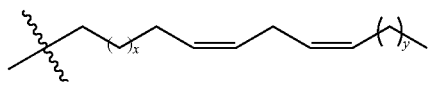

formula (II)

wherein
x is an integer from 1 to 8; and
y is an integer from 1-10. In some embodiments, both of $R^1$ and $R^2$ are of the formula (II). In some embodiments, at least one of the double bonds has an E configuration, e.g., both of the double bonds have an E configuration. In some embodiments, at least one of $R^1$ and $R^2$ is provided in formula (III) below

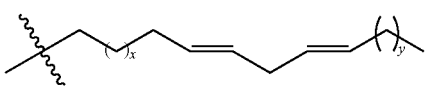

formula (III)

wherein
x is an integer from 1 to 8; and
y is an integer from 1-10.

In some embodiments, each $R^1$ and $R^2$ includes three double bond moieties. In some embodiments, at least one of the double bonds has a Z configuration. In some embodiments, at least two of the double bonds have a Z configuration. In some embodiments, all three of the double bonds have a Z configuration. In some embodiments, at least one of $R^1$ and $R^2$ is provided in formula (IV) below formula (IV)

wherein
x is an integer from 1 to 8; and
y is an integer from 1-10. In some embodiments, both of $R^1$ and $R^2$ are as provided in formula (IV). In some embodiments, at least one of the double bonds has an E configuration. In some embodiments, at least two of the double bonds have an E configuration. In some embodiments, all three of the double bonds have an E configuration. In some embodiments, at least one of $R^1$ and $R^2$ is provided in formula (IV) below

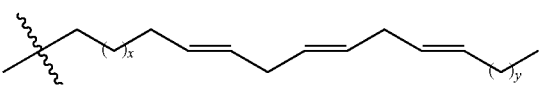

formula (V)

wherein
x is an integer from 1 to 8; and
y is an integer from 1-10. In some embodiments, both of $R^3$ and $R^4$ are as provided in formula (V).

In some embodiments, p is 3.

In some embodiments, L is $NHC(O)C_{1-6}$ alkyl (e.g., $NHC(O)C_3$alkyl). In some embodiments, the compound of formula (XXI) is the compound of (XXI') below:

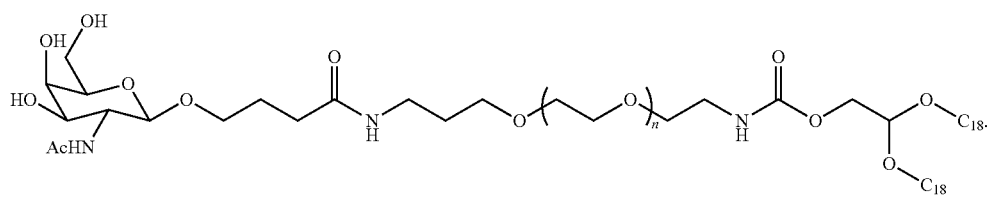

formula (XXI')

In one embodiment, the lipid is a compound of formula (XXII)

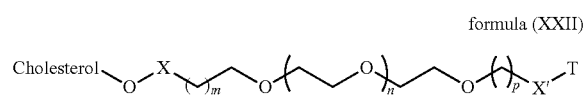

formula (XXII)

wherein;
each X and X' is independently —C(O)NH—, —NHC(O)—, C(S)NH, C(S)NH, —C(O)$C_{1-3}$alkylC(O)NH—; NHC(O)$C_{1-3}$alkylC(O)—; —C(O)$C_{1-3}$alkylC(O)O—; NHC(O)$C_{1-3}$alkyl-; or $C_{1-3}$alkylC(O)NH—;
m is an integer from 0-11 and
n is an integer from 1-500
p is an integer from 1-6, e.g., 3;
T is a targeting moiety such as a glycosyl moiety (e.g., a sugar residue). Examplary targeting moieties include

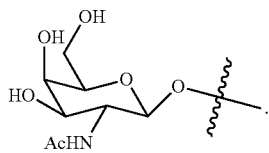 [SMILES: *OC1OC(CO)C(O)C(O)C1NC(C)=O]

In some preferred embodiments, the compound of formula (XXII) is the compound of (XXII') as provided below:

formula (XXII')

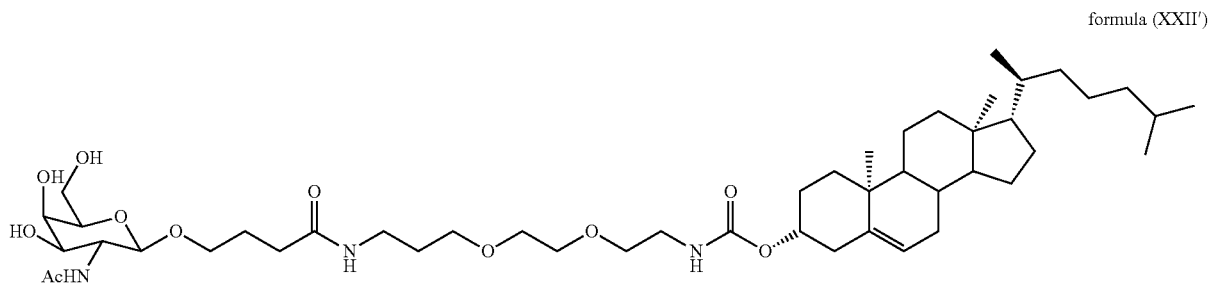

In one aspect, the invention features an association complex comprising a compound preparation comprising a compound described herein (e.g., a compound of formula (I) or a compound of formula (X)) and a nucleic acid such as an RNA a single stranded or double stranded RNA (e.g., siRNA or dsRNA or a DNA). In some embodiments, the association complex is a lipoplex or a liposome. In some embodiments the association complex includes one or more additional components such as a targeting moiety, a fusogenic lipid, a PEGylated lipid, such as a PEG-lipid described herein such as a PEG-lipid having the formula (XV), (XV') or (XVI) or a structural component. In some embodiments, the PEG-lipid is a targeted PEG-lipid as described herein, e.g., a compound of formula (XXI), (XXI'), (XXII), or (XXII').

In one aspect, the invention features a method of forming a liposome comprising contacting a lipid preparation comprising a compound described herein (e.g. a lipid described herein such as a compound of formula (I) or formula (X)) with a therapeutic agent in the presence of a buffer, wherein said buffer:
is of sufficient strength that substantially all amines of the molecules formula I are protonated;
is present at between 100 and 300 mM;
is present at a concentration that provides significantly more protonation of than does the same buffer at 20 mM.

In one aspect, the invention features a liposome made by the method described herein.

In one aspect, the invention features a method of forming a liposome comprising contacting a lipid preparation described herein (e.g., a lipid preparation comprising a compound of formula (I) or a compound of formula (X)) with a therapeutic agent in a mixture comprising at least about 90% ethanol and rapidly mixing the lipid preparation with the therapeutic agent to provide a particle having a diameter of less than about 200 uM. In some embodiments, the particle has a diameter of less than about 50 uM.

In one aspect, the invention features a method of forming a liposome comprising contacting a lipid preparation described herein (e.g., a lipid preparation comprising a compound of formula (I) or a compound of formula (X)) with a therapeutic agent in the presence of a buffer, wherein said buffer has a concentration from about 100 to about 300 mM.

In one aspect, the invention features liposome comprising a preparation described herein (e.g., a lipid preparation comprising a compound of formula (I) or a compound of formula (X)) and a nucleic acid. In some embodiments, the preparation also includes a PEGylated lipid, for example a PEG-lipid described herein, such as a PEG-lipid having the formula (XV), (XV') or (XVI). In some embodiments, the PEG-lipid is a targeted PEG-lipid as described herein, e.g., a compound of formula (XXI), (XXI'), (XXII), or (XXII'). In some embodiments, the preparation also includes a structural moiety such as cholesterol. In some embodiments the preparation of association complex includes compounds of formaulae (I), (XV) and cholesterol. In some embodiments, said nucleic acid is an siRNA, for example said nucleic acid is an siRNA which has been modified to resist degradation, said nucleic acid is an siRNA which has been modified by modification of the polysaccharide backbone, or said siRNA targets the ApoB gene.

In some embodiments, the liposome further comprises a structural moiety and a PEGylated lipid, such as a PEG-lipid described herein, wherein the ratio, by weight, of preparation (e.g., a lipid preparation comprising a compound of formula (I) or a compound of formula (X)), a structural moiety such as cholesterol, PEGylated lipid, and a nucleic acid, is 8-22:4-10:4-12:0.4-2.2. In some embodiments, the structural moiety is cholesterol. In some embodiments, the ratio is 10-20:0.5-8.0:5-10:0.5-2.0, e.g., 15:0.8:7:1. In some embodiments, the average liposome diameter is between 10 nm and 750 nm, e.g., the average liposome diameter is between 30 and 200 nm or the average liposome diameter is between 50 and 100 nm. In some embodiments, the preparation is less than 15%, by weight, of unreacted lipid. In some embodiments, the ratio of the preparation (e.g., a lipid preparation comprising a compound of formula (I) or a compound of formula (X)), the structural moiety such as cholesterol, and the PEG lipid is about 42/48/10 (molar ratio). In some embodiments, the total lipid to nucleic acid (e.g., siRNA) is about 7.5% by weight.

In some embodiments an association complex described herein has a weight ratio of total excipients to nucleic acid of less than about 15:1, for example, about 10:1, 7.5:1 or about 5:1.

In one aspect, the invention features a method of forming an association complex comprising a plurality of lipid moieties and a therapeutic agent, the method comprising: mixing a plurality of lipid moieties in ethanol and aqueous NaOAc buffer to provide a particle; and adding the therapeutic agent to the particle, thereby forming the association complex.

In some embodiments, the lipid moieties are provided in a solution of 100% ethanol.

In some embodiments, the plurality of lipid moieties comprise a cationic lipid.

In some embodiments, the cationic lipid is a lipid described herein, for example, the cationic lipid is a lipid of one of the following or a mixture thereof:

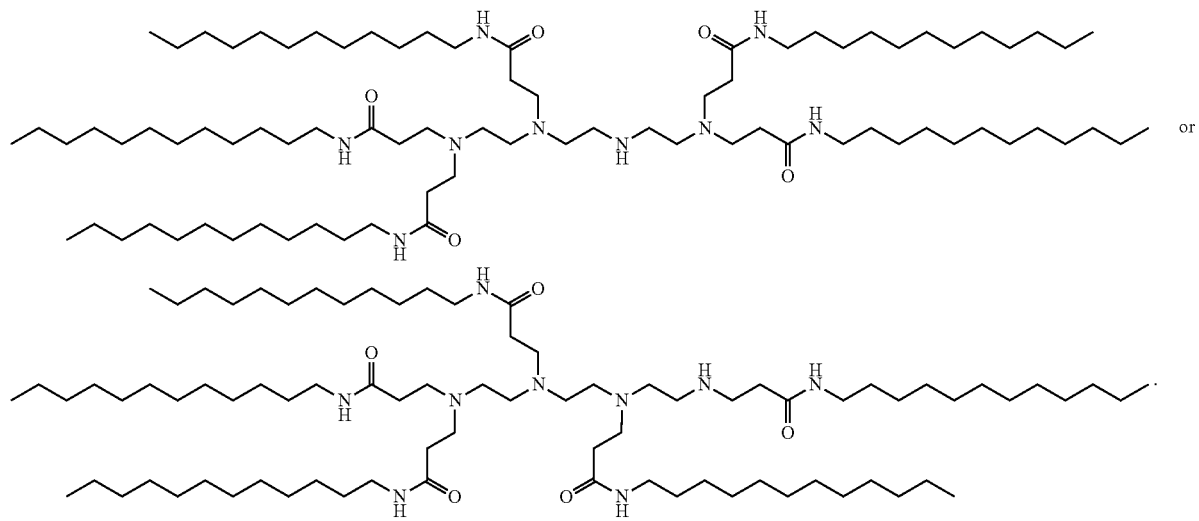

In some preferred embodiments, the cationic lipid is

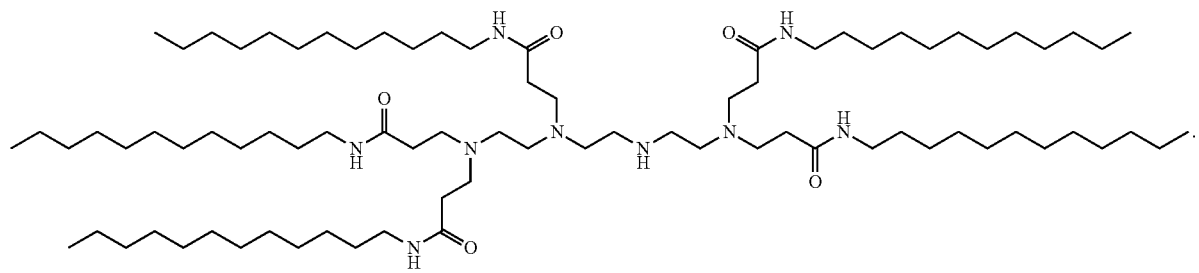 [SMILES: CCCCCCCCCCCCNC(=O)CCN(CCNCCN(CCC(=O)NCCCCCCCCCCCC)CCN(CCC(=O)NCCCCCCCCCCCC)CCC(=O)NCCCCCCCCCCCC)CCC(=O)NCCCCCCCCCCCC]

In some embodiments, the plurality of lipid moieties comprise a PEG-lipid, for example, the PEG-lipid has the following structure:

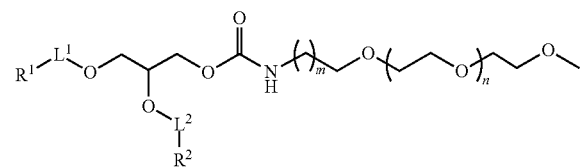

wherein;

each $L^1$ and $L^2$ are independently a bond or C(O);

each $R^1$ and $R^2$ are independently alkyl alkenyl or alkynyl; each of which is optionally substituted with one or more substituents;

X is —C(O)NH—, C(S)NH, —C(O)$C_{1-3}$alkylC(O)NH—; or —C(O)$C_{1-3}$alkylC(O)O—;

m is an integer from 0-11 and n is an integer from 1-500.

In some preferred embodiments, the PEG-lipid is a PEG lipid of formula (XVI), wherein the repeating PEG moiety has an average molecular weight of 2000, for example, with an n value between 42 and 47 or the lipid provided below:

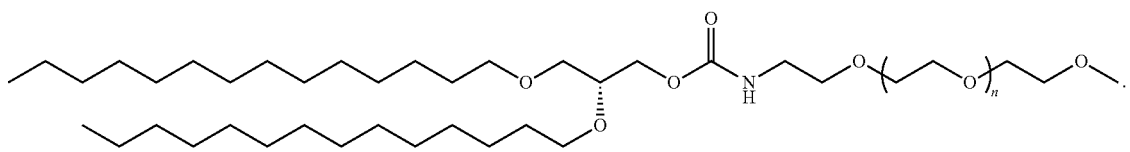

In some embodiments, the plurality of lipid moieties comprises a structural lipid, for example, the structural lipid is cholesterol.

In some embodiments, the PEG-lipid is a targeted PEG-lipid as described herein, e.g., a compound of formula (XXI), (XXI'), (XXII), or (XXII').

In some embodiments, the method includes further comprising extruding the lipid containing particles, for example, prior to addition of the therapeutic agent.

In some embodiments, the therapeutic agent is a nucleic acid, for example, an siRNA, such as an siRNA which has been modified to resist degradation, an siRNA which has been modified by modification of the polysaccharide backbone, or an siRNA conjugated to a Lipophilic moiety. In some embodiments, the siRNA targets the ApoB gene.

In some embodiments, the association complex comprises a cationic lipid, a structural lipid, a PEG-lipid and a nucleic acid. In some embodiments, the molar ratio of the cationic lipid, structural lipid, PEG-lipid and nucleic acid is 36-48:42-54:6-14, for example, 38-46:44-52:8-12 or about 42:48:10. In some embodiments, the weight ratio of total excipient to nucleic acid is less than about 15:1, for example, about 10:1 about 7.5:1 or about 5:1. In some preferred embodiments, the cationic lipid has the following structure;

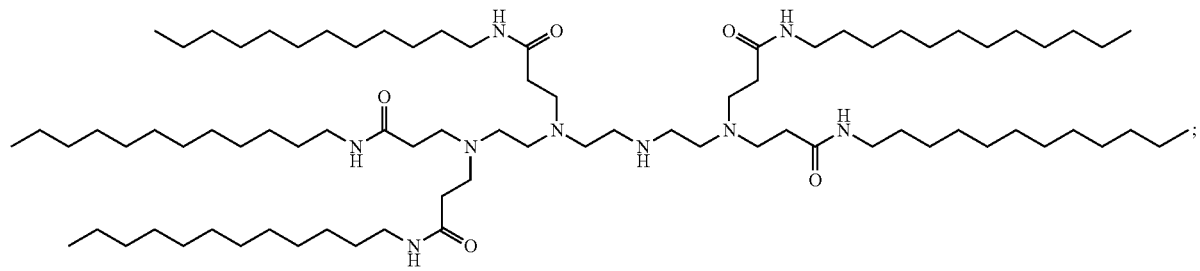 [SMILES: CCCCCCCCCCCCNC(=O)CCN(CCNCCN(CCC(=O)NCCCCCCCCCCCC)CCN(CCC(=O)NCCCCCCCCCCCC)CCC(=O)NCCCCCCCCCCCC)CCC(=O)NCCCCCCCCCCCC]

the PEG-lipid is a PEG lipid of formula (XVI), wherein the repeating PEG moiety has an average molecular weight of 2000, for example, with an n value between 42 and 47 or has the following structure:

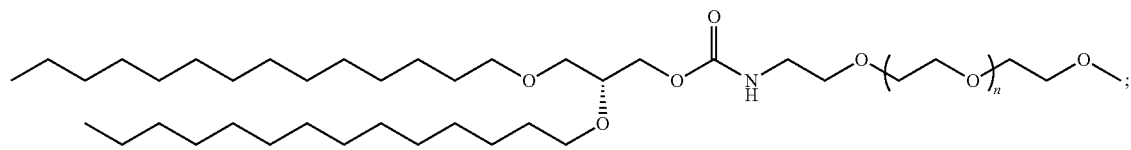

and the structural lipid is cholesterol, for example, wherein the molar ratio of the cationic lipid, structural lipid, is PEG-lipid is 38-46:44-52:8-12, e.g., about 42:48:10. In some preferred embodiments, the weight ratio of total exipient to nucleic acid is less than about 15:1, e.g., about 10:1, about 7.5:1, or about 5:1.

In another aspect, the invention features an association complex made from a method described herein.

In another aspect, the invention features association complex comprising a cationic lipid, a structural lipid, a PEG-lipid and a nucleic acid, wherein the cationic lipid is a lipid of one of the following or a mixture thereof:

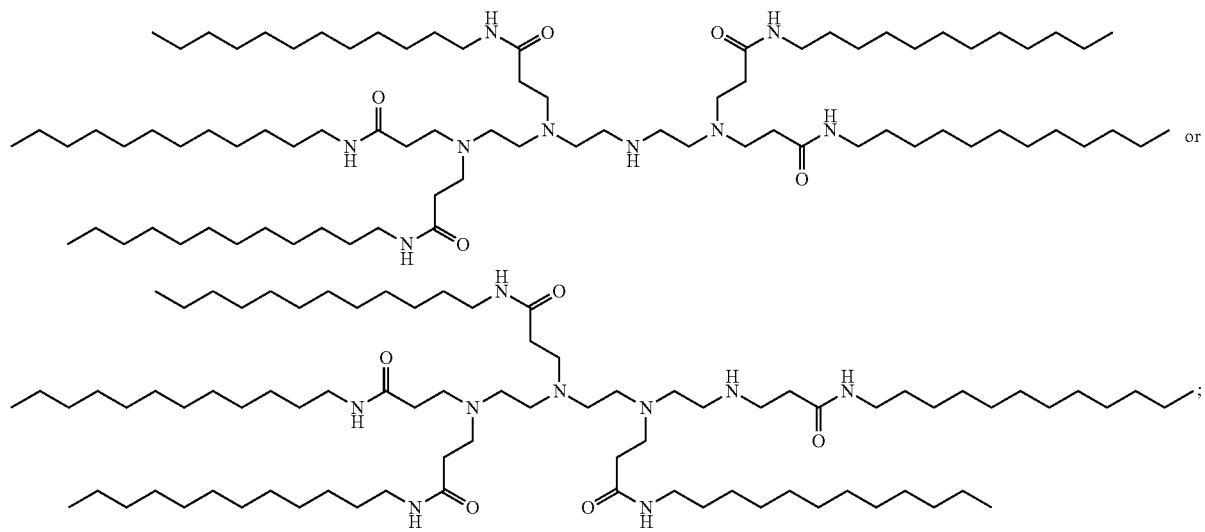

the PEG-lipid is a PEG lipid of formula (XVI), wherein the repeating PEG moiety has an average molecular weight of 2000, for example, with an n value between 42 and 47 or has the following structure:

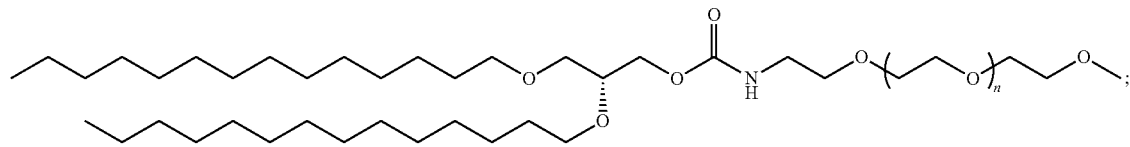

and the structural lipid is cholesterol. In some preferred embodiments, the nucleic acid is an siRNA. In some preferred embodiments, the cationic lipid has the following formula:

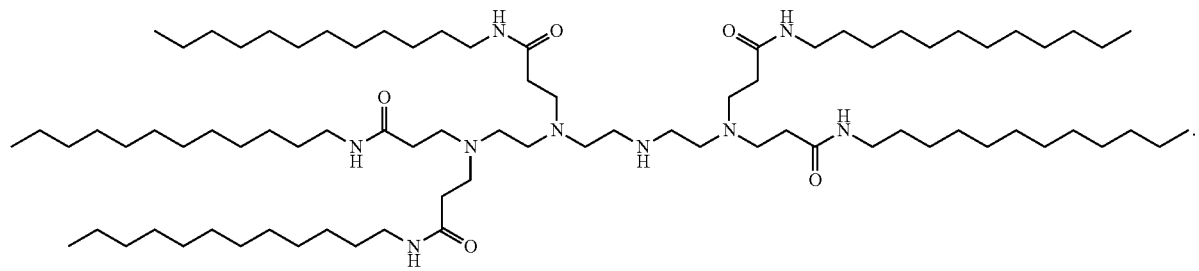 [SMILES: CCCCCCCCCCCCNC(=O)CCN(CCNCCN(CCC(=O)NCCCCCCCCCCCC)CCN(CCC(=O)NCCCCCCCCCCCC)CCC(=O)NCCCCCCCCCCCC)CCC(=O)NCCCCCCCCCCCC]

In some preferred embodiments, the molar ratio of the cationic lipid preparation, structural lipid (e.g., cholesterol), PEG-lipid and nucleic acid is 36-48:42-54:6-14, for example, 38-46:44-52:8-12 or about 42:48:10. In some preferred embodiments, the weight ratio of total exipient to nucleic acid is less than about 15:1, for example, about 10:1, about 7.5:1, or about 5:1.

In some embodiments, an association complex described herein has a mean diameter or particle size of less than about 25000 nm, e.g., from about 20 to 200 nm, about 60, or about 50 nm.

In some embodiments, a nucleic acid as administered in an association complex described herein, demonstrates a serum half life (e.g., in vitro) for at least about 4 hours, e.g., at least about 6 hours, at least about 8 hours, at least about 12 hours, at least about 24 hours, at least about 2 days, at least about 3 days, at least about 4 days, at least about 1 week, at least about 2 weeks, or at least about 3 weeks.

In one aspect, the invention features a pharmaceutically acceptable composition comprising the preparation described herein.

In one aspect, the invention features a pharmaceutically acceptable composition comprising a liposome described herein.

In one aspect, the invention features a method of treating a mammal comprising administering to said mammal a therapeutic amount of a pharmaceutically acceptable composition, for example, an association complex such as a liposome described herein.

DEFINITIONS

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{36}$ alkyl indicates that the group may have from 1 to 136 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "alkylene" refers to a divalent alkyl, e.g., —$CH_2$—, —$CH_2CH_2$—, —$CH_2CH_2CH_2$—, —$CH_2CH_2CH_2CH_2$, —$CH_2CH_2CH_2CH_2CH_2$—, and $CH_2CH_2CH_2CH_2CH_2CH_2$—.

The term "alkenyl" refers to a straight or branched hydrocarbon chain containing 2-36 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkynyl" refers to a straight or branched hydrocarbon chain containing 2-36 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Any atom can be substituted. Suitable substituents include, without limitation, alkyl (e.g., C1, C2, C3, C4, C5, C6, C7, C8, C9, C10, C11, C12 straight or branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkyl amino, $SO_3H$, sulfate, phosphate, methylenedioxy (—O—$CH_2$—O— wherein oxygens are attached to same carbon (geminal substitution) atoms), ethylenedioxy, oxo, thioxo (e.g., C=S), imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

The term "structural isomer" as used herein refers to any of two or more chemical compounds, such as propyl alcohol and isopropyl alcohol, having the same molecular formula but different structural formulas.

The term "geometric isomer" or "stereoisomer" as used herein refers to two or more compounds which contain the same number and types of atoms, and bonds (i.e., the connectivity between atoms is the same), but which have different spatial arrangements of the atoms, for example cis and trans isomers of a double bond, enantiomers, and diasteriomers.

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A" and "U" each generally stand for a nucleotide that contains guanine, cytosine, adenine, and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

As used herein, "target sequence" refers to a contiguous portion of the nucleotide sequence of an mRNA molecule formed during the transcription of the corresponding gene, including mRNA that is a product of RNA processing of a primary transcription product. A target region is a segment in a target gene that is complementary to a portion of the RNAi agent.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, an oligonucleotide agent comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes of the invention.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled.

The terms "complementary", "fully complementary" and "substantially complementary" herein may be used with respect to the base matching between the sense strand and the antisense strand of an oligonucleotide agent, or between the antisense strand of an oligonucleotide agent and a target sequence, as will be understood from the context of their use.

As used herein, a polynucleotide which is "substantially complementary to at least part of" a messenger RNA (mRNA) refers to a polynucleotide which is substantially complementary to a contiguous portion of the mRNA of interest. For example, a polynucleotide is complementary to at least a part of an ApoB mRNA if the sequence is substantially complementary to a non-interrupted portion of a mRNA encoding ApoB.

As used herein, an "oligonucleotide agent" refers to a single stranded oligomer or polymer of ribonucleic acid (RNA) or deoxyribonucleic acid (DNA) or both or modifications thereof, which is antisense with respect to its target. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

Oligonucleotide agents include both nucleic acid targeting (NAT) oligonucleotide agents and protein-targeting (PT) oligonucleotide agents. NAT and PT oligonucleotide agents refer to single stranded oligomers or polymers of ribonucleic acid (RNA) or deoxyribonucleic acid (DNA) or both or modifications thereof. This term includes oligonucleotides composed of naturally occurring nucleobases, sugars, and covalent internucleoside (backbone) linkages as well as oligonucleotides having non-naturally-occurring portions that function similarly. Such modified or substituted oligonucleotides are often preferred over native forms because of desirable properties such as, for example, enhanced cellular uptake, enhanced affinity for nucleic acid target, and/or increased stability in the presence of nucleases. NATs designed to bind to specific RNA or DNA targets have substantial complementarity, e.g., at least 70, 80, 90, or 100% complementary, with at least 10, 20, or 30 or more bases of a target nucleic acid, and include antisense RNAs, microRNAs, antagomirs and other non-duplex structures which can modulate expression. Other NAT oligonucleotide agents include external guide sequence (EGS) oligonucleotides (oligozymes), DNAzymes, and ribozymes. The NAT oligonucleotide agents can target any nucleic acid, e.g., a miRNA, a pre-miRNA, a pre-mRNA, an mRNA, or a DNA. These NAT oligonucleotide agents may or may not bind via Watson-Crick complementarity to their targets. PT oligonucleotide agents bind to protein targets, preferably by virtue of three-dimensional interactions, and modulate protein activity. They include decoy RNAs, aptamers, and the like.

While not wishing to be bound by theory, an oligonucleotide agent may act by one or more of a number of mechanisms, including a cleavage-dependent or cleavage-independent mechanism. A cleavage-based mechanism can be RNAse H dependent and/or can include RISC complex function. Cleavage-independent mechanisms include occupancy-based translational arrest, such as can be mediated by miRNAs, or binding of the oligonucleotide agent to a protein, as do aptamers. Oligonucleotide agents may also be used to alter the expression of genes by changing the choice of splice site in a pre-mRNA. Inhibition of splicing can also result in degradation of the improperly processed message, thus downregulating gene expression.

The term "double-stranded RNA" or "dsRNA", as used herein, refers to a complex of ribonucleic acid molecules, having a duplex structure comprising two anti-parallel and substantially complementary, as defined above, nucleic acid strands. The two strands forming the duplex structure may be different portions of one larger RNA molecule, or they may be separate RNA molecules. Where separate RNA molecules, such dsRNA are often referred to in the literature as siRNA ("short interfering RNA"). Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop", "short hairpin RNA" or "shRNA". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs. In addition, as used in this specification, "dsRNA" may include chemical modifications to ribonucleotides, including substantial modifications at multiple nucleotides and including all types of modifications disclosed herein or known in the art. Any such modifications, as used in an siRNA type molecule, are encompassed by "dsRNA" for the purposes of this specification and claims.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule. For clarity, chemical caps or non-nucleotide chemical moieties conjugated to the 3' end or 5' end of an siRNA are not considered in determining whether an siRNA has an overhang or is blunt ended.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus The term "sense strand," as used herein, refers to the strand of a dsRNA that includes a region that is substantially complementary to a region of the antisense strand.

The terms "silence" and "inhibit the expression of", in as far as they refer to a target gene, herein refer to the at least partial suppression of the expression of the gene, as manifested by a reduction of the amount of mRNA transcribed from the gene which may be isolated from a first cell or group of cells in which the gene is transcribed and which has or have been treated such that the expression of the gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to gene transcription, e.g. the amount of protein encoded by the gene which is secreted by a cell, or the number of cells displaying a certain phenotype, e.g apoptosis. In principle, gene silencing may be determined in any cell expressing the target, either constitutively or by genomic engineering, and by any appropriate assay. However, when a reference is needed in order to determine whether a given dsRNA inhibits the expression of the gene by a certain degree and therefore is encompassed by the instant invention, the assay provided in the Examples below shall serve as such reference.

For example, in certain instances, expression of the gene is suppressed by at least about 20%, 25%, 35%, or 50% by administration of the double-stranded oligonucleotide of the invention. In some embodiment, the gene is suppressed by at least about 60%, 70%, or 80% by administration of the double-stranded oligonucleotide of the invention. In some embodiments, the gene is suppressed by at least about 85%, 90%, or 95% by administration of the double-stranded oligonucleotide of the invention.

As used herein, the terms "treat", "treatment", and the like, refer to relief from or alleviation of pathological processes which can be mediated by down regulating a particular gene. In the context of the present invention insofar as it relates to any of the other conditions recited herein below (other than pathological processes which can be mediated by down regulating the gene), the terms "treat", "treatment", and the like mean to relieve or alleviate at least one symptom associated with such condition, or to slow or reverse the progression of such condition.

As used herein, the phrases "therapeutically effective amount" and "prophylactically effective amount" refer to an amount that provides a therapeutic benefit in the treatment, prevention, or management of pathological processes which can be mediated by down regulating the gene on or an overt symptom of pathological processes which can be mediated by down regulating the gene. The specific amount that is therapeutically effective can be readily determined by ordinary medical practitioner, and may vary depending on factors known in the art, such as, e.g. the type of pathological processes which can be mediated by down regulating the gene, the patient's history and age, the stage of pathological processes which can be mediated by down regulating gene expression, and the administration of other anti-pathological processes which can be mediated by down regulating gene expression. An effective amount, in the context of treating a subject, is sufficient to produce a therapeutic benefit. The term "therapeutic benefit" as used herein refers to anything that promotes or enhances the well-being of the subject with respect to the medical treatment of the subject's cell proliferative disease. A list of nonexhaustive examples of this includes extension of the patients life by any period of time; decrease or delay in the neoplastic development of the disease; decrease in hyperproliferation; reduction in tumor growth; delay of metastases; reduction in the proliferation rate of a cancer cell, tumor cell, or any other hyperproliferative cell; induction of apoptosis in any treated cell or in any cell affected by a treated cell; and/or a decrease in pain to the subject that can be attributed to the patient's condition.

As used herein, a "pharmaceutical composition" comprises a pharmacologically effective amount of an oligonucleotide agent and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof and are described in more detail below. The term specifically excludes cell culture medium.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 9 are bar graphs depicting the efficacy of siRNAs with two targets, FVII and ApoB.

DETAILED DESCRIPTION

Figure 1:
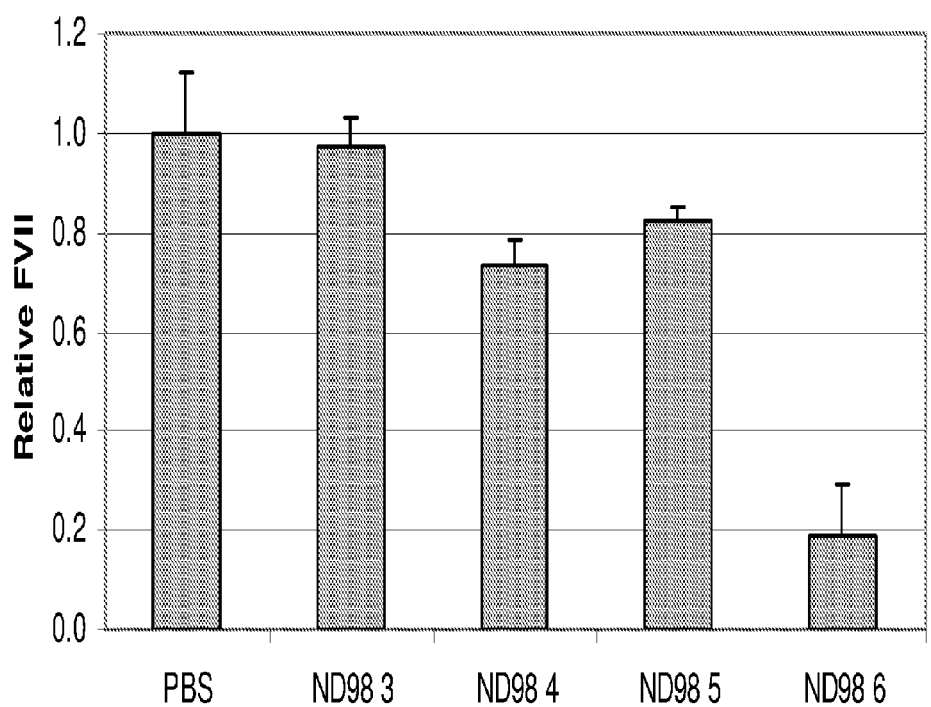
FIG. 1 depicts a bar graph comparing the efficacy of various ND98 compositions.

Lipid preparations and delivery systems useful to administer nucleic acid based therapies such as siRNA are described herein.

Cationic Lipid Compounds and Lipid Preparations

Polyamine Lipid Preparations

Applicants have discovered that certain polyamine lipid moieties provide desirable properties for administration of nucleic acids, such as siRNA. For example, in some embodiments, a lipid moiety is complexed with a Factor VII-targeting siRNA and administered to an animal such as a mouse. The level of secreted serum Factor VII is then quantified (24 h post administration), where the degree of Factor VII silencing indicates the degree of in vivo siRNA delivery. Accordingly, lipids providing enhanced in vivo delivery of a nucleic acid such as siRNA are preferred. In particular, Applicants have discovered polyamines having substitutions described herein can have desirable properties for delivering siRNA, such as bioavailability, biodegradability, and tolerability.

In one embodiment, a lipid preparation includes a polyamine moiety having a plurality of substituents, such as acrylamide or acrylate substituents attached thereto. For example, a lipid moiety can include a polyamine moiety as provided below,

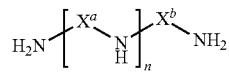

where one or more of the hydrogen atoms are substituted, for example with a substituent including a long chain alkyl, alkenyl, or alkynyl moiety, which in some embodiments is further substituted. $X^a$ and $X^b$ are alkylene moieties. In some embodiments, $X^a$ and $X^b$ have the same chain length, for example $X^a$ and $X^b$ are both ethylene moieties. In other embodiments $X^a$ and $X^b$ are of differing chain lengths. In some embodiments, where the polyamine includes a plurality of X' moieties, X' can vary with one or more occurrences. For example, where the polyamine is spermine, X' in one occurrence is propylene, $X^a$ in another occurrence is butylenes, and $X^b$ is propylene.

Applicants have discovered that in some instances it is desirable to have a relatively high degree of substitution on the polyamine For example, in some embodiments, Applicants have discovered that polyamine preparations where at least 80% (e.g., at least about 85%, at least about 90%, at least about 95%, at least about 97%, at least about 98%, at least about 99%, or substantially all) of the polyamines in the preparation have at least n+2 of the hydrogens substituted with a substituent provide desirable properties, for example for use in administering a nucleic acid such as siRNA.

In some instances it is desirable (preferably) to have one or more of hetero atoms present on the substituent on the nitrogen of polyamine In some embodiments, a preparation comprises a compound of formula (I) or a pharmaceutically acceptable salt thereof,

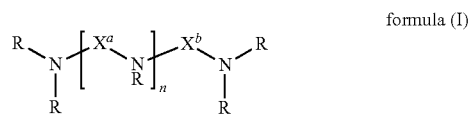

each $X^a$ and $X^b$, for each occurrence, is independently $C_{1-6}$ alkylene; n is 0, 1, 2, 3, 4, or 5; each R is independently H,

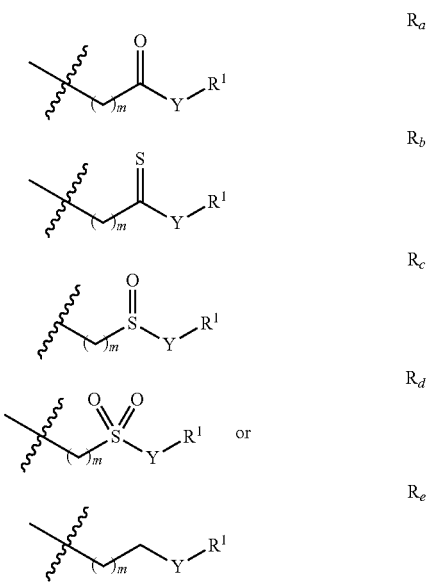

wherein at least n+2 of the R moieties in at least about 80% of the molecules of the compound of formula (I) in the preparation are not H; m is 1, 2, 3 or 4; Y is O, $NR^2$, or S; $R^1$ is alkyl alkenyl or alkynyl; each of which is optionally substituted; and $R^2$ is H, alkyl alkenyl or alkynyl; each of which is optionally substituted; provided that, if n=0, than at least n+3 of the R moieties are not H.

As noted above, the preparation includes molecules containing symmetrical as well as asymmetrical polyamine derivatives. Accordingly, $X^a$ is independent for each occurrence and $X^b$ is independent of $X^a$. For example, where n is 2, $X^a$ can either be the same for each occurrence or can be different for each occurrence or can be the same for some occurrences and different for one or more other occurrences. $X^b$ is independent of $X^a$ regardless of the number of occurrences of X' in each polyamine derivative. X', for each occurrence and independent of $X^b$, can be methylene, ethylene, propylene, butylene, pentylene, or hexylene. Exemplary polyamine derivatives include those polyamines derived from $N^1,N^{1'}$-(ethane-1,2-diyl)diethane-1,2-diamine, ethane-1,2-diamine, propane-1,3-diamine, spermine, spermidine, putrecine, and $N^1$-(2-Aminoethyl)-propane-1,3-diamine. Preferred polyamine derivatives include propane-1,3-diamine and $N^1,N^{1'}$-(ethane-1,2-diyl)diethane-1,2-diamine.

The polyamine of formula (I) is substituted with at least n+2 R moieties that are not H. In general, each non-hydrogen R moiety includes an alkyl, alkenyl, or alkynyl moiety, which is optionally substituted with one or more substituents, attached to a nitrogen of the polyamine derivative via a linker. Suitable linkers include amides, esters, thioesters, sulfones, sulfoxides, ethers, amines, and thioethers. In many instances, the linker moiety is bound to the nitrogen of the polyamine via an alkylene moiety (e.g., methylene, ethylene, propylene, or butylene). For example, an amide or ester linker is attached to the nitrogen of the polyamine through a methylene or ethylene moiety.

Examples of preferred amine substituents are provided below:

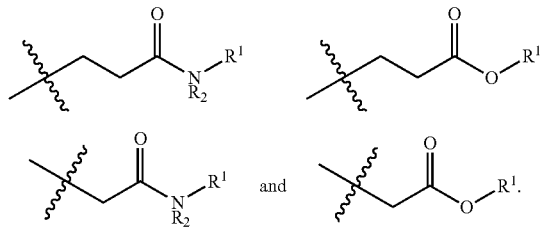

In instances where the amine is bound to the linker-$R^1$ portion via an ethylene group, a 1,4 conjugated precursor acrylate or acrylamide can be reacted with the polyamine to provide the substituted polyamine. In instances where the amine is bound to the linker-$R^1$ portion via a methylene group, an amide or ester including an alpha-halo substituent, such as an alpha-chloro moiety, can be reacted with the polyamine to provide the substituted polyamine. In preferred embodiments, $R^2$ is H.

R moieties that are not H, all require an $R^1$ moiety as provided above. In general, the $R^1$ moiety is a long chain moiety, such as $C_6$-$C_{32}$ alkyl, $C_6$-$C_{32}$ alkenyl, or $C_6$-$C_{32}$ alkynyl.

In some preferred embodiments, $R^1$ is an alkyl moiety. For example $R^1$ is $C_{10}$-$C_{18}$ alkyl, such as $C_{12}$ alkyl. Examples of especially preferred R moieties are provided below.

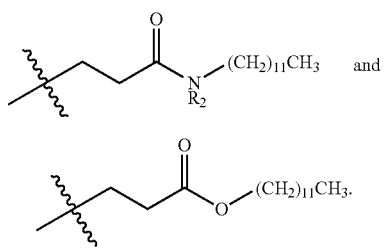

The preparations including a compound of formula (I) can be mixtures of a plurality of compounds of formula (I). For example, the preparation can include a mixture of compounds of formula (I) having varying degrees of substitution on the polyamine moiety. However, the preparations described herein are selected such that at least n+2 of the R moieties in at least about 80% (e.g., at least about 85%, at least about 90%, at least about 95%, at least about 97%, at least about 98%, at least about 99%, or substantially all) of the molecules of the compound of formula (I) in the preparation are not H.

In some embodiments, a preparation includes a polyamine moiety having two amino groups wherein in at least 80% (e.g., at least about 85%, at least about 90%, at least about 95%, at least about 97%, at least about 98%, at least about 99%, or substantially all) of the molecules of formula (I) in the mixture are substituted with three R moieties that are not H. Exemplary compounds of formula (I) are provided below.

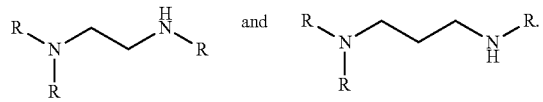

In some preferred embodiments R is

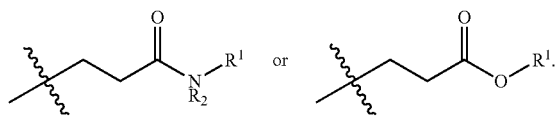

In some preferred embodiments, $R^1$ is $C_{10}$-$C_{18}$ alkyl, or $C_{10}$-$C_{30}$ alkenyl.

In some embodiments, a preparation includes a polyamine moiety having three or four (e.g., four) amino groups wherein at least n+2 of the R moieties in at least about 80% (e.g., at least about 85%, at least about 90%, at least about 95%, at least about 97%, at least about 98%, at least about 99%, or substantially all) of the molecules of formula (I) are not H. Exemplary compounds of formula (I) having 4 amino moieties are provided below.

Examples of polyamine moiety where all (i.e., n+4) R moieties are not H are below:

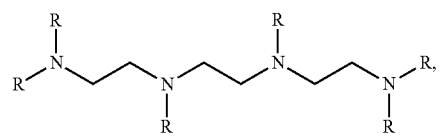

In some preferred embodiments R is

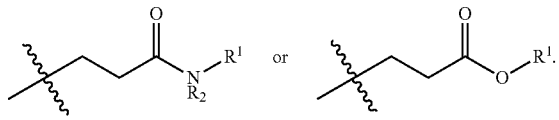

In some preferred embodiments, $R^1$ is $C_{10}$-$C_{18}$ alkyl (e.g., $C_{12}$ alkyl), or $C_{10}$-$C_{30}$ alkenyl.

Examples of polyamine moieties where five (i.e., n+3) R moieties are not H are provided below:

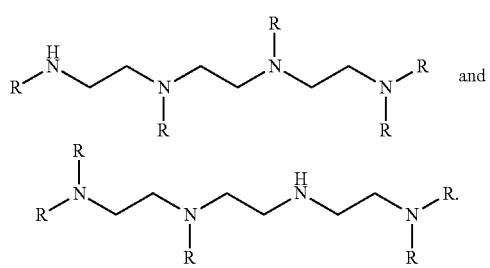

In some preferred embodiments R is

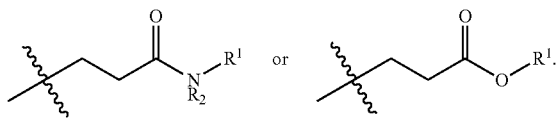

In some preferred embodiments, $R^1$ is $C_{10}$-$C_{18}$ alkyl (e.g., $C_{12}$ alkyl), or $C_{10}$-$C_{30}$ alkenyl.

Examples of polyamine moieties where four (i.e, n+2) R moieties are not H are provided below:

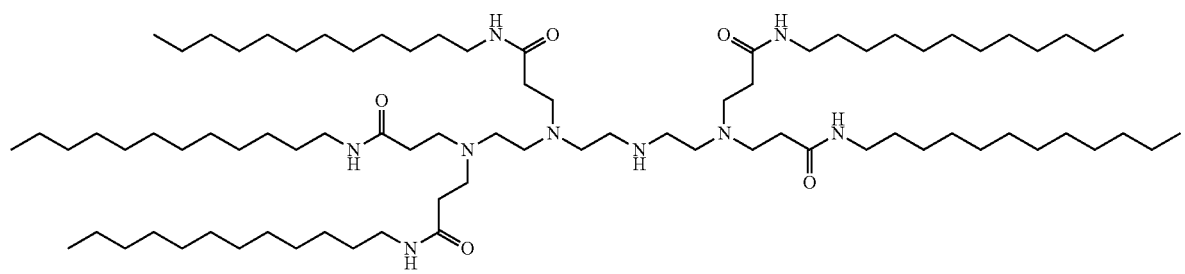

isomer (1)

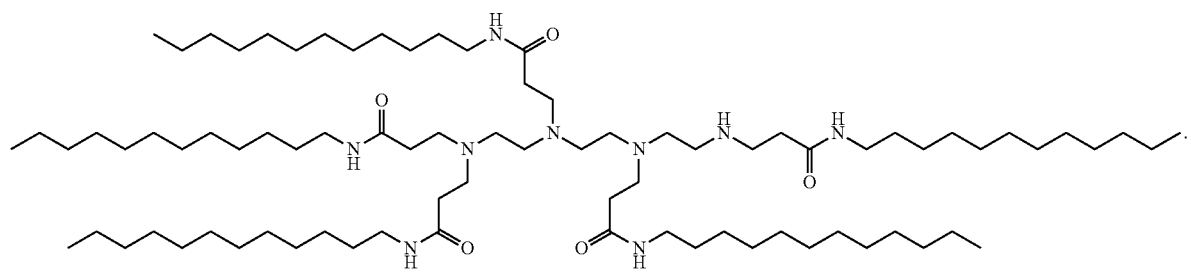

isomer (2)

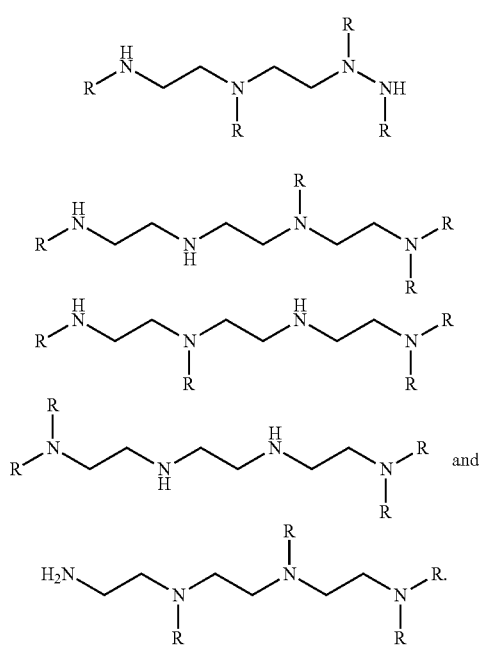

In some preferred embodiments R is

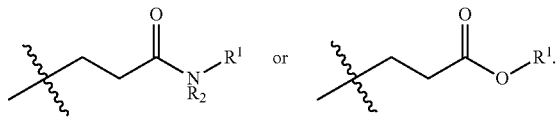

In some preferred embodiments, $R^1$ is $C_{10}$-$C_{18}$ alkyl (e.g., $C_{12}$ alkyl), or $C_{10}$-$C_{30}$ alkenyl.

In some preferred embodiments, the polyamine is a compound of isomer (1) or (2) below, preferably a compound of isomer (1)

In some embodiments, the preparation including a compound of formula (I) includes a mixture of molecules having formula (I). For example, the mixture can include molecules having the same polyamine core but differing R substituents, such as differing degrees of R substituents that are not H.

In some embodiments, a preparation described herein includes a compound of formula (I) having a single polyamine core wherein each R of the polyamine core is either R or a single moiety such as

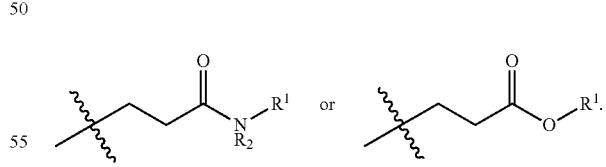

The preparation, therefore includes a mixture of molecules having formula (I), wherein the mixture is comprised of either polyamine compounds of formula (I) having a varied number of R moieties that are H and/or a polyamine compounds of formula (I) having a single determined number of R moieties that are not H where the compounds of formula (I) are structural isomers of the polyamine, such as the structural isomers provided above.

In some preferred embodiments the preparation includes molecules of formula (I) such that at least 80% (e.g., at least about 85%, at least about 90%, at least about 95%, at least about 97%, at least about 98%, at least about 99%, or substantially all) of the molecules are a single structural isomer.

In some embodiments, the preparation includes a mixture of two or more compounds of formula (I). In some embodiments, the preparation is a mixture of structural isomers of the same chemical formula. In some embodiments, the preparation is a mixture of compounds of formula (I) where the compounds vary in the chemical nature of the R substituents. For example, the preparation can include a mixture of the following compounds:

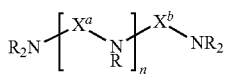

formula (I)

wherein n is 0 and each R is independently H or

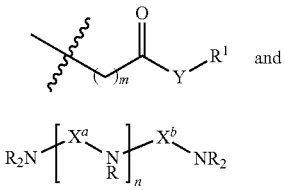

formula (I)

wherein n is 2 and each R is independently H or

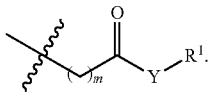

In some embodiments, the compound of formula (I) is in the form of a salt, such as a pharmaceutically acceptable salt. A salt, for example, can be formed between an anion and a positively charged substituent (e.g., amino) on a compound described herein. Suitable anions include fluoride, chloride, bromide, iodide, sulfate, bisulfate, nitrate, phosphate, citrate, methanesulfonate, trifluoroacetate, acetate, fumarate, oleate, valerate, maleate, oxalate, isonicotinate, lactate, salicylate, tartrate, tannate, pantothenate, bitartrate, ascorbate, succinate, gentisinate, gluconate, glucaronate, saccharate, formate, benzoate, glutamate, ethanesulfonate, benzenesulfonate, p-toluenesulfonate, and pamoate. In some preferred embodiments, the compound of formula (I) is a hydrohalide salt, such as a hydrochloride salt.

Compounds of formula (I) can also be present in the form of hydrates (e.g., $(H_2O)_n$) and solvates, which are included herewith in the disclosure.

Biocleavable Cationic Lipids

Applicants have discovered that certain cationic lipids that include one or more biocleavable moieties can be used as a component in an association complex, such as a liposome, for the delivery of nucleic acid therapies (e.g., dsRNA). For example, disclosed herein are cationic lipids that are subject to cleavage in vivo, for example, via an enzyme such as an esterase, an amidase, or a disulfide cleaving enzyme. In some instances, the lipid is cleaved chemically, for example by hydrolysis of an acid labile moiety such as an acetal or ketal. In some embodiments, the lipid includes a moiety that is hydrolyzed in vitro and then subject to enzymatic cleavage by one or more of an esterase, amidase, or a disulfide cleaving enzyme. This can happen in vesicular compartments of the cell such as endosomes. Another acid sensitive cleavable linkage is β-thiopropionate linkage which is cleaved in the acidic environment of endosomes (Jeong et al. Bioconjugate chem. 2003, 4, 1426).

In some embodiments, the invention features a compound of formula (X) or a pharmaceutically acceptable salt thereof, wherein

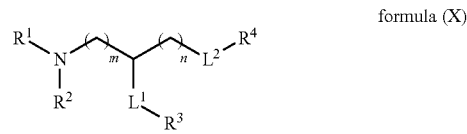

formula (X)

wherein $R^1$ and $R^2$ are each independently H, $C_1$-$C_6$ alkyl, optionally substituted with 1-4 $R^5$, $C_2$-$C_6$ alkenyl, optionally substituted with 1-4 $R^5$, or $C(NR^6)(NR^6)_2$;

$R^3$ and $R^4$ are each independently alkyl, alkenyl, alkynly, each of which is optionally substituted with fluoro, chloro, bromo, or iodo;

$L^1$ and $L^2$ are each independently —$NR^6C(O)$—, —$C(O)NR^6$—, —$OC(O)$—, —$C(O)O$—, —S—S—, —$N(R^6)C(O)N(R^6)$—, —$OC(O)N(R^6)$—, —$N(R^6)C(O)O$—, —O—N=O—, OR—OC(O)NH; or $L^1$-$R^3$ and $L^2$-$R^4$ can be taken together to form an acetal or a ketal;

$R^5$ is fluoro, chloro, bromo, iodo, —$OR^7$, —$N(R^8)(R^9)$, —CN, $SR^{10}$, $S(O)R^{10}$, $S(O)_2R^{10}$ $R^6$ is H, $C_1$-$C_6$ alkyl, $R^7$ is H or $C_1$-$C_6$ alkyl;

each $R^8$ and $R^9$ are independently H or $C_1$-$C_6$ alkyl;

$R^{10}$ is H or $C_1$-$C_6$ alkyl;

m is 1, 2, 3, 4, 5, or 6;

n is 0, 1, 2, 3, 4, 5, or 6;

and pharmaceutically acceptable salts thereof.

In some embodiments, $R^1$ is H, a lower alkyl, such as methyl, ethyl, propyl, or isopropyl, or a substituted alkyl, such as 2-hydroxyethyl.

In some embodiments, $R^2$ is H or a lower alkyl, such as methyl, ethyl, propyl, or isopropyl.

In some embodiments, $R^1$ or $R^2$ form a quanadine moiety with the nitrogen of formula (X).

$L^1$-$R^3$ and $L^2$-$R^4$ or the combination thereof provide at least one moiety that is cleaved in vivo. In some embodiments, both $L^1$-$R^3$ and $L^2$-$R^4$ are biocleavable. For example, both $L^1$-$R^3$ and $L^2$-$R^4$ are independently subject to enzymatic cleavage (e.g., by an esterase, amidase, or a disulfide cleaving enzyme). In some embodiments, both $L^1$ and $L^2$ are the same chemical moiety such as an ester, amide or disulfide. In other instances, $L^1$ and $L^2$ are different, for example, one of $L^1$ or $L^2$ is an ester an the other of $L^1$ or $L^2$ is a disulfide.

In some embodiments, $L^1$-$R^3$ and $L^2$-$R^4$ together form an acetal or ketal moiety, which is hydrolyzed in vivo.

In some embodiments, one of $L^1$-$R^3$ or $L^2$-$R^4$ is subject to enzymatic cleavage. For example, one of $L^1$-$R^3$ or $L^2$-$R^4$ is cleaved in vivo, providing a free hydroxyl moiety or free amine on the lipid, which becomes available to chemically react with the remaining $L^1$-$R^3$ or $L^2$-$R^4$ moiety. Exemplary embodiments are provided below:

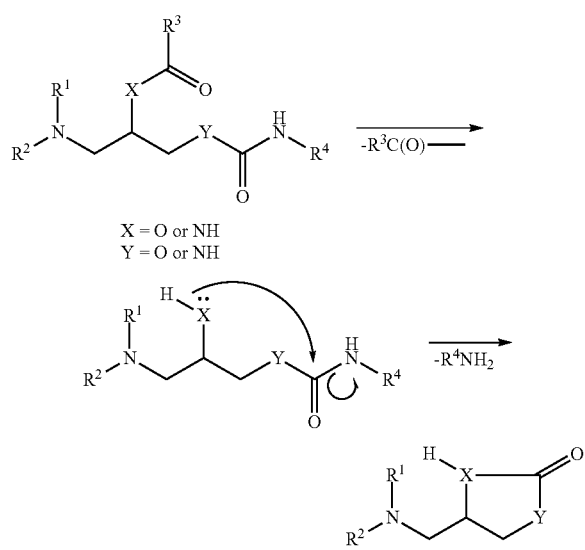

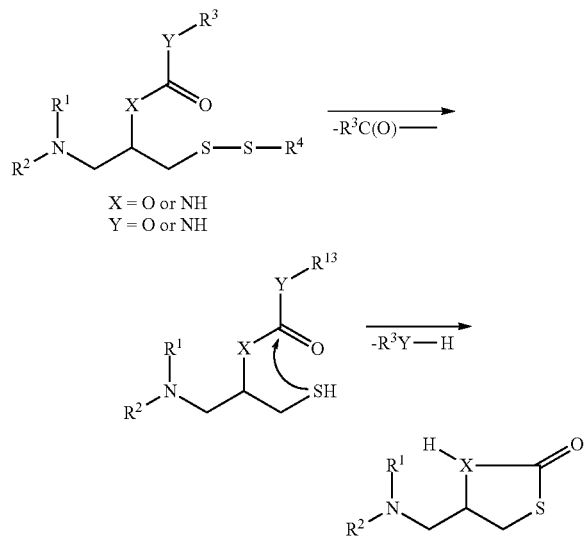

In some preferred embodiments, a carbamate or urea moiety is included in combination with an amide, ester or disulfide moiety. For example, the lipid includes an ester moiety, which upon cleavage (e.g., enzymatic cleavage) becomes available to chemically react with the carbamate or urea moiety. Some preferred combinations of $L^1$ and $L^2$ include two amides, two esters, an amide and an ester, two disulfides, an amide and a disulfide, an ester and a disulfide, a carbamate and a disulfide, and a urea and a disulfide. Exemplary compounds are provided below:

Amide and Ester Linkages with Z Configuration (Two Double Bonds)

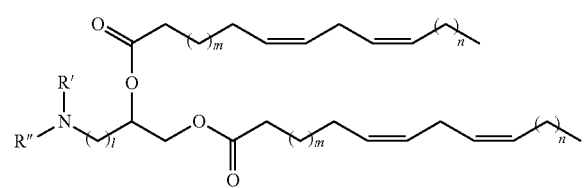

R'=H, Me, Et, propyl, isopropyl or 2-hydroxyethyl and R''=H; l=1 to 6, m=1-8, n=1-10
R'=H, Me, Et, propyl, isopropyl or 2-hydroxyethyl and R''=Me; l=1 to 6, m=1-8, n=1-10
R'=H, Me, Et, propyl, isopropyl or 2-hydroxyethyl and R''=Et; l=1 to 6, m=1-8, n=1-10
R'=H, Me, Et, propyl, isopropyl or 2-hydroxyethyl and R''=propyl; l=1 to 6, m=1-8, n=1-10
R'=H, Me, Et, propyl, isopropyl or 2-hydroxyethyl and R''=isopropyl; l=1 to 6, m=1-8, n=1-10

Amide Ester Linkage with Z Configuration (Three Double Bonds)

R'=H, Me, Et, propyl, isopropyl or 2-hydroxyethyl and R''=H; l=1 to 6, m=1-8, n=1-10
R'=H, Me, Et, propyl, isopropyl or 2-hydroxyethyl and R''=Me; l=1 to 6, m=1-8, n=1-10
R'=H, Me, Et, propyl, isopropyl or 2-hydroxyethyl and R''=Et; l=1 to 6, m=1-8, n=1-10

R'=H, Me, Et, propyl, isopropyl or 2-hydroxyethyl and R"=propyl; l=1 to 6, m=1-8, n=1-10

R'=H, Me, Et, propyl, isopropyl or 2-hydroxyethyl and R"=isopropyl; l=1 to 6, m=1-8, n=1-10

Amides and Ester Linkages with E Configuration (Two Double Bonds)

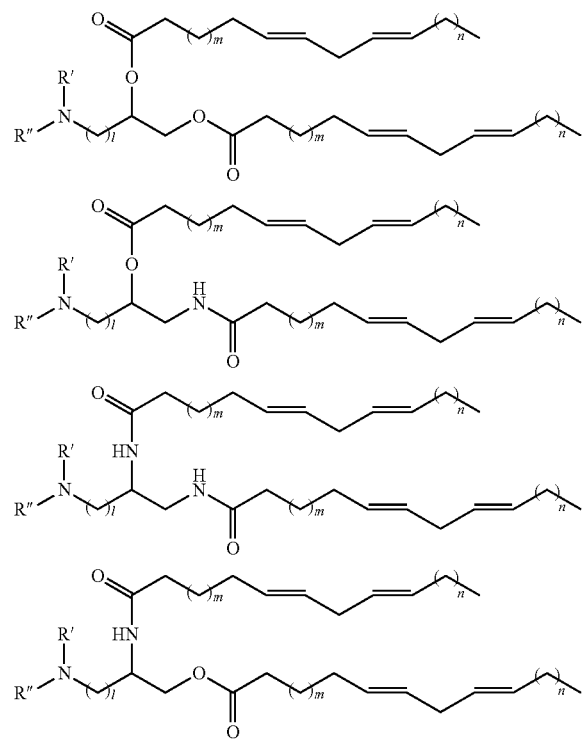

R'=H, Me, Et, propyl, isopropyl or 2-hydroxyethyl and R"=H; l=1 to 6, m=1-8, n=1-10

R'=H, Me, Et, propyl, isopropyl or 2-hydroxyethyl and R"=Me; l=1 to 6, m=1-8, n=1-10

R'=H, Me, Et, propyl, isopropyl or 2-hydroxyethyl and R"=Et; l=1 to 6, m=1-8, n=1-10

R'=H, Me, Et, propyl, isopropyl or 2-hydroxyethyl and R"=propyl; l=1 to 6, m=1-8, n=1-10

R'=H, Me, Et, propyl, isopropyl or 2-hydroxyethyl and R"=isopropyl; l=1 to 6, m=1-8, n=1-10

Amides and Ester Linkages with E Configuration (Three Double Bonds)

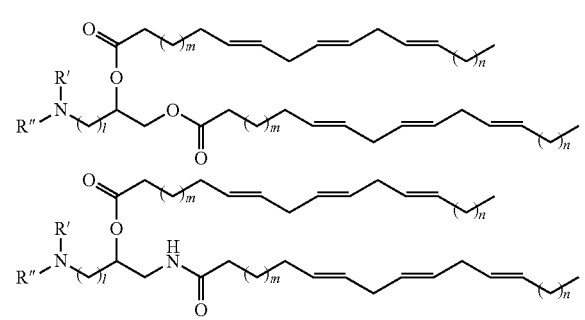

-continued

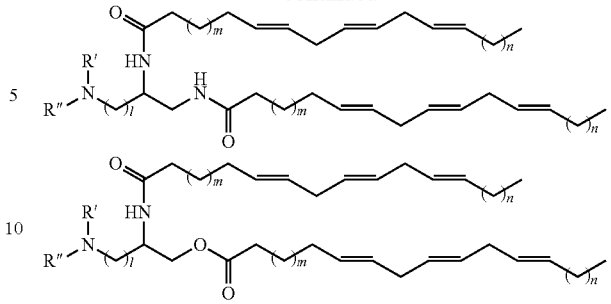

R'=H, Me, Et, propyl, isopropyl or 2-hydroxyethyl and R"=H; l=1 to 6, m=1-8, n=1-10

R'=H, Me, Et, propyl, isopropyl or 2-hydroxyethyl and R"=Me; l=1 to 6, m=1-8, n=1-10

R'=H, Me, Et, propyl, isopropyl or 2-hydroxyethyl and R"=Et; l=1 to 6, m=1-8, n=1-10

R'=H, Me, Et, propyl, isopropyl or 2-hydroxyethyl and R"=propyl; l=1 to 6, m=1-8, n=1-10

R'=H, Me, Et, propyl, isopropyl or 2-hydroxyethyl and R"=isopropyl; l=1 to 6, m=1-8, n=1-10

Disulfide Linkages

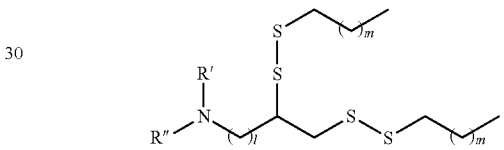

R'=H, Me, Et, propyl, isopropyl or 2-hydroxyethyl and R"=H; l=1 to 6, m=6-28

R'=H, Me, Et, propyl, isopropyl or 2-hydroxyethyl and R"=Me; l=1 to 6, m=6-28

R'=H, Me, Et, propyl, isopropyl or 2-hydroxyethyl and R"=Et; l=1 to 6, m=6-28

R'=H, Me, Et, propyl, isopropyl or 2-hydroxyethyl and R"=propyl; l=1 to 6, m=6-28

R'=H, Me, Et, propyl, isopropyl or 2-hydroxyethyl and R"=isopropyl; l=1 to 6, m=6-28

Disulfide Linkages with Unsaturated Alkyl Chains, E and Z Configuration

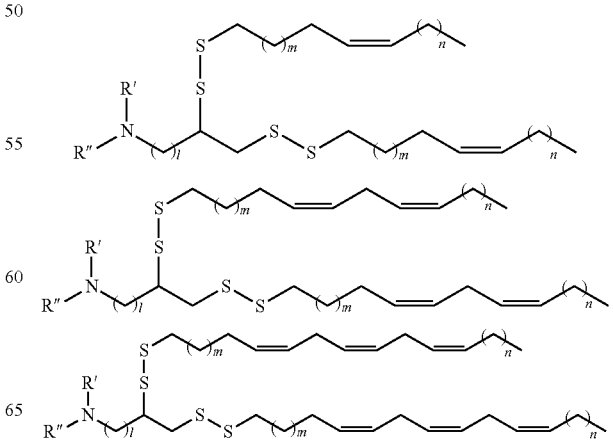

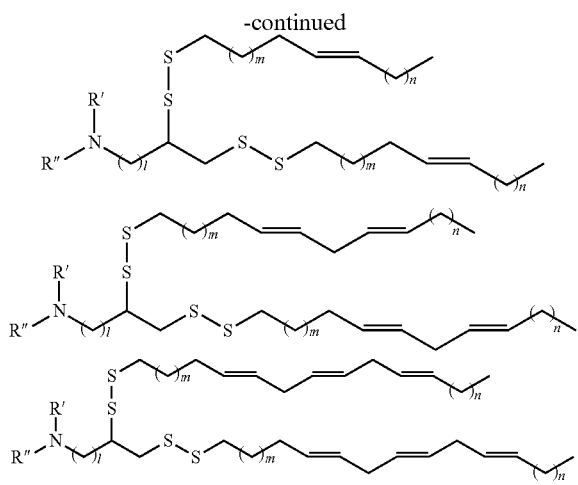

R'=H, Me, Et, propyl, isopropyl or 2-hydroxyethyl and R"=H; l=1 to 6, m=1-8, n=1-10

R'=H, Me, Et, propyl, isopropyl or 2-hydroxyethyl and R"=Me; l=1 to 6, m=1-8, n=1-10

R'=H, Me, Et, propyl, isopropyl or 2-hydroxyethyl and R"=Et; l=1 to 6, m=1-8, n=1-10

R'=H, Me, Et, propyl, isopropyl or 2-hydroxyethyl and R"=propyl; l=1 to 6, m=1-8, n=1-10

R'=H, Me, Et, propyl, isopropyl or 2-hydroxyethyl and R"=isopropyl; l=1 to 6, m=1-8, n=1-10

Amide and Disulfide Linkages with Saturated and Unsaturated Alkyl Chains

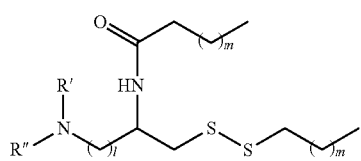

R'=H, Me, Et, propyl, isopropyl or 2-hydroxyethyl and R"=H; l=1 to 6, m=6-28

R'=H, Me, Et, propyl, isopropyl or 2-hydroxyethyl and R"=Me; l=1 to 6, m=6-28

R'=H, Me, Et, propyl, isopropyl or 2-hydroxyethyl and R"=Et; l=1 to 6, m=6-28

R'=H, Me, Et, propyl, isopropyl or 2-hydroxyethyl and R"=propyl; l=1 to 6, m=6-28

R'=H, Me, Et, propyl, isopropyl or 2-hydroxyethyl and R"=isopropyl; l=1 to 6, m=6-28

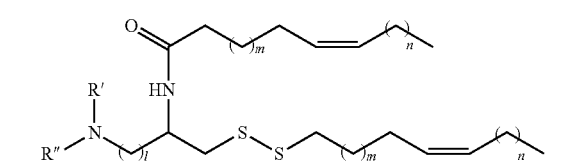

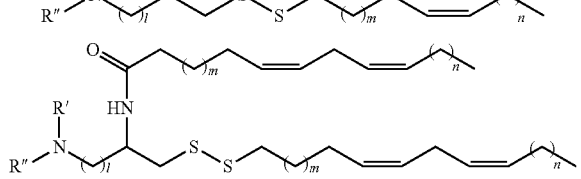

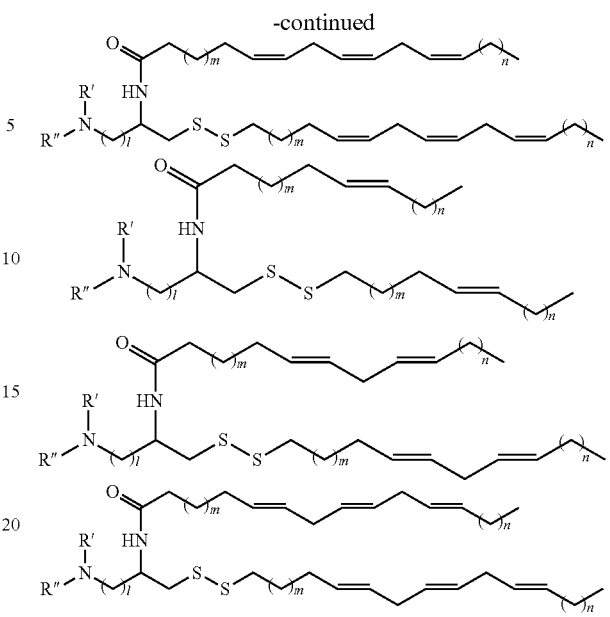

R'=H, Me, Et, propyl, isopropyl or 2-hydroxyethyl and R"=H; l=1 to 6, m=1-8, n=1-10

R'=H, Me, Et, propyl, isopropyl or 2-hydroxyethyl and R"=Me; l=1 to 6, m=1-8, n=1-10

R'=H, Me, Et, propyl, isopropyl or 2-hydroxyethyl and R"=Et; l=1 to 6, m=1-8, n=1-10

R'=H, Me, Et, propyl, isopropyl or 2-hydroxyethyl and R"=propyl; l=1 to 6, m=1-8, n=1-10

R'=H, Me, Et, propyl, isopropyl or 2-hydroxyethyl and R"=isopropyl; l=1 to 6, m=1-8, n=1-10

Ester and Disulfide Linkages with Saturated and Unsaturated Alkyl Chains

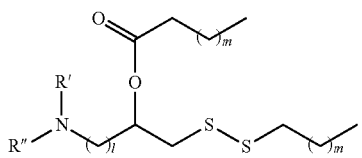

R'=H, Me, Et, propyl, isopropyl or 2-hydroxyethyl and R"=H; l=1 to 6, m=6-28

R'=H, Me, Et, propyl, isopropyl or 2-hydroxyethyl and R"=Me; l=1 to 6, m=6-28

R'=H, Me, Et, propyl, isopropyl or 2-hydroxyethyl and R"=Et; l=1 to 6, m=6-28

R'=H, Me, Et, propyl, isopropyl or 2-hydroxyethyl and R"=propyl; l=1 to 6, m=6-28

R'=H, Me, Et, propyl, isopropyl or 2-hydroxyethyl and R"=isopropyl; l=1 to 6, m=6-28

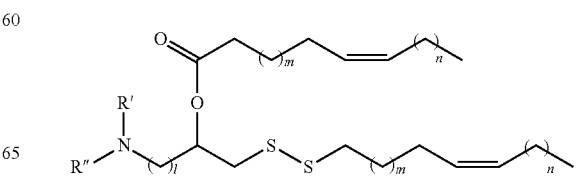

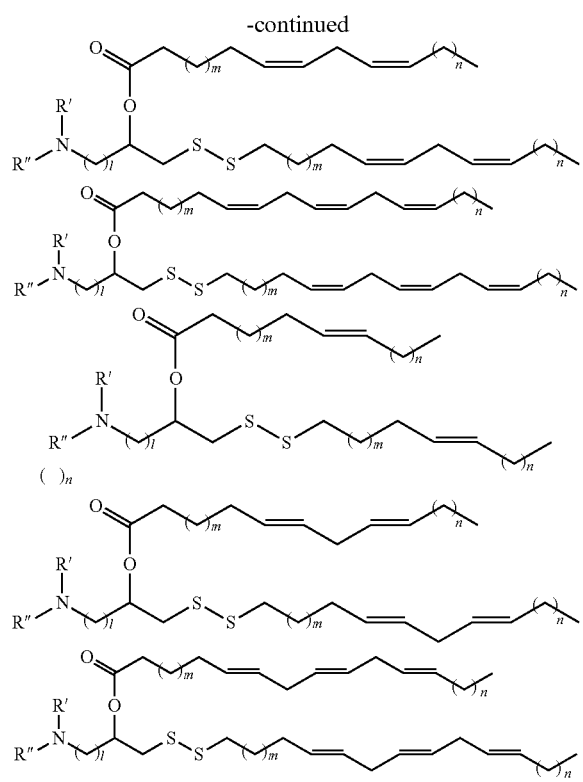

R'=H, Me, Et, propyl, isopropyl or 2-hydroxyethyl and R"=H; l=1 to 6, m=1-8, n=1-10

R'=H, Me, Et, propyl, isopropyl or 2-hydroxyethyl and R"=Me; l=1 to 6, m=1-8, n=1-10

R'=H, Me, Et, propyl, isopropyl or 2-hydroxyethyl and R"=Et; l=1 to 6, m=1-8, n=1-10

R'=H, Me, Et, propyl, isopropyl or 2-hydroxyethyl and R"=propyl; l=1 to 6, m=1-8, n=1-10

R'=H, Me, Et, propyl, isopropyl or 2-hydroxyethyl and R"=isopropyl; l=1 to 6, m=1-8, n=1-10

Carbamate or Urea and Disulfide Linkages with Alkyl Chains

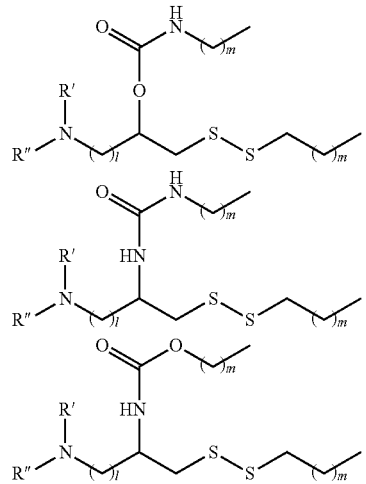

R'=H, Me, Et, propyl, isopropyl or 2-hydroxyethyl and R"=H; l=1 to 6, m=6-28

R'=H, Me, Et, propyl, isopropyl or 2-hydroxyethyl and R"=Me; l=1 to 6, m=6-28

R'=H, Me, Et, propyl, isopropyl or 2-hydroxyethyl and R"=Et; l=1 to 6, m=6-28

R'=H, Me, Et, propyl, isopropyl or 2-hydroxyethyl and R"=propyl; l=1 to 6, m=6-28

R'=H, Me, Et, propyl, isopropyl or 2-hydroxyethyl and R"=isopropyl; l=1 to 6, m=6-28

Carbamate or Urea and Disulfide Linkages with Unsaturated Alkyl Chains

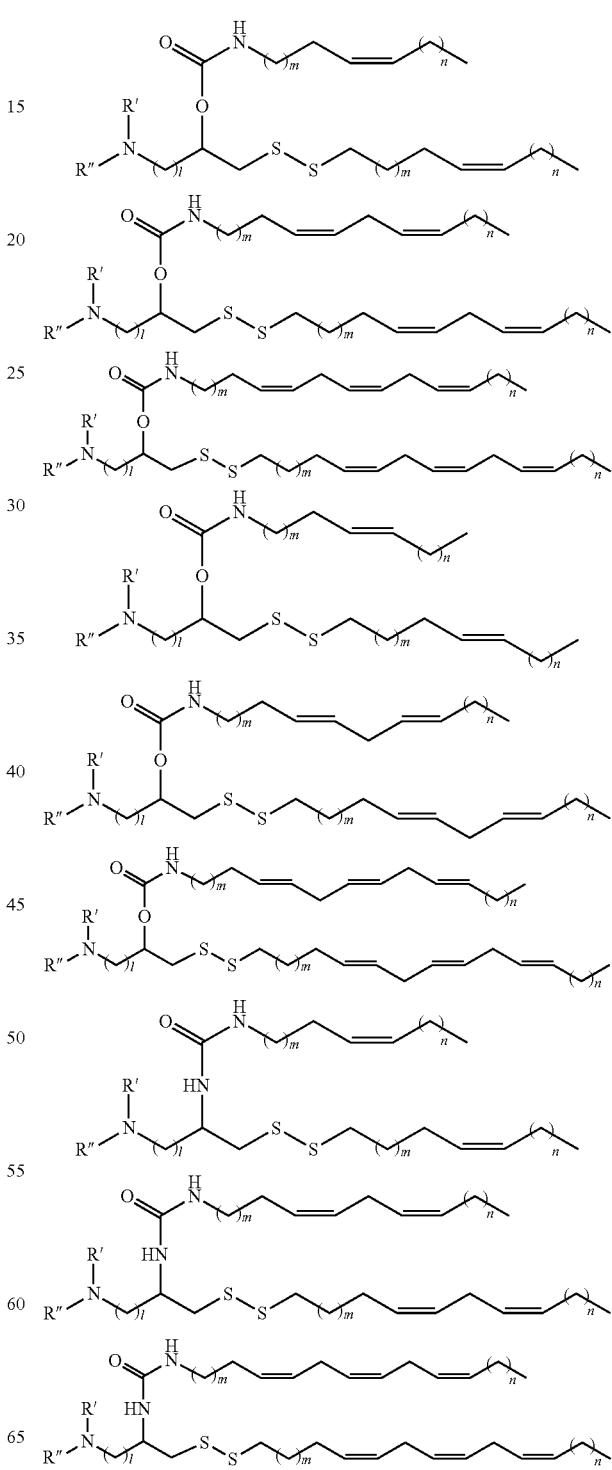

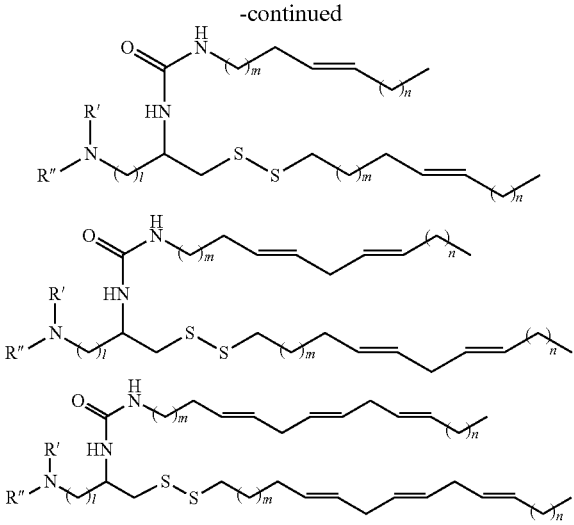

R'=H, Me, Et, propyl, isopropyl or 2-hydroxyethyl and R"=H; l=1 to 6, m=6-28

R'=H, Me, Et, propyl, isopropyl or 2-hydroxyethyl and R"=Me; l=1 to 6, m=6-28

R'=H, Me, Et, propyl, isopropyl or 2-hydroxyethyl and R"=Et; l=1 to 6, m=6-28

R'=H, Me, Et, propyl, isopropyl or 2-hydroxyethyl and R"=propyl; l=1 to 6, m=6-28

R'=H, Me, Et, propyl, isopropyl or 2-hydroxyethyl and R"=isopropyl; l=1 to 6, m=6-28

Carbamate or Urea and Disulfide Linkages with Unsaturated Alkyl Chains

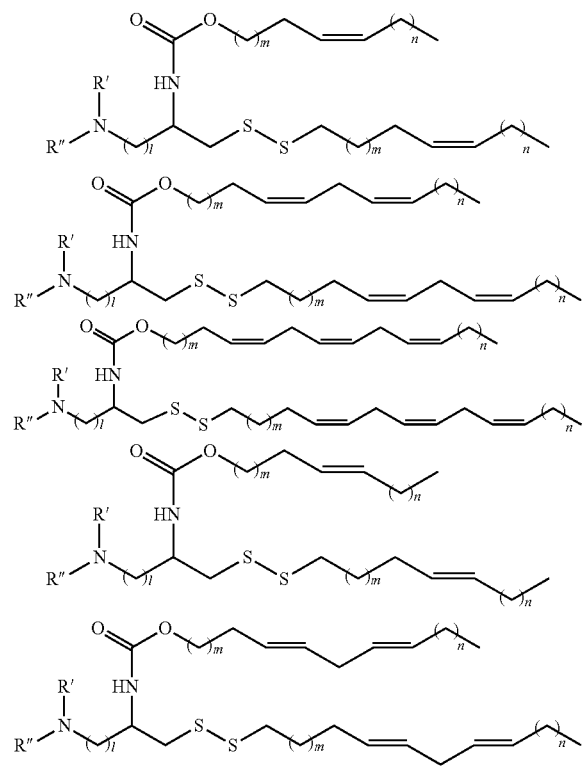

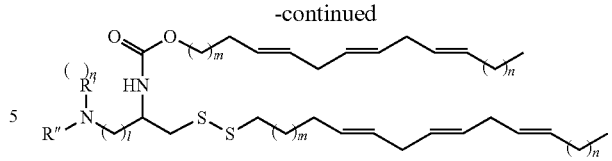

R'=H, Me, Et, propyl, isopropyl or 2-hydroxyethyl and R"=H; l=1 to 6, m=6-28

R'=H, Me, Et, propyl, isopropyl or 2-hydroxyethyl and R"=Me; l=1 to 6, m=6-28

R'=H, Me, Et, propyl, isopropyl or 2-hydroxyethyl and R"=Et; l=1 to 6, m=6-28

R'=H, Me, Et, propyl, isopropyl or 2-hydroxyethyl and R"=propyl; l=1 to 6, m=6-28

R'=H, Me, Et, propyl, isopropyl or 2-hydroxyethyl and R"=isopropyl; l=1 to 6, m=6-28

Carbamate and Urea Linkages with Unsaturated Alkyl Chains

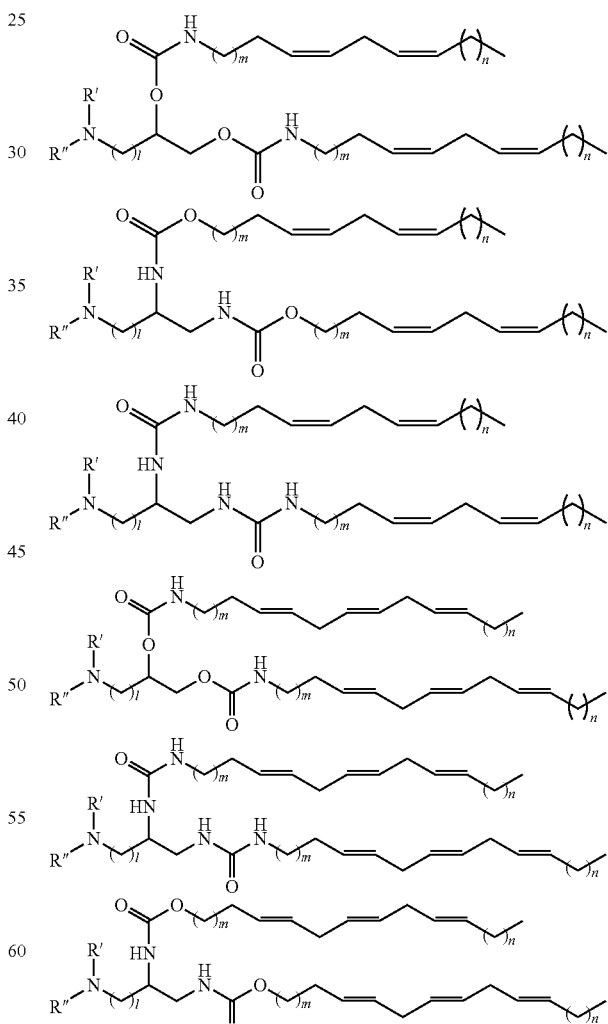

R'=H, Me, Et, propyl, isopropyl or 2-hydroxyethyl and R"=H; l=1 to 6, m=1-10, n=1-10

R'=H, Me, Et, propyl, isopropyl or 2-hydroxyethyl and R"=Me; l=1 to 6, m=1-10, n=1-10

R'=H, Me, Et, propyl, isopropyl or 2-hydroxyethyl and R"=Et; l=1 to 6, m=1-10, n=1-10

R'=H, Me, Et, propyl, isopropyl or 2-hydroxyethyl and R"'=propyl; l=1 to 6, m=1-10, n=1-10

R'=H, Me, Et, propyl, isopropyl or 2-hydroxyethyl and R"'=isopropyl; l=1 to 6, m=1-10, n=1-10

In some embodiments, the lipid includes an oxime or hydrazone, which can undergo acidic cleavage.

$R^3$ and $R^4$ are generally long chain hydrophobic moieties, such as alkyl, alkenyl, or alkynyl. In some embodiments, $R^3$ or $R^4$ are substituted with a halo moiety, for example, to provide a perfluoroalkyl or perfluoroalkenyl moiety. Each of $R^3$ and $R^4$ are independent of each other. In some embodiments, both of $R^3$ and $R^4$ are the same. In some embodiments, $R^3$ and $R^4$ are different.

In some embodiments $R^3$ and/or $R^4$ are alkyl. For example one or both of $R^3$ and/or $R^4$ are $C_6$ to $C_{30}$ alkyl, e.g., $C_{10}$ to $C_{26}$ alkyl, $C_{12}$ to $C_{20}$ alkyl, or $C_{12}$ alkyl.

In some embodiments, $R^3$ and/or $R^4$ are alkenyl. In some preferred embodiments, $R^3$ and/or $R^4$ include 2 or 3 double bonds. For example $R^3$ and/or $R^4$ includes 2 double bonds or $R^3$ and/or $R^4$ includes 3 double bonds. The double bonds can each independently have a Z or E configuration. Exemplary alkenyl moieties are provided below:

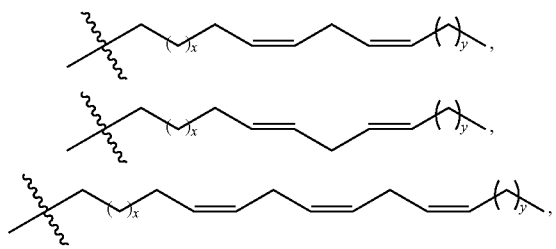

-continued

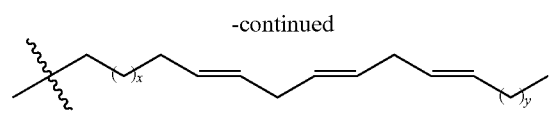

wherein x is an integer from 1 to 8; and y is an integer from 1-10. In some preferred embodiments, $R^3$ and/or $R^4$ are $C_6$ to $C_{30}$ alkenyl, e.g., $C_{10}$ to $C_{26}$ alkenyl, $C_{12}$ to $C_{20}$ alkenyl, or $C_{1-7}$ alkenyl, for example having two double bonds, such as two double bonds with Z configuration. $R^3$ and/or $R^4$ can be the same or different. In some preferred embodiments, $R^3$ and $R^4$ are the same.

In some embodiments, $R^3$ and/or $R^4$ are alkynyl. For example $C_6$ to $C_{30}$ alkynyl, e.g., $C_{10}$ to $C_{26}$ alkynyl, $C_{12}$ to $C_{20}$ alkynyl. $R^3$ and/or $R^4$ can have from 1 to 3 triple bonds, for example, one, two, or three triple bonds.

In some embodiments, the compound of formula (X) is in the form of a salt, such as a pharmaceutically acceptable salt. A salt, for example, can be formed between an anion and a positively charged substituent (e.g., amino) on a compound described herein. Suitable anions include fluoride, chloride, bromide, iodide, sulfate, bisulfate, nitrate, phosphate, citrate, methanesulfonate, trifluoroacetate, acetate, fumarate, oleate, valerate, maleate, oxalate, isonicotinate, lactate, salicylate, tartrate, tannate, pantothenate, bitartrate, ascorbate, succinate, gentisinate, gluconate, glucaronate, saccharate, formate, benzoate, glutamate, ethanesulfonate, benzenesulfonate, p-toluensulfonate, and pamoate. In some preferred embodiments, the compound of formula (X) is a hydrohalide salt, such as a hydrochloride salt.

Compounds of formula (X) can also be present in the form of hydrates (e.g., $(H_2O)_n$) and solvates, which are included herewith in the disclosure.

PEG-Lipid Compounds

Applicants have discovered that certain PEG containing lipid moieties provide desirable properties for administration of a nucleic acid agent such as single stranded or double stranded nucleic acid, for example siRNA. For example, when a PEG containing lipid, such as a lipid described herein, is formulated into an association complex with a nucleic acid moiety, such as siRNA and administered to a subject, the lipid provides enhanced delivery of the nucleic acid moiety. This enhanced delivery can be determined, for example, by evaluation in a gene silencing assay such as silencing of FVII. In particular, Applicants have discovered the PEG-lipids of formula (XV) can have desirable properties for the delivery of siRNA, including improved bioavailability, diodegradability, and tolerability.

In some embodiment, the PEG is attached via a linker moiety to a structure including two hydrophobic moieties, such as a long chanin alkyl moiety. Exemplary PEG-lipids are provided above, for example, those encompassed by formula (XV), (XV'), and (XVI). In some preferred embodiments, the PEG-lipid has the structure below:

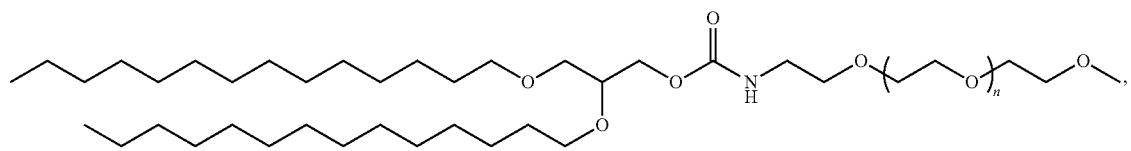

wherein the preferred stereochemistry of the chiral center is 'R' and the repeating PEG moiety has a total average molecular weight of about 2000 daltons.

In some embodiments, a PEG lipid described herein is conjugated to a targeting moiety, e.g., a glycosyl moiety such as a

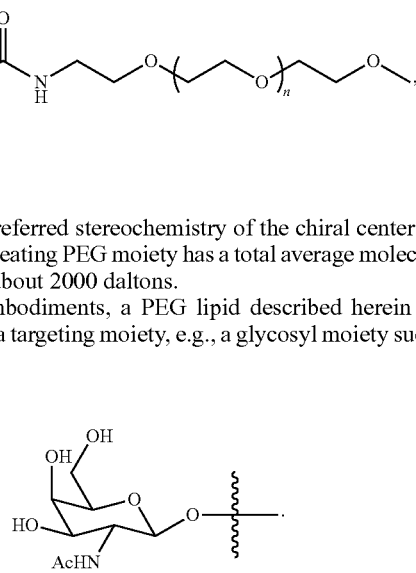

In some embodiments, the targeting moiety is attached to the PEG lipid through a linker, for example a linker described herein. Exemplary targeted PEG lipid compounds are compounds of formula (XXI), (XXI'), (XXII), and (XXII') described herein. Methods of making such lipids are described, for example, in Examples 42 and 43.

Methods of Making Cationic Lipid Compounds and Cationic Lipid Containing Preparations The compounds described herein can be obtained from commercial sources (e.g., Asinex, Moscow, Russia; Bionet, Camelford, England; ChemDiv, SanDiego, Calif.; Comgenex, Budapest, Hungary; Enamine, Kiev, Ukraine; IF Lab, Ukraine; Interbioscreen, Moscow, Russia; Maybridge, Tintagel, UK; Specs, The Netherlands; Timtec, Newark, Del.; Vitas-M Lab, Moscow, Russia) or synthesized by conventional methods as shown below using commercially available starting materials and reagents.

Methods of Making Polyamine Lipids

In some embodiments, a compound of formula (I) can be made by reacting a polyamine of formula (III) as provided below

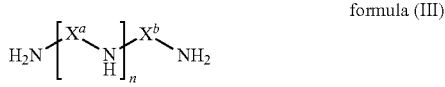

formula (III)

wherein $X^a$, $X^b$, and $n$ are defined as above
with a 1,4 conjugated system of formula (IV)

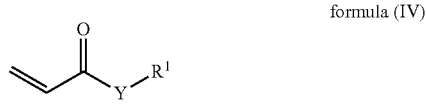

formula (IV)

wherein Y and $R^1$ are defined as above
to provide a compound of formula (I).

In some embodiments, the compounds of formula (III) and (IV) are reacted together neat (i.e., free of solvent). For example, the compounds of formula (III) and (IV) are reacted together neat at elevated temperature (e.g., at least about 60° C., at least about 65° C., at least about 70° C., at least about 75° C., at least about 80° C., at least about 85° C., or at least about 90° C.), preferably at about 90° C.

In some embodiments, the compounds of formula (III) and (IV) are reacted together with a solvent (e.g., a polar aprotic solvent such as acetonitrile or DMF). For example, the compounds of formula (III) and (IV) are reacted together in solvent at an elevated temperature from about 50° C. to about 120° C.

In some embodiments, the compounds of formula (III) and (IV) are reacted together in the presence of a radical quencher or scavenger (e.g., hydroquinone). The reaction conditions including a radical quencher can be neat or in a solvent e.g., a polar aprotic solvent such as acetonitrile or DMF. The reaction can be at an elevated temperature (e.g., neat at an elevated temperature such as 90° C. or with solvent at an elevated temperature such as from about 50° C. to about 120° C.). The term "radical quencher" or "radical scavenger" as used herein refers to a chemical moiety that can absorb free radicals in a reaction mixture. Examples of radical quenchers/scavengers include hydroquinone, ascorbic acid, cresols, thiamine, 3,5-Di-tert-butyl-4-hydroxytoluene, tert-Butyl-4-hydroxyanisole and thiol containing moieties.

In some embodiments, the compounds of formula (III) and (IV) are reacted together in the presence of a reaction promoter (e.g., water or a Michael addition promoter such as acetic acid, boric acid, citric acid, benzoic acid, tosic acid, pentafluorophenol, picric acid aromatic acids, salts such as bicarbonate, bisulphate, mono and di-hydrogen phophates, phenols, perhalophenols, nitrophenols, sulphonic acids, PTTS, etc.), preferably boric acid such as a saturated aqueous boric acid. The reaction conditions including a reaction promoter can be neat or in a solvent e.g., a polar aprotic solvent such as acetonitrile or DMF. The reaction can be at an elevated temperature (e.g., neat at an elevated temperature such as 90° C. or with solvent at an elevated temperature such as from about 50° C. to about 120° C.). The term "reaction promoter" as used herein refers to a chemical moiety that, when used in a reaction mixture, accelerates/enhances the rate of reaction.

The ratio of compounds of formula (III) to formula (IV) can be varied, providing variability in the substitution on the polyamine of formula (III). In general, polyamines having at least about 50% of the hydrogen moieties substituted with a non-hydrogen moiety are preferred. Accordingly, ratios of compounds of formula (III)/formula (IV) are selected to provide for products having a relatively high degree of substitution of the free amine (e.g., at least about 50%, at least about 55%, at least about 60%, at least about 65%, at least about 70%, at least about 75%, at least about 80%, at least about 85%, at least about 90%, at least about 95%, at least about 97%, at least about 99%, or substantially all). In some preferred embodiments n is 0 in the polyamine of formula (III), and the ratio of compounds of formula (III) to compounds of formula (IV) is from about 1:3 to about 1:5, preferable about 1:4. In some preferred embodiments, n is 2 in the polyamine of formula (III), and the ratio of compound of formula (III) to compounds of formula (IV) is from about 1:3 to about 1:6, preferably about 1:5.

In some embodiments, the compounds of formula (III) and formula (IV) are reacted in a two step process. For example, the first step process includes a reaction mixture having from about 0.8 about 1.2 molar equivalents of a compound of formula (III), with from about 3.8 to about 4.2 molar equivalents of a compound of formula (IV) and the second step process includes addition of about 0.8 to 1.2 molar equivalent of compound of formula (IV) to the reaction mixture.

Upon completion of the reaction, one or more products having formula (I) can be isolated from the reaction mixture. For example, a compound of formula (I) can be isolated as a single product (e.g., a single structural isomer) or as a mixture of product (e.g., a plurality of structural isomers and/or a plurality of compounds of formula (I)). In some embodiments, one or more reaction products can be isolated and/or purified using chromatography, such as flash chromatography, gravity chromatography (e.g., gravity separation of isomers using silica gel), column chromatography (e.g., normal phase HPLC or RPHPLC), or moving bed chromatography. In some embodiments, a reaction product is purified to provide a preparation containing at least about 80% of a single compound, such as a single structural isomer (e.g., at least about 85%, at least about 90%, at least about 95%, at least about 97%, at least about 99%).

In some embodiments, a free amine product is treated with an acid such as HCl to prove an amine salt of the product (e.g., a hydrochloride salt). In some embodiments a salt product provides improved properties, e.g., for handling and/or storage, relative to the corresponding free amine product. In some embodiments, a salt product can prevent or reduce the rate of formation of breakdown product such as N-oxide or N-carbonate formation relative to the corresponding free amine. In some embodiments, a salt product can have improved properties for use in a therapeutic formulation relative to the corresponding free amine.

In some embodiments, the reaction mixture is further treated, for example, to purify one or more products or to remove impurities such as unreacted starting materials. In some embodiments the reaction mixture is treated with an immobilized (e.g., polymer bound) thiol moiety, which can trap unreacted acrylamide. In some embodiments, an isolated product can be treated to further remove impurities, e.g., an isolated product can be treated with an immobilized thiol moiety, trapping unreacted acrylamide compounds.

In some embodiments a reaction product can be treated with an immobilized (e.g., polymer bound) isothiocyanate. For example, a reaction product including tertiary amines can be treated with an immobilized isothiocyanate to remove primary and/or secondary amines from the product.

In some embodiments, a compound of formula (I) can be made by reacting a polyamine of formula (III) as provided below

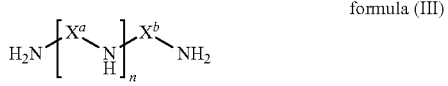

formula (III)

wherein $X^a$, $X^b$, and $n$ are defined as above
with a compound of formula (VI)),

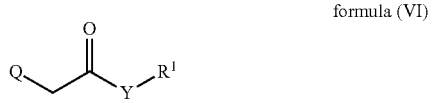

formula (VI)

wherein Q is Cl, Br, or I, and Y and $R^1$ are as defined above.

In some embodiments, the compound of formula (III) and formula (VI) are reacted together neat. In some embodiments, the compound of formula (III) and formula (VI) are reacted together in the presence of one or more solvents, for example a polar aprotic solvent such as acetonitrile or DMF. In some embodiments, the reactants (formula (III) and formula (VI)) are reacted together at elevated temperature (e.g., at least about 50° C., at least about 60° C., at least about 70° C., at least about 80° C., at least about 90° C., at least about 100° C.).

In some embodiments, the reaction mixture also includes a base, for example a carbonate such as $K_2CO_3$.

In some embodiments, the reaction mixture also includes a catalyst.

In some embodiments, the compound of formula (VI) is prepared by reacting an amine moiety with an activated acid such as an acid anhydrate or acid halide (e.g., acid chloride) to provide a compound of formula (VI).

The ratio of compounds of formula (III) to formula (VI) can be varied, providing variability in the substitution on the polyamine of formula (III). In general, polyamines having at least about 50% of the hydrogen moieties substituted with a non-hydrogen moiety are preferred. Accordingly, ratios of compounds of formula (III)/formula (VI) are selected to provide for products having a relatively high degree of substitution of the free amine (e.g., at least about 50%, at least about 55%, at least about 60%, at least about 65%, at least about 70%, at least about 75%, at least about 80%, at least about 85%, at least about 90%, at least about 95%, at least about 97%, at least about 99%, or substantially all). In some preferred embodiments n is 0 in the polyamine of formula (III), and the ratio of compounds of formula (III) to compounds of formula (VI) is from about 1:3 to about 1:5, preferable about 1:4. In some preferred embodiments, n is 2 in the polyamine of formula (III), and the ratio of compound of formula (III) to compounds of formula (VI) is from about 1:3 to about 1:6, preferably about 1:5.

In some embodiments, the compounds of formula (III) and formula (VI) are reacted in a two step process. For example, the first step process includes a reaction mixture having from about 0.8 about 1.2 molar equivalents of a compound of formula (III), with from about 3.8 to about 4.2 molar equivalents of a compound of formula (VI) and the second step process includes addition of about 0.8 to 1.2 molar equivalent of compound of formula (VI) to the reaction mixture.

In some embodiments, one or more amine moieties of formula (III) are selectively protected using a protecting group prior to reacting the polyamine of formula (III) with a compound of formula (IV) or (VI), thereby providing improved selectivity in the synthesis of the final product. For example, one or more primary amines of the polyamine of formula (III) can be protected prior to reaction with a compound of formula (IV) or (VI), providing selectivity for the compound of formula (IV) or (VI) to react with secondary amines. Other protecting group strategies can be employed to provide for selectivity towards primary amines, for example, use of orthogonal protecting groups that can be selectively removed.

Upon completion of the reaction, one or more products having formula (I) can be isolated from the reaction mixture. For example, a compound of formula (I) can be isolated as a single product (e.g., a single structural isomer) or as a mixture of product (e.g., a plurality of structural isomers and/or a plurality of compounds of formula (I)). In some embodiments, on or more reaction products can be isolated and/or purified using chromatography, such as flash chromatography, gravity chromatography (e.g., gravity separation of isomers using silica gel), column chromatography (e.g., normal phase HPLC or RPHPLC), or moving bed chromatography. In some embodiments, a reaction product is purified to provide a preparation containing at least about 80% of a single compound, such as a single structural isomer (e.g., at least about 85%, at least about 90%, at least about 95%, at least about 97%, at least about 99%).

In some embodiments, a free amine product is treated with an acid such as HCl to prove an amine salt of the product (e.g., a hydrochloride salt). In some embodiments a salt product provides improved properties, e.g., for handling and/or storage, relative to the corresponding free amine product. In some embodiments, a salt product can prevent or reduce the rate of formation of breakdown product such as N-oxide or N-carbonate formation relative to the corresponding free amine. In some embodiments, a salt product can have improved properties for use in a therapeutic formulation relative to the corresponding free amine.

In some embodiments, a polyamine cationic lipid can be made in using a regioselective synthesis approach. The regioselective synthetic approach provides a convenient way to make site specific alkylation on nitrogen(s) of the polyamine backbone that leads to synthesis of specific alkylated derivatives of interest. In general a compound of formula (I) is initially reacted with a reagent that selectively reacts with primary amines or terminal amines to block them from reacting or interfering with further reactions and these blockages could be selectively removed at appropriate stages during the synthesis of a target compound. After blocking terminal amines of a compound of formula (I), one or more of the secondary amines could be selectively blocked with an orthogonal amine protecting groups by using appropriate molar ratios of the reagent and reaction conditions. Selective alkylations, followed by selective deprotection of the blocked amines and further alkylation of regenerated amines and appropriate repetition of the sequence of reactions described provides specific compound of interest. For example, terminal amines of triethylenetetramine (1) is selectively blocked with primary amine specific protecting groups (e.g., trifluoroacetamide) under appropriate reaction conditions and subsequently reacted with excess of orthogonal amine protecting reagent [(Boc)$_2$O, for e.g.)] in the presence of a base (for e.g., diisopropylethylamine) to block all internal amines (e.g., Boc). Selective removal of the terminal protecting group and subsequent alkylation of the terminal amines, for instance with an acrylamide provides a fully terminal amine alkylated derivative of compound 1. Deblocking of the internal amine protection and subsequent alkylation with calculated amount of an acrylamide for instance yields a partially alkylated product 7. Another approach to make compound 7 is to react terminally protected compound 1 with calculated amount of an orthogonal amine protecting reagent [(Boc)$_2$O, for e.g.)] to obtain a partially protected derivatives of compound 1. Removal of the terminal amine protecting groups of partially and selectively protected 1 and subsequent alkylation of all unprotected amines with an acrylamide, for instance, yields compound 7 of interest.

Methods of Making Lipids Having a Biocleavable Moiety

In some embodiments, a compound of formula (X) can be made by reacting a compound of formula

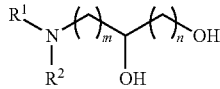

formula (XI)

with a compound of formula (XII)

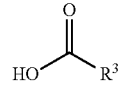

formula (XII)

wherein R$^1$, R$^2$, and R$^3$ are as defined above.

In some embodiments, the compounds of formulas (XI) and (XII) are reacted in the presence of a coupling agent such as a carbodiimide (e.g., a water soluble carbodiimide such as EDCI).

Other chemical reactions and starting materials can be employed to provide a compound of formula (X) having two linking groups L$^1$ and L$^2$. For example, the hydroxyl moieties of formula (XI) could be replaced with amine moieties to provide a precursor to amide or urea linking groups.

Upon completion of the reaction, one or more products having formula (X) can be isolated from the reaction mixture. For example, a compound of formula (X) can be isolated as a single product (e.g., a single structural isomer) or as a mixture of product (e.g., a plurality of structural isomers and/or a plurality of compounds of formula (X)). In some embodiments, on or more reaction products can be isolated and/or purified using chromatography, such as flash chromatography, gravity chromatography (e.g., gravity separation of isomers using silica gel), column chromatography (e.g., normal phase HPLC or RPHPLC), or moving bed chromatography. In some embodiments, a reaction product is purified to provide a preparation containing at least about 80% of a single compound, such as a single structural isomer (e.g., at least about 85%, at least about 90%, at least about 95%, at least about 97%, at least about 99%).

In some embodiments, a free amine product is treated with an acid such as HCl to prove an amine salt of the product (e.g., a hydrochloride salt). In some embodiments a salt product provides improved properties, e.g., for handling and/or storage, relative to the corresponding free amine product. In some embodiments, a salt product can prevent or reduce the rate of formation of breakdown product such as N-oxide or N-carbonate formation relative to the corresponding free amine. In some embodiments, a salt product can have improved properties for use in a therapeutic formulation relative to the corresponding free amine.

Methods of Making PEG-Lipids

The PEG-lipid compounds can be made, for example, by reacting a glyceride moiety (e.g., a dimyristyl glyceride, dipalmityl glyceride, or distearyl glyceride) with an activating moiety under appropriate conditions, for example, to provide an activated intermediate that could be subsequently reacted with a PEG component having a reactive moiety such as an amine or a hydroxyl group to obtain a PEG-lipid. For example, a dalkylglyceride (e.g., dimyristyl glyceride) is initially reacted with N,N'-disuccinimidyl carbonate in the presence of a base (for e.g., triethylamine) and subsequent reaction of the intermediate formed with a PEG-amine (e.g., mPEG2000-NH$_2$) in the presence of base such as pyridine affords a PEG-lipid of interest. Under these conditions the PEG component is attached to the lipid moiety via a carbamate linkage. In another instance a PEG-lipid can be made, for example, by reacting a glyceride moiety (e.g., dimyristyl glyceride, dipalmityl glyceride, distearyl glyceride, dimyristoyl glyceride, dipalmitoyl glyceride or distearoyl glyceride) with succinic anhydride and subsequent activation of the carboxyl generated followed by reaction of the activated intermediate with a PEG component with an amine or a hydroxyl group, for instance, to obtain a PEG-lipid. In one example, dimyristyl glyceride is reacted with succinic anhydride in the presence of a base such as DMAP to obtain a hemi-succinate. The free carboxyl moiety of the hemi-succinate thus obtained is activated using standard carboxyl activating agents such as HBTU and diisopropylethylamine and subsequent reaction of the activated carboxyl with mPEH2000-NH$_2$, for instance, yields a PEG-lipid. In this approach the PEG component is linked to the lipid component via a succinate bridge.

Association Complexes

The lipid compounds and lipid preparations described herein can be used as a component in an association complex, for example a liposome or a lipoplex. Such association complexes can be used to administer a nucleic acid based therapy such as an RNA, for example a single stranded or double stranded RNA such as dsRNA.

The association complexes disclosed herein can be useful for packaging an oligonucleotide agent capable of modifying gene expression by targeting and binding to a nucleic acid. An oligonucleotide agent can be single-stranded or double-stranded, and can include, e.g., a dsRNA, aa pre-mRNA, an mRNA, a microRNA (miRNA), a mi-RNA precursor (pre-miRNA), plasmid or DNA, or to a protein. An oligonucleotide agent featured in the invention can be, e.g., a dsRNA, a microRNA, antisense RNA, antagomir, decoy RNA, DNA, plasmid and aptamer.

Association complexes can include a plurality of components. In some embodiments, an association complex such as a liposome can include an active ingredient such as a nucleic acid therapeutic (such as an oligonucleotide agent, e.g., dsRNA), a cationic lipid such as a lipid described herein. In some embodiments, the association complex can include a plurality of therapeutic agents, for example two or three single or double stranded nucleic acid moieties targeting more than one gene or different regions of the same gene. Other components can also be included in an association complex, including a PEG-lipid such as a PEG-lipid described herein, or a structural component, such as cholesterol. In some embodiments the association complex also includes a fusogenic lipid or component and/or a targeting molecule. In some preferred embodiments, the association complex is a liposome including an oligonucleotide agent such as dsRNA, a lipid described herein such as a compound of formula (I) or (X), a PEG-lipid such as a PEG-lipid described herein (e.g., a PEG-lipid of formula (XV), and a structural component such as cholesterol.

Single Stranded Ribonucleid Acid

Oligonucleotide agents include microRNAs (miRNAs). MicroRNAs are small noncoding RNA molecules that are capable of causing post-transcriptional silencing of specific genes in cells such as by the inhibition of translation or through degradation of the targeted mRNA. An miRNA can be completely complementary or can have a region of non-complementarity with a target nucleic acid, consequently resulting in a "bulge" at the region of non-complementarity. The region of noncomplementarity (the bulge) can be flanked by regions of sufficient complementarity, preferably complete complementarity to allow duplex formation. Preferably, the regions of complementarity are at least 8 to 10 nucleotides long (e.g., 8, 9, or 10 nucleotides long). A miRNA can inhibit gene expression by repressing translation, such as when the microRNA is not completely complementary to the target nucleic acid, or by causing target RNA degradation, which is believed to occur only when the miRNA binds its target with perfect complementarity. The invention also can include double-stranded precursors of miRNAs that may or may not form a bulge when bound to their targets.

In a preferred embodiment an oligonucleotide agent featured in the invention can target an endogenous miRNA or pre-miRNA. The oligonucleotide agent featured in the invention can include naturally occurring nucleobases, sugars, and covalent internucleoside (backbone) linkages as well as oligonucleotides having non-naturally-occurring portions that function similarly. Such modified or substituted oligonucleotides are often preferred over native forms because of desirable properties such as, for example, enhanced cellular uptake, enhanced affinity for the endogenous miRNA target, and/or increased stability in the presence of nucleases. An oligonucleotide agent designed to bind to a specific endogenous miRNA has substantial complementarity, e.g., at least 70, 80, 90, or 100% complementary, with at least 10, 20, or 25 or more bases of the target miRNA.

A miRNA or pre-miRNA can be 18-100 nucleotides in length, and more preferably from 18-80 nucleotides in length. Mature miRNAs can have a length of 19-30 nucleotides, preferably 21-25 nucleotides, particularly 21, 22, 23, 24, or 25 nucleotides. MicroRNA precursors can have a length of 70-100 nucleotides and have a hairpin conformation. MicroRNAs can be generated in vivo from pre-miRNAs by enzymes called Dicer and Drosha that specifically process long pre-miRNA into functional miRNA. The microRNAs or precursor mi-RNAs featured in the invention can be synthesized in vivo by a cell-based system or can be chemically synthesized. MicroRNAs can be synthesized to include a modification that imparts a desired characteristic. For example, the modification can improve stability, hybridization thermodynamics with a target nucleic acid, targeting to a particular tissue or cell-type, or cell permeability, e.g., by an endocytosis-dependent or -independent mechanism. Modifications can also increase sequence specificity, and consequently decrease off-site targeting. Methods of synthesis and chemical modifications are described in greater detail below.

Given a sense strand sequence (e.g., the sequence of a sense strand of a cDNA molecule), an miRNA can be designed according to the rules of Watson and Crick base pairing. The miRNA can be complementary to a portion of an RNA, e.g., a miRNA, a pre-miRNA, a pre-mRNA or an mRNA. For example, the miRNA can be complementary to the coding region or noncoding region of an mRNA or pre-mRNA, e.g., the region surrounding the translation start site of a pre-mRNA or mRNA, such as the 5' UTR. An miRNA oligonucleotide can be, for example, from about 12 to 30 nucleotides in length, preferably about 15 to 28 nucleotides in length (e.g., 16, 17, 18, 19, 20, 21, 22, 23, 24, or 25 nucleotides in length).

In particular, an miRNA or a pre-miRNA featured in the invention can have a chemical modification on a nucleotide in an internal (i.e., non-terminal) region having noncomplementarity with the target nucleic acid. For example, a modified nucleotide can be incorporated into the region of a miRNA that forms a bulge. The modification can include a ligand attached to the miRNA, e.g., by a linker (e.g., see diagrams OT-I through OT-IV below). The modification can, for example, improve pharmacokinetics or stability of a therapeutic miRNA, or improve hybridization properties (e.g., hybridization thermodynamics) of the miRNA to a target nucleic acid. In some embodiments, it is preferred that the orientation of a modification or ligand incorporated into or tethered to the bulge region of a miRNA is oriented to occupy the space in the bulge region. For example, the modification can include a modified base or sugar on the nucleic acid strand or a ligand that functions as an intercalator. These are preferably located in the bulge. The intercalator can be an aromatic, e.g., a polycyclic aromatic or heterocyclic aromatic compound. A polycyclic intercalator can have stacking capabilities, and can include systems with 2, 3, or 4 fused rings. The universal bases described below can be incorporated into the miRNAs. In some embodiments, it is preferred that the orientation of a modification or ligand incorporated into or tethered to the bulge region of a miRNA is oriented to occupy the space in the bulge region. This orientation facilitates the improved hybridization properties or an otherwise desired characteristic of the miRNA.

In one embodiment, an miRNA or a pre-miRNA can include an aminoglycoside ligand, which can cause the miRNA to have improved hybridization properties or improved sequence specificity. Exemplary aminoglycosides include glycosylated polylysine; galactosylated polylysine; neomycin B; tobramycin; kanamycin A; and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-S-acridine has an increased affinity for the HIV Rev-response element (RRE). In some embodiments the guanidine analog (the guanidinoglycoside) of an aminoglycoside ligand is tethered to an oligonucleotide agent. In a guanidinoglycoside, the amine group on the amino acid is exchanged for a guanidine group. Attachment of a guanidine analog can enhance cell permeability of an oligonucleotide agent.

In one embodiment, the ligand can include a cleaving group that contributes to target gene inhibition by cleavage of the target nucleic acid. Preferably, the cleaving group is tethered to the miRNA in a manner such that it is positioned in the bulge region, where it can access and cleave the target RNA. The cleaving group can be, for example, a bleomycin (e.g., bleomycin-$A_5$, bleomycin-$A_2$, or bleomycin-$B_2$), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a miRNA or a pre-miRNA to promote cleavage of the target RNA, e.g., at the bulge region. For example, 1,8-dimethyl-1,3,6,8,10,13-hexaazacyclotetradecane (cyclam) can be conjugated to a peptide (e.g., by an amino acid derivative) to promote target RNA cleavage. The methods and compositions featured in the invention include miRNAs that inhibit target gene expression by a cleavage or non-cleavage dependent mechanism.

An miRNA or a pre-miRNA can be designed and synthesized to include a region of noncomplementarity (e.g., a region that is 3, 4, 5, or 6 nucleotides long) flanked by regions of sufficient complementarity to form a duplex (e.g., regions that are 7, 8, 9, 10, or 11 nucleotides long).

For increased nuclease resistance and/or binding affinity to the target, the miRNA sequences can include 2'-O-methyl, 2'-fluorine, 2'-O-methoxyethyl, 2'-O-aminopropyl, 2'-amino, and/or phosphorothioate linkages. Inclusion of locked nucleic acids (LNA), 2-thiopyrimidines (e.g., 2-thio-U), 2-amino-A, G-clamp modifications, and ethylene nucleic acids (ENA), e.g., 2'-4'-ethylene-bridged nucleic acids, can also increase binding affinity to the target. The inclusion of furanose sugars in the oligonucleotide backbone can also decrease endonucleolytic cleavage. An miRNA or a pre-miRNA can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3' end of oligonucleotide. Even small alkyl chains, aryl groups, or heterocyclic conjugates or modified sugars (D-ribose, deoxyribose, glucose etc.) can block 3'-5'-exonucleases.

The 5'-terminus can be blocked with an aminoalkyl group, e.g., a 5'-O-alkylamino substituent. Other 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5' end of oligonucleotide. Even small alkyl chains, aryl groups, or heterocyclic conjugates or modified sugars (D-ribose, deoxyribose, glucose etc.) can block 3'-5'-exonucleases.

In one embodiment, an miRNA or a pre-miRNA includes a modification that improves targeting, e.g. a targeting modification described herein. Examples of modifications that target miRNA molecules to particular cell types include carbohydrate sugars such as galactose, N-acetylgalactosamine, mannose; vitamins such as folates; other ligands such as RGDs and RGD mimics; and small molecules including naproxen, ibuprofen or other known protein-binding molecules.

An miRNA or a pre-miRNA can be constructed using chemical synthesis and/or enzymatic ligation reactions using procedures known in the art. For example, an miRNA or a pre-miRNA can be chemically synthesized using naturally occurring nucleotides or variously modified nucleotides designed to increase the biological stability of the molecules or to increase the physical stability of the duplex formed between the miRNA or a pre-miRNA and target nucleic acids, e.g., phosphorothioate derivatives and acridine substituted nucleotides can be used. Other appropriate nucleic acid modifications are described herein. Alternatively, the miRNA or pre-miRNA nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Antisense-Type Oligonucleotide Agents

The single-stranded oligonucleotide agents featured in the invention include antisense nucleic acids. An "antisense" nucleic acid includes a nucleotide sequence that is complementary to a "sense" nucleic acid encoding a gene expression product, e.g., complementary to the coding strand of a double-stranded cDNA molecule or complementary to an RNA sequence, e.g., a pre-mRNA, mRNA, miRNA, or pre-miRNA. Accordingly, an antisense nucleic acid can form hydrogen bonds with a sense nucleic acid target.

Given a coding strand sequence (e.g., the sequence of a sense strand of a cDNA molecule), antisense nucleic acids can be designed according to the rules of Watson and Crick base pairing. The antisense nucleic acid molecule can be complementary to a portion of the coding or noncoding region of an RNA, e.g., a pre-mRNA or mRNA. For example, the antisense oligonucleotide can be complementary to the region surrounding the translation start site of a pre-mRNA or mRNA, e.g., the 5' UTR. An antisense oligonucleotide can be, for example, about 10 to 25 nucleotides in length (e.g., 11, 12, 13, 14, 15, 16, 18, 19, 20, 21, 22, 23, or 24 nucleotides in length). An antisense oligonucleotide can also be complementary to a miRNA or pre-miRNA.

An antisense nucleic acid can be constructed using chemical synthesis and/or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and target nucleic acids, e.g., phosphorothioate derivatives and acridine substituted nucleotides can be used. Other appropriate nucleic acid modifications are described herein. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

An antisense agent can include ribonucleotides only, deoxyribonucleotides only (e.g., oligodeoxynucleotides), or both deoxyribonucleotides and ribonucleotides. For example, an antisense agent consisting only of ribonucleotides can hybridize to a complementary RNA, and prevent access of the translation machinery to the target RNA transcript, thereby preventing protein synthesis. An antisense molecule including only deoxyribonucleotides, or deoxyribonucleotides and ribonucleotides, e.g., DNA sequence flanked by RNA sequence at the 5' and 3' ends of the antisense agent, can hybridize to a complementary RNA, and the RNA target can be subsequently cleaved by an enzyme, e.g., RNAse H. Degradation of the target RNA prevents translation. The flanking RNA sequences can include 2'-O-methylated nucleotides, and phosphorothioate linkages, and the internal DNA sequence can include phosphorothioate internucleotide linkages. The internal DNA sequence is preferably at least five nucleotides in length when targeting by RNAseH activity is desired.

For increased nuclease resistance, an antisense agent can be further modified by inverting the nucleoside at the 3'-terminus with a 3'-3' linkage. In another alternative, the 3'-terminus can be blocked with an aminoalkyl group.

In one embodiment, an antisense oligonucleotide agent includes a modification that improves targeting, e.g. a targeting modification described herein.

Decoy-Type Oligonucleotide Agents

An oligonucleotide agent featured in the invention can be a decoy nucleic acid, e.g., a decoy RNA. A decoy nucleic acid resembles a natural nucleic acid, but is modified in such a way as to inhibit or interrupt the activity of the natural nucleic acid. For example, a decoy RNA can mimic the natural binding domain for a ligand. The decoy RNA therefore competes with natural binding target for the binding of a specific ligand. The natural binding target can be an endogenous nucleic acid, e.g., a pre-miRNA, miRNA, premRNA, mRNA or DNA. For example, it has been shown that over-expression of HIV trans-activation response (TAR) RNA can act as a "decoy" and efficiently bind HIV tat protein, thereby preventing it from binding to TAR sequences encoded in the HIV RNA.

In one embodiment, a decoy RNA includes a modification that improves targeting, e.g. a targeting modification described herein.

The chemical modifications described above for miRNAs and antisense RNAs, and described elsewhere herein, are also appropriate for use in decoy nucleic acids.

Aptamer-Type Oligonucleotide Agents

An oligonucleotide agent featured in the invention can be an aptamer. An aptamer binds to a non-nucleic acid ligand, such as a small organic molecule or protein, e.g., a transcription or translation factor, and subsequently modifies (e.g., inhibits) activity. An aptamer can fold into a specific structure that directs the recognition of the targeted binding site on the non-nucleic acid ligand. An aptamer can contain any of the modifications described herein.

In one embodiment, an aptamer includes a modification that improves targeting, e.g. a targeting modification described herein.

The chemical modifications described above for miRNAs and antisense RNAs, and described elsewhere herein, are also appropriate for use in decoy nucleic acids.

The details of one or more embodiments of the invention are set forth in the accompanying drawings and the description below. Other features and advantages of the invention will be apparent from the description and drawings, and from the claims.

This application incorporates all cited references, patents, and patent applications by references in their entirety for all purposes.

In one aspect, the invention features antagomirs. Antagomirs are single stranded, double stranded, partially double stranded and hairpin structured chemically modified oligonucleotides that target a microRNA.

An antagomir consisting essentially of or comprising at least 12 or more contiguous nucleotides substantially complementary to an endogenous miRNA and more particularly agents that include 12 or more contiguous nucleotides substantially complementary to a target sequence of an miRNA or pre-miRNA nucleotide sequence. Preferably, an antagomir featured in the invention includes a nucleotide sequence sufficiently complementary to hybridize to a miRNA target sequence of about 12 to 25 nucleotides, preferably about 15 to 23 nucleotides. More preferably, the target sequence differs by no more than 1, 2, or 3 nucleotides from a sequence shown in Table 1, and in one embodiment, the antagomir is an agent shown in Table 2a-e. In one embodiment, the antagomir includes a non-nucleotide moiety, e.g., a cholesterol moiety. The non-nucleotide moiety can be attached, e.g., to the 3' or 5' end of the oligonucleotide agent. In a preferred embodiment, a cholesterol moiety is attached to the 3' end of the oligonucleotide agent.

Antagomirs are stabilized against nucleolytic degradation such as by the incorporation of a modification, e.g., a nucleotide modification. In another embodiment, the antagomir includes a phosphorothioate at least the first, second, or third internucleotide linkage at the 5' or 3' end of the nucleotide sequence. In yet another embodiment, the antagomir includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In a particularly preferred embodiment, the antagomir includes at least one 2'-O-methyl-modified nucleotide, and in some embodiments, all of the nucleotides of the antagomir include a 2'-O-methyl modification.

An antagomir that is substantially complementary to a nucleotide sequence of an miRNA can be delivered to a cell or a human to inhibit or reduce the activity of an endogenous miRNA, such as when aberrant or undesired miRNA activity, or insufficient activity of a target mRNA that hybridizes to the endogenous miRNA, is linked to a disease or disorder. In one embodiment, an antagomir featured in the invention has a nucleotide sequence that is substantially complementary to miR-122 (see Table 1), which hybridizes to numerous RNAs, including aldolase A mRNA, N-myc downstram regulated gene (Ndrg3) mRNA, IQ motif containing GTPase activating protein-1 (Iqgap1) mRNA, HMG-CoA-reductase (Hmgcr) mRNA, and citrate synthase mRNA and others. In a preferred embodiment, the antagomir that is substantially complementary to miR-122 is antagomir-122 (Table 2a-e). Aldolase A deficiencies have been found to be associated with a variety of disorders, including hemolytic anemia, arthrogryposis complex congenita, pituitary ectopia, rhabdomyolysis, hyperkalemia. Humans suffering from aldolase A deficiencies also experience symptoms that include growth and developmental retardation, midfacial hypoplasia, hepatomegaly, as well as myopathic symptoms. Thus a human who has or who is diagnosed as having any of these disorders or symptoms is a candidate to receive treatment with an antagomir that hybridizes to miR-122.

Double-Stranded Ribonucleic Acid (dsRNA)

In one embodiment, the invention provides a double-stranded ribonucleic acid (dsRNA) molecule packaged in an association complex, such as a liposome, for inhibiting the expression of a gene in a cell or mammal, wherein the dsRNA comprises an antisense strand comprising a region of complementarity which is complementary to at least a part of an mRNA formed in the expression of the gene, and wherein the region of complementarity is less than 30 nucleotides in length, generally 19-24 nucleotides in length, and wherein said dsRNA, upon contact with a cell expressing said gene, inhibits the expression of said gene by at least 40%. The dsRNA comprises two RNA strands that are sufficiently complementary to hybridize to form a duplex structure. One strand of the dsRNA (the antisense strand) comprises a region of complementarity that is substantially complementary, and generally fully complementary, to a target sequence, derived from the sequence of an mRNA formed during the expression of a gene, the other strand (the sense strand) comprises a region which is complementary to the antisense strand, such that the two strands hybridize and form a duplex structure when combined under suitable conditions. Generally, the duplex structure is between 15 and 30, more generally between 18 and 25, yet more generally between 19 and 24, and most generally between 19 and 21 base pairs in length. Similarly, the region of complementarity to the target sequence is between 15 and 30, more generally between 18 and 25, yet more generally between 19 and 24, and most generally between 19 and 21 nucleotides in length. The dsRNA of the invention may further comprise one or more single-stranded nucleotide overhang(s). The dsRNA can be synthesized by standard methods known in the art as further discussed below, e.g., by use of an automated DNA synthesizer, such as are commercially available from, for example, Biosearch, Applied Biosystems, Inc.

The dsRNAs suitable for packaging in the association complexes described herein can include a duplex structure of between 18 and 25 basepairs (e.g., 21 base pairs). In some embodiments, the dsRNAs include at least one strand that is at least 21 nt long. In other embodiments, the dsRNAs include at least one strand that is at least 15, 16, 17, 18, 19, 20, or more contiguous nucleotides.

The dsRNAs suitable for packaging in the association complexes described herein can contain one or more mismatches to the target sequence. In a preferred embodiment, the dsRNA contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity.

In one embodiment, at least one end of the dsRNA has a single-stranded nucleotide overhang of 1 to 4, generally 1 or 2 nucleotides. Generally, the single-stranded overhang is located at the 3'-terminal end of the antisense strand or, alternatively, at the 3'-terminal end of the sense strand. The dsRNA may also have a blunt end, generally located at the 5'-end of the antisense strand. Such dsRNAs have improved stability and inhibitory activity, thus allowing administration at low dosages, i.e., less than 5 mg/kg body weight of the recipient per day. Generally, the antisense strand of the dsRNA has a nucleotide overhang at the 3'-end, and the 5'-end is blunt. In another embodiment, one or more of the nucleotides in the overhang is replaced with a nucleoside thiophosphate.

In yet another embodiment, a dsRNA packaged in an association complex, such as a liposome, is chemically modified to enhance stability. Such nucleic acids may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Chemical modifications may include, but are not limited to 2' modifications, modifications at other sites of the sugar or base of an oligonucleotide, introduction of non-natural bases into the oligonucleotide chain, covalent attachment to a ligand or chemical moiety, and replacement of internucleotide phosphate linkages with alternate linkages such as thiophosphates. More than one such modification may be employed.

Chemical linking of the two separate dsRNA strands may be achieved by any of a variety of well-known techniques, for example by introducing covalent, ionic or hydrogen bonds; hydrophobic interactions, van der Waals or stacking interactions; by means of metal-ion coordination, or through use of purine analogues. Such chemically linked dsRNAs are suitable for packaging in the association complexes described herein. Generally, the chemical groups that can be used to modify the dsRNA include, without limitation, methylene blue; bifunctional groups, generally bis-(2-chloroethyl) amine; N-acetyl-N'-(p-glyoxylbenzoyl)cystamine; 4-thiouracil; and psoralen. In one embodiment, the linker is a hexaethylene glycol linker In this case, the dsRNA are produced by solid phase synthesis and the hexa-ethylene glycol linker is incorporated according to standard methods (e.g., Williams, D. J., and K. B. Hall, *Biochem.* (1996) 35:14665-14670). In a particular embodiment, the 5'-end of the antisense strand and the 3'-end of the sense strand are chemically linked via a hexaethylene glycol linker. In another embodiment, at least one nucleotide of the dsRNA comprises a phosphorothioate or phosphorodithioate groups. The chemical bond at the ends of the dsRNA is generally formed by triple-helix bonds.

In yet another embodiment, the nucleotides at one or both of the two single strands may be modified to prevent or inhibit the degradation activities of cellular enzymes, such as, for example, without limitation, certain nucleases. Techniques for inhibiting the degradation activity of cellular enzymes against nucleic acids are known in the art including, but not limited to, 2'-amino modifications, 2'-amino sugar modifications, 2'-F sugar modifications, 2'-F modifications, 2'-alkyl sugar modifications, 2'-O-alkoxyalkyl modifications like 2'-O-methoxyethyl, uncharged and charged backbone modifications, morpholino modifications, 2'-O-methyl modifications, and phosphoramidate (see, e.g., Wagner, *Nat. Med.* (1995) 1:1116-8). Thus, at least one 2'-hydroxyl group of the nucleotides on a dsRNA is replaced by a chemical group, generally by a 2'-F or a 2'-O-methyl group. Also, at least one nucleotide may be modified to form a locked nucleotide. Such locked nucleotide contains a methylene bridge that connects the 2'-oxygen of ribose with the 4'-carbon of ribose. Oligonucleotides containing the locked nucleotide are described in Koshkin, A. A., et al., Tetrahedron (1998), 54: 3607-3630) and Obika, S. et al., *Tetrahedron Lett.* (1998), 39: 5401-5404). Introduction of a locked nucleotide into an oligonucleotide improves the affinity for complementary sequences and increases the melting temperature by several degrees (Braasch, D. A. and D. R. Corey, Chem. Biol. (2001), 8:1-7).

Conjugating a ligand to a dsRNA can enhance its cellular absorption as well as targeting to a particular tissue or uptake by specific types of cells such as liver cells. In certain instances, a hydrophobic ligand is conjugated to the dsRNA to facilitate direct permeation of the cellular membrane and or uptake across the liver cells. Alternatively, the ligand conjugated to the dsRNA is a substrate for receptor-mediated endocytosis. These approaches have been used to facilitate cell permeation of antisense oligonucleotides as well as dsRNA agents. For example, cholesterol has been conjugated to various antisense oligonucleotides resulting in compounds that are substantially more active compared to their non-conjugated analogs. See M. Manoharan *Antisense & Nucleic Acid Drug Development* 2002, 12, 103. Other lipophilic compounds that have been conjugated to oligonucleotides include 1-pyrene butyric acid, 1,3-bis-O-(hexadecyl)glycerol, and menthol. One example of a ligand for receptor-mediated endocytosis is folic acid. Folic acid enters the cell by folate-receptor-mediated endocytosis. dsRNA compounds bearing folic acid would be efficiently transported into the cell via the folate-receptor-mediated endocytosis. Li and coworkers report that attachment of folic acid to the 3'-terminus of an oligonucleotide resulted in an 8-fold increase in cellular uptake of the oligonucleotide. Li, S.; Deshmukh, H. M.; Huang, L. *Pharm. Res.* 1998, 15, 1540. Other ligands that have been conjugated to oligonucleotides include polyethylene glycols, carbohydrate clusters, cross-linking agents, porphyrin conjugates, delivery peptides and lipids such as cholesterol. Other chemical modifications for siRNAs have been described in Manoharan, M. RNA interference and chemically modified small interfering RNAs. Current Opinion in Chemical Biology (2004), 8(6), 570-579.

In certain instances, conjugation of a cationic ligand to oligonucleotides results in improved resistance to nucleases. Representative examples of cationic ligands are propylammonium and dimethylpropylammonium. Interestingly, antisense oligonucleotides were reported to retain their high binding affinity to mRNA when the cationic ligand was dispersed throughout the oligonucleotide. See M. Manoharan *Antisense & Nucleic Acid Drug Development* 2002, 12, 103 and references therein.

The ligand-conjugated dsRNA of the invention may be synthesized by the use of a dsRNA that bears a pendant reactive functionality, such as that derived from the attachment of a linking molecule onto the dsRNA. This reactive oligonucleotide may be reacted directly with commercially-available ligands, ligands that are synthesized bearing any of a variety of protecting groups, or ligands that have a linking moiety attached thereto. The methods of the invention facilitate the synthesis of ligand-conjugated dsRNA by the use of, in some preferred embodiments, nucleoside monomers that have been appropriately conjugated with ligands and that may further be attached to a solid-support material. Such ligand-nucleoside conjugates, optionally attached to a solid-support material, are prepared according to some preferred embodiments of the methods of the invention via reaction of a selected serum-binding ligand with a linking moiety located on the 5' position of a nucleoside or oligonucleotide. In certain instances, a dsRNA bearing an aralkyl ligand attached to the 3'-terminus of the dsRNA is prepared by first covalently attaching a monomer building block to a controlled-pore-glass support via a long-chain aminoalkyl group. Then, nucleotides are bonded via standard solid-phase synthesis techniques to the monomer building-block bound to the solid support. The monomer building block may be a nucleoside or other organic compound that is compatible with solid-phase synthesis.

The dsRNA used in the conjugates of the invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

Teachings regarding the synthesis of particular modified oligonucleotides may be found in the following U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541, 307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587, 361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; U.S. Pat. Nos. 6,262,241, and 5,459,255, drawn to, inter alia, methods of synthesizing 21-fluoro-oligonucleotides.

In the ligand-conjugated dsRNA and ligand-molecule bearing sequence-specific linked nucleosides of the invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. Oligonucleotide conjugates bearing a variety of molecules such as steroids, vitamins, lipids and reporter molecules, has previously been described (see Manoharan et al., PCT Application WO 93/07883). In a preferred embodiment, the oligonucleotides or linked nucleosides of the invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

The dsRNAs packaged in the association complexes described herein can include one or more modified nucleosides, e.g., a 2'-O-methyl, 2'-O-ethyl, 2'-O-propyl, 2'-O-allyl, 2'-O-aminoalkyl or 2'-deoxy-2'-fluoro group in the nucleosides. Such modifications confer enhanced hybridization properties to the oligonucleotide. Further, oligonucleotides containing phosphorothioate backbones have enhanced nuclease stability. Thus, functionalized, linked nucleosides can be augmented to include either or both a phosphorothioate backbone or a 2'-O-methyl, 2'-O-ethyl, 2'-O-propyl, 2'-O-aminoalkyl, 2'-O-allyl or 2'-deoxy-2'-fluoro group. A summary listing of some of the oligonucleotide modifications known in the art is found at, for example, PCT Publication WO 200370918.

In some embodiments, functionalized nucleoside sequences possessing an amino group at the 5'-terminus are prepared using a DNA synthesizer, and then reacted with an active ester derivative of a selected ligand. Active ester derivatives are well known to those skilled in the art. Representative active esters include N-hydrosuccinimide esters, tetrafluorophenolic esters, pentafluorophenolic esters and pentachlorophenolic esters. The reaction of the amino group and the active ester produces an oligonucleotide in which the selected ligand is attached to the 5'-position through a linking group. The amino group at the 5'-terminus can be prepared utilizing a 5'-Amino-Modifier C6 reagent. In one embodiment, ligand molecules may be conjugated to oligonucleotides at the 5'-position by the use of a ligand-nucleoside phosphoramidite wherein the ligand is linked to the 5'-hydroxy group directly or indirectly via a linker. Such ligand-nucleoside phosphoramidites are typically used at the end of an automated synthesis procedure to provide a ligand-conjugated oligonucleotide bearing the ligand at the 5'-terminus.

Examples of modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative United States Patents relating to the preparation of the above phosphorus-atom-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, each of which is herein incorporated by reference.

Examples of modified internucleoside linkages or backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Representative United States patents relating to the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In certain instances, an oligonucleotide included in an association complex, such as a liposome, may be modified by a non-ligand group. A number of non-ligand molecules have been conjugated to oligonucleotides in order to enhance the activity, cellular distribution or cellular uptake of the oligonucleotide, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such oligonucleotide conjugates have been listed above. Typical conjugation protocols involve the synthesis of oligonucleotides bearing an amino-linker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

The modifications described above are appropriate for use with an oligonucleotide agent as described herein.

Fusogenic Lipids

The term "fusogenic" refers to the ability of a lipid or other drug delivery system to fuse with membranes of a cell. The membranes can be either the plasma membrane or membranes surrounding organelles, e.g., endosome, nucleus, etc. Examples of suitable fusogenic lipids include, but are not limited to dioleoylphosphatidylethanolamine (DOPE), DODAC, DODMA, DODAP, or DLinDMA. In some embodiments, the association complex include a small molecule such as an imidzole moiety conjugated to a lipid, for example, for endosomal release.

PEG or PEG-Lipids

In addition to cationic and fusogenic lipids, the association complexes include a bilayer stabilizing component (BSC) such as an ATTA-lipid or a PEG-lipid. Examplary lipids are as follows: PEG coupled to dialkyloxypropyls (PEG-DAA) as described in, e.g., WO 05/026372, PEG coupled to diacylglycerol (PEG-DAG) as described in, e.g., U.S. Patent Publication Nos. 20030077829 and 2005008689), PEG coupled to phosphatidylethanolamine (PE) (PEG-PE), or PEG conjugated to ceramides, or a mixture thereof (see, U.S. Pat. No. 5,885,613). In a preferred embodiment, the association includes a PEG-lipid described here, for example a PEG-lipid of formula (XV), (XV') or (XVI). In one preferred embodiment, the BSC is a conjugated lipid that inhibits aggregation of the SPLPs. Suitable conjugated lipids include, but are not limited to PEG-lipid conjugates, ATTA-lipid conjugates, cationic-polymer-lipid conjugates (CPLs) or mixtures thereof.

In one preferred embodiment, the SPLPs comprise either a PEG-lipid conjugate or an ATTA-lipid conjugate together with a CPL.

PEG is a polyethylene glycol, a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S—NHS), monomethoxypolyethylene glycol-amine (MePEG-NH.sub.2), monomethoxypolyethylene glycol-tresylate (MePEG-TRES), and monomethoxypolyethylene glycol-imidazolyl-carbonyl (MePEG-IM). In addition, monomethoxypolyethyleneglycol-acetic acid (MePEG-CH.sub.2COOH), is particularly useful for preparing the PEG-lipid conjugates including, e.g., PEG-DAA conjugates.

In a preferred embodiment, the PEG has an average molecular weight of from about 550 daltons to about 10,000 daltons, more preferably of about 750 daltons to about 5,000 daltons, more preferably of about 1,000 daltons to about 5,000 daltons, more preferably of about 1,500 daltons to about 3,000 daltons and, even more preferably, of about 2,000 daltons, or about 750 daltons. The PEG can be optionally substituted by an alkyl, alkoxy, acyl or aryl group. PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—0-), succinyl (—(O)CCH.sub.2CH.sub.2C(O)—), succinamidyl (—NHC(O)CH.sub.2CH.sub.2C(O—)NH—), ether, disulphide, etc. as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Targeting Agents

In some embodiments, the association complex includes a targeting agent. For example, a targeting agent can be included in the surface of the association complex (e.g., liposome) to help direct the association complex to a targeted area of the body. An example of targeting agents galactose, mannose, and folate. Other examples of targeting agents include small molecule receptors, peptides and antibodies. In some embodiments, the targeting agent is conjugated to the therapeutic moiety such as oligonucleotide agent. In some embodiments, the targeting moiety is attached directly to a lipid component of an association complex. In some embodiments, the targeting moiety is attached directly to the lipid component via PEG preferably with PEG of average molecular weight 2000 amu. In some embodiments, the targeting agent is unconjugated, for example on the surface of the association complex.

Structural Components

In some embodiments, the association complex includes one or more components that improves the structure of the complex (e.g., liposome). In some embodiments, a therapeutic agents such as dsRNA can be attached (e.g., conjugated) to a lipophilic compound such as cholesterol, thereby providing a lipophilic anchor to the dsRNA. In some embodiments conjugation of dsRNA to a lipophilic moiety such as cholesterol can improve the encapsulation efficiency of the association complex.

Properties of Association Complexes

Association complexes such as liposomes are generally particles with hydrodynamic diameter ranging from about 25 nm to 500 nm. In some preferred embodiments, the association complexes are less than 500 nm, e.g., from about 25 to about 400 nm, e.g., from about 25 nm to about 300 nm, preferably about 120 nm or less.

In some embodiments, the weight ratio of total excipients within the association complex to RNA is less than about 20:1, for example about 15:1. In some preferred embodiments, the weight ratio is less than 10:1, for example about 7.5:1.

In some embodiments the association complex has a pKa such that the association complex is protonated under endozomal conditions (e.g., facilitating the rupture of the complex), but is not protonated under physiological conditions.

In some embodiments, the association complex provides improved in vivo delivery of an oligonucleotide such as dsRNA. In vivo delivery of an oligonucleotide can be measured, using a gene silencing assay, for example an assay measuring the silencing of Factor VII.

In vivo Factor VII Silencing Experiments

C57BL/6 mice received tail vein injections of saline or various lipid formulations. Lipid-formulated siRNAs are administered at varying doses in an injection volume of 10 μL/g animal body weight. Twenty-four hours after administration, serum samples are collected by retroorbital bleed. Serum Factor VII concentrations are determined using a chromogenic diagnostic kit (Coaset Factor VII Assay Kit, DiaPharma) according to manufacturer protocols.

Methods of Making Association Complexes

In some embodiments, an association complex is made by contacting a therapeutic agent such as an oligonucleotide with a lipid in the presence of solvent and a buffer. In some embodiments, a plurality of lipids are included in the solvent, for example, one or more of a cationic lipid (e.g., a polyamine containing lipid or a lipid including a biocleavable moiety as described herein), a PEG-lipid, a targeting lipid or a fusogenic lipid.

In some embodiments, the buffer is of a strength sufficient to protonate substantially all amines of an amine containing lipid such as lipid described herein, e.g., a lipid of formula (I) or formula (X).

In some embodiments, the buffer is an acetate buffer, such as sodium acetate (pH of about 5). In some embodiments, the buffer is present in solution at a concentration of from about 100 mM and about 300 mM.

In some embodiments, the solvent is ethanol. For example, in some embodiments, the mixture includes at least about 90% ethanol, or 100% ethanol.

In some embodiments, the method includes extruding the mixture to provide association complexes having particles of a size with hydrodynamic diameter less than about 500 nm (e.g., a size from about 25 nm to about 300 nm, for example in some preferred embodiments the particle sizes ranges from about 40-120 nm). In some embodiments, the method does not include extrusion of the mixture.

In one embodiment, a liposome is prepared by providing a solution of a lipid described herein mixed in a solution with cholesterol, PEG, ethanol, and a 25 mM acetate buffer to provide a mixture of about pH 5. The mixture is gently vortexed, and to the mixture is added sucrose. The mixture is then vortexed again until the sucrose is dissolved. To this mixture is added a solution of siRNA in acetate buffer, vortexing lightly for about 20 minutes. The mixture is then extruded (e.g., at least about 10 times, e.g., 11 times or more) through at least one filter (e.g., two 200 nm filters) at 40° C., and dialyzed against PBS at pH 7.4 for about 90 minutes at RT.

In one embodiment, a liposome is prepared without extruding the liposome mixture. A lipid described herein is combined with cholesterol, PEG, and siRNA in 100% ethanol, water, and an acetate buffer having a concentration from about 100 mM to about 300 mM (pH of about 5). The combination is rapidly mixed in 90% ethanol. Upon completion, the mixture is dialyzed (or treated with ultrafiltration) against an acetate buffer having a concentration from about 100 mM to about 300 mM (pH of about 5) to remove ethanol, and then dialyzed (or treated with ultrafiltration) against PBS to change buffer conditions.

Association complexes can,be formed in the absence of a therapeutic agent such as single or double stranded nucleic acid, and then upon formation be treated with one or more therpauetically active single or double stranded nucleic acid moieties to provide a loaded association complex, i.e., an association complex that is loaded with the therpaueitcally active nucleic acids. The nucleic acid can be entrapped within the association complex, adsorbed to the surface of the association complex or both. For example, methods of forming association complexes such as liposomes above can be used to form association complexes free of a therapeutic agent, such as a nucleic acid, for example a single or double stranded RNA such as siRNA. Upon formation of the association complex, the complex can then be treated with the therapeutic agent such as siRNA to provide a loaded association complex.

In one embodiment, a mixture including cationic lipid such as a lipid described in formula (I), preferably a cationic lipid of the following formula are provided in ethanol (e.g., 100% ethanol) and combined with an aqueous buffer such as aqueous NaOAc, to provide unloaded association complexes. The association complexes are then optionally extruded, providing a more uniform size distribution of the association complexes. The association complexes are then treated with the thereapeutic agent such as siRNA in ethanol (e.g., 35% ethanol) to thereby provide a loaded association complex. In some embodiments, the association complex is then treated with a process that removes the ethanol, such as dialysis.

Characterization of Association Complexes

Association complexes prepared by any of the methods above are characterized in a similar manner Association complexes are first characterized by visual inspection. In general, preferred association complexes are whitish translucent solutions free from aggregates or sediment. Particle size and particle size distribution of lipid-nanoparticles are measured by dynamic light scattering using a Malvern Zetasizer Nano ZS (Malvern, USA). Preferred particles are 20-300 nm, more preferrably, 40-100 nm in size. In some preferred embodiments, the particle size distribution is unimodal. The total siRNA concentration in the formulation, as well as the entrapped fraction, is estimated using a dye exclusion assay. A sample of the formulated siRNA is incubated with the RNA-binding dye Ribogreen (Molecular Probes) in the presence or absence of a formulation disrupting surfactant, 0.5% Triton-X100. The total siRNA in the formulation is determined by the signal from the sample containing the surfactant, relative to a standard curve. The entrapped fraction is determined by subtracting the "free" siRNA content (as measured by the signal in the absence of surfactant) from the total siRNA content. Percent entrapped siRNA is typically >85%.

Methods of Using Association Complexes and Compositions Including the Same

Pharmaceutical Compositions Comprising Oligonucleotide Agents

An oligonucleotide agent assembled in an association complex can be administered, e.g., to a cell or to a human, in a single-stranded or double-stranded configuration. An oligo-

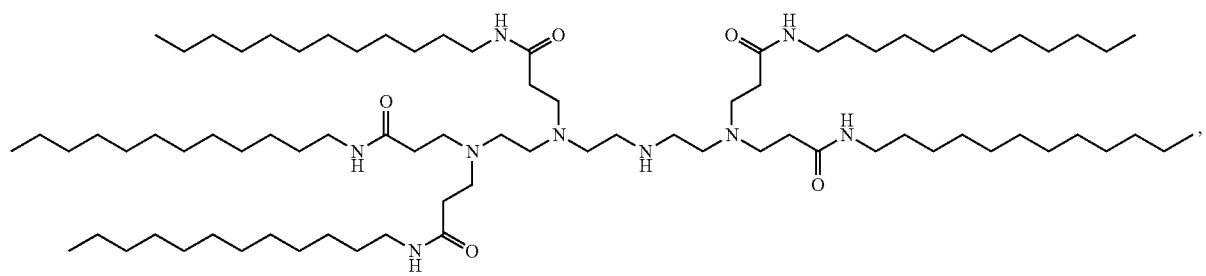 [SMILES: CCCCCCCCCCCCNC(=O)CCN(CCNCCN(CCC(=O)NCCCCCCCCCCCC)CCN(CCC(=O)NCCCCCCCCCCCC)CCC(=O)NCCCCCCCCCCCC)CCC(=O)NCCCCCCCCCCCC]

cholesterol, and a PEG-lipid, for example a PEG-lipid described herein, such as the PEG-lipid below,

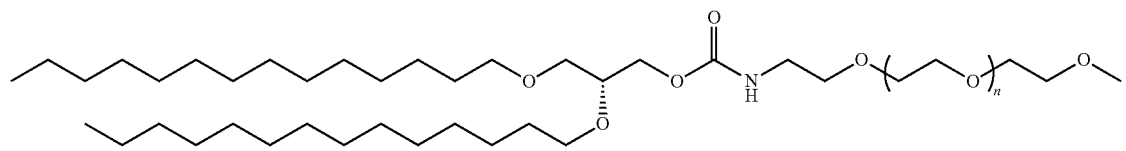

nucleotide agent that is in a double-stranded configuration is bound to a substantially complementary oligonucleotide strand. Delivery of an oligonucleotide agent in a double stranded configuration may confer certain advantages on the oligonucleotide agent, such as an increased resistance to nucleases.

In one embodiment, the invention provides pharmaceutical compositions including an oligonucleotide agent packaged in an association complex, such as a liposome, as described herein, and a pharmaceutically acceptable carrier. The pharmaceutical composition comprising the packaged oligonucleotide agent is useful for treating a disease or disorder associated with the expression or activity of a target gene, such as a pathological process which can be mediated by down regulating gene expression. Such pharmaceutical compositions are formulated based on the mode of delivery. One example is compositions that are formulated for delivery to a specific organ/tissue, such as the liver, via parenteral delivery.

The pharmaceutical compositions featured in the invention are administered in dosages sufficient to inhibit expression of a target gene.

In general, a suitable dose of a packaged oligonucleotide agent will be such that the oligonucleotide agent delivered is in the range of 0.01 to 5.0 milligrams per kilogram body weight of the recipient per day, generally in the range of 1 microgram to 1 mg per kilogram body weight per day. The pharmaceutical composition may be administered once daily, or the oligonucleotide agent may be administered as two, three, or more sub-doses at appropriate intervals throughout the day or even using continuous infusion or delivery through a controlled release formulation. In that case, the oligonucleotide agent contained in each sub-dose must be correspondingly smaller in order to achieve the total daily dosage. The dosage unit can also be compounded for delivery over several days, e.g., using a conventional sustained release formulation which provides sustained release of the packaged oligonucleotide agent over a several day period. Sustained release formulations are well known in the art.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual oligonucleotide agents packaged in the association complexes can be made using conventional methodologies or on the basis of in vivo testing using an appropriate animal model, as described elsewhere herein.

Advances in mouse genetics have generated a number of mouse models for the study of various human diseases. Such models are used for in vivo testing of oligonucleotide agents packaged in lipophilic compositions, as well as for determining a therapeutically effective dose.

Any method can be used to administer an oligonucleotide agent packaged in an association complex, such as a liposome, to a mammal. For example, administration can be direct; oral; or parenteral (e.g., by subcutaneous, intraventricular, intramuscular, or intraperitoneal injection, or by intravenous drip). Administration can be rapid (e.g., by injection), or can occur over a period of time (e.g., by slow infusion or administration of slow release formulations).

An oligonucleotide agent packaged in an association complex can be formulated into compositions such as sterile and non-sterile aqueous solutions, non-aqueous solutions in common solvents such as alcohols, or solutions in liquid or solid oil bases. Such solutions also can contain buffers, diluents, and other suitable additives. For parenteral, intrathecal, or intraventricular administration, an oligonucleotide agent can be formulated into compositions such as sterile aqueous solutions, which also can contain buffers, diluents, and other suitable additives (e.g., penetration enhancers, carrier compounds, and other pharmaceutically acceptable carriers).

The oligonucleotide agents packaged in an association complex can be formulated in a pharmaceutically acceptable carrier or diluent. A "pharmaceutically acceptable carrier" (also referred to herein as an "excipient") is a pharmaceutically acceptable solvent, suspending agent, or any other pharmacologically inert vehicle. Pharmaceutically acceptable carriers can be liquid or solid, and can be selected with the planned manner of administration in mind so as to provide for the desired bulk, consistency, and other pertinent transport and chemical properties. Typical pharmaceutically acceptable carriers include, by way of example and not limitation: water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

EXAMPLES

Example 1

Syntheses and Purification of Compounds 3, 4 and 4, 5: Alkylation of Triethylenetetramine Under Michael Addition Condition—Method 1 (Scheme 1)

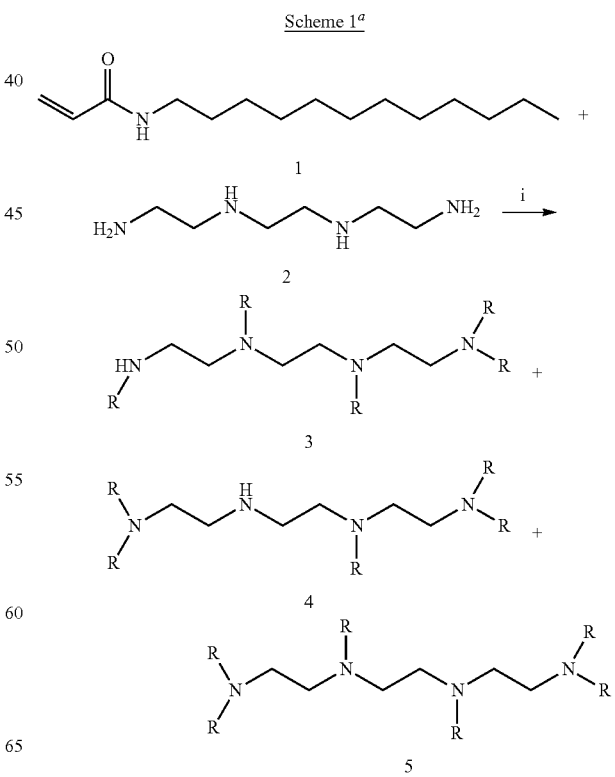

R = 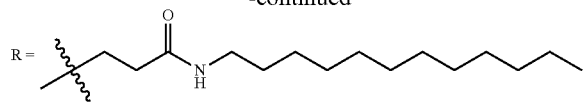

*a* (i) 90° C., Neat, 5 days

In a 350 mL pressure bottle N-dodecylacrylamide 1 (84 g, 0.35 mol) [Slee, Deborah H.; Romano, Suzanne J.; Yu, Jinghua; Nguyen, Truc N.; John, Judy K.; Raheja, Neil K.; Axe, Frank U.; Jones, Todd K.; Ripka, William C. Journal of Medicinal Chemistry (2001), 44(13), 2094-2107] was taken and the solid was melted under argon by gently heating the vessel. To this melt was added triethylenetetramine 2 (10.2 g, 0.07 mol) and the mixture was heated at 90° C. for 5 days. Michael addition of triethylenetetramine 2 to the acrylamide 1 yielded two five and the sole six alkylated products along with minor amounts of low alkylated products under neat reaction condition. The reaction mixture was analyzed by TLC using $CH_2Cl_2$:MeOH:$NEt_3$ (90:5:5) as the eluent. The TLC showed the near complete consumption of the starting acrylamide 1. The reaction mixture was dissolved in dichloromethane (40 mL), loaded on a pre-packed column of silica gel and the mixture was separated using eluent $CH_2Cl_2$:MeOH:$NEt_3$ (48:1:1 to 8:1:1). In order to achieve complete separation, multiple columns using the same conditions were performed and the following pure products were obtained. The required five addition products 3 and 4 were isolated along with the six addition product 5. In this reaction mixture some of the lower addition products were also detected in the TLC and the LC-MS of the crude reaction mixture.

N-Dodecyl-3-((2-dodecylcarbamoyl-ethyl)-{2-[(2-dodecylcarbamoyl-ethyl)-2-{(2-dodecylcarbamoyl-ethyl)-[2-(2-dodecylcarbamoyl-ethylamino)-ethyl]-amino}-ethyl-amino) propionamide. One of the two 5-alkylated derivatives, compound 3 (isomer I), was isolated as light yellow foam (12 g, 13%). MS m/z 672 (M+2H/2), 448 (M+3H/3). $^1$H NMR $CDCl_3$ δ 0.87 (t, J=6.5 Hz, 15H), 1.20-1.39 (m, 92H), 1.46-1.57 (m, 12H), 2.20-2.50 (m, 16H), 2.60-2.78 (m, 10H), 3.10-3.25 (m, 12H), 6.98 (bs, 3H), 7.41 (bs, 1H), 7.63 (bs, 1H), 8.85 (bs, 1H). $^{13}$C NMR $CDCl_3$ δ 14.33, 22.90, 27.37, 29.59, 29.67, 29.88, 29.89, 29.92, 32.13, 39.74, 172.77.

(3-[(2-{2-[{2-Bis-(2-dodecylcarbamoyl-ethyl)-amino]-ethyl}-(2-dodecylcarbamoyl-ethyl)-amino]-ethylamino}-ethyl)-(2-dodecylcarbamoyl-ethyl)-amino]-N-dodecyl-propionamide). Second 5-alkylated derivative, compound 4 (isomer II) was isolated as a white powder (13.7 g, 14%). MS m/z 672 (M+2H/2), 448 (M+3H/3). $^1$H NMR $CDCl_3$ δ 0.87 (t, J=6.5 Hz, 15H), 1.20-1.39 (m, 92H), 1.44-1.54 (m, 12H), 2.30-2.45 (m, 8H), 2.46-2.54 (m, 8H), 2.55-2.85 (m, 10H), 3.15-3.30 (m, 12H), 6.98 (bs, 3H), 7.41 (bs, 1H), 7.63 (bs, 1H), 8.85 (bs, 1H). $^{13}$C NMR $CDCl_3$ δ 14.33, 22.89, 27.28, 27.38, 29.59, 29.69, 29.88, 29.89, 29.92, 32.13, 39.65, 39.74, 50.84, 172.63, 172.75, 172.81.

Along with this a pure mixture of compounds 3 and 4 (11.6 g, 12%) in 2:3 (3:4) ratio was also isolated.

3-[{2-[{2-[2-[Bis-(2-dodecylcarbamoyl-ethyl)-amino]-ethyl}-(2-dodecylcarbamoyl-ethyl)-amino]-ethyl}-(2-dodecylcarbamoyl-ethyl)-amino]-ethyl}-(2-dodecylcarbamoyl-ethyl)-amino]-N-dodecyl-propionamide. The six alkylated product 5 was isolated as a cream powder (16.3 g, 17%). MS m/z 792 (M+2H/2), 528 (M+3H/3). $^1$H NMR DMSO-$d_6$ δ 0.87 (t, J=7 Hz, 18H), 1.15-1.40 (m, 112H), 1.45-1.53 (m, 12H), 2.20-2.35 (m, 12H), 2.37-2.50 (m, 12H), 2.64-2.78 (m, 12H), 3.10-3.25 (m, 12H), 7.26 (bs, 4H), 7.64 (bs, 2H). $^{13}$C NMR $CDCl_3$ δ 14.32, 22.89, 27.34, 27.38 29.59, 29.69, 29.90, 29.92, 32.13, 39.77, 50.85, 172.80.

Example 2

Syntheses and Purification of Compounds 3, 4 and 4: Alkylation of Triethylenetetramine Under Michael Addition Condition—Method 2 (Scheme 2)

In another experiment, in order to prevent the polymerization of the starting acrylamide 1 at high temperature, a radical quencher benzoquinone was added to the reaction mixture.

Scheme 2*a*

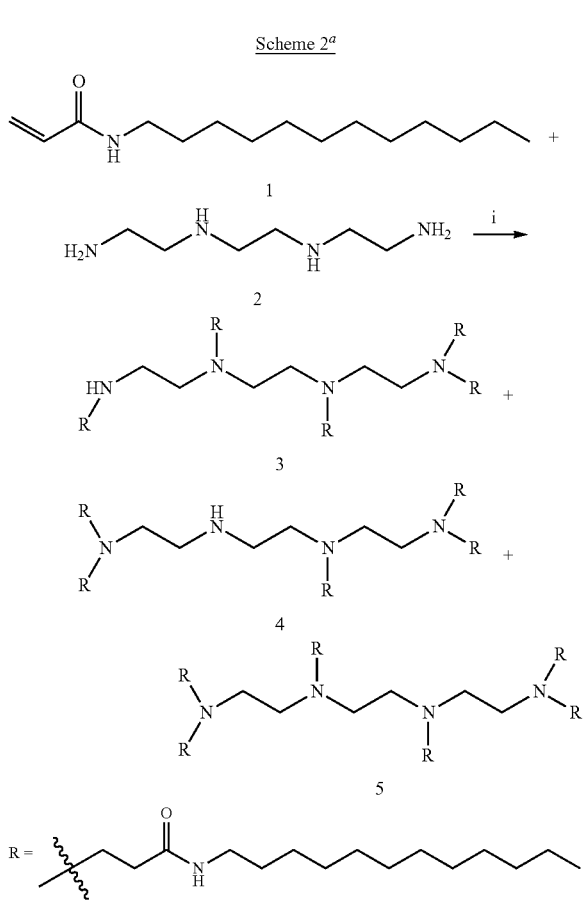

*a* (i) 90° C., Catalytic amount (15 mg) of benzoquinone, 5 days

In this method a similar reaction to that of Method 1 (Example 1) was performed except that, a radical quencher benzoquinone was added to the reaction mixture. In a 150 mL pressure bottle N-dodecylacrylamide 1 (24 g, 100 mmol) was taken and to this 15 mg of benzoquinone was added and the solid acrylamide was melted under argon by gently heating the vessel. To this melt was added triethylenetetramine 2 (2.9 g, 20 mmol) and the mixture was heated at 90° C. for 5 days. The reaction mixture was analyzed by TLC using $CH_2Cl_2$:MeOH:$NEt_3$ (90:5:5) as the eluent. The TLC showed the near complete consumption of the starting acrylamide 1. The reaction mixture was dissolved in dichloromethane (40 mL) and the desired products 3, 4 and 5 were isolated as described in Example 1. In this case a slight increase in the amount of six addition product was observed.

Compound 3: The five addition product, isomer I, was isolated as light yellow foam (3.4 g, 13%). The analytical and spectral data for this compound was identical to that of 3 obtained by Method 1.

Compound 4: The five addition product, isomer II, was isolated as a white powder (3.9 g, 14%). The analytical and spectral data for this compound was identical to that of 4 obtained by Method 1. A pure mixture of isomers 3 and 4 (1.9 g, 7%) was also isolated.

Compound 5: The six addition product was isolated as a cream powder (6.9 g, 26%). The analytical and spectral data for this compound was identical to that of 5 obtained by Method 1.

Example 3

Syntheses and Purification of Compounds 3, 4 and 4: Alkylation of Triethylenetetramine Under Michael Addition Condition—Method 3 (Scheme 3)

In this method the Michael addition was performed in the presence of a promoter like boric acid (Chaudhuri, Mihir K.; Hussain, Sahid; Kantam, M. Lakshmi; Neelima, B. *Tetrahedron Letters* (2005), 46(48), 8329-8331.) in order to enhance the rate of the reaction.

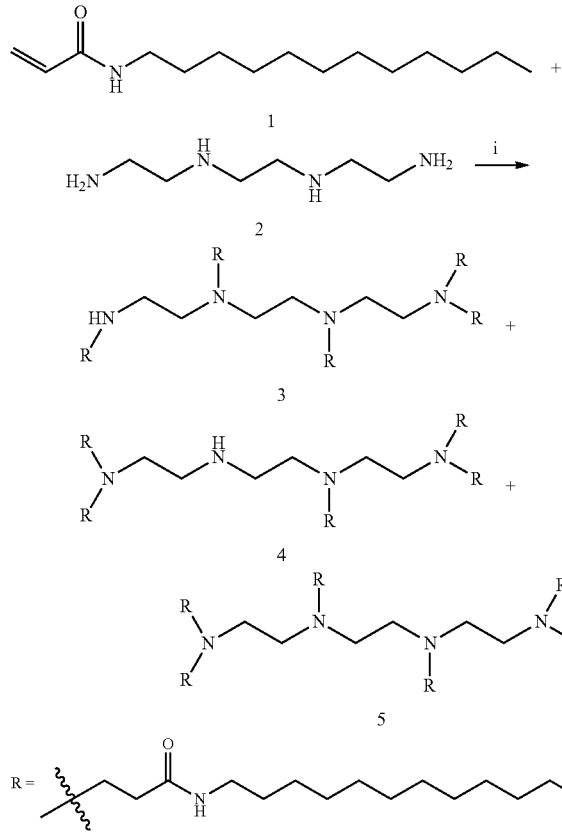

$^a$ (i) 90° C., aq. boric acid, 2 days

In this method a similar reaction to that of Method 1 (Example 1) was performed except that, a Michael addition promoter, saturated aqueous boric acid was added to the reaction mixture. In a 150 mL pressure bottle N-dodecyl-acrylamide 1 (24 g, 100 mmol) was melted under argon by gently heating the vessel and to this 3 mL of aqueous boric acid was added. To this melt was added triethylenetetramine 2 (2.9 g, 20 mmol) and the mixture was heated at 90° C. for 2 days. The reaction mixture was analyzed by TLC using $CH_2Cl_2$:MeOH:$NEt_3$ (90:5:5) as the eluent. The TLC showed the near complete consumption of the starting acrylamide 1. The reaction mixture was dissolved in dichloromethane (100 mL) and the solution was stirred with solid sodium bicarbonate and the organic layer was filtered and concentrated in a rotory evaporator. This crude product was purified by column chromatography (silica gel) using $CH_2Cl_2$:MeOH:$NEt_3$ (48:1:1 to 8:1:1). In order to achieve complete separation, multiple columns using the same conditions were performed and the following pure products were obtained. Under this reaction condition an increase in yields of compound 4 (isomer II) and six addition product 5 were achieved.

Compound 3: The five addition product 3, isomer I, was isolated as light yellow foam (3.1 g, 11%). The analytical and spectral data for this compound was identical to that of 3 obtained by Method 1.

Compound 4: The five addition product 4, isomer II, was isolated as a white powder (5.7 g, 20%). The analytical and spectral data for this compound was identical to that of 4 obtained by Method 1. A pure mixture of isomers 3 and 4 (2.1 g, 7%) was also isolated.

Compound 5: The six addition product 5 was isolated as a cream powder (7.6 g, 28%). The analytical and spectral data for this compound was identical to that of 5 obtained by Method 1.

Example 4

Syntheses and Purification of Compounds 3 and 4: Alkylation of Triethylenetetramine Under Michael Addition Condition—Method 4 (Scheme 4)

In another experiment, in order to minimize the formation of the six addition product 5, use of solvent was attempted.

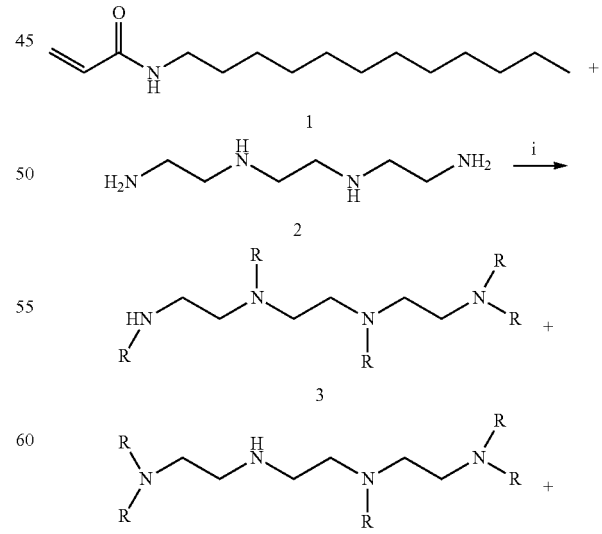

4- 3- and 2- addition products

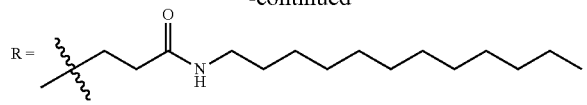

*a* (i) 90° C., acetonitrile or DMF, 5 days

In this method a similar reaction to that of Method 1 (Example 1) and Method 2 (Example 2) was performed except that, the reactions were performed in the presence of solvents at 90° C. with stirring. In a 150 mL pressure bottle N-dodecylacrylamide 1 (10 g, 41.8 mmol) was dissolved in 20 mL of either acetonitrile or DMF. To this solution was added triethylenetetramine 2 (1 g, 6 8 mmol) and the mixture was heated at 90° C. for 5 days. The reaction mixture was analyzed by TLC using $CH_2Cl_2$:MeOH:$NEt_3$ (90:5:5) as the eluent. The TLC showed the formation of only minor amounts of the required five addition product. The major product in this reaction was a mixture of four addition products along with very polar lower addition products.

Example 5

Separation of Unreacted Acrylamide from the Reaction Mixture and/or the Isolated Products 3, 4 and 5

To remove unreacted acrylamide 1 from the reaction mixture, the reaction mixture is diluted with ethyl acetate or DMF and stirred with polystyrene or polymer bound thiol (or mercaptan) to capture all the acrylamide. The immobilized thiol was added to the solution and gently shaken at ambient temperature and filter off the solid. Michael addition of immobilized thiol to acrylamide capture all unreacted acrylamide. Traces of acrylamide as contaminant after isolation of each desired isomer could also be completely removed under the same condition. The isolated product 3 (or 4 or 5) is dissolved in DMF or ethyl acetate and gently shaken with the immobilized acrylamide quencher, filter and evaporation of the filtrate in vacuo affords a pure compound 3 (or 4 or 5) free of acrylamide contamination.

Example 6

Separation of Primary and Secondary Amine Contaminant from Compound 5

After column chromatographic separation of compound 5, to remover traces of primary and secondary amine contaminants, the compound is dissolved in ethyl acetate or DMF and stirred with solid bound or immobilized isothiocyanate at ambient temperature overnight. Filter off the solid and evaporation of the filtrate affords a pure compound 5 free of any primary or secondary amine contamination.

Example 7

Separation of Primary Amine Contaminants from Compound 3 and 4

After the completion of the reaction the reaction mixture is treated with tetrachlorophthalic anhydride in the presence of triethylamine in dichloromethane at room temperature and the solvent is evaporated and the residue stirred with ethyl acetate and the solid is filtered and the filtrate is concentrated to get the products which lacks the primary amine contaminant.

TABLE 1

Methods of synthesizing products 3 and 4

| Method | Temperature | Promoter | Solvent | Radical Quencher | Remarks |
|---|---|---|---|---|---|
| 1 | 90° C. | None | Neat | None | Formation of 3 and 4 in a combined isolated yield of 39%. The six addition product 5 was isolated in 17%. Reaction took six days for completion. |
| 2 | 90° C. | None | Neat | Benzoquinone | Benzoquinone was used to prevent the polymerization of acrylamide 1. The combined yield of 3 and 4 was 34%. However 26% of 5 was also isolated. Reaction time same as Method 1. |
| 3 | 90° C. | Boric acid | Neat | None | Reaction rate enhanced. The reaction was completed in two days. The combined yield of 3 and 4 was 38%. Additional 28% of 5 was also isolated. |
| 4 | 80-120° C. | None | DMF | None | Reaction very sluggish. Only lower addition products formed. |

Example 8

Methods of Preparation of the Hydrochloride Salts of the Products 3, 4 and 5

In order to improve the ease of handling and increase the stability of the compounds listed above, they were converted into their corresponding hydrochloride salts 6, 7 and 8.

Hydrochloride of compound 3 (6): The amine 3 (9.4 g) was dissolved in 100 mL of hot anhydrous 1,4-dioxane and 100 mL of 4M HCl in dioxane was added and the mixture was stirred at room temperature overnight. Nitrogen was bubbled into the reaction mixture for 1 h to remove the excess HCl and the remaining solution was concentrated to ~10 mL. To this heterogeneous mixture 100 mL of EtOAc:hexanes (1:1) was added and the precipitated product was filtered, washed with ethyl acetate (50 mL), hexanes (100 mL) and the resulting powder was dried under vacuum to get the pure product 6 (9.99 g, 96%) as a cream powder. $^1$H NMR $CDCl_3$ δ 0.83 (t, J=6.5 Hz, 15H), 1.20-1.39 (m, 92H), 2.64-2.70 (m, 8H), 2.90-3.10 (m, 16H), 3.25-3.45 (m, 12H), 3.46-3.64 (m, 4H), 5.20-6.0 (bs, 2H), 8.05-8.15 (m, 5H), 10. (bs, 3H). $^{13}$C NMR $CDCl_3$ δ 13.83, 22.04, 26.48, 28.69, 28.79, 28.90, 29.04, 31.26, 38.71, 168.38, 168.53. Elemental Analysis Calcd. $C_{81}H_{163}N_9O_5$·4HCl·3$H_2O$: C, 63.05; H, 11.30; N, 8.17; Cl, 9.19. Found: C, 63.13; H, 11.06; N, 8.21; Cl, 9.21.

Scheme 5[a]

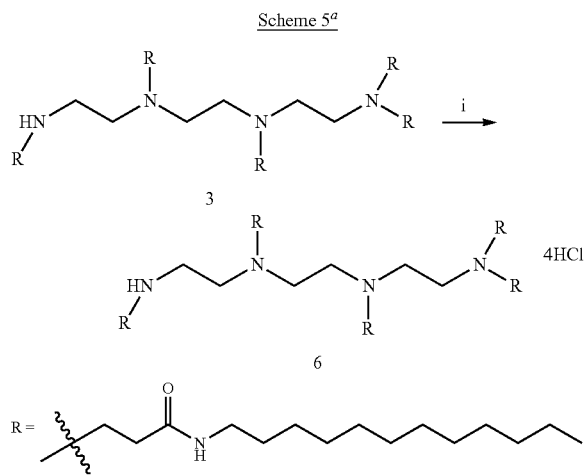

[a] (i) 4M HCl in 1,4-dioxane, rt., 12 h

Scheme 7[a]

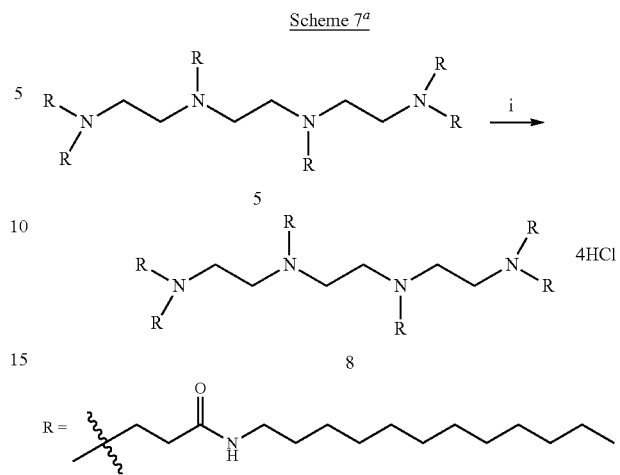

[a] (i) 4M HCl in 1,4-dioxane, rt., 12 h.

Compound 7

The amine 4 (13.7 g, 10 2 mmol) was converted to the corresponding HCl salt 7 using a similar procedure used above for 3 to obtain 6. The tetrahydrochloride salt 7 was isolated as a white powder (14.6, 96%). $^1$H NMR CDCl$_3$ δ 0.82 (t, J=6.5 Hz, 15H), 1.20-1.41 (m, 92H), 2.52-2.72 (m, 8H), 2.90-3.10 (m, 16H), 3.25-3.45 (m, 12H), 3.46-3.64 (m, 4H), 5.20-6.0 (bs, 2H), 8.05-8.15 (m, 5H), 10. (bs, 3H). $^{13}$C NMR CDCl$_3$ δ 8.42, 13.84, 22.04, 26.48, 28.69, 28.79, 29.00, 31.26, 45.44, 168.53, 168.60. Elemental Analysis: Calcd: $C_{81}H_{163}N_9O_5 \cdot 4HCl \cdot 2H_2O$: C, 63.79; H, 11.30; N, 8.17; Cl, 9.34. Found: C, 63.78; H, 11.04; N, 8.40; Cl, 9.73.

Scheme 6[a]

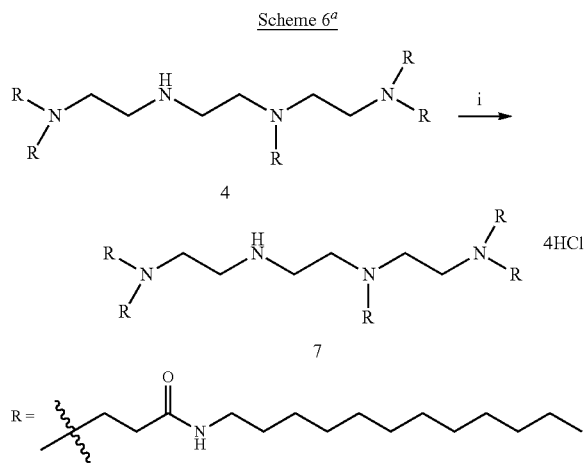

[a] (i) 4M HCl in 1,4-dioxane, rt., 12 h

Compound 8

The amine 5 (13.7 g, 1.2 mmol) was converted to the corresponding HCl 8 using a procedure similar to that described above for the salt 6. The tetrahydrochloride salt 8 was isolated as a white powder (1.3 g, 96%). $^1$H NMR DMSO-d$_6$ δ 0.87 (t, J=7 Hz, 18H), 1.13-1.30 (m, 112H), 1.35-1.53 (m, 12H), 2.10-2.25 (m, 12H), 2.30-2.40 (m, 12H), 2.60-2.76 (m, 12H), 3.10-3.25 (m, 12H), 7.26 (bs, 4H), 7.64 (bs, 2H), 10.1 (bs, 4H).

Example 9

Selective Protection of Amino Groups on Triethylenetetramine for Directed Synthesis of Compounds 3 and 4

Step 1: Preparation of compound 10: Triethylenetetramine, 2 (20.55 g, 140.52 mmol, purchased from Sigma-Aldrich) in acetonitrile (500 mL) was cooled over an ice bath under constant stirring. Ethyl trifluoroacetate (35.20 mL, 295.09 mmol) was added to the stirring solution and stirred for 20 h. Solvent and volatiles were removed under reduced pressure and dried under high vacuum to get 9 as white solid (44.4 g, 94%). The product thus obtained could be used for the next reaction without further purification (Wender P. A. et al. *Organic Letters*, 2005 7, 4815).

Crude compound 9 (23.70, 70 mmol) was dissolved in acetonitrile (400 mL) and stirred over an ice bath. N-(Benzyloxycarbonyloxy) succinate (Z—OSu, 43.73 g, 175 mmol, purchased from Novabiochem) and triethylamine (23.40 mL, 210 mmol) were added to the reaction mixture and stirred overnight. Solvents were removed and the residue was extracted into dichloromethane (DCM), washed successively with water (two times) and brine, dried over anhydrous sodium sulfate. Solvent was removed in vacuo and residue thus obtained was purified by silica gel column chromatography (gradient elution, 30-70% EtOAc/Hexanes) to obtain compound 10 as white solid (38.2 g, 89%). $^1$H NMR (DMSO-d6, 400 MHz) δ=9.60-9.50(m, 2H), 7.40-7.20(m, 10H), 5.02 (s, 4H), 3.40-3.20(m, 12H). MS: $C_{26}H_{28}F_6N_4O_6$ Cal. 606.19. Found. 607.2 (M$^+$).

Step 2: Preparation of compound 11: Compound 10 (12.60 g, 20.78 mmol) was suspended in methanol (MeOH, 150 mL) at ambient temperature and 8M solution of methylamine in ethanol (40 ml) was added to the suspension under constant stirring. All the solids went into solution, after stirring for 1 h at ambient temperature, the mixture was warmed to 50° C. and stirred for 8 h. Reaction was monitored by TLC. All the solvents were removed under reduced pressure and the residue was purified by silica gel column chromatography (gradient elution, 10% MeOH/DCM to 10:10:80, MeOH:TEA: DCM) to yield the product 11 (7.80 g, 91%) as pale yellow gummy liquid. $^1$H NMR (DMSO-d6, 400 MHz) δ=7.80-7.40

(m, 10H), 5.02-4.94(m, 4H), 3.45-3.05(m, 8H), 2.70-2.55(m, 4H), 2.20(bs, 4H). MS: $C_{22}H_{30}N_4O_4$ Cal. 414.23. Found 415.20 ($M^+$)

Step 3: Preparation of compound 13: Compound 12 was prepared from triethylenetetramine, 100 (10.25 g, 70.09 mmol) as described in step 1 for the synthesis of compound 9 by reacting with 1.1 molar equivalent of ethyl trifluoroacetate (8.80 mL, 77.10 mmol). Crude 12 thus obtained was dissolved in anhydrous DCM (400 ml) and cooled to 0° C. (Boc)$_2$O (53.53 mmol, 245.31 mmol) and triethylamine (48 ml, 350 mmol) were added and reaction mixture was allowed to stir overnight. Progress of the reaction was monitored by TLC. Solvents were removed in vacuo and the residue was extracted into DCM, washed with water, brine and dried. DCM was removed and the residue was purified by silica gel chromatography (gradient elution 50% EtOAc/Hexane to EtOAc) to obtain the desired product 13 (34.20 g, 92%) as white solid. $^1$H NMR (DMSO-d6, 400 MHz) δ=9.51-9.38(m, 1H), 6.82(bs, 1H), 3.30-3.00(m, 12H), 1.58-1.30(s, 27H). MS: $C_{23}H_{41}F_3N_4O_7$ Cal. 542.29. Found 543.4($M^+$).

Step 4: Preparation of 14: A solution of compound 13 (25 g, 47.32 mmol) in MeOH (200 mL) was stirred with $K_2CO_3$ (50 g) in the presence of water (1 mL) at 50° C. overnight. Progress of the reaction was monitored by TLC. Solid $K_2CO_3$ was filtered off, washed with MeOH, combined washing and solvents were removed in vacuo. Residue obtained was purified by silica gel column chromatography to yield the desired product 14 (10.2 g, 50%) as white solid. $^1$H NMR (DMSO-d6, 400 MHz) δ=6.83 (bs, 1H), 2.95-3.30 (m, 12H), 2.62-2.50(m, 2H), 1.25-1.45(m, 27H). MS: $C_{21}H_{42}N_4O_6$ Cal. 446.31. Found 447.4($M^+$).

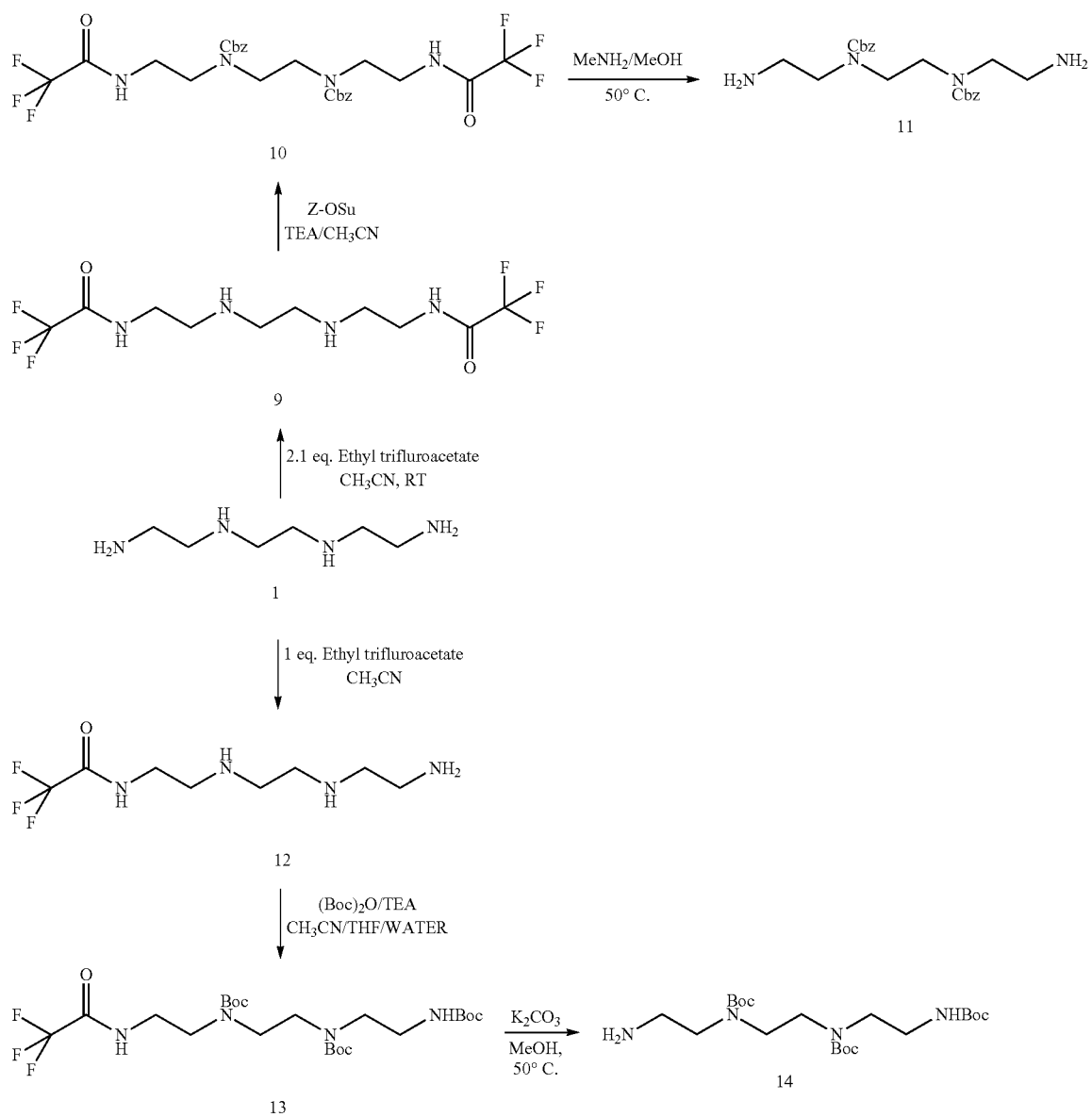

Scheme 8[a]

[a] Selective protection of triethylenetetramine nitrogens.

Step 5: Preparation of compound 15: Compound 9 (23.0 g, 68.02 mmol) was dissolved in a mixture of acetonitrile/dichloromethane (1:1, 300 mL) and cooled to 0° C. Z—OSu (17.00 g, 69 mmol) was added to the solution and stirred for 10 minutes. Triethylamine (23.40 mL, 210 mmol) was subsequently added to the reaction mixture and allowed to stir overnight. Solvents and triethylamine were removed in vacuo and the residue was extracted into DCM, washed with water (two times), brine and dried. After removing solvent, the residue was purified by silica gel column chromatography (eluted initially with 20-60% EtOAc/Hexane, then with 5% MeOH/DCM) to obtain the desired product 15 (13.3 g) as white solid along with side product 10 (8.5 g). $^1$H NMR (DMSO-d6, 400 MHz) δ=9.60 (bs, 1H), 9.30(bs, 1H), 7.40-7.28(m, 5H), 5.01(s, 2H), 3-40-3.10(m, 8H), 2.70-2.50(m, 4H). MS: $C_{18}H_{22}F_6N_4O_4$ Cal. 472.15. Found 473.1($M^+$).

Step 6: Preparation of compound 16: Treatment of compound 15 (13.4 g, 28.38 mmol) with methylamine (50 ml, 8M solution in EtOH) as described in step 2 yielded a colorless liquid compound 16 (6.10 g, 79%). The product thus obtained could be used for next reaction without further purification. $^1$H NMR (DMSO-d6, 400 MHz) δ=7.45-7.20(m, 6H), 5.07(s, 2H), 3.45-2.90(m, 8H), 2.60-2.30(m, 4H). MS: $C_{14}H_{24}N_4O_2$ Cal. 280.19 Found 281.2($M^+$).

(3.47 g, 14.50 mmol) were taken together in a pressure tube and heated at 90° C. for 5 days. The reaction was monitored by TLC. Once the reaction is over, the mixture is dissolved in dichloromethane and purified by flash chromatography to get the products 17, 18 and 19.

Step 2: Preparation of compound 20: Compound 19 (2.00 g, 1.46 mmol) is dissolved in a mixture of ethylacetate and methanol (1:2, 15 ml) to that 2 eq. of acetic acid is added. The mixture is hydrogenated under pressure (50 psi) using palladium/carbon (0.200 g, 10% wt) as a catalyst to get the desired product 20.

Step 3: Preparation of single isomer 4: Compound 20 (1.50 g, 1.36 mmol) and the acrylamide 1 (0.325 mmol, 1.36 mmol) is dissolved in toluene (4 mL) and heated at 90° C. days to form compound 4. Progress of the reaction is monitored by TLC. After completion of reaction, the mixture is cooled to room temperature, dissolved in DCM and purified by flash silica gel column chromatography to obtain the desired product 4.

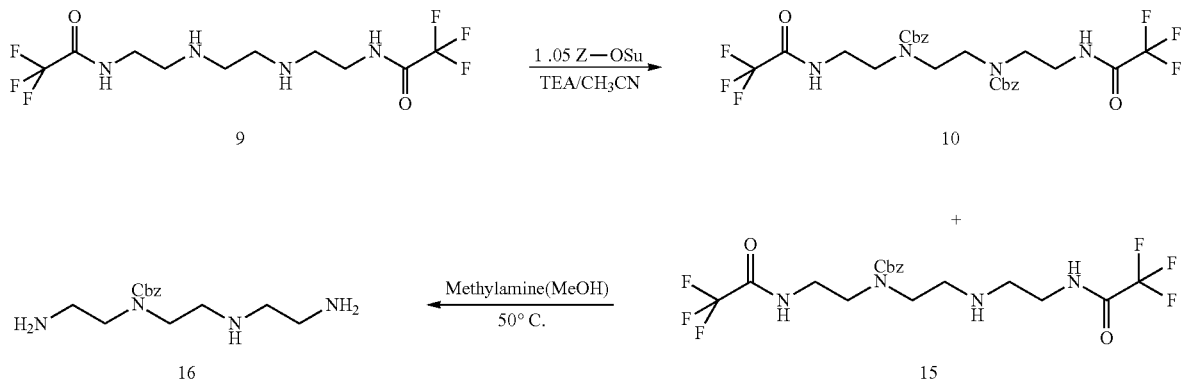

Scheme 9$^a$ $^a$ Selective blocking of single secondary nitrogen of triethylenetetramine Example 10

Synthesis of 5-Alkylated Single Isomer 4-Method 1

Step 1: Reaction of 11 with N-dodecylacrylamide: Diamine 11 (1.00 g, 2.41 mmol) and N-dodecylacrylamide Scheme 10

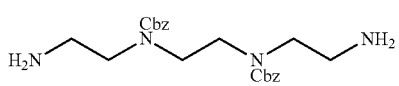

11

N-Dodecylacrylamide
Neat, 90° C.

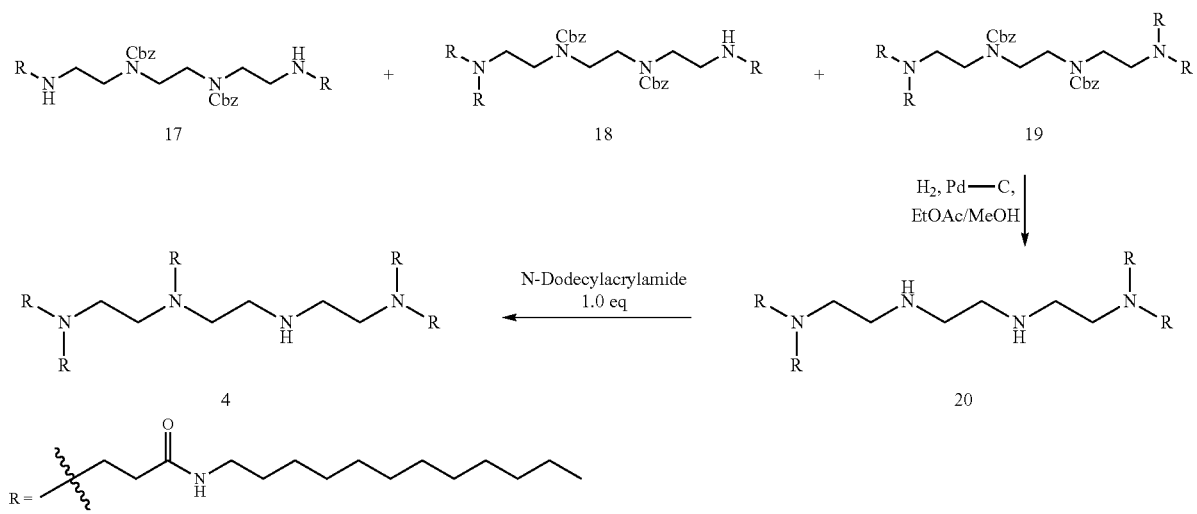

Example 11

Synthesis of 5-Alkylated Single Isomer 4-Method 2

Step 1: Preparation of compound 21: Compound 16 (1.0 g, 3.56 mmol) and N-dodecylacrylamide (6.00 g, 7 eq) are taken together in a pressure tube and heated to obtain compound 21. Progress of the reaction is monitored by TLC. After completion of the reaction the mixture is dissolved in DCM and purified by flash silica gel chromatography to afford the desired compound 21.

Step 2: Preparation of compound 4 from 21: Compound 21 (2.00 g, 1.35 mmol) is dissolved in a mixture of ethyl acetate and methanol (1:2, 15 ml) to that 2 eq. of acetic acid is added. The mixture is hydrogenated under pressure (50 psi) over palladium-carbon (0.200 g, 10% wt) to afford the desired single isomer 4.

Example 12

Synthesis of 5-Alkylated Single Isomer 3-Method 1

Step 1: Preparation of compound 22: Compound 14 (5.06 g, 11.30 mmol) and N-dodecylacrylamide (2.94 g, 12.43 mmol) were taken in toluene and heated at 90° C. for five days. TLC was checked and showed the formation of product. The reaction mixture was directly loaded on a pre-packed column of column silica gel and purified by flash chromatography (5% MeOH/DCM) to afford compound 22 (4.82 g, 62%). $^1$H NMR (DMSO-d6, 400 MHz) δ=8.17(bs, 1H), 6.60 (bs, 1H), 3.30-2.95(m, 12H), 2.70(t, J=5.80 Hz, 2H), 2.60(t, J=6.00 Hz, 2H), 2.18(t, J=6.40 Hz, 2H), 1.35(m, 29H), 1.26-1.15(m, 18H), 0.83(t, J=6.00 Hz, 3H). MS: $C_{36}H_{71}N_5O_7$ Cal. 685.54. Found 686.5(M$^+$).

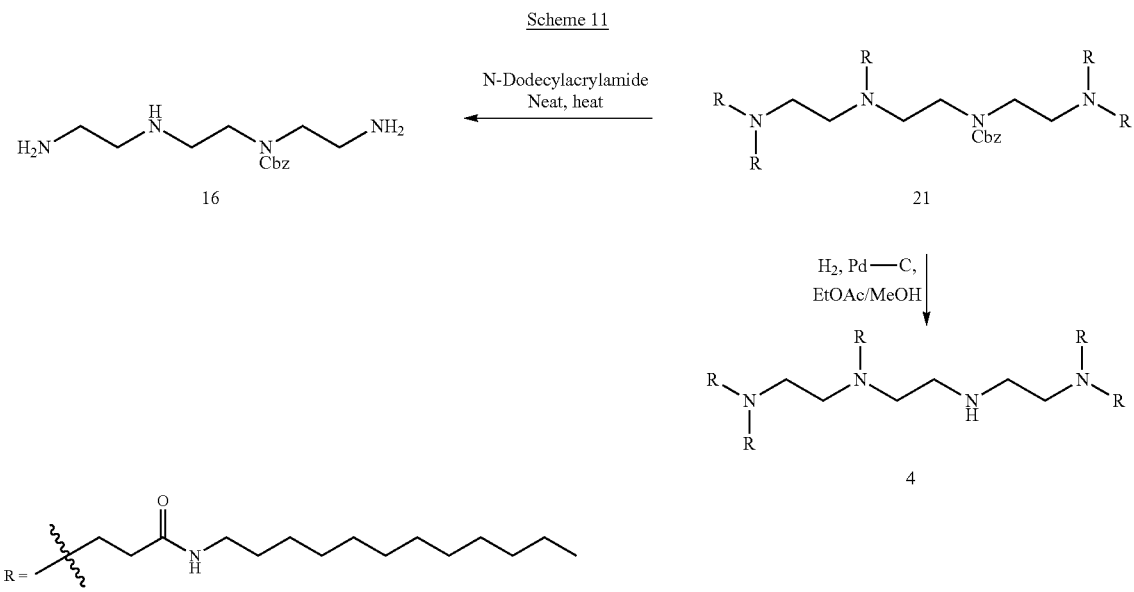

Step 2: Preparation of compound 23: Compound 22 (4.75 g, 6.92 mmol) was dissolved in dichloromethane (100 mL) and cooled to 0° C. Z—OSu (2.59 g, 1.5 eq) was added to the solution and stirred for 10 minutes. The reaction mixture was subsequently stirred with triethylamine (2.82 mL, 20.76 mmol) overnight. Solvent and triethylamine were removed in vacuo and the residue was extracted into dichloromethane, washed successively with water (two times) and brine, and dried over anhydrous sodium sulfate. After removing solvent the residue was purified by flash silica gel column chromatography (5-10% MeOH/DCM) to obtain the desired compound 23 (5.33 g, 94%). $^1$H NMR (CDCl$_3$, 400 MHz) δ=7.49-7.25(m, 5H), 5.11(s, 2H), 3.60-3.02 (m, 14H), 2.45-45(m, 4H), 1.50-1.35(m, 27H), 1.24-1.20(m, 18H), 0.87(t, J=6.00 Hz, 3H). MS: C$_{44}$H$_{77}$N$_5$O$_9$ Cal. 819.57. Found 820.7(M).

Step 3: Preparation of compound 24: 4M HCl in dioxane (50 mL) was added into a solution of compound 23 (5.30 g, 6.50 mmol) in dioxane (100 ml). The reaction mixture was then allowed to stir overnight. Product was precipitated out during the course of the reaction. Solvent and HCl were removed under vacuum to yield a white solid. The residue was taken in MeOH containing excess triethylamine and the suspension was stirred for 1 h to obtain a homogeneous solution. Solvents were removed in vacuo and the residue was triturated with EtOAc, filtered off the triethylamine hydrochloride salt. Combined filtrate was evaporated under vacuum to obtain a gummy liquid 24 (3.30 g, 98%). $^1$H NMR (CDCl$_3$, 400MHz) δ=7.37-7.28(m, 5H), 5.05(s, 2H), 3.60-3.20(m, 4H), 3.10-2.70(m, 10H), 2.40-2.20(m, 4H), 1.40-1.30(m, 2H), 1.25-1.17(m, 18H), 0.81(t, J=6.00 Hz, 3H). MS: C$_{29}$H$_{53}$N$_5$O$_3$ Cal. 519.41. Found 520.4(M$^+$).

Step 4: Preparation of compound 25: Compound 24 (1.00 g, 1.925 mmol) and N-dodecylacrylamide (3.70 g, 8 eq) are taken together in a pressure tube and heated at elevated temperature to form desired compound 25. Formation of the product is monitored by TLC and is subsequently purified by flash silica gel column chromatography to afford a pure compound 25.

Step 5: Preparation of compound 3: Compound 25 (2.00 g, 1.35 mmol) is dissolved in a mixture of ethyl acetate and methanol (1:2, 15 ml) to that 2 eq. of acetic acid is added. The mixture is hydrogenated under pressure (50 psi) over palladium-carbon (0.200 g, 10% wt) to afford the desired product 3.

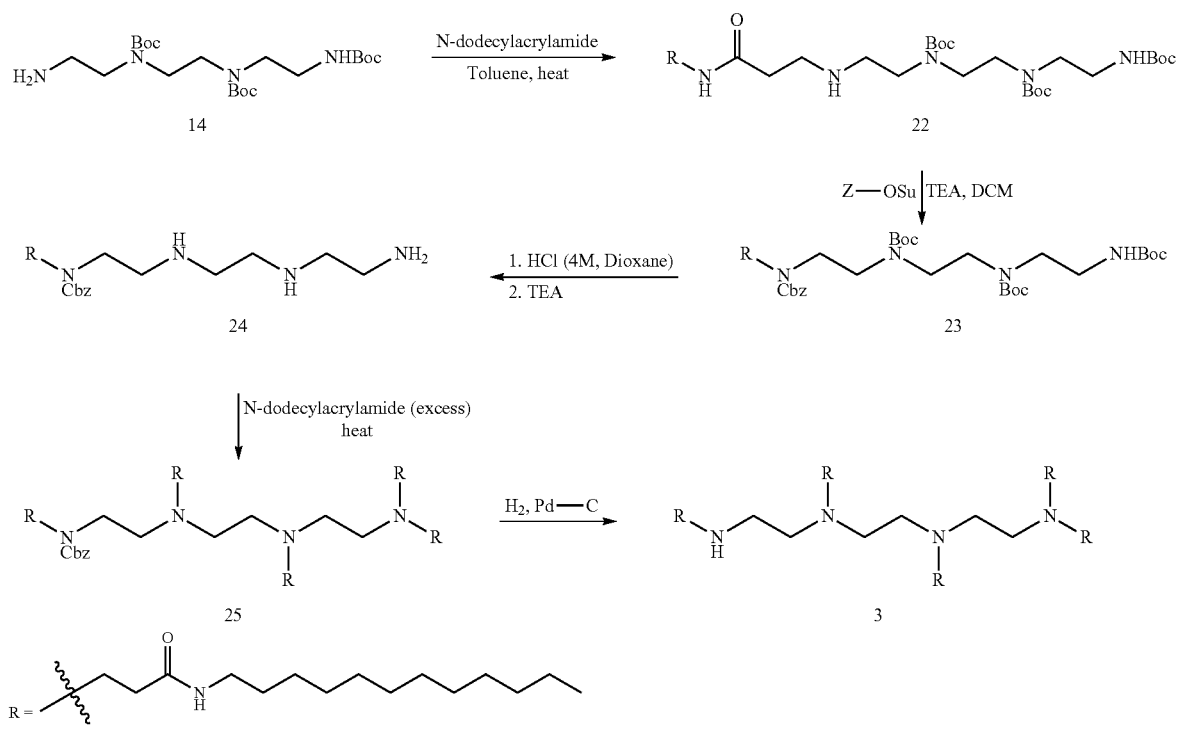

Scheme 12

Example 13

Synthesis of 5-Alkylated Single Isomer 3-Method 2

Step 1: Preparation of compound 26: Benzyl bromide (1.25 ml, 1.5 eq) to a suspension of compound 22 (4.80 g, 7.00 mmol) and K$_2$CO$_3$ (9.67 g, 10 eq) in DMF (100 mL) and the mixture was stirred overnight. Progress of the reaction was monitored by TLC. Solids were filtered off, washed with MeOH and ethyl acetate. Combined filtrate was concentrated under reduced pressure and the residue thus obtained was purified by silica gel column chromatography (50-100% EtOAc/Hexane) to afford the desired compound 26 (3.30 g, 61%). $^1$H NMR (DMSO-d6, 400 MHz) δ=7.77(bs, 2H), 7.28-7.23(m, 5H), 6.85-6.70(m, 1H), 3.59(s, 2H), 3.20-2.20(m, 18H), 1.35(s, 27H), 1.30-1.23(m, 2H), 1.20-1.15(m, 18H), 6.81(t, J=6.00 Hz, 3H). MS: C$_{43}$H$_{77}$N$_5$O$_7$ Cal. 775.58. Found 776.5(M$^+$)

Step 2: Preparation of compound 27: Compound 26 (3.30 g, 4.25 mmol) in dioxane (50 ml) was stirred with 4M HCl (50 mL) in dioxane overnight. Formation of white precipitate was seen during the course of the reaction. Solvent and acid were removed under vacuum and white residue thus obtained was redissolved in methanol containing excess triethylamine. The homogeneous solution was then evaporated under reduced pressure to obtain while residue. The residue was triturated with EtOAc and filtered off triethylamine hydrochloride salt. Filtrate was evaporated under vacuum to afford the desired compound 27 (2.36 g, 99%) as gummy liquid. $^1$H NMR (CDCl$_3$, 400 MHz) δ=8.05(t, J=5.5 Hz, 1H), 7.40-7.20(m, 5H), 3.58(s, 2H), 3.10-2.30(m, 18H), 1.40-1.30(m, 2H), 1.25-1.15(m, 18H), 0.82(t, J=6.00 Hz, 3H). MS: C$_{28}$H$_{53}$N$_5$O Cal. 475.43. Found. 498.4(M+Na)

Step 3: Preparation of compound 28: Neat compound 27 (1.00 g, 2.10 mmol) and N-dodecylacrylamide (4.0 g, 8 eq) are mixed in a pressure tube and heated to elevated temperature to form compound 28. Formation of 28 is monitored by TLC and LC-MS. After completion of the reaction the product is isolated by chromatographic purification to afford pure compound 28.

Step 4: Preparation of compound 3 from compound 28: Compound 28 (2.00 g, 1.40 mmol) is dissolved in a mixture of ethyl acetate and methanol (1:2, 15 ml) to that 6 eq. of acetic acid is added. The mixture is hydrogenated under pressure (50 psi) over palladium-carbon (0.200 g, 10% wt) to obtain compound 3 washed with water and bicarbonate and dried over sodium sulfate. DCM was removed and the residue was purified by silica gel column chromatography (2:2:96 to 10:10:80% MeOH/TEA/DCM) to get compounds 30 (1.86 g) $^1$H NMR (CDCl$_3$, 400 MHz) δ=7.05(bs, 2H), 3.21 (q, J=6.30 Hz, 4H), 2.87(t, J=6.00 Hz, 4H), 2.73(s, 4H), 2.34(t, J=6.00 Hz, 4H), 1.57(bs, 2H), 1.49-1.45(m, 4H), 1.28-1.19(m, 40H), 0.87(t, J=6.8 Hz, 6H) MS: C$_{32}$H$_{66}$N$_4$O$_2$ Cal. 538.52. Found 539.50 (M$^+$). 31 (3.50 g) $^1$H NMR (DMSO-d6, 400 MHz) δ=8.20(bs, 1H), 3.20-2.15 (m, 22H), 1.36-1.30(m, 6H), 1.25-1.15(m, 30H), 0.81(t, J=6.00 Hz, 9H), MS: C$_{47}$H$_{95}$N$_5$O$_3$ Cal. 777.74. Found 778.7(M$^+$) and 32 (1.75 g) $^1$H NMR (DMSO-d6, 400 MHz) δ=3.23-2.15 (m, 28H), 1.35-1.45 (m, 8H), 1.26-1.15 (m, 40H), 0.82 (t, J=6.00 Hz, 12H). MS: C$_{62}$H$_{124}$N$_6$O$_4$ Cal. 1016.97. Found 1018.0 (M$^+$).

Step 2: Preparation of compound 33: Compound 31 (1.55 g, 2 mmol) and K$_2$CO$_3$ (2.76 g, 20 mmol) are taken in DMF. To that chloroacetaldehyde dimethyl acetal (0.453 ml, 4.00 mmol) is added and stirred for 24 h. Reaction is monitored by TLC, filtered off K$_2$CO$_3$ washed with MeOH. Solvents are removed under reduced pressure and the residue is subjected to chromatographic purification to afford compound 33.

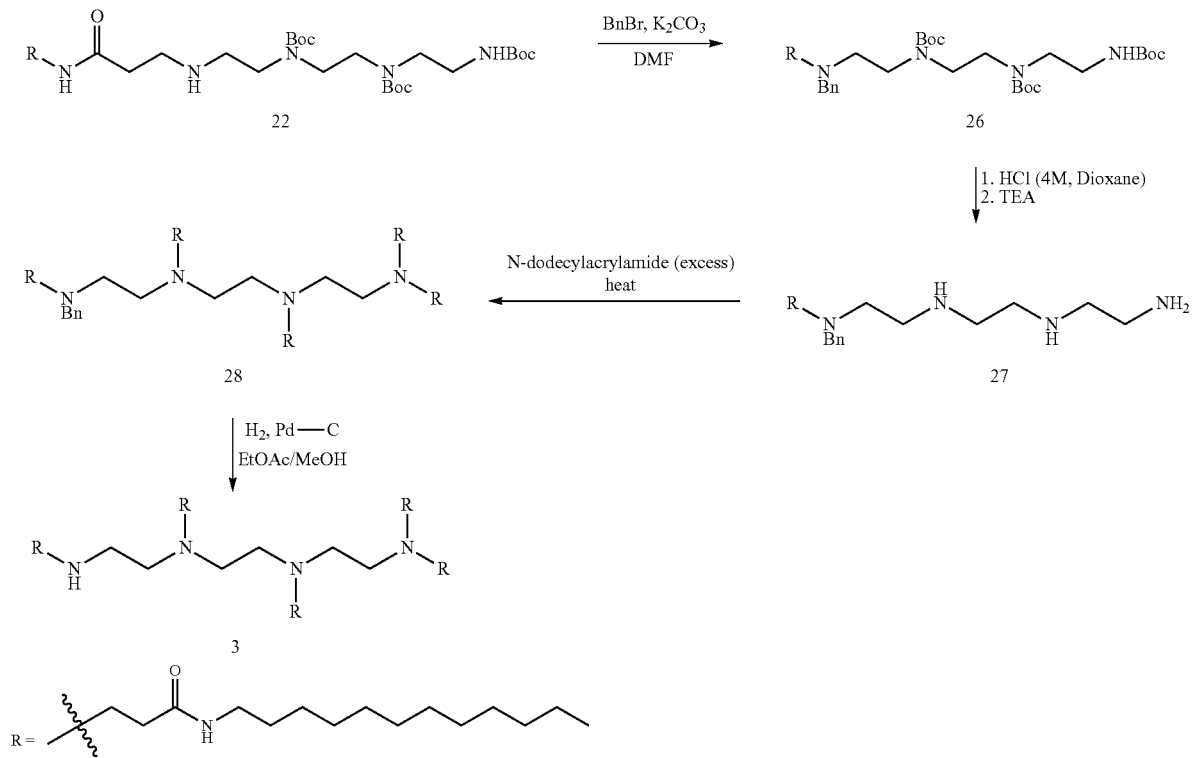

Scheme 13

Example 14

Convergent Synthesis of Isomer 3—Method 1

Step 1: Preparation of compounds 30, 31 and 32: Ethylenediamine 29 (0.978 ml, 14.63 mmol), N-dodecylacrylamide (7.00 g, 29.26 mmol) and boric acid (100 mg) were taken in 5 mL of water and heated at 90° C. for four days. Complete disappearance of acrylamide was ascertained by TLC analysis. The reaction mixture was dissolved in DCM, Step 3: Preparation of compound 34: Compound 33 (2.00 g, 2.31 mmol) is taken in a mixture of MeOH and DCM, to that PTSA (2.0 eq) is added and reaction mixture is stirred overnight. The solution is neutralized with sodium bicarbonate solution and extract with DCM and dried. Compound is purified by chromatographic separation to afford the desired product 34.

Step 4: Preparation of single isomer 3 from 34: Compound 34 (2.00 g, 2.43 mmol) and 30 (1.31 g, 2.43 mmol) are taken in DCM; to that activated molecular sieves is added and stirred for 3 h. The reaction is monitored by TLC. Once the reaction is over solvents is removed. The residue is dissolved in THF and sodium triacetoxyborohydride (5 eq.) and acetic acid are added and stirred overnight. Solvents are removed and extracts with DCM, chromatographic separation of the residue affords pure isomer 3.

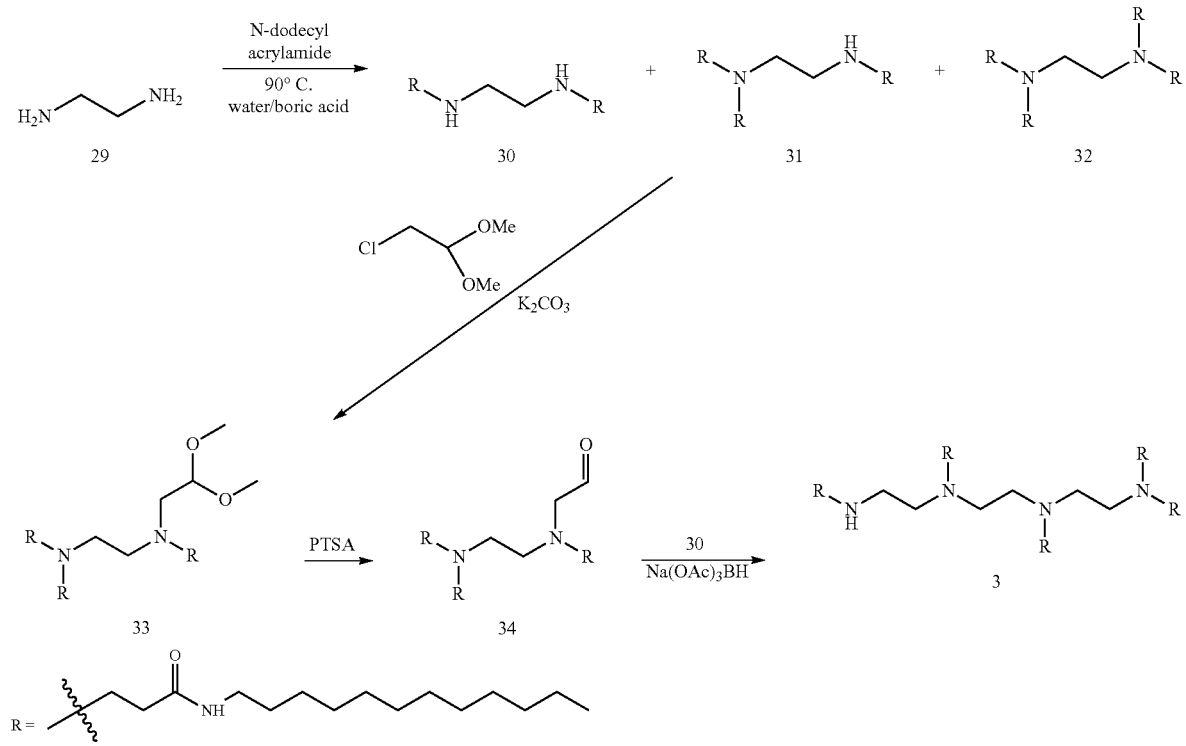

Example 15

Convergent Synthesis of Isomer 3—Method 2

The desired single isomer 3 is also prepared from compound 30 by selective protection of one of the nitrogen to obtain compound 35. Compound 35 is subsequently reacted with aldehyde 34 under reductive conditions to obtain compound 36. Acid treatment of 36 affords desired compound 3.

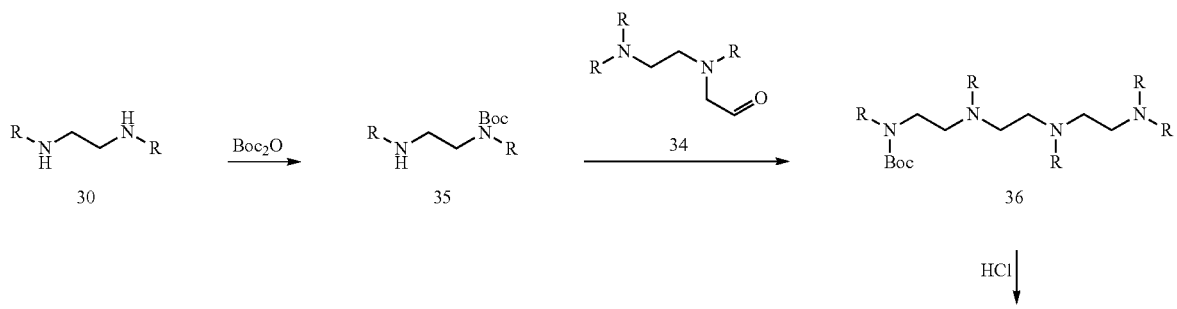

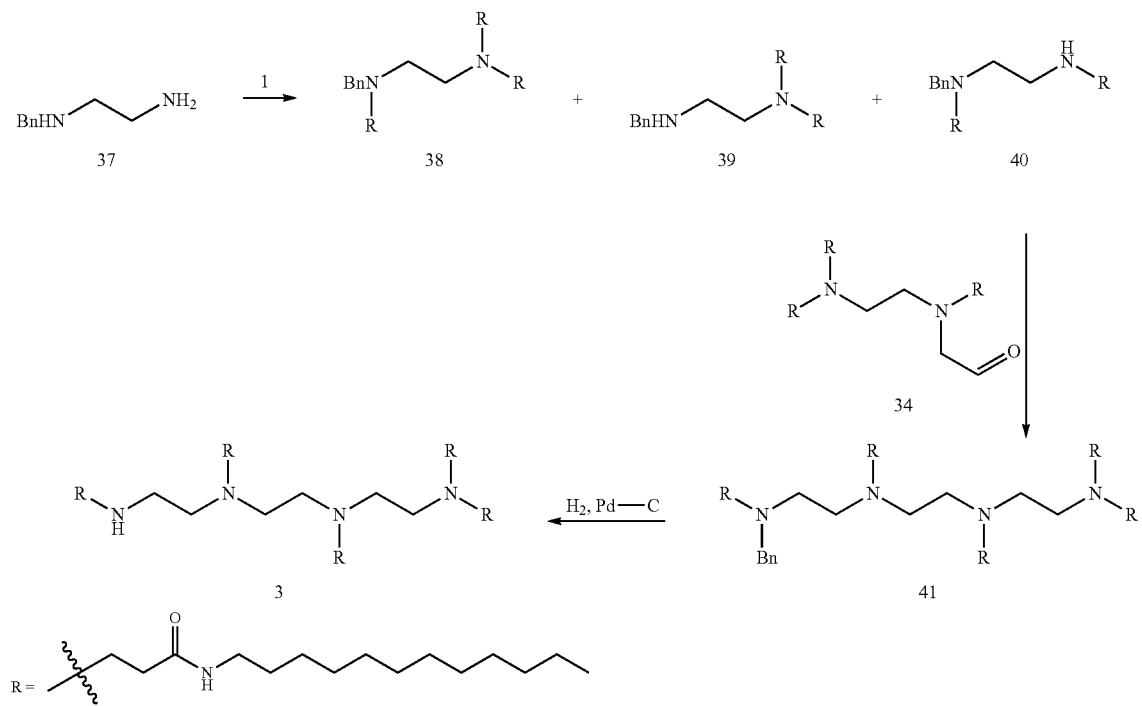

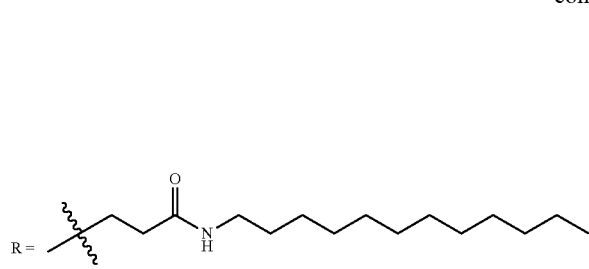

Example 16

Convergent Synthesis of Isomer 3—Method 3

The desired single isomer 3 is also prepared from monobenzyl ethylenediamine 37. Alkylation of 37 with 1 affords a mixture of compounds 38, 39 and 40. Compound 40 is reacted with aldehyde 34 under reductive conditions to obtain compound 41. Hydrogenolysis of 41 affords the desired compound 3.

of the starting acrylamide 1. The reaction mixture was dissolved in dichloromethane (100 mL) and the solution was stirred with solid sodium bicarbonate and the organic layer was filtered and concentrated in a rotory evaporator. This crude product was purified by column chromatography (silica gel) using $CH_2Cl_2$:MeOH:$NEt_3$ (48:1:1 to 8:1:1). The major product in this reaction is the double addition product 43. Minor amounts of mono adduct was also observed.

Step 2: Preparation of compound 44: Compound 43 (2.00 g, 3.13 mmol) is taken in dioxane (50 mL) to that HCl (20 mL,

Example 17

Convergent Synthesis of Isomer 4—Method 1

Step 1: Preparation of compounds 43: In a 150 mL pressure bottle N-dodecyl-acrylamide 1 (16.4 g, 68 8 mmol) was melted under argon by gently heating the vessel and to this 3 mL of aqueous boric acid was added. To this melt was added Boc protected ethylenediamine 42 (5 g, 31.2 mmol) and the mixture was heated at 90° C. overnight. The reaction mixture was analyzed by TLC using $CH_2Cl_2$:MeOH:$NEt_3$ (90:5:5) as the eluent. The TLC showed the near complete consumption 4M solution in dioxane) is added and stirred overnight. Solvent is removed to get the compound 44.

Step 3: Preparation of single isomer 4 from 34 and 44: Compound 34 (2.00 g, 2.43 mmol) and 44 (1.31 g, 2.43 mmol) are taken in DCM; to that activated molecular sieves is added and stirred for 3 h. The reaction is monitored by TLC. Once the reaction is over solvents are removed. The residue is dissolved in THF and sodium triacetoxy borohydride (5 eq.) and acetic acid are added and stirred overnight. Solvents are removed and extracts with DCM, chromatographic separation of the residue affords pure isomer 4.

Scheme 17

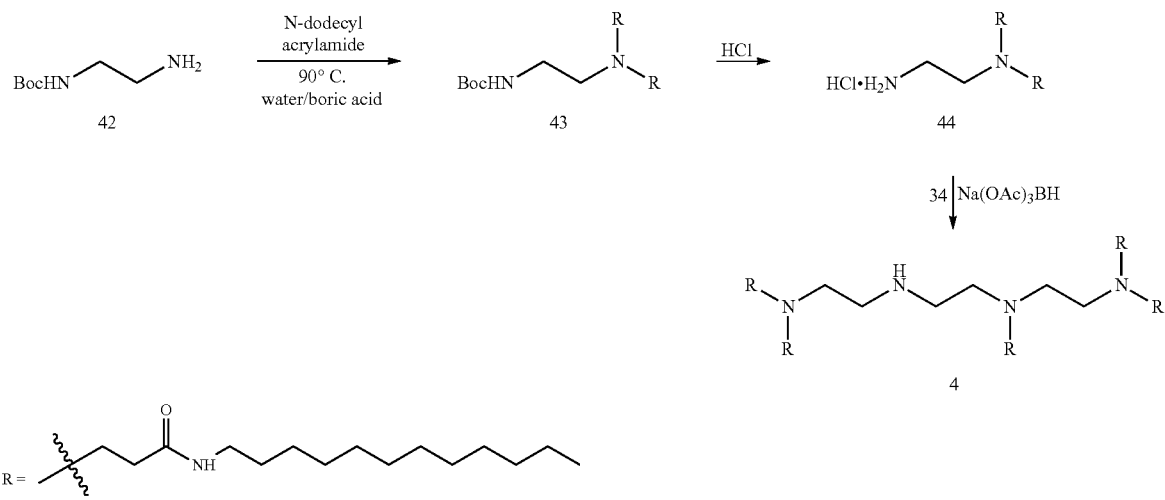

Example 18

Addition of N-dodecylacrylamide to 1,3-diaminopropane and Subsequent Reduction of the Amide to Amine In order to study the effect of number of charges in the cationic lipid the Michael adducts of acrylamide 1 with 1,3-diaminopropane 45 was investigated.

Step 1: Synthesis of 46, 47 and 48: In a 150 mL pressure bottle N-dodecyl-acrylamide 1 (15.4 g, 64 mmol) was melted under argon by gently heating the vessel and to this 3 mL of aqueous boric acid was added. To this melt was added 1,3-diaminopropane 44 (1.58 g, 21 mmol) and the mixture was heated at 90° C. overnight. The reaction mixture was analyzed by TLC using $CH_2Cl_2$:MeOH:$NEt_3$ (90:5:5) as the eluent. The TLC showed the near complete consumption of the starting acrylamide 1. The reaction mixture was dissolved in

Scheme 18$^a$

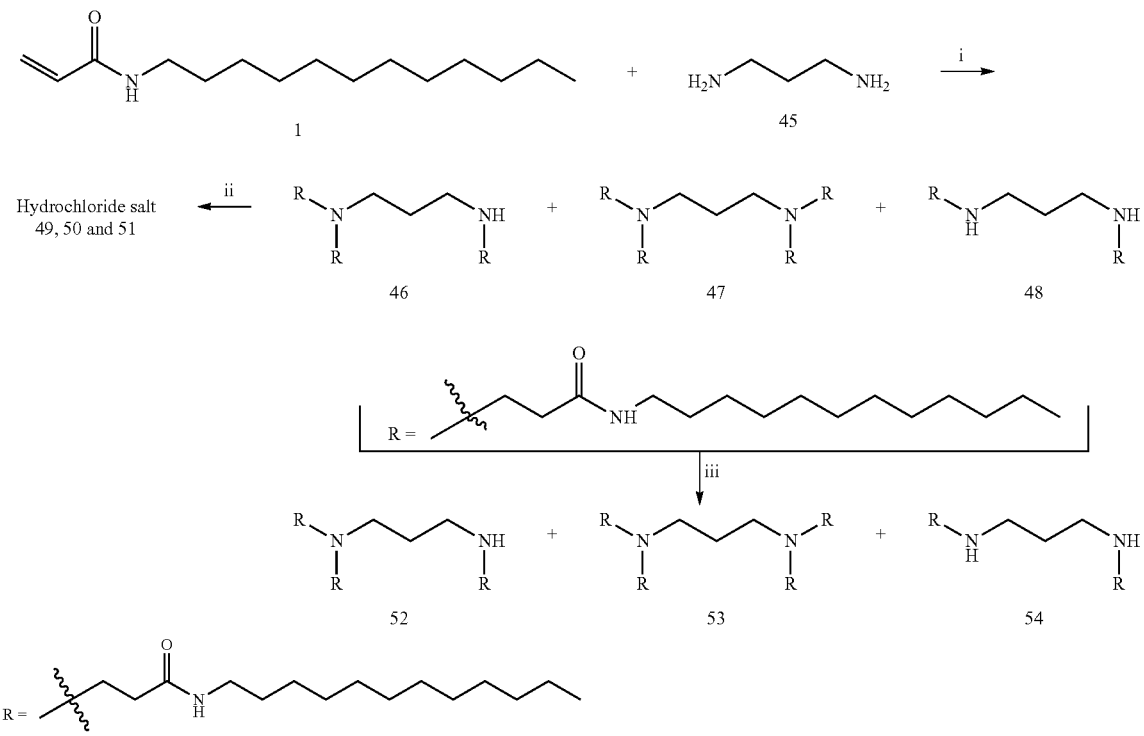

$^a$ (i) 90° C., aq. boric acid, 16 h; (ii) 4M HCl in 1,4-dioxane, rt., 12 h and (iii) $BH_3$ dichloromethane (100 mL) and the solution was stirred with solid sodium bicarbonate and the organic layer was filtered and concentrated in a rotory evaporator. This crude product was purified by column chromatography (silica gel) using CH$_2$Cl$_2$:MeOH:NEt$_3$ (48:1:1 to 8:1:1). The major product in this reaction is the triple addition product 46. Minor amounts of tetra adduct 47 and bis adduct 48 were also isolated.

N-Dodecyl-3-{(2-dodecylcarbamoyl-ethyl)-[3-(2-dodecylcarbamoyl-ethylamino)-propyl]-amino}-propionamide 46. The three addition product 46 was isolated as a white powder (5.7 g, 35%). MS m/z 793 (MH$^+$). $^1$H NMR CDCl$_3$ δ 0.87 (t, J=6.6 Hz, 9H), 1.20-1.30 (m, 60H), 1.42-1.66 (m, 6H), 2.33 (t, J=6 Hz, 4H), 2.38-2.46 (m, 4H), 2.60-2.70 (m, 4H), 2.84 (t, 2H), 3.15-3.28 (m, 6H), 6.65 (bs, 1H), 6.99 (bs, 3H).

4-[{3-[Bis-(2-dodecylcarbamoyl-ethyl)-amino]-propyl}-(2-dedecylcarbamoyl-ethyl)amino]-N-dodecyl-butyramide 47. The four addition product 47 was also isolated in minor amounts.

N-Dodecyl-3-[-(2-dodecylcarbamoyl-ethylamino)-propylamino]-propionamide 48. The diadduct 48 was isolated as a cream powder (1.6 g, 10%). MS m/z 553 (MH$^+$). $^1$H NMR CDCl$_3$ δ 0.89 (t, J=6.6 Hz, 6H), 1.10-1.20 (m, 40H), 1.42-1.66 (m, 4H), 2.20 (t, J=6 Hz, 4H), 2.55 (t, 4H), 2.60 (t, 4H), 3.00 (m, 4H), 8.00 (bs, 2H).

Step 2: Conversion of Amines 4, 35 and 36 to their Corresponding Hydrochloride Salts 49, 50 and 51.

The amine 46 (5.5 g) was converted to the corresponding HCl 49 using a procedure similar to the described in Example 8 and the dihydrochloride salt 49 was isolated as a white powder (5.73 g, 92%). $^1$H NMR DMSO-d$_6$ δ 0.88 (t, J=7 Hz, 9H), 1.17-1.30 (m, 66H), 1.35-1.45 (m, 6H), 2.10-2.25 (m, 2H), 2.55-2.70 (m, 6H), 2.95-3.15 (m, 10H), 3.20-3.35 (m, 6H), 8.16 (t, 1H), 8.24 (t, 1H), 9.15 (bs, 1H), 10.65 (bs, 1H).

In a similar procedure to that described in Example 8 the amine 47 is treated with 4M HCl to obtain the dihydrochloride salt 50.

In a similar procedure to that described in Example 8 the amine 48 is treated with 4M HCl to obtain the dihydrochloride salt 51.

Step 3: Reduction of amides 46, 47 and 48 to amines 52, 53 and 54: Amine 46 is refluxed in THF with excess of diborane overnight and subsequent treatment with 4M HCl affords hydrochloride salt of polyamine 52.

A similar treatment of amines 47 and 48 affords the corresponding reduced product 53 and 54 as their respective hydrochloride salt.

Example 19

Reduction of Polyamides 3, 4 and 5 to the Corresponding Polyamine Dendrimers

Compound 3 is refluxed with large excess of diborane in THF to obtain the corresponding reduced product 55. After completion of the reaction, the reaction mixture is treated with 4M HCl prior to work-up and the product is isolated as its hydrochloride salt. Hydrochloride salts of 56 and 57 are also obtained from the corresponding precursors 4 and 5 respectively.

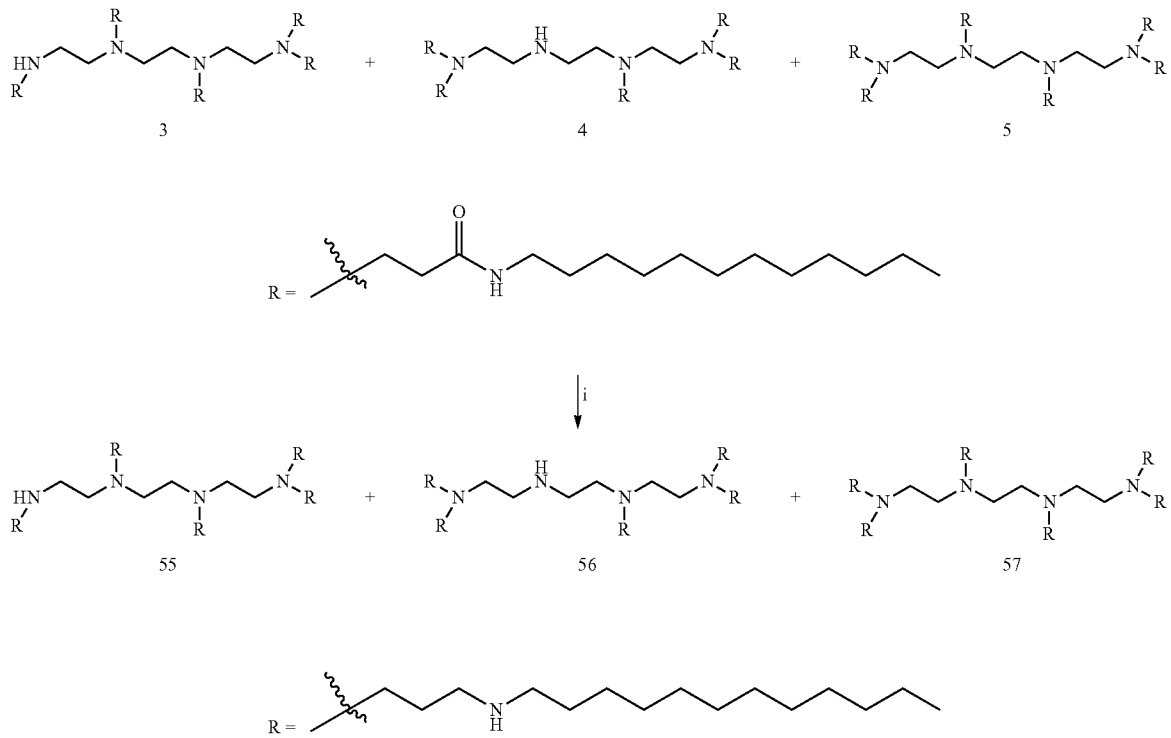

Scheme 19$^a$ $^a$ (i) BH$_3$, THF, reflux

Example 20

Polyamino Alkyl Lipids—Reduction of Amides to Amines

Preparation of polyamines 60 from 32: Compound 32 (1.02 g, 1 mmol) is taken in THF (20 ml), to that $BH_3$·THF (60 ml, 1M in THF) is added and refluxed for two days. Reaction is monitored by TLC. Removal of THF gives a white residue, which is treated with 1M HCl and extracts into DCM. Chromatographic separation of the crude products yields pure compound 60.

Preparation of polyamines 58 and 59 from 30 and 31: Reduction of amides 30 and 31 under similar conditions described for the preparation 60 respectively affords 58 and 59.

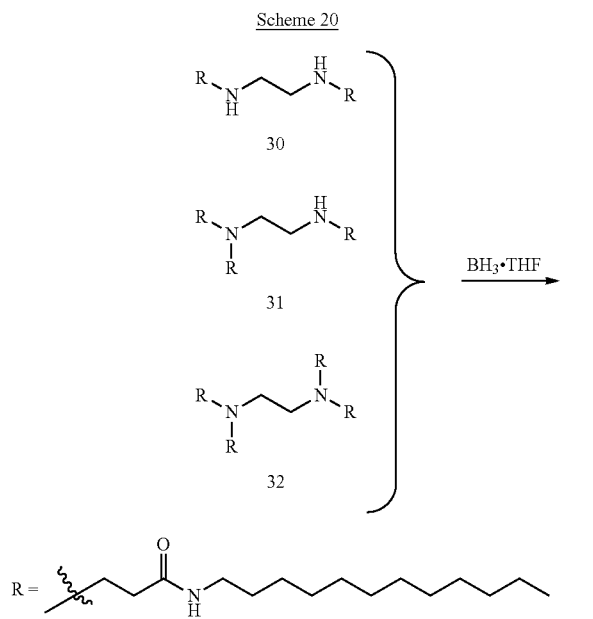

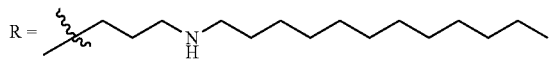

Example 21

Synthesis of Polyamido-Polyamino Alkyls—Alkylation of Amines Using Alkyl Halides Step 1: preparation of compound 62: A solution of chloroacetyl chloride (10.31 mL, 129.37 mmol) in DCM (200 mL) was cooled over an ice bath and to this a solution of dodecylamine (61, 20.00 g, 107.81 mmol) in dichloromethane containing TEA (36.70 ml, 269.5 mmol) was added dropwise over a period of 1 hr. The reaction mixture tuned brownish-black by this time, continued the stirring for another hour at 0° C. The reaction mixture was filtered through a sintered funnel, washed with EtOAc, diluted with chloroform, washed successively with water, sodium bicarbonate solution, 1M HCl and brine. Organic layer was dried over sodium sulfate. Solvents were removed and the residue was purified by silica gel column chromatography (5-50% EtOAc/Hexane) to afford compound 62 (26.00 g, 92%) as brown solid. $^1$H NMR (CDCl$_3$, 400 MHz) δ=6.59(bs, 1H), 4.03(s, 2H), 3.25 (q, J=6.00 Hz, 2H), 1.54-1.49(m, 2H), 1.45-1.15(m, 18H), 0.86 (t, J=6.00 Hz, 3H). MS: $C_{14}H_{28}ClNO$ Cal. 261.19. Found 262.20(M$^+$).

Step 2: Preparation of 63, 64 and 65: Triethylenetetramine 2 (1.00 g, 6.83 mmol) and chloroacetamide 62 (10.00 g, 5.5 eq) are taken together in a mixture of $CH_3CN$/DMF (1:3), to that $K_2CO_3$ (9.43 g, 10 eq) and KI (50 mg) are added and heated at 85° C. for three days. The reaction mixture is filtered to remove solids, wash with DCM, solvents are removed in vacuo and chromatographic separation of the crude residue affords pure compounds 63, 64 and 65.

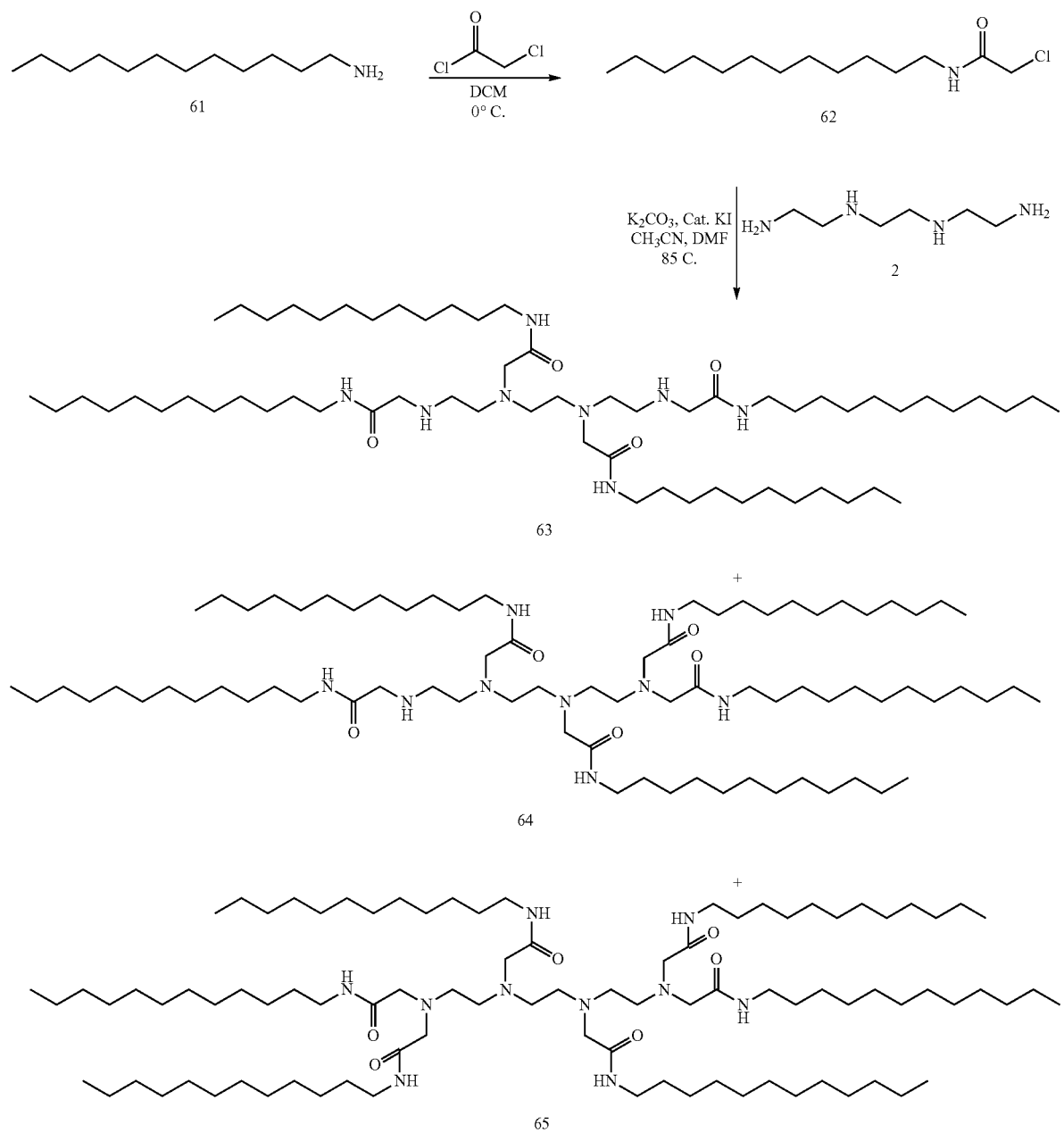

Example 22

Synthesis of Polyamido-Polyamino Alkyls—Alkylation of Amines Using Alkyl Halides with Branched Aminoalkyls Step 1: Preparation of 67: Chloroacetyl chloride (4.05 mL, 51 mmol) was taken in DCM (100 mL) and cooled down to 0° C. To this a dichloromethane solution of N,N-didodecylamine (66, 15.00 g, 42.41 mmol) and TEA (14.43 ml, 2.5 eq.) were added dropwise over a period of 1 hr. The reaction mixture tuned brownish-black by this time, after the addition the reaction mixture was stirred for 24 h at ambinet temperature. The reaction mixture was filtered through a sintered funnel, washed with EtOAc, diluted with chloroform, washed successively with water, sodium bicarbonate solution, 1M HCl and brine. Organic layer was dried over sodium sulfate. Solvents were removed in vacuo and the residue was purified by silica gel column chromatography (5-50% EtOAc/Hexane to obtian the required product 67 (12.5 g, 69%) as brownish liquid. 1H NMR (CDCl$_3$, 400 MHz) δ=4.04(s, 2H), 3.30(m, 4H), 1.50-1.45(m, 2H), 1.40-1.20(m, 18H), 0.87(t, J=6.00 Hz, 3H). MS: C$_{26}$H$_{52}$ClNO Cal. 430.15. Found 431.2(M$^+$).

Step 2: Preparation of 68, 69 and 70: Triethylenetetramine 2 (0.500 g, 6.83 mmol) and chloroacetamide 67 (8.10 g, 5.5 eq) are taken together in a mixture of CH$_3$CN/DMF (1:3), to that K$_2$CO$_3$ (4.72 g, 10 eq) and KI (30 mg) are added and heated at 85° C. for three days. The reaction mixture was filtered to remove insoluble solids, wash with DCM, solvents are removed and chromatographic separation of the residue affords t 68, 69 and 70.

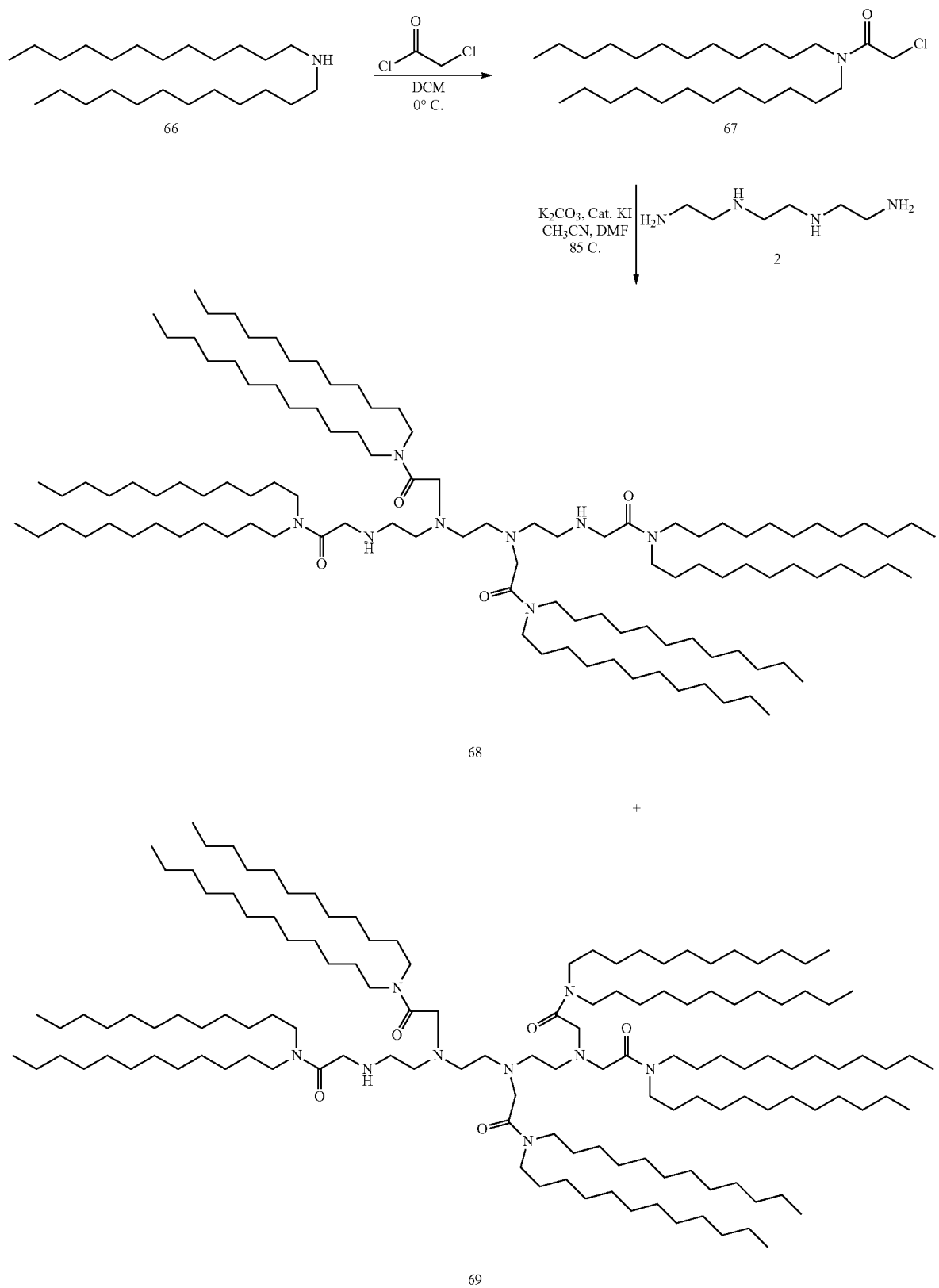

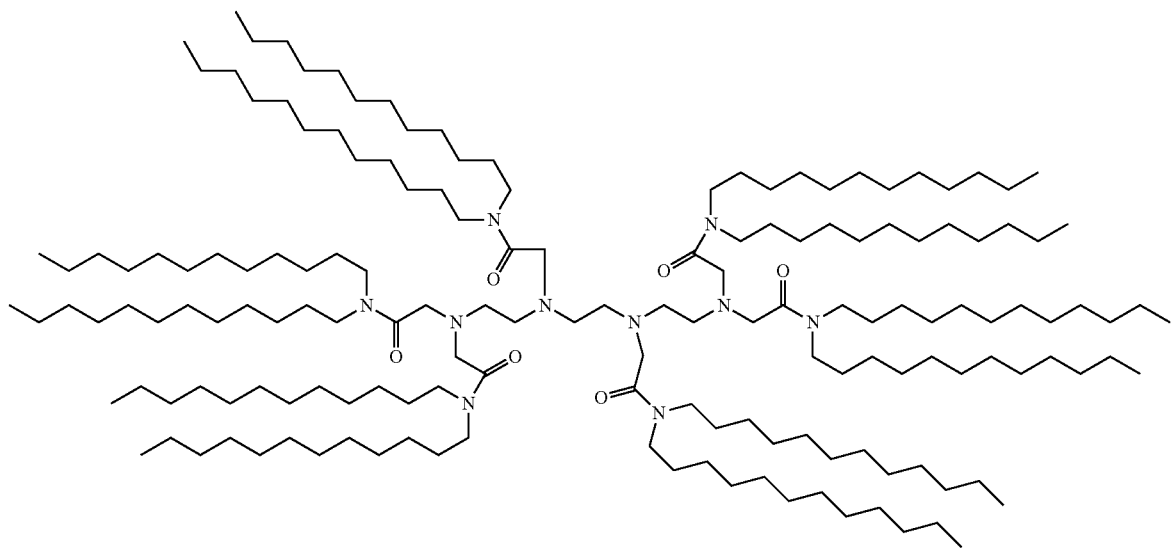
70
Example 23
Addition of N,N-dialkylacrylamide to Polyamines
In order to study the effect of adding more hydrophobic chains to the cationic lipids, didodecylamine was used as a precursor to the acrylamide.
Scheme 23$^a$
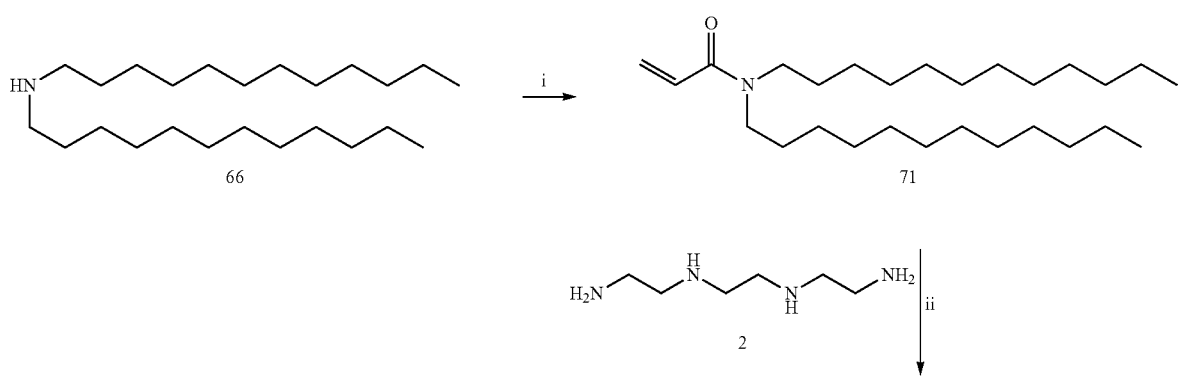

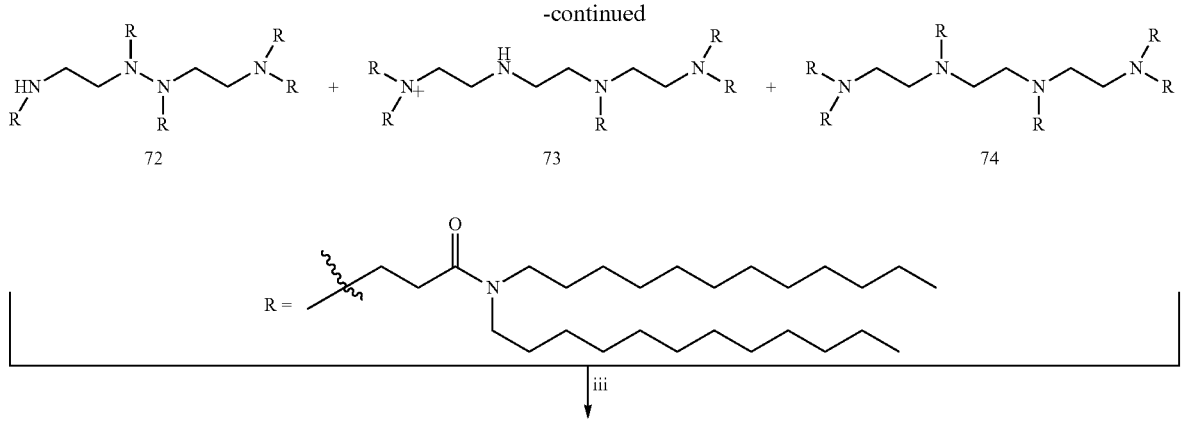

$^a$ (i) Acryyloyl chloride, -10-0° C., DIPEA, CH$_2$Cl$_2$, 4 h, (ii) 90° C., Neat, 5 days and (iii) HCl/Dioxane Step 1: Synthesis of N,N-Didodecylacrylamide 71

To a solution of didodecylamine 66 (25 g, 70 7 mmol) and diisopropylethylamine (18 g, 141 mmol) in anhydrous CH$_2$Cl$_2$ (700 mL) at −10° C., a solution of acryloyl chloride (7.68 g, 85 mmol) in CH$_2$Cl$_2$ (100 mL) was added dropwise over a period of 20 min. After the completion of the addition the reaction mixture was stirred for 4 h at 0° C. after which the TLC of the reaction mixture showed the completion of the reaction. The reaction mixture was washed with satd. NaHCO$_3$ solution (200 mL), water (200 mL), brine (100 mL) and dried over NaSO$_4$. Concentration of the organic layer provided the product 71 (28.4 g, 100%) which was used as such in the next step. $^1$H NMR CDCl$_3$ δ 0.94 (t, J=6.5 Hz, 6H), 1.05-1.69 (m, 40H), 3.15-3.60 (dt, 4H), 5.64 (d, 1H), 6.36 (d, 1H), 6.63 (m, 1H).

Step 2: Reaction of triethyelentetramine 2 and 71

The acrylamide 71 is treated with the amine 2 and after usual work-up and column purification the Michael addition products 72, 73 and 74 are isolated.

Step 3: Synthesis of hydrochloride salts 75, 76 and 77:

Each single compound obtained is taken in dioxane and 4M HCl in dioxane is added to the solution and stirred as described in example 8 to yield the corresponding hydrochloride salt.

Example 24

Alkenylation of Polyamines Using Mono Unsaturated N-Alkyl Acrylamide Under Michael Addition Condition In order to study the effect of double bond in the alkyl chain oleylamine was used as a precursor to the acrylamide 79.

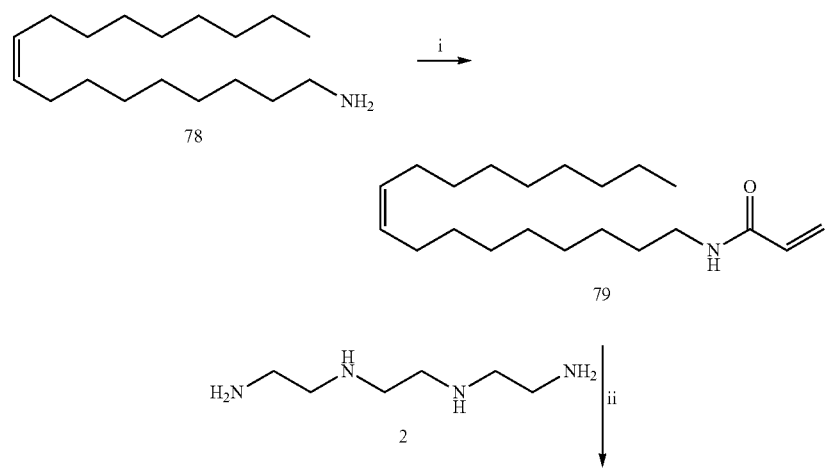

Scheme 24$^a$

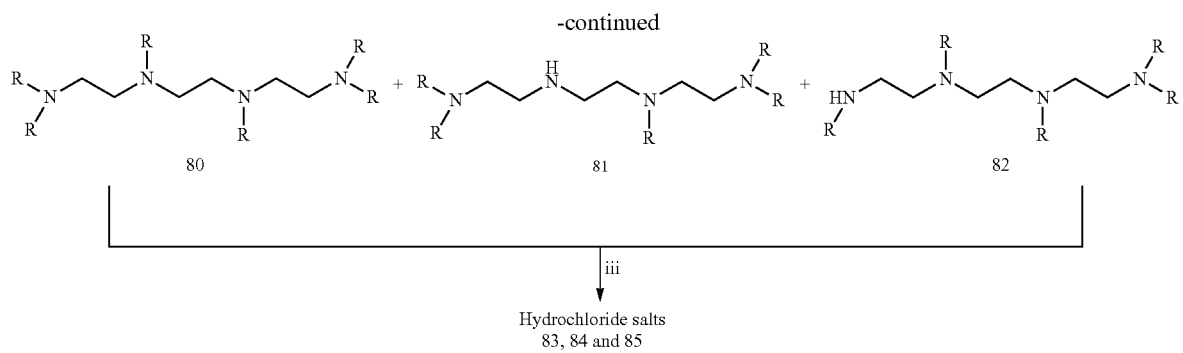

80 + 81 + 82

↓ iii

Hydrochloride salts
83, 84 and 85

*(i) Acryloyl chloride, -10-0° C., DIPEA, CH₂Cl₂, 4 h, (ii) 90° C., Neat, 5 days and (iii) HCl/Dioxane

R =

Step 1: Synthesis of compound 79: To a solution of oleylamine 78 (26.75 g, 100 mmol) and triethylamine (20 g, 200 mmol) in anhydrous $CH_2Cl_2$ (200 mL) at −10° C., a solution of acryloyl chloride (9.9 g, 110 mmol) in $CH_2Cl_2$ (100 mL) was added dropwise over a period of 20 min. After the completion of the addition the reaction mixture was stirred for 4 h at 0° C. after which the TLC of the reaction mixture showed the completion of the reaction. The reaction mixture was washed with satd. $NaHCO_3$ solution (200 mL), water (200 mL), brine (100 mL) and dried over $NaSO_4$. Concentration of the organic layer provided the product 79 (32 g, 100%) which was used as such in the next step. $^1$H NMR $CDCl_3$ δ 0.91 (t, J=6.5 Hz, 3H), 1.05-1.35 (m, 24H), 1.42 (t, 2H), 1.96 (m, 4H), 5.31 (t, 1H), 5.33-5.36 (m, 1H), 5.54 (dd, 1H), 6.02 (dd, 1H), 6.18 (dd, 1H), 8.03 (bs, 1H).

Step 2: Reaction of Compound 79 with Triethylenetetramine

The acrylamide 79 is treated with triethylenetetramine 2 and after usual work-up and column purification of the Michael addition products affords pure compounds 80, 81 and 82.

Step 3: Synthesis of hydrochloride salts 83, 84 and 85: Each single compound (80, 81 or 82) obtained is taken in dioxane and 4M HCl in dioxane is added to the solution and stirred as described in example 8 to yield the corresponding hydrochloride salt.

Example 25

Alkenylation of Diamines Using Mono Unsaturated N-Alkyl Acrylamide Under Michael Addition Condition Scheme 25ᵃ

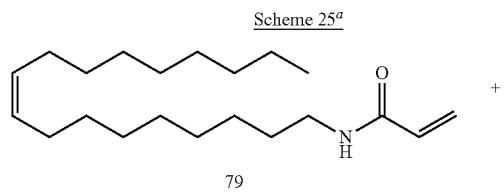

79

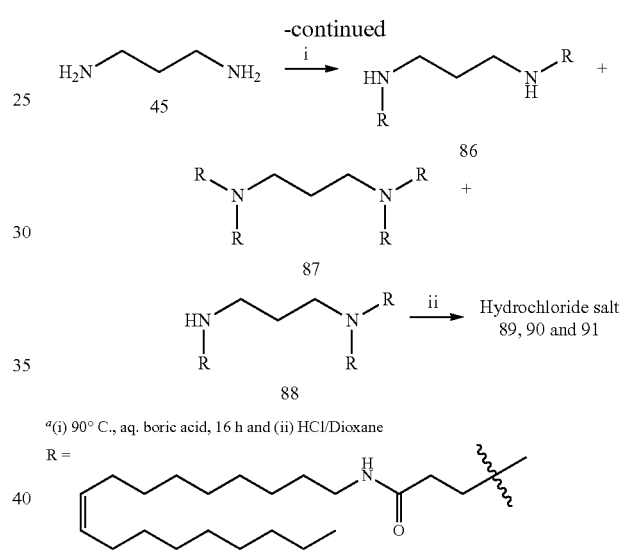

*(i) 90° C., aq. boric acid, 16 h and (ii) HCl/Dioxane

R =

In a similar procedure to that of Example 24 the acrylamide 79 is treated with the diamine 45 and after usual work-up and column purification the Michael addition products 86, 87 and 88 are isolated. Treatment of the free amine thus obtained with HCl in dioxane affords the corresponding hydrochloride salts 89, 90 and 91 respectively.

Example 26

Alkenylation of Polyamines Using Poly Unsaturated N-Alkyl Acrylamide Under Michael Addition Condition In order to study the effect of polyunsaturation in the alkyl chain linoleylamine 92 was used as a precursor to the acrylamide 93.

Scheme 26[a]

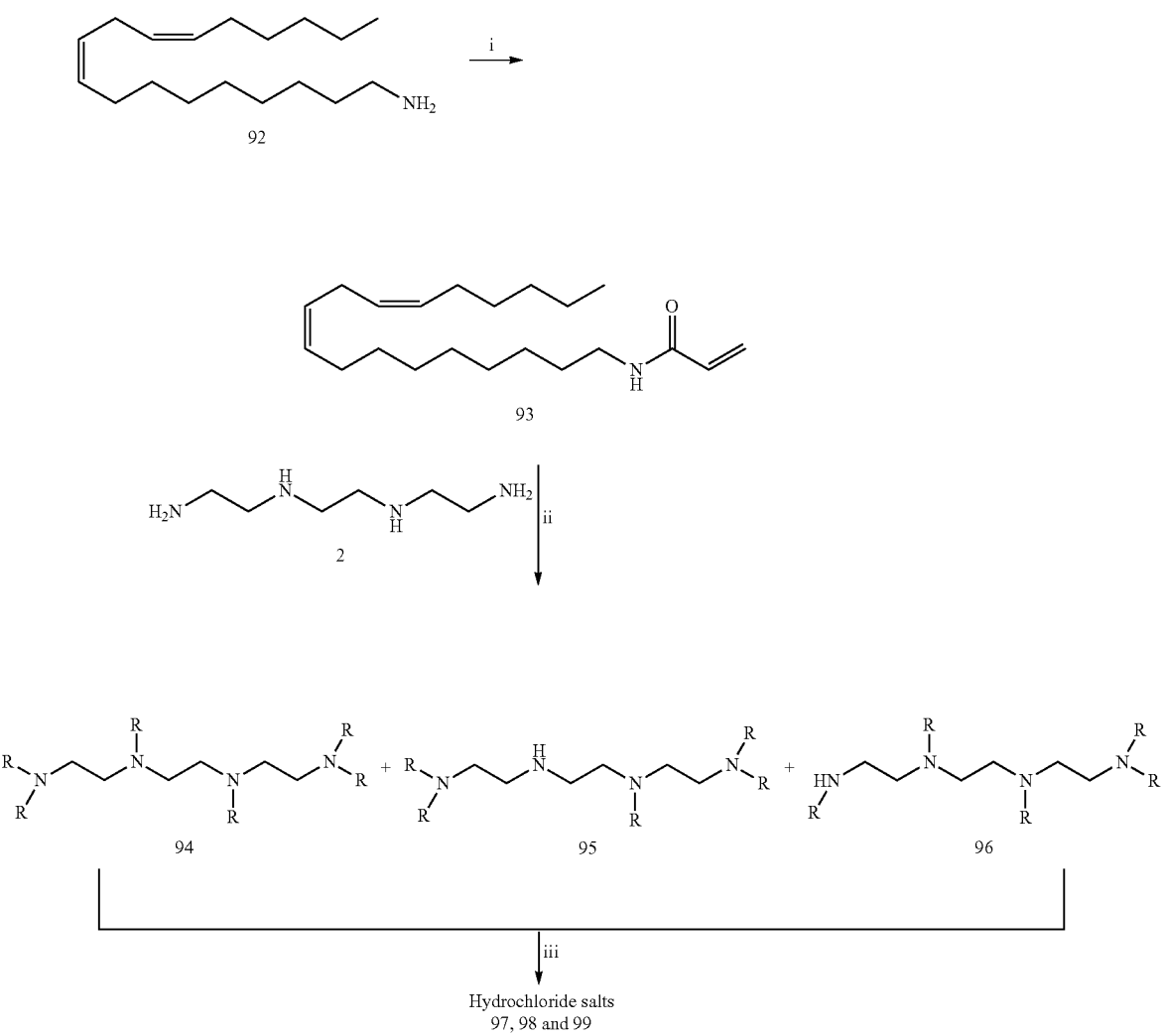

[a](i) Acrloyl chloride, -10-0° C., DIPEA, CH₂Cl₂, 4 h, (ii) 90° C., Neat, 5 days and (iii) HCl/Dioxane

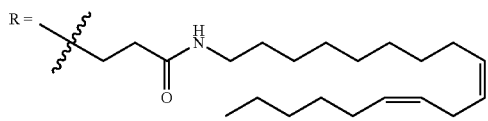

Step 1: Compound 93: Linolylamine 92 is treated with acryloyl chloride in a similar procedure to that of Example 24, step 1 and the corresponding acrylamide 93 is isolated.

Step 2: Reaction of Compound 93 with Triethylenetetramine

The acrylamide 93 is treated with triethylenetetramine 2 in the presence of boric acid as described in Example 3 and after usual work-up and column purification of the Michael addition products affords pure compounds 94, 95 and 96.

Step 3: Synthesis of hydrochloride salts 97, 98 and 99: Each single compound (94, 95 or 96) obtained is taken in dioxane and 4M HCl in dioxane is added to the solution and stirred as described in example 8 to yield the corresponding hydrochloride salt.

Example 27
Alkenylation of Diamines Using Poly Unsaturated N-Alkyl Acrylamide Under Michael Addition Condition

Scheme 27[a]

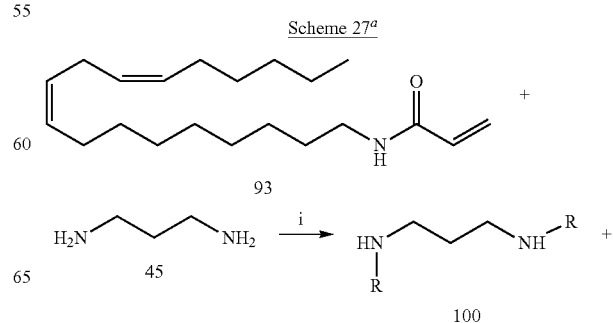

-continued

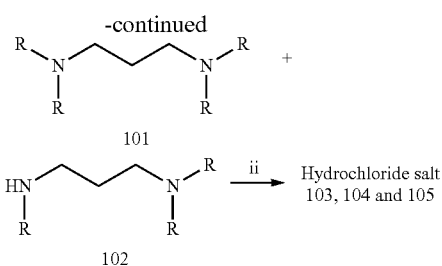

101

102

$^a$(i) 90° C., aq. boric acid, 16 h and (ii) HCl/Dioxane

R =

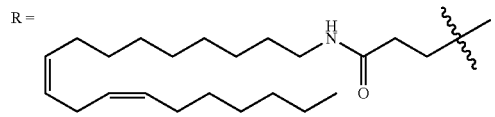

In a similar procedure to that of Example 3 the acrylamide 93 is treated with the diamine 45 in the presence of boric acid and after usual work-up and column purification the Michael addition products 100, 101 and 102 are isolated. Treatment of the free amine thus obtained with HCl in dioxane affords the corresponding hydrochloride salts 103, 104 and 105 respectively.

Example 28

Alkenylation of Polymines Using Alkyl Acrylates Under Michael Addition Condition Scheme 28$^a$

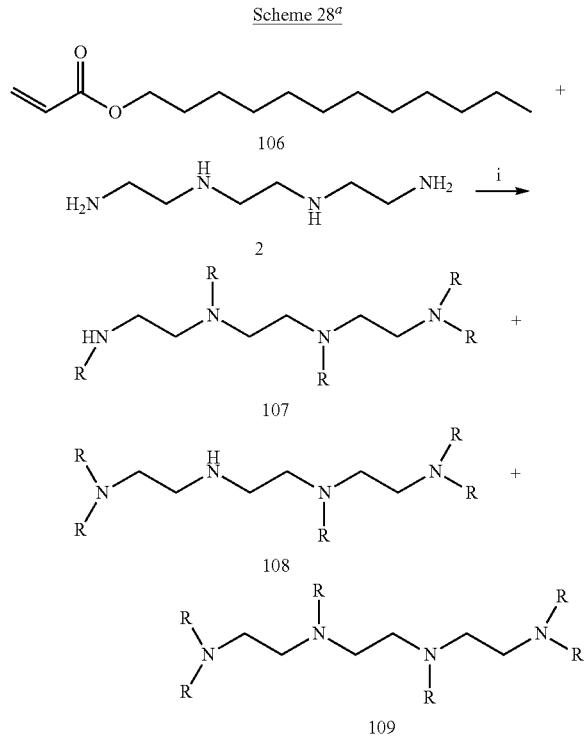

$^a$(i) Methanol-water, 40° C. or Methanol, water, boric acid, room temperature

R =

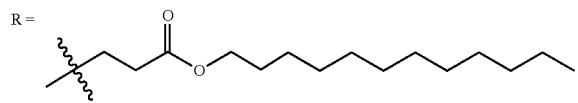

Method 1: n-Dodecylacrylate (106) is stirred with triethylenetetramine 2 in methanol-water at 40° C. to obtain compounds 107, 108 and 109. The products are isolated by chromatographic separation.

Method 2: n-Dodecylacrylate (106) is stirred with triethylenetetramine 2 in the presence of boric acid in methanol-water at 40° C. to obtain compounds 107, 108 and 109. The products are isolated by chromatographic separation.

Example 29

Alkenylation of Diamines Using Alkyl Acrylates Under Michael Addition Condition

Scheme 29$^a$

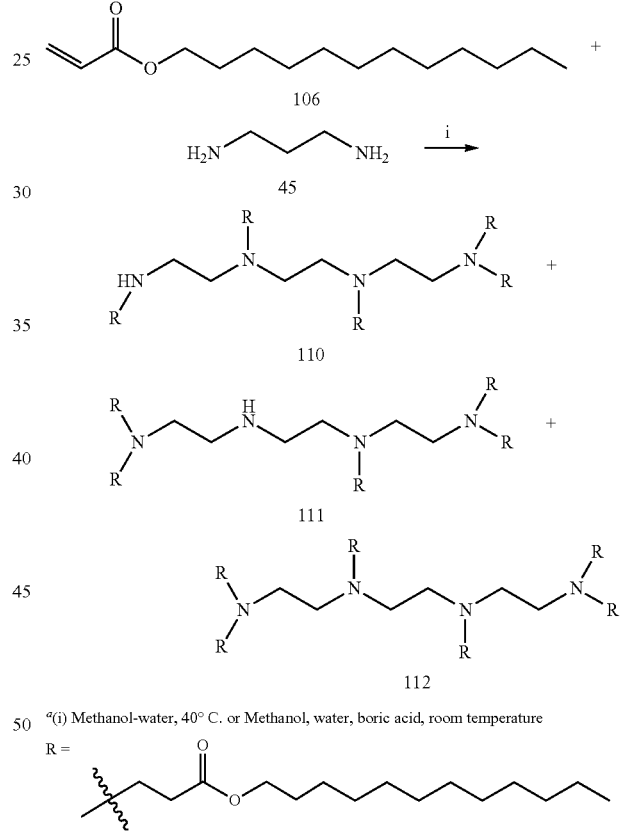

$^a$(i) Methanol-water, 40° C. or Methanol, water, boric acid, room temperature

R =

Method 1: n-Dodecylacrylate (106) is stirred with triethylenetetramine 2 in methanol-water at 40° C. to obtain compounds 110, 111 and 112. The products are isolated by chromatographic separation.

Method 2: n-Dodecylacrylate (106) is stirred with triethylenetetramine 2 in the presence of boric acid in methanol-water at 40° C. to obtain compounds 110, 111 and 112. The products are isolated by chromatographic separation.

Example 30

Synthesis of Octadeca-9,12-dienoic acid 3-dimethylamino-2-octadeca-9,12-dienoyloxy-propyl ester 3

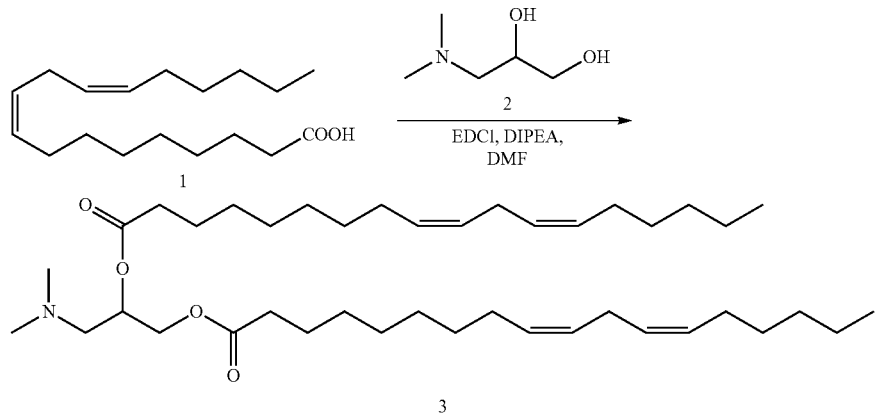

To a solution of the linoleic acid (25 g, 89.1 mmol) in anhydrous DMF (60 mL), diisopropyl ethylamine (17 mL, 100 mml) was added at room temperature with stirring followed by 3-(dimethylamino)-1,2-propanediol (4.8 g, 40.5 mmol) and EDCI (17.25 g, 89.9 mmol) and the mixture was stirred at room temperature overnight. The TLC of the reaction mixture (eluent 20% EtOAc in hexanes) showed the completion of the reaction. The reaction mixture was poured into ice water and extracted with ethyl acetate (2×100 mL). The combined organic layers were washed with water (100 mL), saturated NaHCO$_3$ (100 mL) and dried over Na$_2$SO$_4$. Concentration of the organic layer provided the crude product which was purified by column chromatography (silica gel, eluent: 20% EtOAc in hexanes). The fractions containing pure product was pooled and concentrated. The pure ester was isolated as a clear liquid (5.7 g, 22%). MS m/z 645 (M+H). $^1$H NMR CDCl$_3$ δ 0.88 (t, J=6.3 Hz, 6H), 1.20-1.39 (m, 28H), 1.61 (t, J=4.9 Hz, 12H), 2.03-2.08 (m, 8H), 2.26-2.38 (m, 10H), 2.44-2.56 (m, 2H), 2.76 (t, J=6.3 Hz, 4H), 4.09 (dd, J=6.1 Hz & 11.9 Hz, 1H), 4.36 (dd, J=3.3 & 11.9 Hz, 1H), 5.29-5.34 (m, 1H), 5.34-5.41 (m, 8H). $^{13}$C NMR CDCl$_3$ δ 14.30, 22.79, 25.08, 25.10, 25.83, 27.40, 29.26, 29.30, 29.34, 29.42, 29.55, 29.83, 31.73, 34.32, 34.58, 46.01, 59.37, 64.02, 128.08, 128.24, 130.21, 130.42, 173.39, 173.65.

Example 31

Exemplary Procedure for Making a Liposome Using Extrusion

Prepare stock solutions of ND98 (120 mg/ml), cholesterol (25 mg/ml), and C16-PEG-Cer-2000 (100 mg/ml) in 100% ethanol. Store at −20° C. Warm in 37° C. water bath prior to preparing formulations (up to 30 minutes is helpful—it takes a while for the cholesterol to dissolve completely).

2×2 ml Prep

To a 15 ml Falcon tube, add:
1) 125 ul of lipid
2) 200 ul of cholesterol
3) 70 ul of PEG
4) 5 ul of 100% ethanol
5) 600 ul of 25 mM sodium acetate pH 5
6) Mix gently (setting 5) on a vortex
7) Add 20 mg sucrose
8) Vortex again until sucrose has dissolved
9) Add 1 ml of a freshly-prepared (in a new Falcon tube) 1 mg/ml solution of siRNA in 25 mM sodium acetate (=100 ul of 10 mg/ml siRNA+900 ul of 25 mM sodium acetate)
10) Vortex lightly (setting 1, with Falcon tube holder adapter) for 20 minutes
11) After 15 minutes (5 minutes remaining), clean extruder
12) Extrude 11 times through two 200 nm filters at 40° C.
13) Dialyze against PBS, pH 7.4 for 90 minutes at RT in 3,500 MWCO Pierce cassettes

Example 32

Exemplary Procedure for Making a Liposome without Using Extrusion

Prepare stock solutions of ND98 (120 mg/ml), cholesterol (25 mg/ml), and C16-PEG-Cer-2000 (100 mg/ml) in 100% ethanol. Store at −20° C. Warm in 37° C. water bath prior to preparing formulations (up to 30 minutes is helpful—it takes a while for the cholesterol to dissolve completely).

To a 15 ml Falcon tube, add:
1) 125 ul of lipid
2) 200 ul of cholesterol
3) 70 ul of PEG
4) 495 ul of 100% ethanol
5) 100 ul of water
6) Prepare 1 ml of 1 mg/ml siRNA in 100-300 mM sodium acetate, pH ~5
7) Rapidly mix lipids in 90% ethanol with siRNA in acetate buffer
8) Dialyze (or use ultrafiltration) against 100-300 mM sodium acetate, pH ~5 to remove ethanol
9) Dialyze (or use ultrafiltration) against PBS to change buffer conditions

Example 33

Exemplary Protocol for Quantification of RNA in a Liposome Sample

The procedure below can be used to quantify (1) the proportion of entrapped siRNA and (2) the total amount of siRNA in a liposome.

Materials:
RiboGreen (Molecular Probes)
2% Triton X-100
TE buffer

Protocol (96-Well Plate Format)
1. Dilute samples to be tested in TE buffer such that siRNA concentration is ~2 ug/mL (0.4-4 ug/mL). Note dilution of samples.
2. Array 50 uL of each sample into 2 wells (e.g. samples arrayed into 2 rows of microplate)
3. Add 50 uL of TE buffer to one of each of the 2 samples (e.g. top row samples). This sample will be used to determine "free" siRNA.
4. Add 50 uL of 2% Triton X-100 to the remaining of the 2 samples (e.g. bottom row samples). This sample will be used to determine "total" siRNA.
5. Prepare standard siRNA dilutions by using known amounts of the siRNA to be quantified. Start with 50 uL of 4 ug/mL, and do 2-fold dilutions. Add 50 uL of 2% Triton X-100 to each of the standard sample dilutions.
6. Incubate for 15 min at room temperature.
7. Add 100 uL of diluted RiboGreen to all of the samples. Diluted RiboGreen to be used at 1:100 dilution.
8. Read plate in fluorimeter (Victor2) using FITC settings.

Calculations:
Final volume in wells will be 200 uL.
RiboGreen will be at 1:200 final dilution.
Triton X-100 will be at 0.5%.
Standards will be dilutions starting from 1 ug/mL.
Plot Standard Curve, perform linear fit.
Determine Entrapment %=100*(1-"free" signal/"total" signal)
Determine [siRNA]: First convert "total" signal to concentration using the standard curve, then multiply by dilution factor.

Example 34

Comparison of Lipid Moieties as Formulated into Liposomes

The effectiveness of lipid compositions can be tested by determining the relative ability of a lipid to deliver an siRNA moiety to a target. For example, the silencing of a target indicates that the siRNA is delivered into the cell. Applicants have compared liposome complexes that include each of the following lipid moieties together with siRNA that is used to silence Factor VII (FVII).

Initially unpurified reaction mixtures were used. Different ND98 reaction mixtures were generated by synthesizing product at different ND:98 monomer ratios: ND:98=1:1, 2:1, 3:1, 4:1, 5:1, and 6:1. ND98 is generated by reacting ND, the structure of which is provided below:

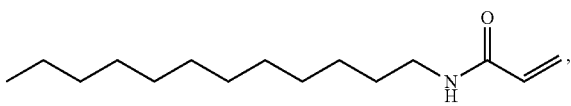 [SMILES: C=CC(=O)NCCCCCCCCCCCC]

with amine 98, the structure of which is provided below

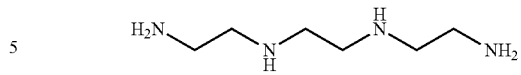

in the ratios provided above (i.e., ND:98=1:1, 2:1, 3:1, 4:1, 5:1, and 6:1).

Liposomes were formulated at ND98:cholesterol: FED2000-CerC16:siRNA=15:0.8:7:1 (wt ratios). Liposomes prepared with ND:98=1:1 and 2:1 precipitated drying formulation and were not characterized further.

Table 1, below provides the average particle size and percent entrapment of the liposomes using the various monomer ratios (i.e, the number indicating the ratio of ND relative to 98).

TABLE 1

|  | Z-Avg. Particle size (nm) | % Entrapment |
| --- | --- | --- |
| ND98 3 | 56 | >95 |
| ND98 4 | 56 | >95 |
| ND98 5 | 81 | 93 |
| ND98 6 | 72 | 74 |

FIG. 1 provides the results of the FVII silencing assay for the various monomer ratios using an experimental dosing of 2 mg/kg siRNA. The results suggest that the ND98 5 tail moiety and/or ND 98 6 tail moiety are the active species as these are the most abundants species on the ND98 6:1 preparation. As described a 5 tail moiety indicates a compound where 5 of the hydrogens on the starting amine 98 have been reacted with a starting acrylamide moiety ND. A 6 tail moiety indicates a compound where 6 of the hydrogens on the starting amine 98 have been reacted with an acrylamide moiety ND. Accordingly, the number of "tails" indicates the number of reacted hydrogens on the starting amine.

Example 35

Determination of Preferred Lipid Isomer

Applicants purified ND98 lipid products. ND98 lipid moieties are the lipid moieties resulting in the reaction of ND, the structure of which is provided below:

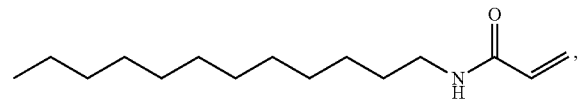 [SMILES: C=CC(=O)NCCCCCCCCCCCC]

with amine 98, the structure of which is provided below

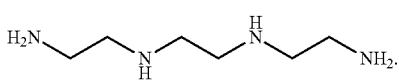

Applicants tested 4-tail mixed isomers of ND98 (i.e., where four of the amine hydrogens have been reacted with the ND acrylamide above), single structural isomers of 5-tail ND98 (i.e., where for of the amine hydrogens have been reacted with the ND acrylamide above). Examples of the two 5 tail isomers are provided below:

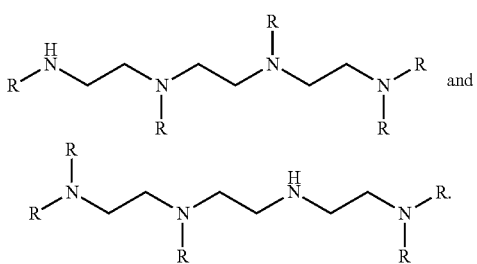

Liposomes of the purified ND98 products were formulated with the following components in the following ratios: ND98:cholesterol:PEG2000-CerC16:siRNA=15:5:7:1 (wt ratios).

Table 2, below provides the average particle size and percent entrapment of the liposomes using the various monomer ratios (i.e, the number indicating the ratio of ND relative to 98).

TABLE 2

|  | Z-Avg. Particle size (nm) | % Entrapment |
|---|---|---|
| ND98 1 | 88 | >95 |
| ND98 2 | 104 | 86 |
| ND98 3 | 115 | 86 |
| ND98 4 | 92 | >95 |

Figure 2:
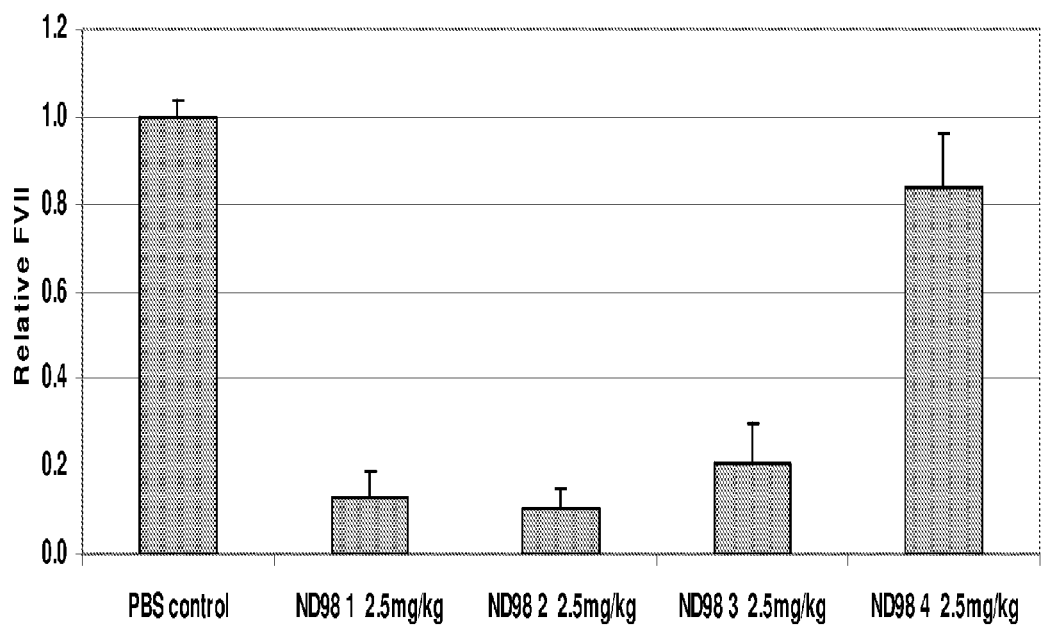
FIG. 2 depicts a bar graph comparing the efficacy of various ND98 compositions.

For the purposes of table 2 and FIG. 2:
ND98 1 = 5-tailed (isomer I);
ND98 2 = 5-tailed (isomer I + II);
ND98 3 = 5-tailed (isomer II);
and ND98 4 = 4-tailed.

The liposomes where administered with siRNA at a does of 2.5 mg/kg, and evaluated for the silencing of FVII. FIG. 2 provides the results of the 4 tailed isomer mixture, the single 5 tailed isomers (i.e., isomer I and II) and the mixture of 5 tailed isomers (i.e., isomer I and II).

Example 36

Determination of Preferred ND98 Isomer

Figure 3:
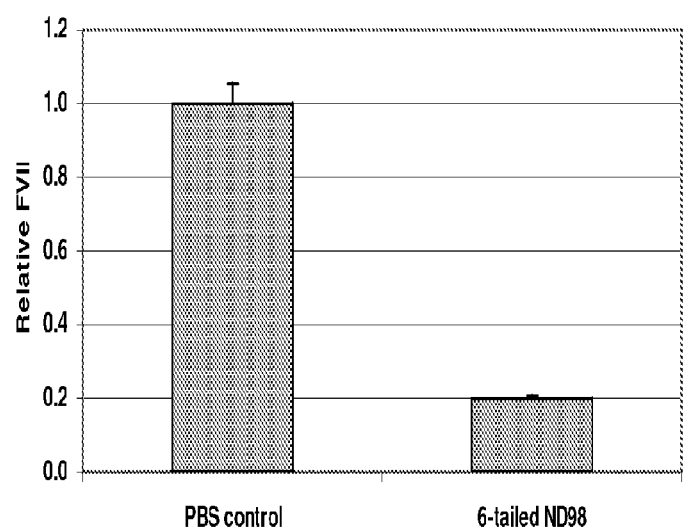
FIG. 3 depicts a bar graph demonsrating the efficacy of a 6-tailed isomer of ND98.

A purified isomer of 6 tailed ND98 was prepared and purified. ND98 structure corresponds with those described in examples 34 and 35 above. The 6 tail indicates that all of the hydrogens of amine 98 have been reacted with the ND starting material. With this lipid starting material, liposomes were formulated at the following ratios: ND98:cholesterol:PEG2000-CerC16:siRNA=15:5:7:1 (wt ratios). FIG. 3 demonstrates the effectiveness of the ND98 6 tail isomer in delivery of siRNA, which effectively silenced FVII.

Example 37

Liposome Particle Size Using Various ND98 Lipid Starting Materials

A plurality of lipid starting materials having the ND98 structures (as provided in examples 34 and 35 above) were formulated into liposomes. The particle size of the liposomes were evaluated, the results of which are provided in table 3 below:

| Formulation | Particle Diameter (nm) |
|---|---|
| ND98 3 (Exp 1) | 56 |
| ND98 4 (Exp 1) | 56 |
| ND98 5 (Exp 1) | 81 |
| ND98 6 (Exp 1) | 72 |
| ND98 1 (Exp 2) | 88 |
| ND98 2 (Exp 2) | 104 |
| ND98 3 (Exp 2) | 115 |
| ND98 4 (Exp 2) | 92 |
| 6-tailed ND98 (Exp 3) | 127 |

Example 38

Extrusion Free Liposome Formulation

Liposome complexes were prepared using ND98 lipids. The formulations include the following ratios: ND98:cholesterol:PEG2000-CerC16:siRNA=15:5:7:1 (wt. ratios). The liposomes were prepared without extrusion, as generally described in Example 32 above. Two samples were prepared, a first sample having the following: 100 mM=siRNA prepared in 100 mM sodium acetate with a first dialysis step in 100 mM acetate; and a second sample having 300 mM=siRNA prepared in 300 mM sodium acetate with a first dialysis step in 300 mM acetate.

Figure 4:
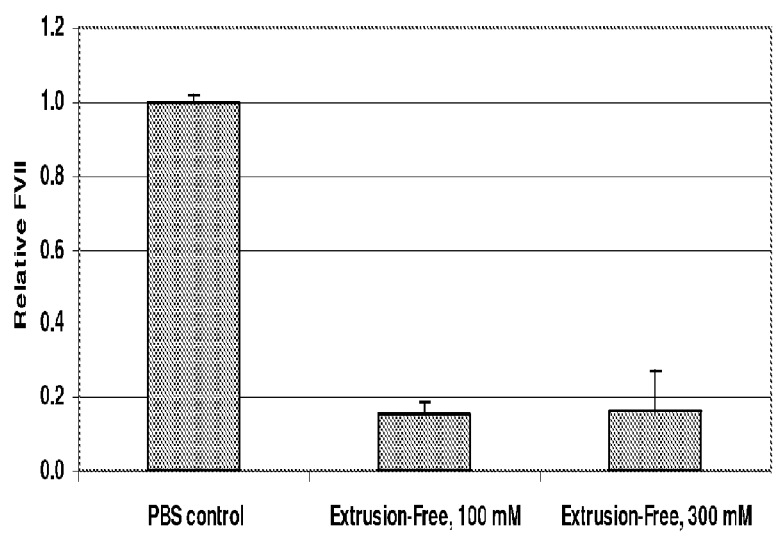
FIG. 4 depicts a bar graph comparing the efficacy of association complexes prepared using two different procedures.

FIG. 4 shows the results of an FVII silencing assay, demonstrating the comparative activity of the formulations made using the various processes.

Example 39

Regioselective Synthesis of Cationic Lipid 7—Strategy 1

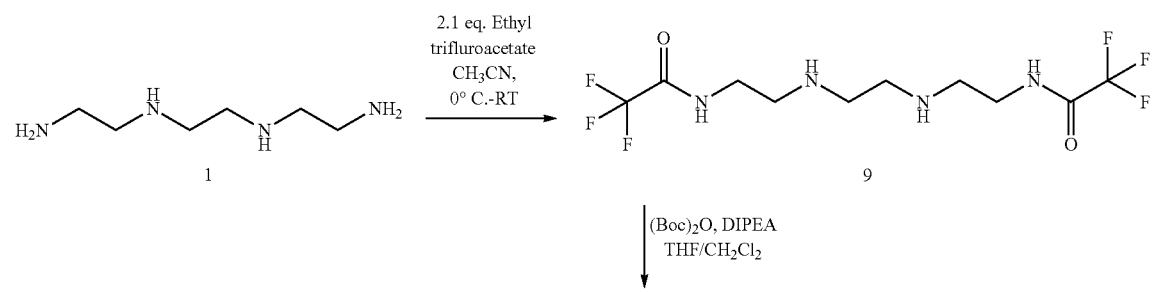

Scheme 31$^a$

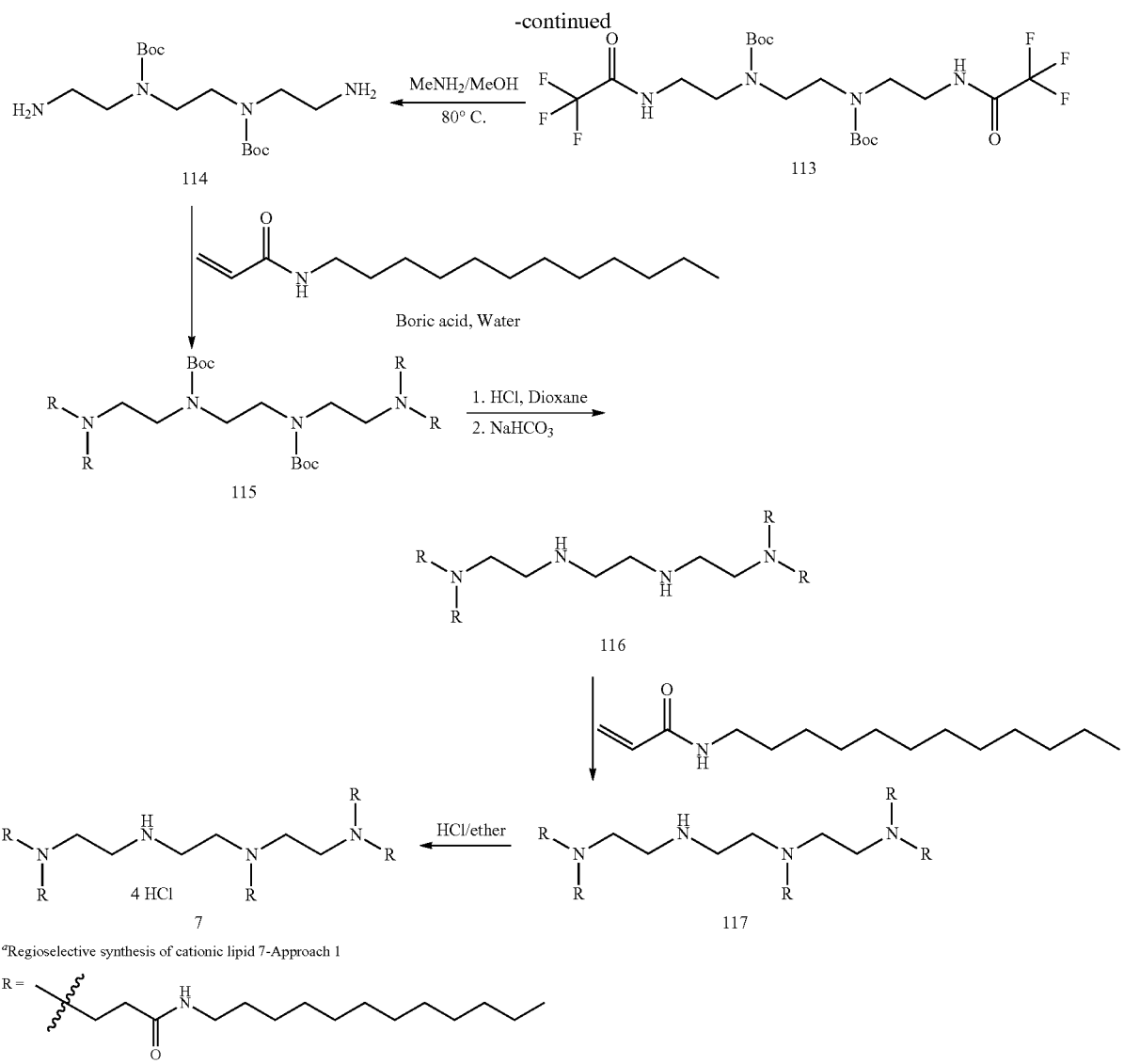

<sup>a</sup>Regioselective synthesis of cationic lipid 7-Approach 1

Step 1. Preparation of compound 9: Triethylenetetramine, 1 (48.83 g, 0.334 mol, purchased from Sigma-Aldrich) in anhydrous acetonitrile (500 mL) was cooled over an ice bath under constant stirring. Ethyl trifluoroacetate (79.6 mL, 0.668 mol) was added to the solution and after completion of the addition the reaction mixture was allowed to warm to room temperature and stirred for 20 h. Solvent and volatiles were removed under reduced pressure and the residue was dissolved in minimum amount of warm dichloromethane (100 mL) and to it cold hexanes was added with stirring. The precipitated product was cooled in ice and filtered to get a white solid (112.2 g, 99%).

Step 2. Synthesis of (2-{tert-butoxycarbonyl-[2-(2,2,2-trifluoro-acetylamino)ethyl]-amino}-2-(2,2,2-trifluoro-acetylamino)ethyl]-carbamic acid tert-butyl ester 113

The trifluoroacetamide 9 (112.2 g, 0.332 mol) was dissolved in $CH_2Cl_2$/THF (600 mL/100 mL) and to it diisopropylethylamine (129.25 g, 1 mol) was added and stirred over an ice bath. Di-tert-butyl dicarbonate (145 g, 0.664 mol, purchased from Sigma Aldrich) in $CH_2Cl_2$ (100 mL) was added drop wise to the reaction mixture and stirred overnight. Solvents were removed and the residue was stirred with a saturated solution of $NaHCO_3$ (400 mL) and filtered and washed with hexanes (100 mL) and dried in vacuo at 45° C. overnight to obtain the pure diboc compound as a white solid (167 g, 94%). $^1H$ NMR for 113 (DMSO-d6, 400 MHz) δ=9.60-9.40(m, 2H), 3.35-3.15(m, 12H), 1.36(s, 18H) MS: $C_{15}H_{24}F_6N_4O_4$ Cal. 438.17. Found 439.20 ($M^+$) MS: $C_{20}H_{32}F_6N_4O_6$ Cal. 538.22. Found 539.20($M^+$).

Step 3. Synthesis of (2-amino-ethyl)-{2-[(2-amino-ethyl)-tert-butoxycarbonyl-amino]-ethyl}carbamic acid tert-butyl ester The acetamide 113 (167 g, 0.31 mol) was taken in a stainless steel pressure reactor and to it a solution of methylamine (33% by wt) in ethanol (200 ml) was added. The mixture was warmed to 90° C. and stirred for 24 h. Reaction was monitored by mass spectra. All the solvents were removed under reduced pressure and the residue was subjected to high vacuum at 80° C. to yield the product 114 (103 g, 96%) as gummy liquid and this compound could be used for the next reaction with out further purification. $^1H$ NMR (CDCl$_3$, 400 MHz) δ=3.20-3.00(m, 4H), 2.62-2.38(m, 8H), 1.32(s, 9H). MS: $C_{11}H_{26}N_4O_2$ Cal. 246.21. Found 246.20($M^+$).

Step 4. Synthesis of Michael addition product 115

The diamine 114 (103 g, 0.297 mmol), N-dodecylacrylamide (356 g, 1.487 mol) and saturated solution of boric acid in water (30 mL) were taken together in a pressure reactor and heated at 90° C. for 4 days. The reaction was monitored by TLC and Mass spectra. The reaction mixture was extracted into dichloromethane (DCM), washed successively with NaHCO$_3$ solution and brine, dried over anhydrous sodium sulfate. Solvent was removed in vacuo and residue thus obtained was purified by silica gel column chromatography (gradient elution-Ethyl acetate then 3-10% MeOH/DCM) to obtain 115 as a pale yellow solid (228 g, 59%). MS: $C_{76}H_{150}N_8O_8$ Cal. 1303.16. Found 1304.20 (M$^+$).

Step 5. Preparation of diamine-116

4M HCl in dioxane (500 mL) was added to a solution of the diboc compound 115 (228 g, 0.175 mol) in methanol (100 mL) and the mixture was stirred at room temperature for 2 days. The reaction was monitored by Mass spectra. After the complete disappearance of the starting diboc compound, the precipitated hydrochloride salt was filtered, washed with THF (100 mL) and dried to get the pure salt as a white powder (178 g, 93%). The above salt was treated with saturated NaHCO$_3$ (1 L) and extracted with dichloromethane (3×600 mL). The combined organic extracts were dried and concentrated to isolate the tetramer as a white solid (164 g, 85%). MS: $C_{66}H_{134}N_8O_4$ Cal. 1103.05. Found 1104.10 (M$^+$).

Step 6. Synthesis of 117: Compound 116 (164 g, 149 mmol), N-dodecylacrylamide (35.6 g, 149 mmol) and saturated solution of boric acid in water (30 mL) were taken together in a pressure reactor and heated at 90° C. for 3 days. Progress of the reaction was monitored by TLC and Mass spectra. The reaction mixture extracted into dichloromethane (DCM), washed successively with NaHCO$_3$ solution and brine, dried over anhydrous sodium sulfate. Solvent was removed in vacuo and residue thus obtained was purified by silica gel (2 Kg) column chromatography (gradient elution- 0:5:95-10:10:80% TEA/MeOH/DCM) to obtain 117 as a pale yellow solid (83.8 g, 42%). MS: $C_{76}H_{150}N_8O_8$ Cal. 1303.16. Found 1304.20 (M$^+$). The material was compared with authentic sample TLC (qualitative), HPLC and Mass spectra. MS: $C_{81}H_{163}N_9O_5$ Cal. 1342.28. Found 1343.30 (M$^+$).

Step 7. Synthesis of the Hydrochloride Salt 7

The amine 117 (54 g, 40 mmol) was dissolved ethanol (100 mL) and to it 200 mL of 2M HCl in ether was added and the mixture was stirred at room temperature overnight. Nitrogen was bubbled to the reaction mixture and the outlet was passed through dryrite and to a 10% solution of KOH. After 30 minute, the reaction mixture was concentrated to dryness and the residue was re-dissolved in 500 mL of anhydrous ethanol and the mixture was concentrated in a rotary evaporator. This process was again repeated once again and the thus obtained residue was dried in a vacuum oven at 43° C. overnight. The pure product was isolated as a cream powder (59.5 g, 99%).

Example 40

Regioselective Synthesis of Cationic Lipid 7—Strategy 2

Method 1

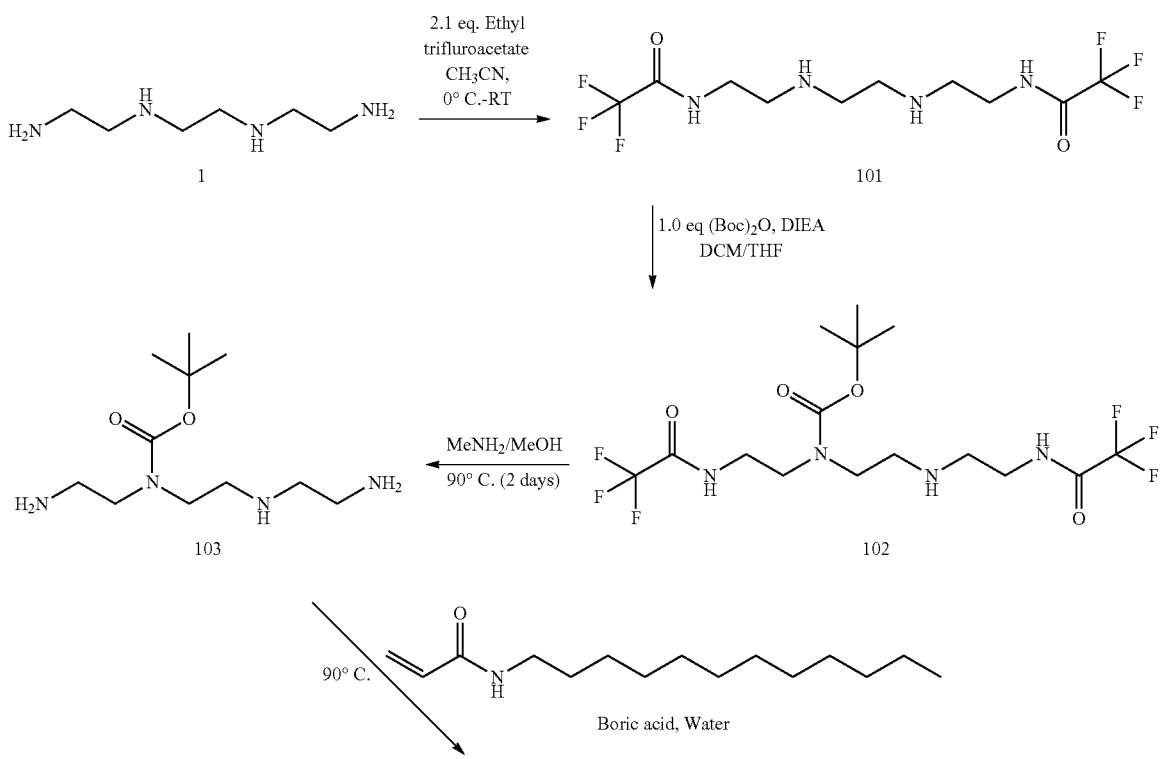

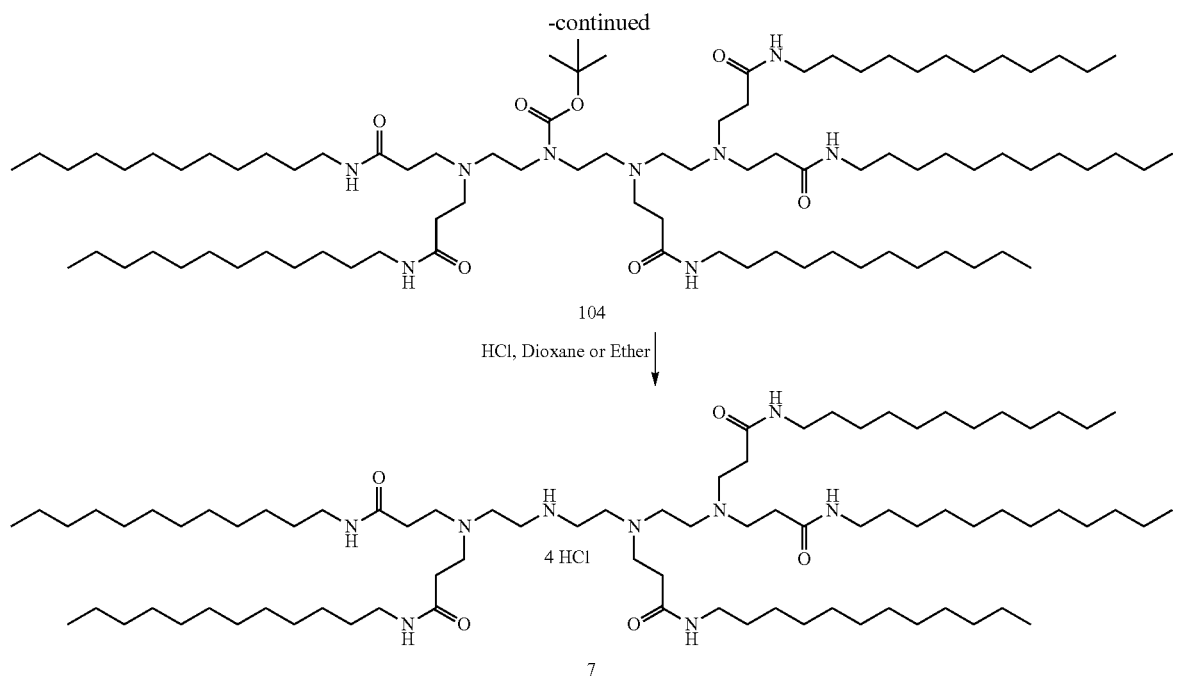

Step 1: Triethylenetetramine, 1 (200 g g, 1.37 mol, purchased from Sigma-Aldrich) in acetonitrile (2 L) in a 4 neck 5 L flask with overhead stirrer was cooled over an ice bath under constant stirring. Ethyl trifluoroacetate (388.5 g, 2.74 mol) was added to the stirring solution and stirred for 20 h. Solvent and volatiles were removed under reduced pressure; the residue was triturated with a mixture of DCM/Hexane and filtered to get 101 as white solid (429 g, 93%). The product thus obtained could be used for the next reaction without further purification. MS: $C_{10}H_{16}F_6N_4O_2$ Cal. 338.12. Found 339.0 ($M^+$).

Step 2: Crude compound 101 (427 g, 1.26 mol) was dissolved in a mixture of solvents (3 L, THF/DCM (1:2)) and stirred over an ice-water bath. Di-tert-butyl dicarbonate (($Boc)_2O$, 270 g, 1.26 mol, purchased from Sigma Aldrich) and DIEA (500 mL, 2.86 mol) were added to the reaction mixture and stirred overnight. Solvents were removed and the residue was extracted into dichloromethane (DCM, 1000 mL), washed successively with NaHCO3 solution (500 mL), water (500 mL×2) and brine, dried over anhydrous sodium sulfate. Solvents were removed in vacuo and residue thus obtained was triturated with DCM/Hexane (2:1) and filtered. Solvents were removed and the residue was dried under high vacuum to get the compound 102 as gummy liquid (523 g).

Part of the compound 102 was purified by silica gel chromatography (gradient elution, Ethyl acetate, followed by 3-10% MeOH/DCM) to obtain compound 102 as gummy liquid (102.00 g). $^1H$ NMR for 102 (DMSO-d6, 400 MHz) δ=9.60-9.10(m, 3H), 3.35-3.25(m, 4H), 3.25-3.20(2, 2H), 3.20-3.10(m, 2H), 2.68-2.58(m, 4H), 1.35(s, 9H). MS: $C_{15}H_{24}F_6N_4O_4$ Cal. 438.17. Found 439.20($M^+$).

Step 3: Purified compound 102 (102.0 g, 233.40 mmol) was dissolved in Ethanol/Methyl amine (400 ml, 33 wt % methylamine solution in EtOH) at ambient temperature in a pressure reactor. The mixture was warmed to 90° C. and stirred for two days. Reaction was monitored by mass spectra. All the solvents were removed under reduced pressure and the residue was subjected to high vacuum at 80° C. to yield the product 103 (58.00 g, 99%) as gummy liquid and this compound could be used for the next reaction with out further purification. $^1H$ NMR (CDCl$_3$, 400 MHz) δ=3.20-3.00(m, 4H), 2.62-2.38 (m, 8H), 1.32(s, 9H). MS: $C_{11}H_{26}N_4O_2$ Cal. 246.21. Found 247.20($M^+$).

Step 4: Triamine 103 (56.00 g, 227.64 mmol), N-dodecylacrylamide (327.00 g, 1365 mmol) and saturated solution of boric acid in water (50 mL) were taken together in a pressure reactor and heated at 90° C. for 6 days. The reaction was monitored by TLC and Mass spectra. The reaction mixture extracted into dichloromethane (DCM), washed successively with NaHCO$_3$ solution (400 mL) and dried over anhydrous sodium sulfate. Solvent was removed in vacuo and residue thus obtained was purified by silica gel column chromatography (gradient elution-Ethyl acetate then 3-10% MeOH/DCM) to obtain 104 as a pale yellow solid (186 g, 57%). $^1H$ NMR (CDCl$_3$, 400 MHz) δ=7.20(bs, 1H), 7.05(bs, 1H), 6.85 (bs, 1H), 6.74(bs, 1H), 3.25-3.03 (m, 12H), 2.80-2.60(m, 8H), 2.55-2.21(m, 12H) 1.52-1.45(m, 10H), 1.42 (s, 9H), 1.34-1.20(m, 100H), 0.87(t, J=6.5 Hz, 15H). MS: $C_{86}H_{171}N_9O_7$ Cal. 1442.33. Found 1443.30($M^+$).

Step 5: 4M HCl in dioxane (400 mL) was added into a solution of compound 105 (184.00 g, 127.23 mmol) in dioxane (300 mL). The reaction mixture was then allowed to stir for overnight. The reaction was monitored by Mass spectra. Excess HCl was removed by passing nitrogen through the solution. Solvents were removed under vacuum and residue was co evaporated three times with ethanol (500 mL×3) to yield a pale yellow gummy solid 7 (186.00 g, 98%) as tetrahydrochloride salt. The material was compared with authentic sample TLC (qualitative), HPLC and Mass spectra. MS: $C_{81}H_{163}N_9O_5$ Cal. 1342.28. Found 1343.30 ($M^+$).

Method 2

Compound 102 was prepared as described in Method 1: steps 1 and 2. The crude product obtained from step 2 of Method 1 was used for the next reaction without further purification.

Step 1: Compound 102 (103.45 g, 238.90 mmol, crude compound from step 2, Method 1 was dissolved in Ethanol/Methyl amine (400 ml, 33 wt % methylamine solution in EtOH) at ambient temperature in a pressure reactor. The mixture was warmed to 90° C. and stirred for two days. Reaction was monitored by mass spectra. All the solvents were removed under reduced pressure and the residue was subjected to high vacuum at 80° C. over a water bath to yield the product 103 (63.50 g) as pale yellow gummy liquid and this compound could be used for the next reaction with out further purification.

Step 4: Triamine 103 (63.50 g, 238 mmol), N-dodecylacrylamide (320.00 g, 1338 mmol) and saturated solution of boric acid in water (50 mL) were taken together in a pressure reactor and heated at 90° C. for 6 days as described in step 4, Method 1. The reaction was monitored by TLC and Mass spectra. The reaction mixture extracted into dichloromethane (DCM), washed successively with NaHCO$_3$ solution (400 mL) and dried over anhydrous sodium sulfate. Solvent was removed in vacuo and residue thus obtained was purified by silica gel column chromatography (gradient elution-Ethyl acetate then 3-10% MeOH/DCM) to obtain 104 as a pale yellow solid (65.2 g, 20%).

Step 5: 2M HCl in ether (800 mL) was added to compound 105 (65.00 g, 45 mmol). The reaction mixture was then allowed to stir for overnight. The reaction was monitored by Mass spectra. Excess HCl was removed by passing nitrogen through the solution. Solvents were removed under vacuum and residue was co evaporated three times with ethanol (500 mL×3) to yield a pale yellow gummy solid 7 (66 g, 98%) as tetra hydrochloride salt. The material was compared with authentic sample TLC (qualitative), HPLC and Mass spectra. MS: $C_{81}H_{163}N_9O_5$ Cal. 1342.28. Found 1343.30 (M$^+$).

Method 3

Compound 102 was prepared as described in Method 1: steps 1 and 2. The crude product obtained from step 2 of Method 1 was used for the next reaction without further purification.

Step 3: Compound 102 (105.20 g, 240 mmol, crude compound from method I) was dissolved in Ethanol/Methyl amine (400 ml, 33 wt % methylamine solution in EtOH) at ambient temperature in a pressure reactor. The mixture was warmed to 90° C. and stirred for two days. Reaction was monitored by mass spectra. All the solvents were removed under reduced pressure and the residue was subjected to high vacuum at 80° C. over a water bath to yield the product 103 (64.70 g) as pale yellow gummy liquid and this compound could be used for the next reaction with out further purification.

Step 4: Triamine 103 (64.70 g, 240 mmol), N-dodecylacrylamide (370.00 g, 1569 mmol) and saturated solution of boric acid in water (50 mL) were taken together in a pressure reactor and heated at 90° C. for 6 days. The reaction was monitored by TLC and Mass spectra. The reaction mixture extracted into dichloromethane (DCM), washed successively with NaHCO$_3$ solution (400 mL) and dried over anhydrous sodium sulfate. Solvent was removed in vacuo and residue thus obtained was purified by silica gel column chromatography (gradient elution-Ethyl acetate then 3-10% MeOH/DCM) to obtain 104 as a pale yellow solid (192 g).

Step 5: The desired compound 7 was obtained as hydrochloride salt from compound 104 as described in step 5, Method 1 of Example 40. Compound 7: 194 g (98%) as tetrahydrochloride salt. The material was compared with authentic sample TLC (qualitative), HPLC and Mass spectra. MS: $C_{81}H_{163}N_9O_5$ Cal. 1342.28. Found 1343.30 (M$^+$).

Example 41

Figure 5:
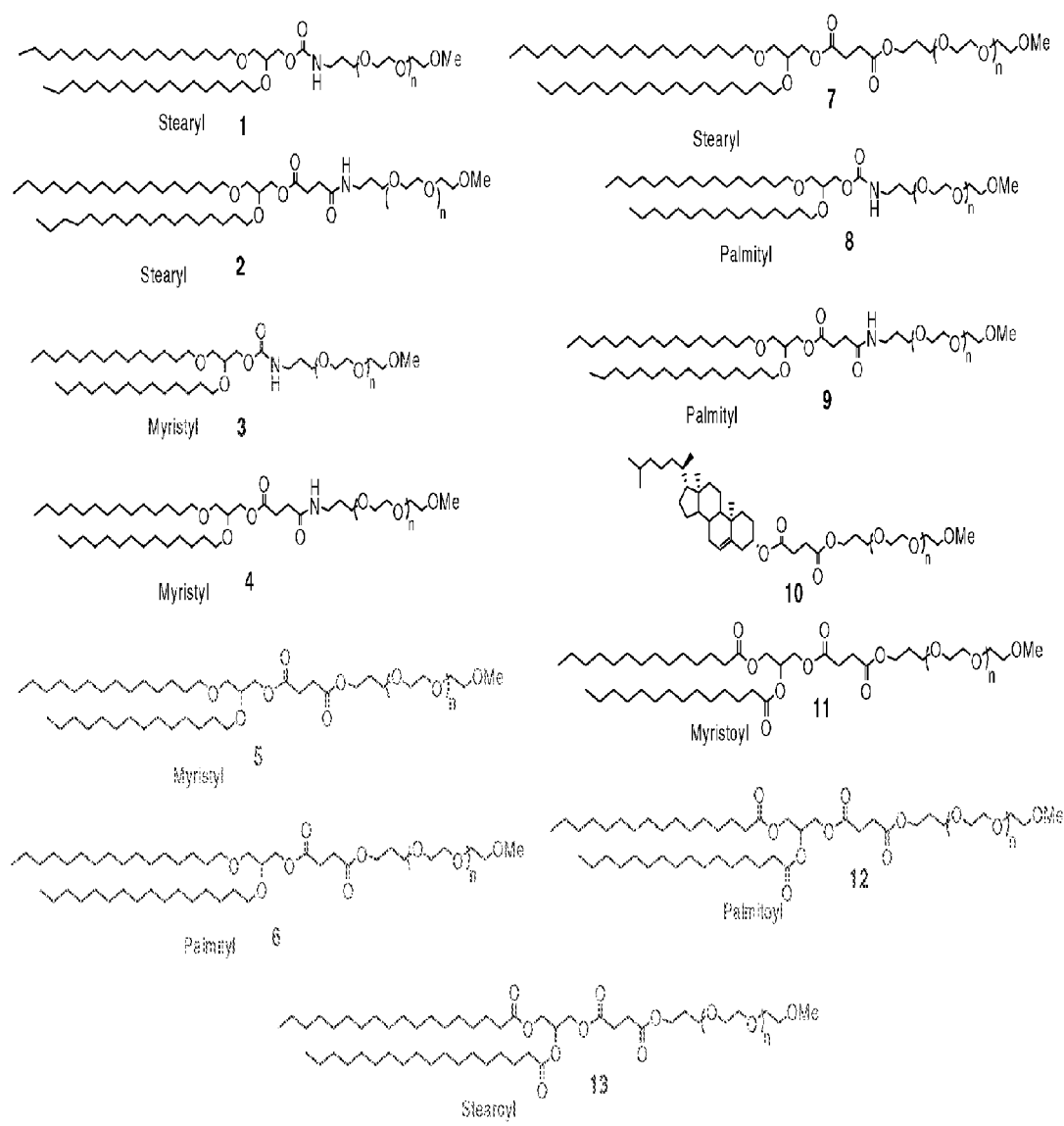
FIG. 5 depicts various PEG lipid moieties, including those having various chain lengths.

Comparison of Activity of siRNA Formulated into Various Association Complexes Having Differing Peg-Lipid Moieties The effectiveness of lipid compositions can be tested by determining the relative ability of a lipid to deliver an siRNA moiety to a target. For example, the silencing of a target indicates that the siRNA is delivered into the cell. Applicants have compared association complexes that include one of 13 different PEG-lipid moieties as provided in FIG. 5, together with siRNA that is used to silence Factor VII (FVII).

PEG-lipids 1-13 were synthesized using the following procedures:

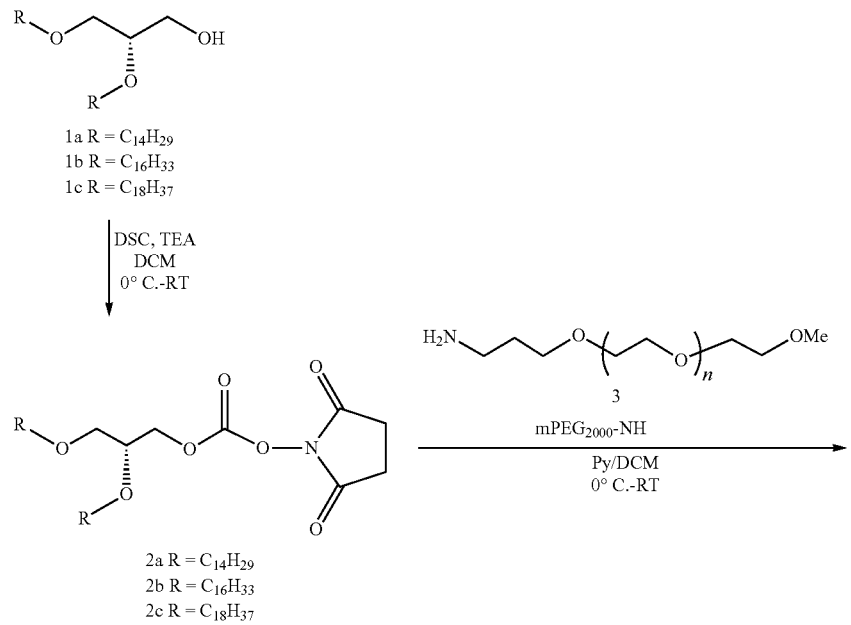

Scheme 1$^a$

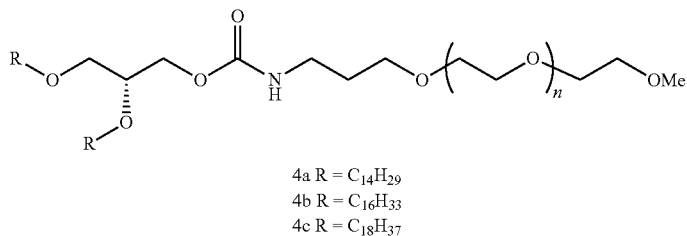

4a R = C₁₄H₂₉
4b R = C₁₆H₃₃
4c R = C₁₈H₃₇

<sup>a</sup>Scheme 1: mPEG2000-1,2-Di-O-alkyl-sn3-carbomoylglyceride

Preparation of compound 5: 1,2-Di-O-tetradecyl-sn-glyceride 1 (30 g, 61.80 mmol) and N,N'-succinimidylcarboante (DSC, 23.76 g, 1.5 eq) were taken in dichloromethane (DCM, 500 mL) and stirred over an ice water mixture. Triethylamine (25.30 mL, 3 eq) was added to stirring solution and subsequently the reaction mixture was allowed to stir overnight at ambient temperature. Progress of the reaction was monitored by TLC. The reaction mixture was diluted with DCM (400 mL) and the organic layer was washed with water (2×500 mL), aqueous NaHCO₃ solution (500 mL) followed by standard work-up. Residue obtained was dried at ambient temperature under high vacuum overnight. After drying the crude carbonate 3 thus obtained was dissolved in dichloromethane (500 mL) and stirred over an ice bath. To the stirring solution mPEG$_{2000}$-NH₂ (4, 103.00 g, 47.20 mmol, purchased from NOF Corporation, Japan) and anhydrous pyridine (80 mL, excess) were added under argon. The reaction mixture was then allowed stir at ambient temperature overnight. Solvents and volatiles were removed under vacuum and the residue was dissolved in DCM (200 mL) and charged on a column of silica gel packed in ethyl acetate. The column was initially eluted with ethyl acetate and subsequently with gradient of 5-10% methanol in dichloromethane to afford the desired PEG-Lipid 5 as a white solid (105.30 g, 83%). ¹H NMR (CDCl₃, 400 MHz) δ=5.20-5.12(m, 1H), 4.18-4.01(m, 2H), 3.80-3.70(m, 2H), 3.70-3.20(m, —O—CH₂—CH₂—O—, PEG-CH₂), 2.10-2.01(m, 2H), 1.70-1.60 (m, 2H), 1.56-1.45 (m, 4H), 1.31-1.15(m, 48H), 0.84(t, J=6.5 Hz, 6H). MS range found: 2660-2836.

Preparation of 4b: 1,2-Di-O-hexadecyl-sn-glyceride 1b (1.00 g, 1.848 mmol) and DSC (0.710 g, 1.5 eq) were taken together in dichloromethane (20 mL) and cooled down to 0° C. in an ice water mixture. Triethylamine (1.00 mL, 3 eq) was added to that and stirred overnight. The reaction was followed by TLC, diluted with DCM, washed with water (2 times), NaHCO₃ solution and dried over sodium sulfate. Solvents were removed under reduced pressure and the residue 2b under high vacuum overnight. This compound was directly used for the next reaction without further purification. MPEG$_{2000}$-NH₂ 3 (1.50 g, 0.687 mmol, purchased from NOF Corporation, Japan) and compound from previous step 2b (0.702 g, 1.5 eq) were dissolved in dichloromethane (20 mL) under argon. The reaction was cooled to 0° C. Pyridine (1 mL, excess) was added to that and stirred overnight. The reaction was monitored by TLC. Solvents and volatiles were removed under vacuum and the residue was purified by chromatography (first Ethyl acetate then 5-10% MeOH/DCM as a gradient elution) to get the required compound 4b as white solid (1.46 g, 76%). ¹H NMR (CDCl₃, 400 MHz) δ=5.17(t, J=5.5 Hz, 1H), 4.13(dd, J=4.00 Hz, 11.00 Hz, 1H), 4.05(dd, J=5.00 Hz, 11.00 Hz, 1H), 3.82-3.75(m, 2H), 3.70-3.20(m, —O—CH₂—CH₂—O—, PEG-CH₂), 2.05-1.90(m, 2H), 1.80-1.70 (m, 2H), 1.61-1.45(m, 6H), 1.35-1.17(m, 56H), 0.85(t, J=6.5 Hz, 6H). MS range found: 2716-2892.

Preparation of 4c: 1,2-Di-O-octadecyl-sn-glyceride 1c (4.00 g, 6.70 mmol) and DSC (2.58 g, 1.5 eq) were taken together in dichloromethane (60 mL) and cooled down to 0° C. in an ice water mixture. Triethylamine (2.75 mL, 3 eq) was added to that and stirred overnight. The reaction was followed by TLC, diluted with DCM, washed with water (2 times), NaHCO₃ solution and dried over sodium sulfate. Solvents were removed under reduced pressure and the residue under high vacuum overnight. This compound was directly used for the next reaction with further purification. MPEG$_{2000}$-NH₂ 3 (1.50 g, 0.687 mmol, purchased from NOF Corporation, Japan) and compound from previous step 2c (0.760 g, 1.5 eq) were dissolved in dichloromethane (20 mL) under argon. The reaction was cooled to 0° C. Pyridine (1 mL, excess) was added to that and stirred overnight. The reaction was monitored by TLC. Solvents and volatiles were removed under vacuum and the residue was purified by chromatography (first Ethyl acetate then 5-10% MeOH/DCM as a gradient elution) to get the required compound 4 c as white solid (0.92 g, 48%). ¹H NMR (CDCl₃, 400 MHz) δ=5.22-5.15(m, 1H), 4.16 (dd, J=4.00 Hz, 11.00 Hz, 1H), 4.06(dd, J=5.00 Hz, 11.00 Hz, 1H), 3.81-3.75(m, 2H), 3.70-3.20(m, —O—CH₂—CH₂—O—, PEG-CH₂), 1.80-1.70 (m, 2H), 1.60-1.48(m, 4H), 1.31-1.15(m, 64H), 0.85(t, J=6.5 Hz, 6H). MS range found: 2774-2948.

Scheme 2[a]

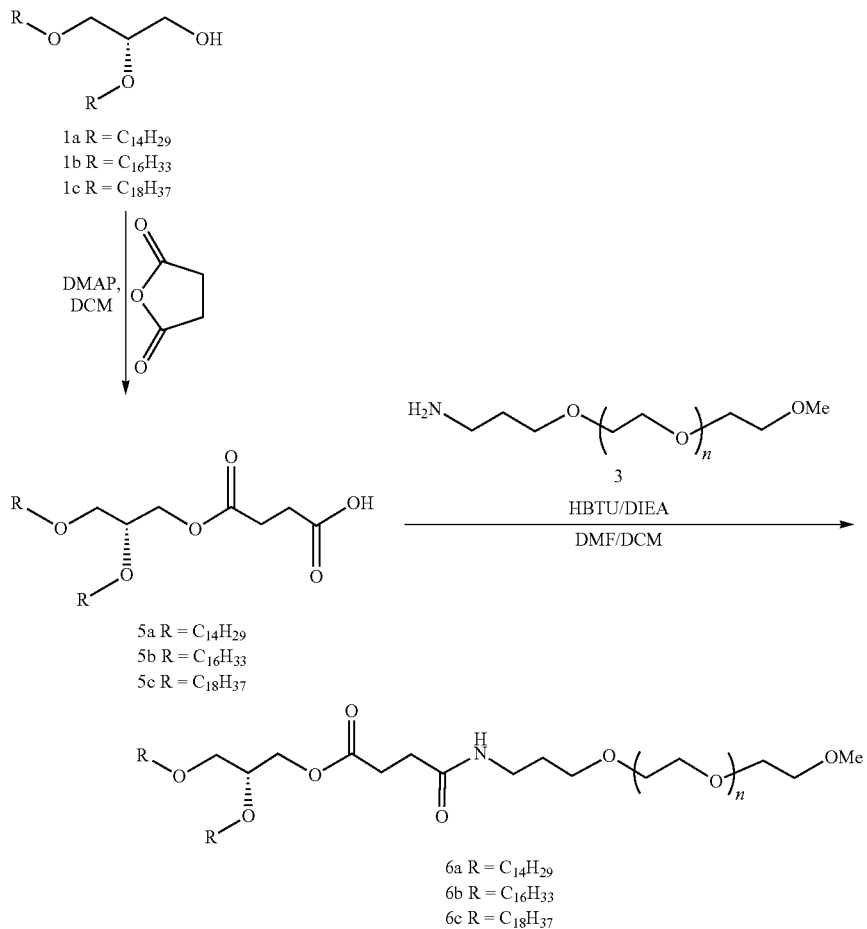

[a]Scheme 2: mPEG2000-1,2-Di-O-alkyl-sn3-succinylglyceride

Preparation of compound 6a: 1,2-Di-O-tetradecyl-sn-glyceride 1a (1.00 g, 2.06 mmol), succinic anhydride (0.416 g, 2 eq) and DMAP (0.628 g, 2.5 eq) were taken together in dichloromethane (20 mL) and stirred overnight. The reaction was followed by TLC, diluted with DCM, washed with cold dilute citric acid, water and dried over sodium sulfate. Solvents were removed under reduced pressure and the residue under high vacuum overnight. This compound was directly used for the next reaction with further purification. MPEG$_{2000}$-NH$_2$ 3 (1.50 g, 0.687 mmol, purchased from NOF Corporation, Japan), compound from previous step 5a (0.66 g, 1.12 eq) and HBTU (0.430 g, 1.13 mmol) were dissolved in a mixture of dichloromethane/DMF (2:1, 20 mL) under argon. DIEA (0.358 mL, 3 eq.) was added to that and stirred overnight. The reaction mixture was transferred to a large flask and removed the solvents and volatiles under reduced pressure. The residue was dried under high vacuum overnight and purified by chromatography (first ethyl acetate then 5-10% MeOH/DCM as a gradient elution) to get the required compound 6a as white solid (0.822 g, 43%). $^1$H NMR (CDCl$_3$, 400 MHz) δ=6.34-6.30(m, 1H), 4.16(dd, J=4.00 Hz, 11.00 Hz, 1H), 4.08(dd, J=5.00 Hz, 11.00 Hz, 1H), 3.82-3.78 (m, 2H), 3.70-3.30(m, —O—CH$_2$—CH$_2$—O—, PEG-CH$_2$), 2.64 (t, J=7.00 Hz, 2H), 2.43(t, J=6.80 Hz, 2H), 1.76-1.72 (m, 2H), 1.56-1.48(m, 4H), 1.34-1.16(m, 48H), 0.85(t, J=6.5 Hz, 6H). MS range found 2644-2804.

Preparation of compound 6b: 1,2-Di-O-hexadecyl-sn-glyceride 1b (1.00 g, 1.848 mmol), succinic anhydride (0.0.369 g, 2 eq) and DMAP (0.563 g, 2.5 eq) were taken together in dichloromethane (20 mL) and stirred overnight. The reaction was followed by TLC, diluted with DCM, washed with cold dilute citric acid, water and dried over sodium sulfate. Solvents were removed under reduced pressure and the residue under high vacuum overnight. This compound was directly used for the next reaction with further purification. MPEG$_{2000}$-NH$_2$ 3 (1.50 g, 0.687 mmol, purchased from NOF Corporation, Japan), compound from previous step 5b (0.66 g, 1.03 eq) and HBTU (0.400 g, 1.05 mmol) were dissolved in a mixture of dichloromethane/DMF (2:1, 20 mL) under argon. DIEA (0.358 mL, 3 eq.) was added to that and stirred overnight. The reaction mixture was transferred to a large flask and removed the solvents and volatiles under reduced pressure. The residue was dried under high vacuum overnight and purified by chromatography (first ethyl acetate then 5-10% MeOH/DCM as a gradient elution) to get the required compound 6b as white solid (0.300 g, 16%). $^1$H NMR (CDCl$_3$, 400 MHz) δ=6.33-6.28(m, 1H), 4.18(dd, J=4.00 Hz, 11.00 Hz, 1H), 4.08(dd, J=5.00 Hz, 11.00 Hz, 1H), 3.82-3.76(m, 2H), 3.70-3.30(m, —O—CH$_2$—CH$_2$—O—, PEG-CH$_2$), 2.65 (t, J=7.08 Hz, 2H), 2.44(t, J=6.83 Hz, 2H), 1.76-1.68 (m, 2H), 1.57-1.48(m, 4H), 1.32-1.17(m, 56H), 0.86(t, J=6.6 Hz, 6H). MS range found: 2640-2822.

Preparation of compound 6c: 1,2-Di-O-octadecyl-sn-glyceride 1c (5.00 g, 8.37 mmol), succinic anhydride (1.70 g, 2 eq) and DMAP (2.55 g, 2.5 eq) were taken together in dichloromethane (50 mL) and stirred overnight. The reaction was followed by TLC, diluted with DCM, washed with cold dilute citric acid, water and dried over sodium sulfate. Solvents were removed under reduced pressure and the residue under high vacuum overnight. This compound was directly used for the next reaction with further purification. MPEG$_{2000}$-NH$_2$ 3 (1.50 g, 0.687 mmol, purchased from NOF Corporation, Japan), compound from previous step 5c (0.718 g, 1.03 mmol) and HBTU (0.410 g, 1.08 mmol) were dissolved in a mixture of dichloromethane/DMF (2:1, 20 mL) under argon. DIEA (0.350 mL, 3 eq.) was added to that and stirred overnight. The reaction mixture was transferred to a large flask and removed the solvents and volatiles under reduced pressure. The residue was dried under high vacuum overnight and purified by chromatography (first ethyl acetate then 5-10% MeOH/DCM as a gradient elution) to get the required compound 6c as white solid (1.1 g, 56%). $^1$H NMR (CDCl$_3$, 400 MHz) δ=6.38-6.33(m, 1H), 4.19(dd, J=4.00 Hz, 11.00 Hz, 1H), 4.07(dd, J=5.00 Hz, 11.00 Hz, 1H), 3.81-3.74(m, 2H), 3.70-3.20(m, —O—CH$_2$—CH$_2$—O—, PEG-CH$_2$), 2.63 (t, J=7.03 Hz, 2H), 2.43(t, J=6.87 Hz, 2H), 1.76-1.68 (m, 2H), 1.57-1.48(m, 4H), 1.32-1.17(m, 64H), 0.86(t, J=6.60 Hz, 6H). MS range found: 2680-2922 removed under reduced pressure and the resulting residue was purified by chromatography (first eluted with EtOAc, followed by 5-10% DCM/MeOH gradient elution) to get the compound 8a as a white solid (0.590 g, 48%). $^1$H NMR (CDCl$_3$, 400 MHz) δ=4.25-4.18(m, 2H), 4.08(dd, J=5.60 Hz, 11.50 Hz, 1H), 3.80-3.73(m, 2H), 3.70-3.30(m, —O—CH$_2$—CH$_2$—O—, PEG-CH$_2$), 1.56-1.47(m, 4H), 1.30-1.15(m, 48H), 0.85(t, J=6.60 Hz, 6H). MS range found: 2440-2708

Preparation of compound 8b: 1,2-Di-O-hexadecyl-sn-glyceride 1b 0.334 g, 0.618 mmol), MPEG-Succinate 7 (1.00 g, 0.476 mmol, purchased from NOF Corporation, Japan), DCC (0.127 g, 1.3 eq) and DMAP (0.058 g, 0.476 mmol) were taken in dichloromethane (20 mL) under argon and stirred overnight. Reaction was monitored by TLC. The reaction mixture was cooled to 0° C. after stirring overnight and filtered off the precipitated solid. Volatiles and solvents were removed under reduced pressure and the resulting residue was purified by chromatography (first eluted with EtOAc, followed by 5-10% DCM/MeOH gradient elution) to get the compound 8b as a white solid (0.930 g, 74%). $^1$H NMR (CDCl$_3$, 400 MHz) δ=4.25-4.17(m, 2H), 4.09(dd, J=5.50 Hz, 11.50 Hz, 1H), 3.81-3.73(m, 2H), 3.70-3.30(m, —O—CH$_2$—CH$_2$—O—, PEG-CH$_2$), 1.58-1.47(m, 4H), 1.30-1.17(m, 56H), 0.86(t, J=6.60 Hz, 6H). MS range found: 2452-2760.

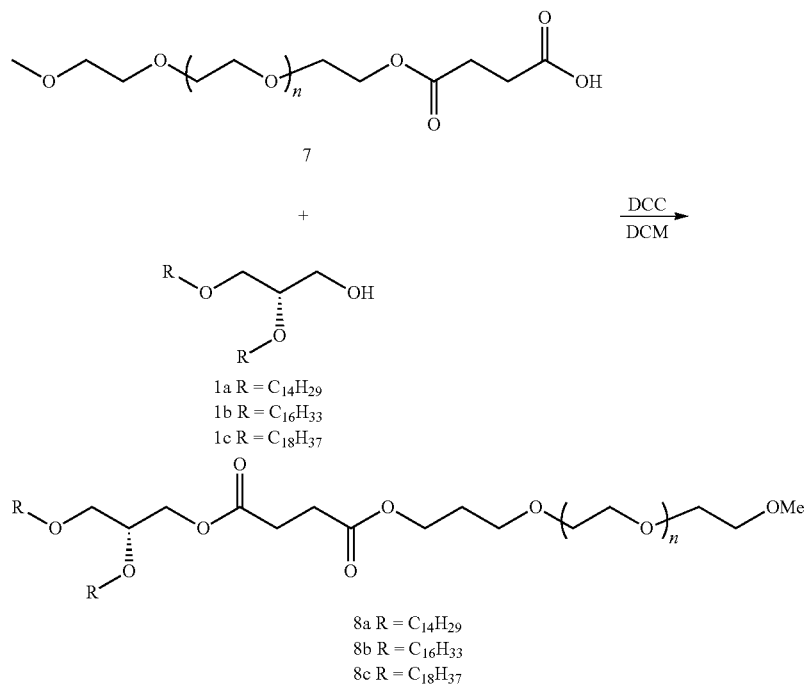

Scheme 3: mPEG2000-1,2-Di-O-alkyl-sn3-succinylglyceride

Preparation of compound 8a: 1,2-Di-O-tetradecyl-sn-glyceride 1a (0.300 g, 0.618 mmol), MPEG-Succinate 7 (1.00 g, 0.476 mmol, purchased from NOF Corporation, Japan), DCC (0.127 g, 1.3 eq) and DMAP (0.058 g, 0.476 mmol) were taken in dichloromethane (20 mL) under argon and stirred overnight. Reaction was monitored by TLC. The reaction mixture was cooled to 0° C. after stirring overnight and filtered off the precipitated solid. Volatiles and solvents were Preparation of compound 8c: 1,2-Di-O-octadecyl-sn-glyceride 1c (0.369 g, 0.618 mmol), MPEG-Succinate 7 (1.00 g, 0.476 mmol, purchased from NOF Corporation, Japan), DCC (0.127 g, 1.3 eq) and DMAP (0.058 g, 0.476 mmol) were taken in dichloromethane (20 mL) under argon and stirred overnight. Reaction was monitored by TLC. The reaction mixture was cooled to 0° C. after stirring overnight and filtered off the precipitated solid. Volatiles and solvents were removed under reduced pressure and the resulting residue was purified by chromatography (first eluted with EtOAc, followed by 5-10% DCM/MeOH gradient elution) to get the compound 8c as a white solid (0.960 g, 75%). $^1$H NMR (CDCl$_3$, 400 MHz) δ=4.27-4.20(m, 2H), 4.10(dd, J=5.80 Hz, 11.50 Hz, 1H), 3.83-3.74(m, 2H), 3.70-3.35(m, —O—CH$_2$—CH$_2$—O—, PEG-CH$_2$), 1.54-1.46(m, 4H), 1.30-1.17(m, 64H), 0.86(t, J=6.60 Hz, 6H). MS range found: 2508-2816.

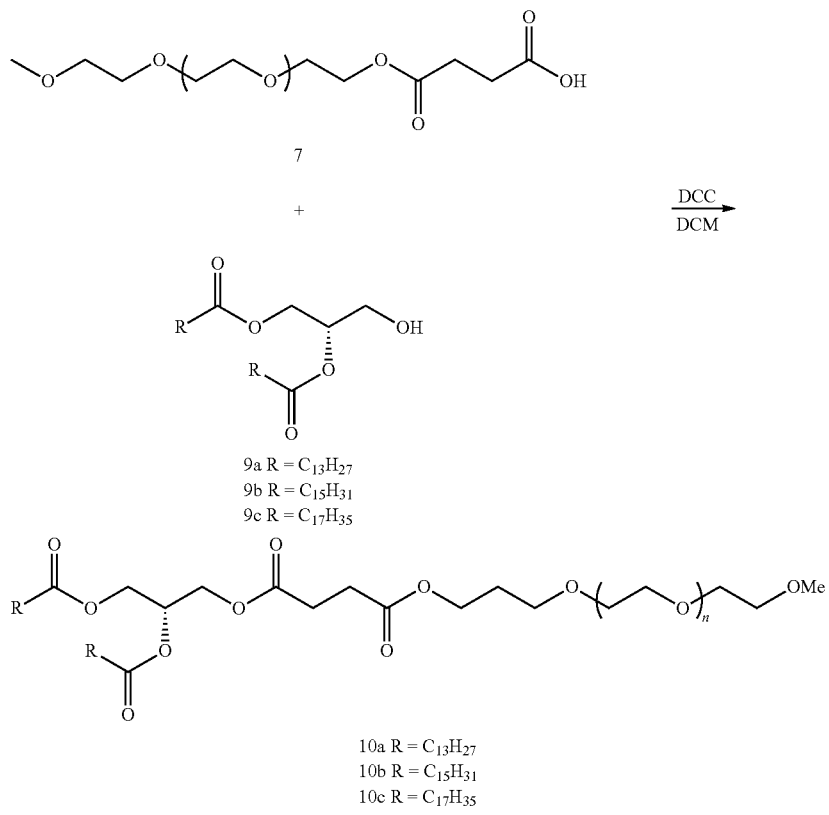

$^a$ Scheme 4: mPEG2000-1,2-Di-O-acyl-sn3-succinylglyceride

Preparation of compound 10a: 1,2-Dimyristoyl-sn-glycerol 9a (0.317 g, 0.618 mmol), MPEG-Succinate 7 (1.00 g, 0.476 mmol, purchased from NOF Corporation, Japan), DCC (0.127 g, 1.3 eq) and DMAP (0.058 g, 0.476 mmol) were taken in dichloromethane (20 mL) under argon and stirred overnight. Reaction was monitored by TLC. The reaction mixture was cooled to 0° C. after stirring overnight and filtered off the precipitated solid. Volatiles and solvents were removed under reduced pressure and the resulting residue was purified by chromatography (first eluted with EtOAc, followed by 5-10% DCM/MeOH gradient elution) to get the compound 10a as a white solid (0.960 g, 78%). $^1$H NMR (CDCl$_3$, 400 MHz) δ=5.26-5.20(m, 1H), 4.30-4.08(m, 6H), 3.81-3.73(m, 2H), 3.70-3.40(m, —O—CH$_2$—CH$_2$—O—, PEG-CH$_2$), 2.65-2.60(m, 4H), 2.35-2.28 (m, 4H), 1.63-1.52 (m, 4H), 1.30-1.15(m, 44H), 0.86(t, J=6.60 Hz, 6H). MS range found: 2468-2732.

Preparation of compound 10b: 1,2-Dipalmitoyl-sn-glycerol 9b (0.352 g, 0.618 mmol), MPEG-Succinate 7 (1.00 g, 0.476 mmol, purchased from NOF Corporation, Japan), DCC (0.127 g, 1.3 eq) and DMAP (0.058 g, 0.476 mmol) were taken in dichloromethane (20 mL) under argon and stirred overnight. Reaction was monitored by TLC. The reaction mixture was cooled to 0° C. after stirring overnight and filtered off the precipitated solid. Volatiles and solvents were removed under reduced pressure and the resulting residue was purified by chromatography (first eluted with EtOAc, followed by 5-10% DCM/MeOH gradient elution) to get the compound 10b as a white solid (1.02 g, 81%). $^1$H NMR (CDCl$_3$, 400 MHz) δ=5.26-5.19(m, 1H), 4.30-4.05(m, 6H), 3.80-3.40(m, —O—CH$_2$—CH$_2$—O—, PEG-CH$_2$), 2.65-2.60(m, 4H), 2.33-2.24(m, 4H), 1.63-1.50(m, 4H), 1.30-1.15 (m, 52H), 0.85(t, J=6.60 Hz, 6H). MS range found: 2524-2792.

Preparation of compound 10c: 1,2-Distearoyl-sn-glycerol 9c (0.387 g, 0.618 mmol), MPEG-Succinate 7 (1.00 g, 0.476 mmol, purchased from NOF Corporation, Japan), DCC (0.127 g, 1.3 eq) and DMAP (0.058 g, 0.476 mmol) were taken in dichloromethane (20 mL) under argon and stirred overnight. Reaction was monitored by TLC. The reaction mixture was cooled to 0° C. after stirring overnight and filtered off the precipitated solid. Volatiles and solvents were removed under reduced pressure and the resulting residue was purified by chromatography (first eluted with EtOAc, followed by 5-10% DCM/MeOH gradient elution) to get the compound 10c as a white solid (1.04 g, 80%). $^1$H NMR (CDCl$_3$, 400 MHz) δ=5.26-5.19(m, 1H), 4.30-4.05(m, 6H), 3.80-3.40(m, —O—CH$_2$—CH$_2$—O—, PEG-CH$_2$), 2.66-

2.59(m, 4H), 2.31-2.26(m, 4H), 1.63-1.52(m, 4H), 1.30-1.15 (m, 52H), 0.85(t, J=6.60 Hz, 6H). MS range found: 2540-2844.

gradient elution) to get the required compound 13 as white solid (5.05 g, 68%). $^1$H NMR (CDCl$_3$, 400 MHz) δ=5.35-5.25(m, 1H), 4.60-4.50(m, 1H), 4.22-4.18(m, 2H), 3.80-3.76 (m, 2H), 3.72-3.40(m, —O—CH$_2$—CH$_2$—O—, PEG-CH$_2$), 2.64-2.56(m, 4H), 2.31-2.20(m, 3H), 2.01-0.8(m, 44H).MS range found: 2390-2654.

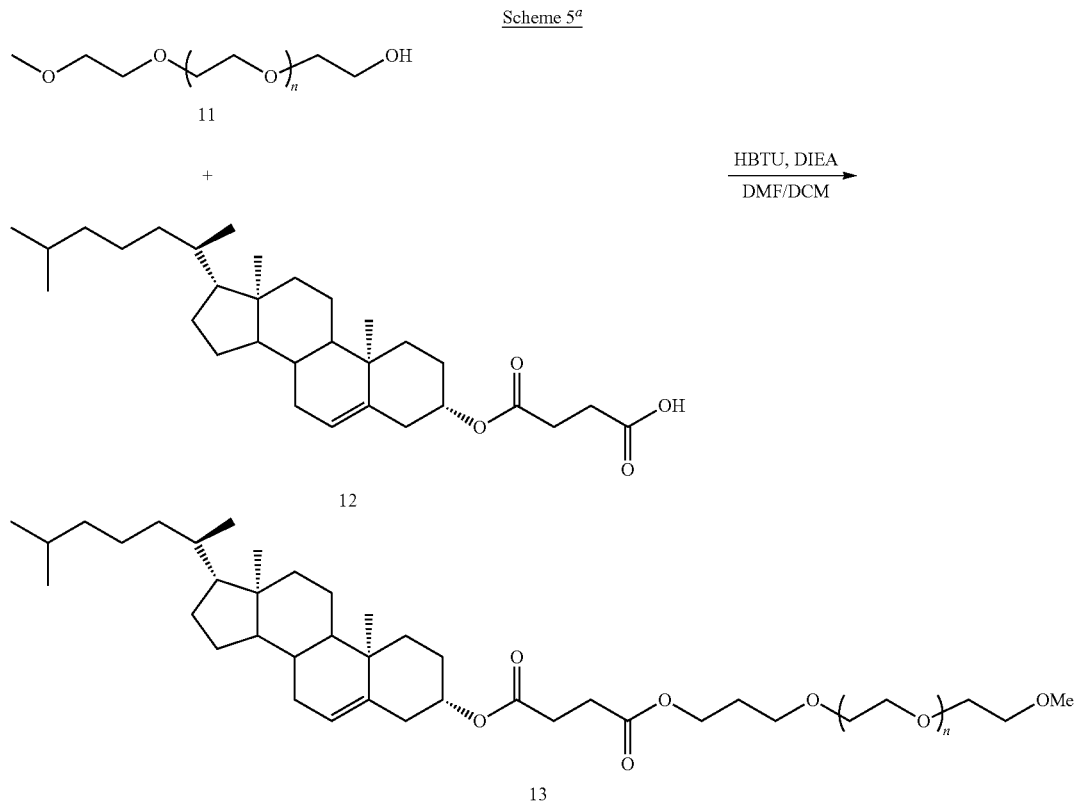

<sup>a</sup>Scheme 5: Cholesteryl-mPEG2000

Preparation of compound 13: mPEG$_{2000}$-OH 11 (6.00 g, 3 mmol, purchased from Sigma-Aldrich), Cholesterol hemisuccinate 12 (1.50 g, 3.08 mmol mmol) and HBTU (1.23 g, 3.23 mmol) were dissolved in a mixture of dichloromethane/DMF (2:1, 100 mL) under argon. DIEA (1.60 mL, 3 eq.) was added to that and stirred overnight. Solvents and volatiles were removed under reduced pressure. The residue was dried under high vacuum overnight and purified by chromatography (first ethyl acetate then 5-10% MeOH/DCM as a Example 42

Targeted PEG-Lipids

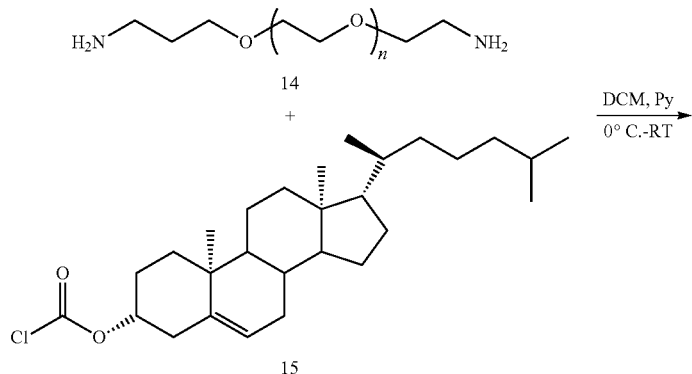

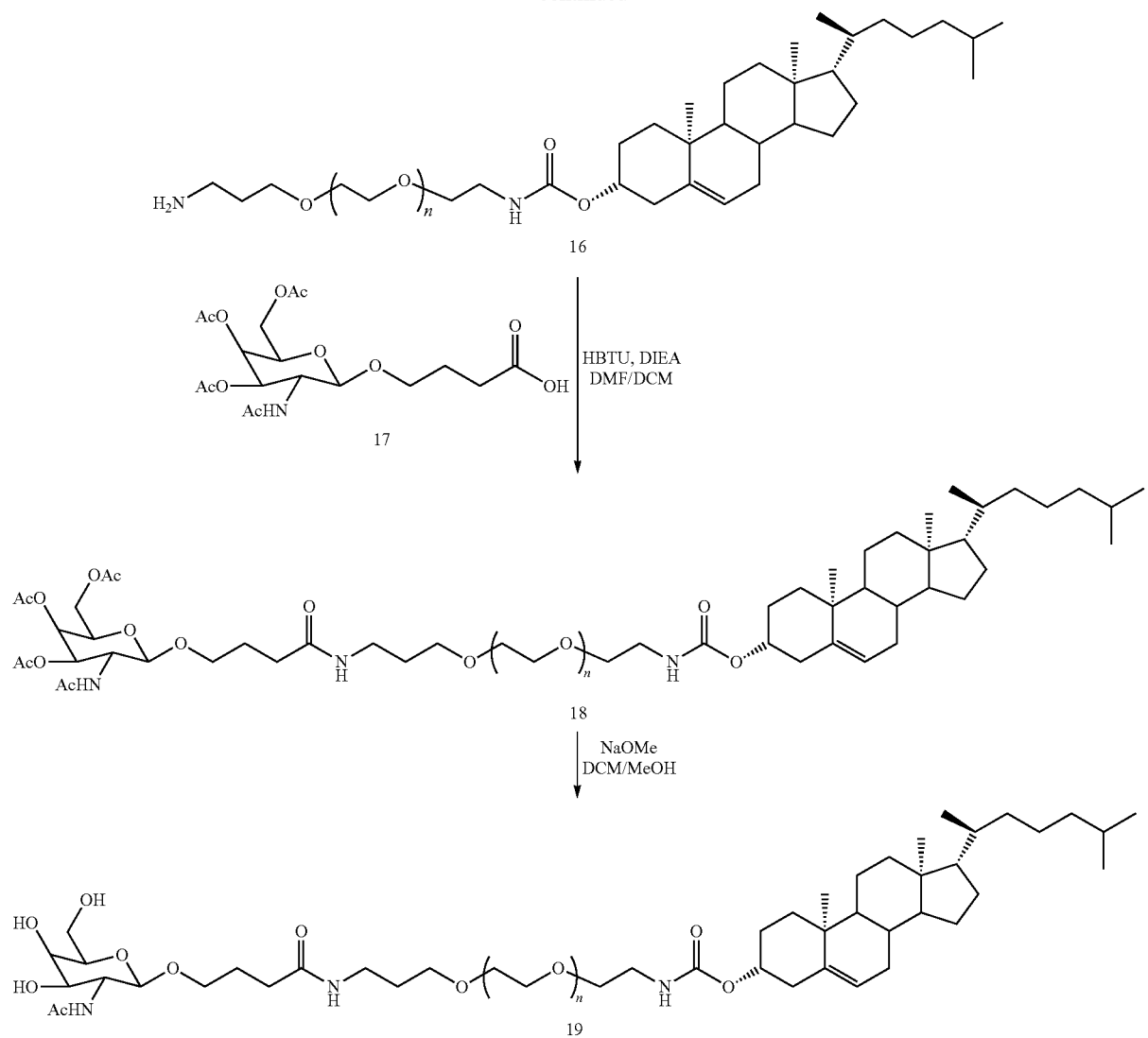

Preparation of 19:

Step 1: Compound 14 (2.00 g, 1.01 mmol) and cholesterol chloroformate 15 (0.453 g, 1.01 mmol) were taken together in dichloromethane (20 mL). The mixture was cooled in an ice-water bath. Triethylamine (0.448 ml) was added and the reaction mixture was stirred overnight. Reaction was monitored by TLC. Solvent was removed and the residue was purified by silica gel chromatography (Ethyl acetate followed by 5-10% MeOH/DCM) to get the desired compound 16 (1.10 g, 45.40%). $^1$H NMR (CDCl$_3$, 400 MHz) δ=5.35(m, 1H), 5.15(m, 1H), 3.40-3.85(m, O—CH$_2$—CH$_2$—O), 3.10-3.25(m, 10H), 0.80-2.38(m, 44H, Cholesterol). MS range found: 2220-2490.

Step 2: Compound 16 (1.00 g, 0.417 mmol), 17 (0.235 g, 0.542 mmol) and HBTU (0.190 g, 0.5 mmol) were taken in a mixture of DCM/DMF (20 mL, 2:1). To that DIEA was added and stirred overnight. Reaction was monitored by TLC, solvents were removed under reduced pressure and the residue was purified by chromatography (5-10% MeOH/DCM) to get the desired compound 18 (1.02 g, 87%). $^1$H NMR (DMSO-d6, 400 MHz) δ=7.52(d, J=8.06 Hz, 1H), 7.33(t, J=7.02 Hz, 1H), 7.25(t, J=7.32 Hz, 1H), 5.27(m, 1H), 5.18(d, J=3.2 Hz, 1H), 4.92(dd, J=3.17, 11.23 Hz, 1H), 4.43(m, 1H), 3.60-4.02 (m, 5H), 3.20-3.55(m, O—CH$_2$—CH$_2$—O), 2.90-3.10(m, 10H), 2.05(s, 3H), 1.96(s, 3H), 1.84(s, 3H), 1.77(s, 3H), 0.80-2.38(m, 44H, Cholesterol). MS range found: 2680-2990.

Step 3: Compound 18 (1.02 g, 0.362 mmol) was dissolved in a mixture of MeOH/DCM (10 mL) to that 0.5 M solution of NaOMe in methanol (excess) was added and stirred overnight. Progress of the reaction was monitored by TLC. The mixture was neutralized with AcOH. Solvents were removed under vacuum and the residue was purified by chromatography (5-10% MeOH/DCM) to get compound 19 (280 mg, 30%). $^1$H NMR (CDCl$_3$, 400 MHz) δ=5.38(m, 1H), 4.02-4.06(m, 7H), 3.30-3.80(m, O—CH$_2$—CH$_2$—O), 3.20-3.29 (m, 8H), 2.08(s, 3H), 0.80-2.38(m, 44H, Cholesterol). MS range found: 2600-2900.

Example 43

Targeted PEG-Lipids

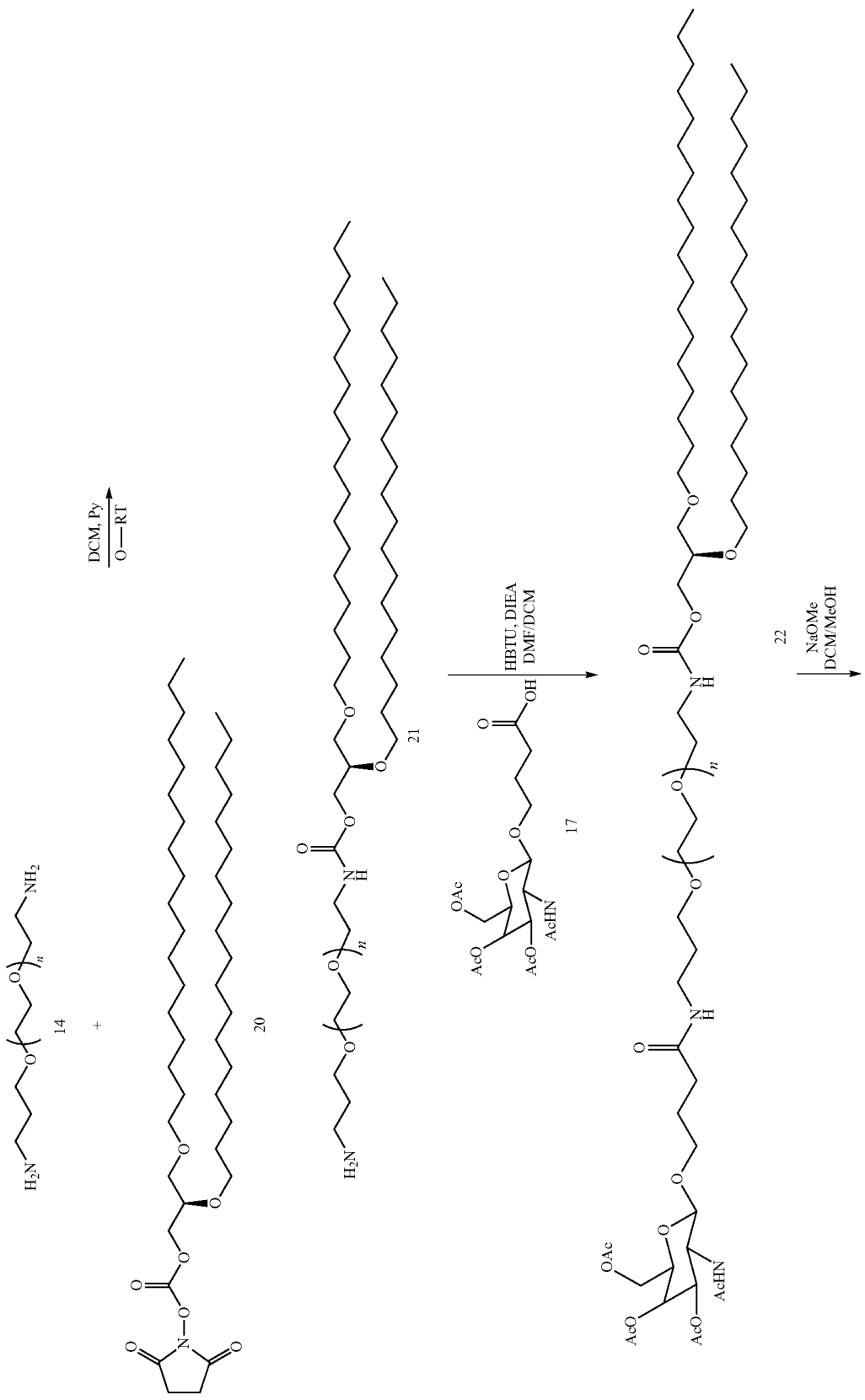

-continued
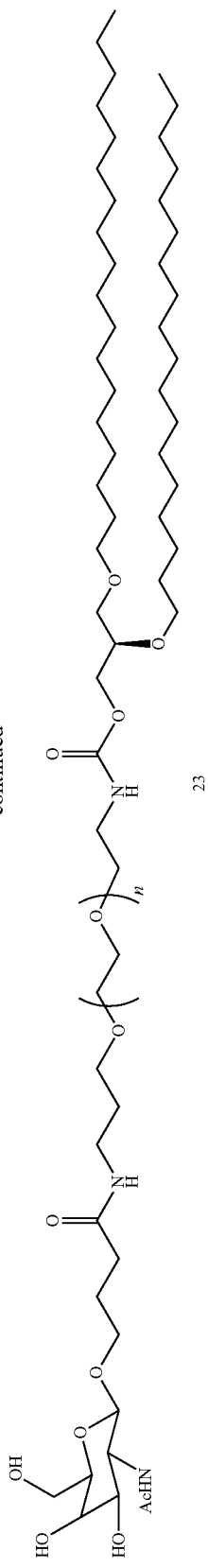

Preparation of 23:

Step 1: Compound 14 (2.00 g, 1.01 mmol) and compound 20 (0.453 g, 1.01 mmol) were taken together in dichloromethane (20 mL). The mixture was cooled in an ice-water bath. Pyridine (1 mL, excess) was added and the reaction mixture was stirred overnight. Reaction was monitored by TLC. Solvent was removed and the residue was purified by silica gel chromatography (Ethyl acetate followed by 5-10% MeOH/DCM) to get the desired compound 21 (400 mg, 15%). $^1$H NMR (CDCl$_3$, 400 MHz) δ=5.20(m, 1H), 4.05-4.20(m, 2H), 3.20-3.80(m, O—CH$_2$—CH$_2$—O), 1.70-1.82 (m, 4H), 1.50-1.61(m, 2H), 1.18-1.38(m, 60H), 0.87(t, J=6.30 Hz, 6H). MS range found: 2400-2750.

Step 2: Compound 21 (0.415 g, 0.159 mmol), 17 (0.100 g, 1.3 eq) and HBTU (0.90 g, 1.15 eq) were taken in a mixture of DCM/DMF (20 mL, 2:1). To that DIEA (0.2 mL) was added and stirred overnight. Reaction was monitored by TLC, solvents were removed under reduced pressure and the residue was purified by chromatography (3-10% MeOH/DCM) to get the desired compound 22 (0.450 g, 94%). $^1$H NMR (CDCl$_3$, 400 MHz) δ=6.21(d, J=8.70 Hz, 1H), 5.33(d, J=2.70 Hz, 1H), 5.15-5.20(m, 2H), 4.55(d, J=8.15 Hz, 1H), 4.01-4.20(m, 4H), 3.20-3.90(m, O—CH$_2$—CH$_2$—O), 2.14(s, 3H), 2.03(s, 3H), 1.99(s, 3H), 1.93(s, 3H), 1.70-1.82(m, 4H), 1.50-1.61(m, 4H), 1.17-1.38(m, 60H), 0.86(t, J=6.32 Hz, 6H). MS range found: 2800-3200.

Step 3: Compound 22 (0.450 g, 0.359 mmol) was dissolved in a mixture of MeOH/DCM (5 mL) to that 0.5 M solution of NaOMe in methanol (excess) was added and stirred overnight. Progress of the reaction was monitored by TLC. The mixture was neutralized with AcOH. Solvents were removed under vacuum and the residue was purified by chromatography (5-10% MeOH/DCM) to get compound 23 (365 mg, 85%). $^1$H NMR (CDCl$_3$, 400 MHz) δ=5.18(m, 1H), 4.05-4.20(m, 4H), 3.20-3.90(m, O—CH$_2$—CH$_2$—O), 2.05(s, 3H), 1.71-1.80(m, 4H), 1.50-1.61(m, 4H), 1.17-1.38(m, 60H), 0.87(t, J=6.32 Hz, 6H). MS range found: 2760-3000.

Figure 6:
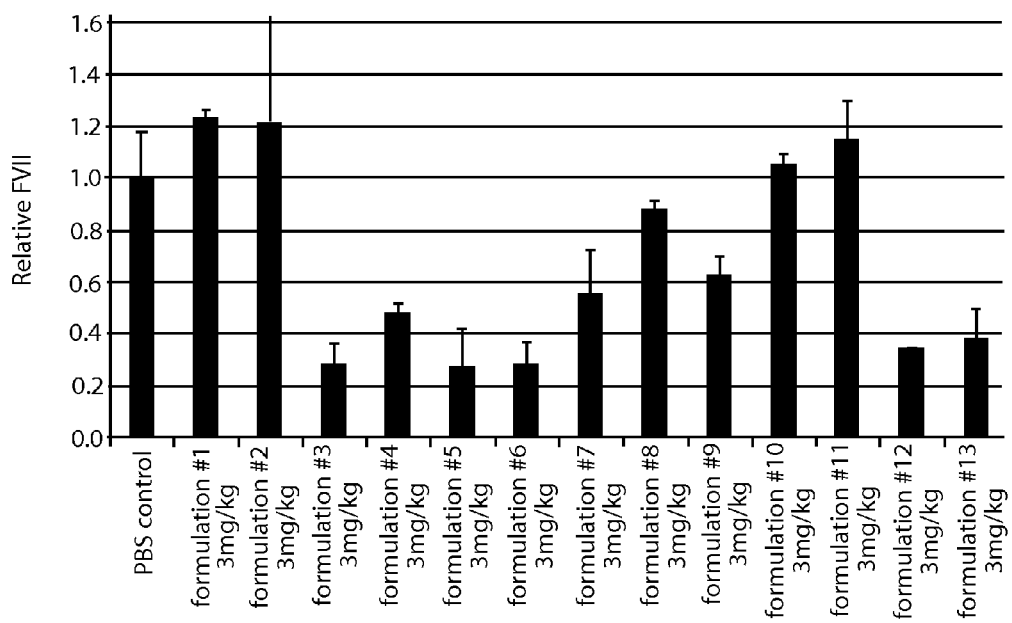
FIG. 6 depicts a bar graph comparing the efficacy of association complexes.

As provided in FIG. 6, the formulations, when administered to a subject, provided a varying degree of silencing of FVII. For example, formulation 3 provided a relative high degree of silencing of FVII, as did formulation 5, 6, and 12.

Example 44

Tolerability of Formulation LNP01 as Dosed in Mice

Figure 7:
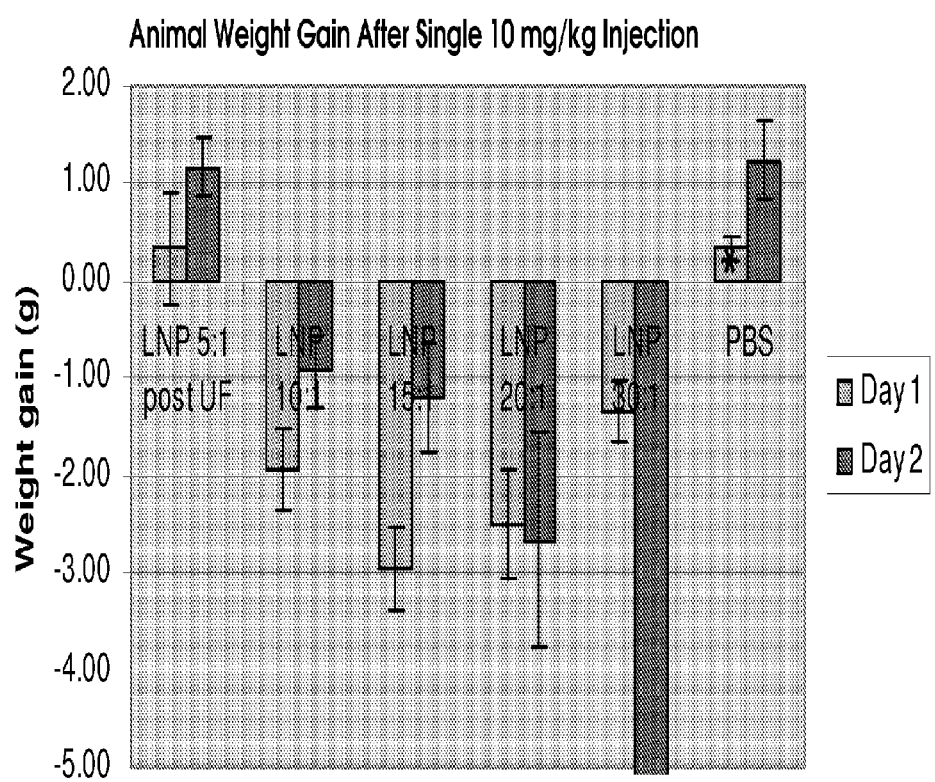
FIG. 7 depicts a bar graph comparing the tolerability of various complexes as the ratio of lipid to siRNA is reduced.

Empty liposomes with composition ND98:cholesterol: PEG-C14=42:48:10 (molar ratio) were prepared as described in Example 45. Different amounts of siRNA were then added to the pre-formed, extruded empty liposomes to yield formulations with initial total excipient:siRNA ratios of 30:1, 20:1, 15:1, 10:1, and 5:1 (wt:wt). Preparation of a formulation at a total excipient:siRNA ratio of 5:1 results in an excess of siRNA in the formulation, saturating the lipid loading capacity. Excess siRNA was then removed by tangential flow filtration using a 100,000 MWCO membrane against 5 volumes of PBS. The resulting formulations were then administered to C57BL/6 mice via tail vein injection at 10 mg/kg siRNA dose. Tolerability of the formulations was assessed by measuring the body weight gain of the animals 24 h and 48 h post administration of the formulation, the results of which are provided in FIG. 7.

Example 45

Figure 8:
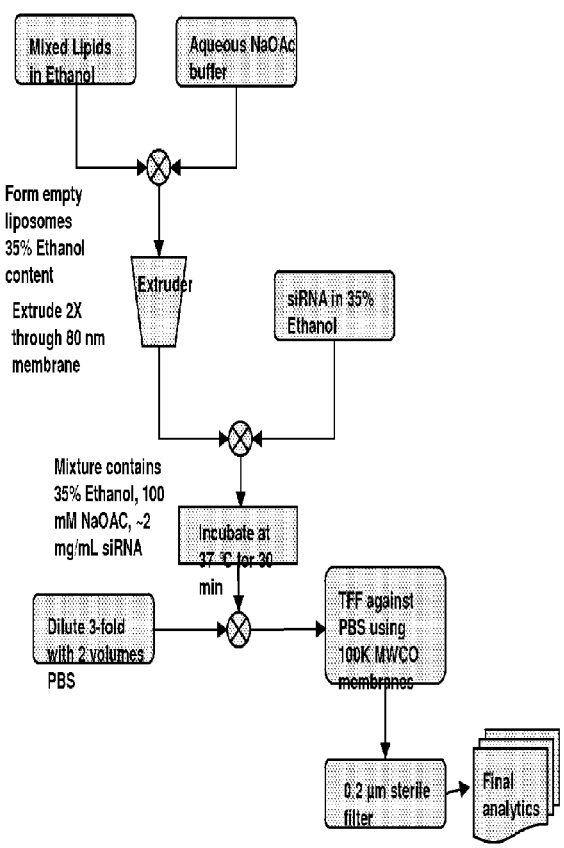
FIG. 8 is a flow chart of a process for making an association complex loaded with nucleic acid.

Formation of Association Complexes by First Forming Unloaded Complexes and then Treating the Unloaded Complexes with siRNA and Administration of Association Complexes Including Two Therapeutic Agents Association complexes having two different nucleic acid moieties were prepared as follows. Stock solutions of ND98, cholesterol, and PEG-C14 in ethanol were prepared at the following concentrations: 133 mg/mL, 25 mg/mL, and 100 mg/mL for ND98, cholesterol, and PEG-C14, respectively. The lipid stocks were then mixed to yield ND98:cholesterol: PEG-C14 molar ratios of 42:48:10. This mixture was then added to aqueous buffer resulting in the spontaneous formulation of lipid nanoparticles in 35% ethanol, 100 mM sodium acetate, pH 5. The unloaded lipid nanoparticles were then passed twice through a 0.08 μm membrane (Whatman, Nucleopore) using an extruder (Lipex, Northern Lipids) to yield unimodal vesicles 20-100 nm in size. The appropriate amount of siRNA in 35% ethanol was then added to the pre-sized, unloaded vesicles at a total excipient:siRNA ratio of 7.5:1 (wt:wt). The resulting mixture was then incubated at 37° C. for 30 min to allow for loading of siRNA into the lipid nanoparticles. After incubation, ethanol removal and buffer exchange was performed by either dialysis or tangential flow filtration against PBS. The final formulation was then sterile filtered through a 0.2 μm filter. A flow chart demonstrating the order of addition of exhipients and therapeutic agents is provided in FIG. 8.

A 1:1 mixture of siRNAs targeting ApoB and Factor VII were formulated as described in Example 44. Separately, the same ApoB- and Factor VII-targeting siRNAs were individually formulated as described in Example 31. The three formulations were then administered at varying doses in an injection volume of 10 μL/g animal body weight. Forty-eight hours after administration, serum samples were collected by retroorbital bleed, animals were sacrificed, and livers were harvested. Serum Factor VII concentrations were determined using a chromogenic diagnostic kit (Coaset Factor VII Assay Kit, DiaPharma) according to manufacturer protocols. Liver mRNA levels of ApoB and Factor VII were determined using a branched-DNA (bDNA) assay (Quantigene, Panomics), the results of which are provided in FIG. 9. No evidence of inhibition between the two therapeutic agents was observed. Rather, both of the therapeutic agents demonstrated effectiveness when administered.

Example 46

Methods of Making Association Complexes Using Preformed Vesicles

Lipid Stock Preparation

Stock solutions of lipidoid ND98.4HCl (MW 1487), cholesterol, and PEG-C14 were prepared in ethanol at the following concentrations: 133 mg/mL, 25 mg/mL, and 100 mg/mL for ND98, cholesterol, and PEG-C14, respectively. Stock solutions were warmed at 50° C. to assist in bring lipids into solution.

Empty Vesicle Preparation

The lipid stocks were then mixed according to the volumes listed below to yield ND98:cholesterol:PEG-C14 molar ratios of 42:48:10. An aqueous mixture was also prepared according to the volumes listed in the table below.

| Volume Lipid Mixture (mL) | | | |
|---|---|---|---|
| ND98 | Cholesterol | PEG | Total |
| 56.250 | 90.000 | 31.500 | 177.750 |

| Aqueous Mixture (mL) | | | |
|---|---|---|---|
| Water | 3M NaOAc | Ethanol | Total |
| 378.000 | 27.000 | 40.327 | 445.327 |

The ethanolic Lipid Mixture was then added to the Aqueous Mixture while rapidly stirring on a magnetic stir plate. Upon mixing, lipidoid vesicles formed spontaneously. The resulting vesicles were then extruded (2 passes) through a 0.08μ membrane (Whatman, Nucleopore) to size the empty vesicles. All manipulations were performed at room temperature.

Loading of Empty Vesicles with siRNA

An siRNA stock solution was prepared by dissolving desalted duplex siRNA in 50 mM sodium acetate pH 5 at a concentration of 10 mg/mL. An appropriate volume of this siRNA stock was mixed with the appropriate volume of ethanol to yield a diluted siRNA solution in 35% (vol) ethanol (see table below).

| siRNA Dilution | | | |
|---|---|---|---|
| siRNA Stock (mg/mL) | siRNA (50 nM NaOAc) | Ethanol | Total |
| 10 | 180.000 | 96.923 | 276.923 |

277 mL of diluted siRNA solution was added to 623 mL of empty vesicle mixture while rapidly stirring on a magnetic stir plate. The resulting combined mixture was then incubated at 37° C. for 30 min to allow for loading of siRNA.

Ultrafiltration and Terminal 0.2 p Filtration

After incubation, the 900 mL loaded nanoparticle mixture was diluted into 1.8 L of PBS to yield a 2.7 L diluted mixture. This diluted mixture was then concentrated to ~1 L and diafiltered by tangential flow filtration against 10 volumes of PBS using a Sartorius TFF system utilizing two stacked 100,000 MWCO cartridges. No back-pressure was applied to the cartridge and the pump speed was set to 300 rpm. After buffer exchange the resulting solution was concentrated to roughly 2 mg/mL siRNA.

Terminal filtration was performed by passing the solution through a 0.2μ filter capsule (Whatman, Polycap 36 AS).

Figure 10:
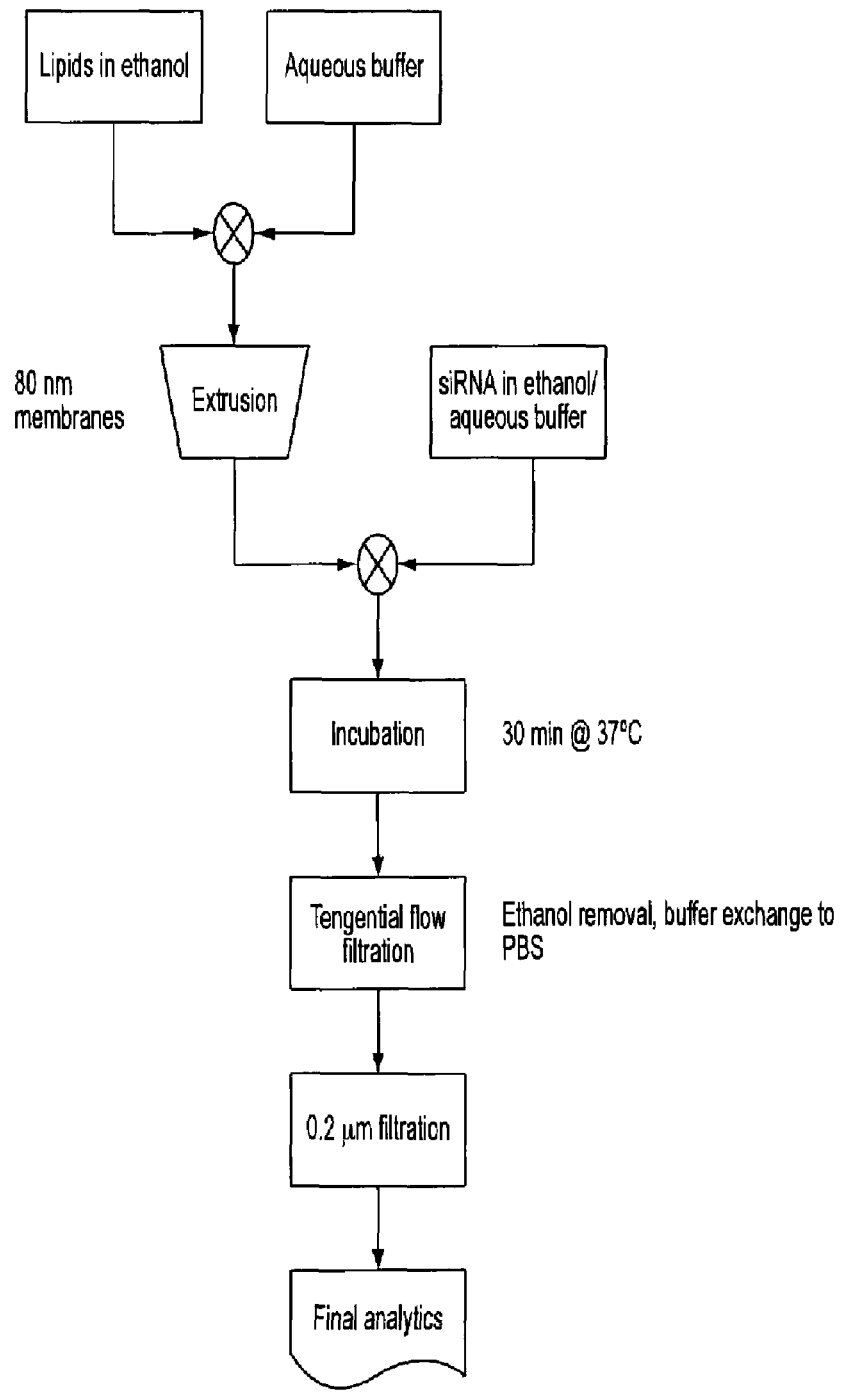
FIG. 10 is a flow chart of a process for making an association complex loaded with nucleic acid.

A flow chart illustrating this process is shown in FIG. 10.

Example 47

Comparison of Particle Size on Efficacy

Association complexes were formed using the procedure generally described in Example 46. However, because the complexes were being evaluated based on size, different extrusion membranes were used to produce particles having the following diameters: 150 nm, 85 nm, 60 nm, and 50 nm. The siRNAs loaded in the complexes targeted factor VII.

Figure 11:
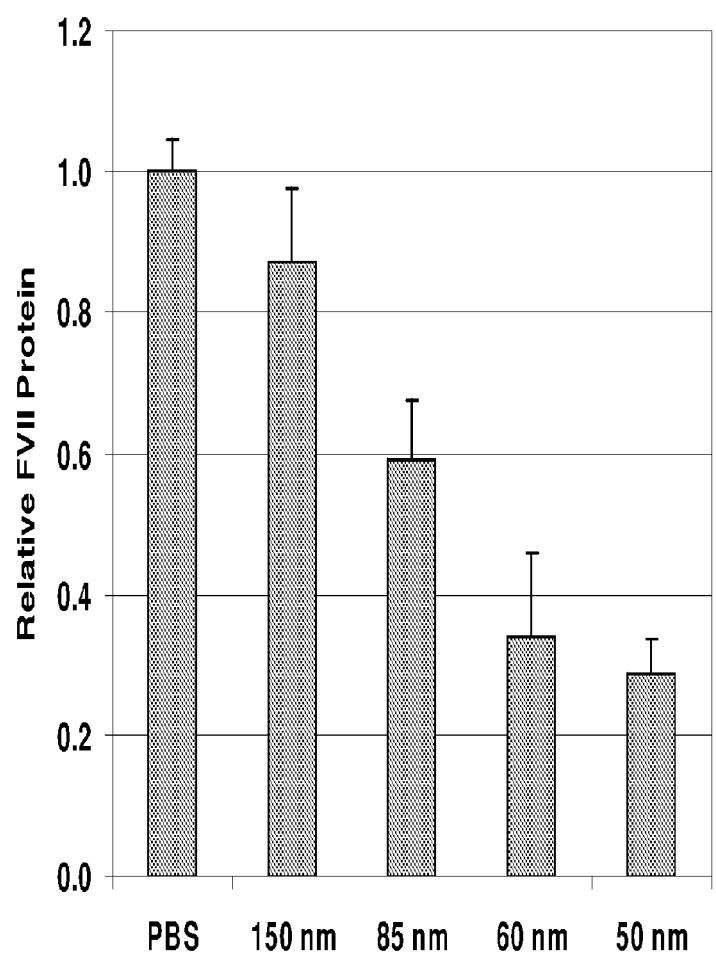
FIG. 11 is a bar graph depicting the effect of particle size of association complexes on the efficacy of a nucleic acid in a silencing assay.

The particles were evaluated in a Factor VII silencing assay, demonstrating that the 50 nm particles were the most efficacious relative to the 150 nm, 85 nm, and 60 nm particles. The results of the assay are depicted in FIG. 11.

Example 48

Figure 12A:
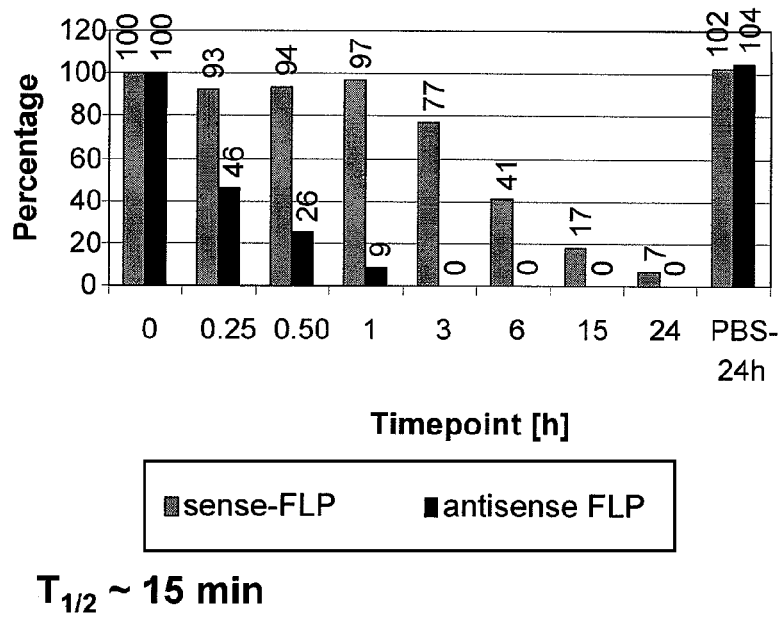
FIGS. 12a and 12b are bar graphs comparing the serum half life of nucleic acid therapeutics in unformulated and formulated forms.
Figure 12B:
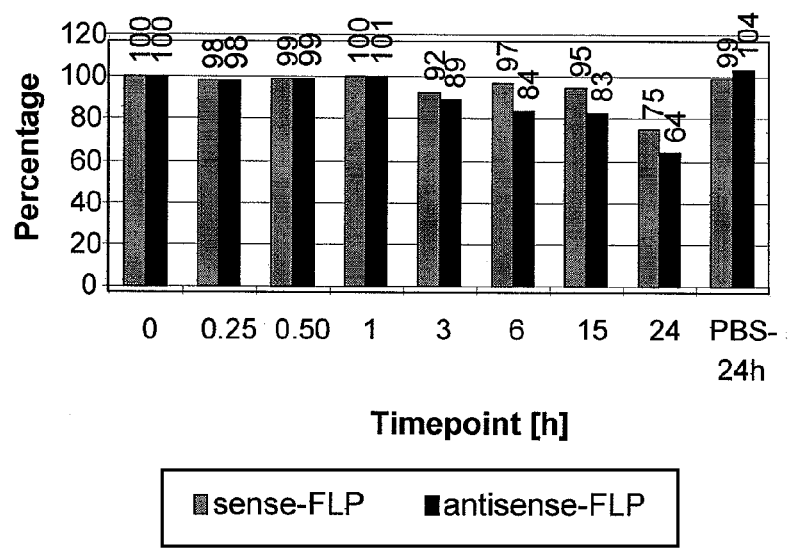

Comparison of Half Life of Nucleic Acid Agents Unformulated Versus Formulated into an Association Complex The half life of siRNA formulated in association complexes was evaluated in vitro in human serum at 37° C. The association complexes were prepared as in Example 46. For purposes of comparison, unformulated siRNA was also evaluated in vitro in human serum. The percent of full length product determined by HPLC was evaluated for both the formulated and unformulated siRNA. As demonstrated in FIG. 12, the formulated siRNA had a significantly improved half life in vitro in human serum.

Example 49

Comparison of Efficacy of Association Having Peg Lipids of Varied Chain Length

Figure 13:
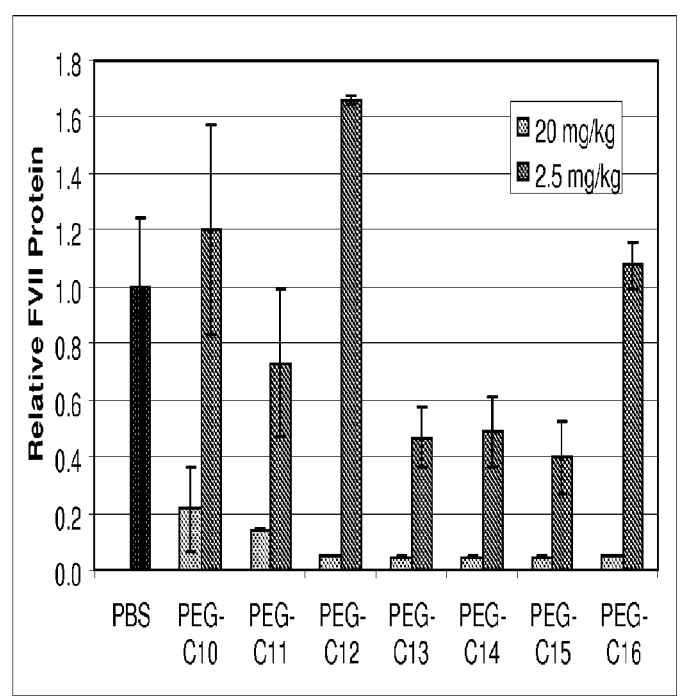
FIG. 13 is a bar graph comparing the efficacy of association complexes having PEG lipids with varied chain lengths.

Association complexes were prepared as in Example 46 with variation on the length of the alkyl chain of the PEG lipid. Alkyl chain lengths of 10, 11, 12, 13, 14, 15, and 16 were evaluated and compared for efficacy in a Factor VII silencing assay. As shown in FIG. 13, chain lengths of 13, 14, and 15 demonstrated the most silencing as measured in the assay.

A number of embodiments of the invention have been described. Nevertheless, it will be understood that various modifications may be made without departing from the spirit and scope of the invention. Accordingly, other embodiments are within the scope of the following claims.

What is claimed is:

1. A compound having the formula (XV):

formula (XV)

$$R^1-L^1-O-CH_2-CH(O-L^2-R^2)-CH_2-O-X-(CH_2)_m-O-(CH_2CH_2O)_n-CH_3$$

wherein
L$^1$ and L$^2$ are both a bond;
each R$^1$ and R$^2$ are independently alkyl, alkenyl, or alkynyl, each of which is optionally substituted with one or more substituents;
X is —C(O)NH—, C(S)NH, —C(O)—C$_{1-3}$alkyl-C(O)NH—, or —C(O)—C$_{1-3}$alkyl-C(O)O—;
m is an integer from 0-11; and
n is an integer from 1-500.

2. The compound of claim 1, wherein R$^1$ and R$^2$ are independently unsubstituted C$_6$-C$_{28}$ alkyl.

3. The compound of claim 1, wherein R$^1$ and R$^2$ are independently unsubstituted C$_{10}$-C$_{18}$ alkyl.

4. The compound of claim 1, wherein the substituents for R$_1$ and R$^2$ are selected from alkyl, cycloalkyl, haloalkyl, aryl, heteroaryl, arylalkyl, heteroarylalkyl, heterocyclyl, alkenyl, alkynyl, cycloalkenyl, heterocycloalkenyl, alkoxy, haloalkoxy, halo, hydroxy, carboxy, carboxylate, cyano, nitro, amino, alkyl amino, SO₃H, sulfate, phosphate, methylenedioxy (—O—CH₂—O— wherein oxygens are attached to same carbon (geminal substitution) atoms), ethylenedioxy, oxo, thioxo, imino, $S(O)_n$alkyl (where n of $S(O)_n$alkyl is 0-2), $S(O)_n$aryl (where n of $S(O)_n$aryl is 0-2), $S(O)_n$heteroaryl (where n of $S(O)_n$heteroaryl is 0-2), $S(O)_n$heterocyclyl (where n of $S(O)_n$heterocyclyl is 0-2), amine, ester, amide, and sulfonamide.

5. A compound having the formula

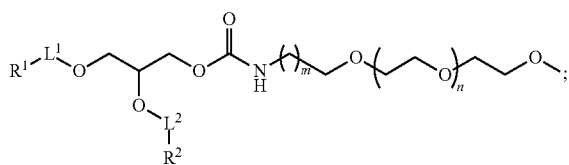

wherein
$L^1$ and $L^2$ are both a bond;
each $R^1$ and $R^2$ are independently alkyl, alkenyl, or alkynyl; each of which is optionally substituted with one or more substituents;
m is an integer from 0-11 and
n is an integer from 1-500.

6. The compound of claim 5, wherein the substituents for $R^1$ and $R^2$ are selected from alkyl, cycloalkyl, haloalkyl, aryl, heteroaryl, arylalkyl, heteroarylalkyl, heterocyclyl, alkenyl, alkynyl, cycloalkenyl, heterocycloalkenyl, alkoxy, haloalkoxy, halo, hydroxy, carboxy, carboxylate, cyano, nitro, amino, alkyl amino, SO₃H, sulfate, phosphate, methylenedioxy (—O—CH₂—O— wherein oxygens are attached to same carbon (geminal substitution) atoms), ethylenedioxy, oxo, thioxo, imino, $S(O)_n$alkyl (where n of $S(O)_n$alkyl is 0-2), $S(O)_n$aryl (where n of $S(O)_n$aryl is 0-2), $S(O)_n$heteroaryl (where n of $S(O)_n$heteroaryl is 0-2), $S(O)_n$heterocyclyl (where n of $S(O)_n$heterocyclyl is 0-2), amine, ester, amide, and sulfonamide.

7. The compound of claim 5, wherein $R^1$ and $R^2$ are independently unsubstituted $C_6$-$C_{28}$ alkyl.

8. The compound of claim 5, wherein $R^1$ and $R^2$ are independently unsubstituted $C_{10}$-$C_{18}$ alkyl.

9. The compound of claim 7, wherein $R^1$ and $R^2$ are straight chain alkyl having the same length.

10. The compound of claim 8, wherein $R^1$ and $R^2$ are straight chain alkyl having the same length.

11. The compound of claim 5, wherein $R^1$ and $R^2$ are unsubstituted $C_{14}$ alkyl.

12. The compound of claim 5, wherein $R^1$ and $R^2$ are unsubstituted $C_{18}$ alkyl.

13. The compound of claim 5, wherein m is 2.

14. The compound of claim 5, wherein n is from 40 to 400.

15. The compound of claim 5, wherein n is from 40 to 50.

16. The compound of claim 5, wherein n is from 42 to 47.

17. The compound of claim 5, wherein $L^1$ and $L^2$ are both bonds, $R^1$ and $R^2$ are both alkyl, and n is an integer from about 40-400.

18. The compound of claim 17, wherein $R^1$ and $R^2$ are unsubstituted $C_6$-$C_{28}$ alkyl.

19. The compound of claim 17, wherein $R^1$ and $R^2$ are unsubstituted $C_{10}$-$C_{18}$ alkyl.

20. The compound of claim 17, wherein $R^1$ and $R^2$ are unsubstituted $C_{14}$ alkyl.

21. The compound of claim 5, wherein the compound has the formula:

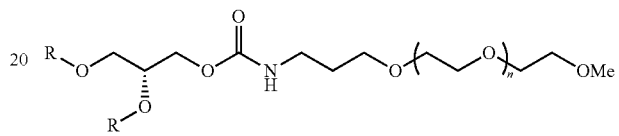

wherein each R is $C_{14}H_{29}$ and n is from 42 to 47.

22. The compound of claim 21, wherein the average molecular weight of the PEG moiety is 2000.

23. The compound of claim 5, wherein the compound has the formula:

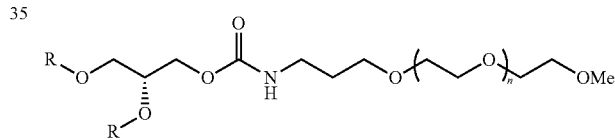

wherein each R is $C_{18}H_{37}$ and n is from 42 to 47.

24. The compound of claim 23, wherein the average molecular weight of the PEG moiety is 2000.

25. The compound of claim 5, wherein the compound has the formula:

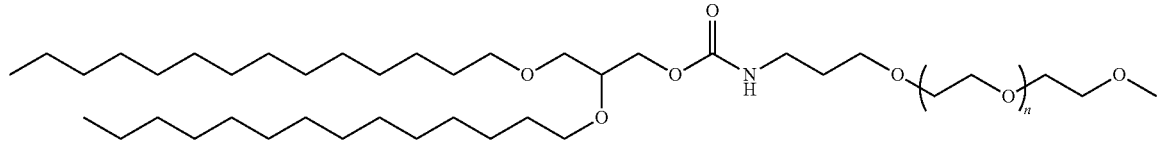

wherein n is an integer from 1-500.

26. The compound of claim 25, wherein n is between 42 and 47.

27. A lipid particle comprising a compound of claim 5.

28. The compound of claim 1, wherein, each of $R^1$ and $R^2$ are independently $C_6$-$C_{28}$ alkyl or $C_6$-$C_{30}$ alkenyl and X is —C(O)NH—.

* * * * *